US008372410B2

(12) United States Patent
Meinke et al.

(10) Patent No.: US 8,372,410 B2
(45) Date of Patent: Feb. 12, 2013

(54) S. EPIDERMIDIS ANTIGENS

(75) Inventors: Andreas Meinke, Pressbaum (AU); Min Bui Duc, Vienna (AU); Eszter Nagy, Vienna (AU)

(73) Assignee: Intercell AG, Vienna (AT)

( * ) Notice: Subject to any disclaimer, the term of this patent is extended or adjusted under 35 U.S.C. 154(b) by 0 days.

(21) Appl. No.: 13/540,696

(22) Filed: Jul. 3, 2012

(65) Prior Publication Data

US 2012/0269843 A1  Oct. 25, 2012

Related U.S. Application Data

(62) Division of application No. 12/625,053, filed on Nov. 24, 2009, now Pat. No. 8,236,325, which is a division of application No. 10/551,492, filed as application No. PCT/EP2004/003398 on Mar. 31, 2004, now Pat. No. 7,628,994.

(30) Foreign Application Priority Data

Mar. 31, 2003  (EP) ..................................... 03450078

(51) Int. Cl.
*A61K 39/085* (2006.01)
*C07K 14/31* (2006.01)

(52) U.S. Cl. .................. 424/243.1; 424/190.1; 530/300; 530/350

(58) Field of Classification Search .................. None
See application file for complete search history.

(56) References Cited

U.S. PATENT DOCUMENTS

| | | | |
|---|---|---|---|
| 6,380,370 B1 | 4/2002 | Doucette-Stamm et al. |
| 7,410,647 B2 | 8/2008 | Foster et al. |
| 7,628,994 B2 | 12/2009 | Meinke et al. |
| 8,236,325 B2 | 8/2012 | Meinke et al. |

FOREIGN PATENT DOCUMENTS

| | | |
|---|---|---|
| DE | 197 42 706 A1 | 4/1999 |
| WO | WO-99/16873 A1 | 4/1999 |
| WO | WO-01/34809 A2 | 5/2001 |
| WO | WO-02/059148 A2 | 8/2002 |
| WO | WO-02/077183 A2 | 10/2002 |
| WO | WO-03/011899 A2 | 2/2003 |

OTHER PUBLICATIONS

Abaza et al., Effects of amino acid substitutions outside an antigenic site on protein binding to monoclonal antibodies of predetermined specificity obtained by peptide immunization: demonstration with region 94-100 (antigenic site 3) of myoglobin, J. Protein Chem., 1992;11:433-44.
Bowie et al., Deciphering the message in protein sequences: tolerance to amino acid substitutions, Science, 1990;247:1306-10.
Colman, Effects of amino acid sequence changes on antibody-antigen interactions, Res. Immunol., 1994;145:33-6.
Database EMBL, Database accession No. ABN92018, 2002.
Database EMBL, Database accession No. ABP39473, 2003.
Database EMBL, Database accession No. ABU43096, 2002.
Database EMBL, Database accession No. ACA46966, 2003.
Database EMBL, Database accession No. AE015929, 2002.
Database EMBL, Database accession No. AE016751 2002.
Database EMBL, Database accession No. Q8CQX2, 2003.
Greenspan et al., Defining epitopes: its not as easy as it seems, Nature Biotechnology, 1999;7:936-937.
Henics et al., Small-fragment genomic libraries for the display of putative epitopes from clinically significant pathogens, Biotechniques, 2003;35:196-209.
Herbert et al., In: The Dictionary of Immunology, Academic Press, 3·sup·rd Edition, London, 1985, pp. 58-59.
Holmes, PSMA specific antibodies and their diagnostic and therapeutic use, Exp. Opin. Invest. Drugs, 2001;10:511-19.
Office Communication, issued in U.S. Appl. No. 10/551,492, mailed Dec. 7, 2006.
Office Communication, issued in U.S. Appl. No. 10/551,492, mailed Oct. 2, 2007.
Office Communication, issued in U.S. Appl. No. 10/551,492, mailed May 13, 2008.
Office Communication, issued in U.S. Appl. No. 10/551,492, mailed Oct. 28, 2008.
Roitt et al., In: Immunology, Mosby, 4·sup·th Edition, St. Louis 1993 pp. 7.7-7.8.
Shinefield et al., Use of a Staphylococcus aureus Conjugate Vaccine in Patients Receiving Hemodialysis, N. Eng. J. Med., 2002;346:491-496.
Sjölund et al., Persistence of resistant *Staphylococcus epidermidis* after single course of clarithromycin. Emerg Infect Dis. Sep. 2005;1 1(9):1389-93.
Zhang et al., Genome-based analysis of virulence genes in a non-biofilm-forming *Staphylococcus epidermis* strain, Molecular Microbiology, 2003;49:1577-1593.

*Primary Examiner* — Padma V Baskar

(74) *Attorney, Agent, or Firm* — Wolf, Greenfield & Sacks, P.C.

(57) ABSTRACT

Hyperimmune serum reactive antigens and fragments thereof are disclosed. In addition, methods for isolating such antigens and specific uses thereof, including the treatment of *S. epidermidis* infections, are disclosed.

14 Claims, 4 Drawing Sheets

A.

B.

| Total (trimmed) | | 409 | (100.0 %) |
| --- | --- | --- | --- |
| ORF (+/+, +/-) | ○ | 248 | (60.7 %) |
| non-ORF (+/+, +/-) | ▦ | 93 | (22.7 %) |
| chimeric | ◇ | 18 | (4.4 %) |
| non-blastable | | 50 | (12.2 %) |

A

B

S. EPIDERMIDIS ANTIGENS

CROSS-REFERENCE TO RELATED APPLICATIONS

This application is a divisional application of U.S. application Ser. No. 12/625,053 filed on Nov. 24, 2009, which is a divisional of U.S. application Ser. No. 10/551,492 filed on Oct. 13, 2006, which is a national phase application under 35 U.S.C. §371 of International Application No. PCT/EP2004/003398 filed Mar. 31, 2004, which claims priority to European Application No. 03450078.5 filed Mar. 31, 2003. The above-referenced applications are incorporated herein by reference in their entirety.

BACKGROUND

The present invention relates to isolated nucleic acid molecules, which encode antigens for *Staphylococcus epidermidis*, which are suitable for use in preparation of pharmaceutical medicaments for the prevention and treatment of bacterial infections caused by *Staphylococcus epidermidis*.

Staphylococci are opportunistic pathogens, which can cause illnesses, which range from minor infections to life threatening diseases. Of the large number of Staphylococci at least 3 are commonly associated with human disease: *S. aureus, S. epidermidis* and rarely *S. saprophyticus* (Crossley, K. B. and Archer G. L, eds. (1997). The Staphylococci in Human Disease. Churchill Livingston Inc.) Staphylococcal infections are imposing an increasing threat in hospitals world-wide. The appearance and disease causing capacity of Staphylococci are related to the wide-spread use of antibiotics, which induced and continue to induce multi-drug resistance. Both *S. aureus* and *S. epidermidis* have become resistant to many commonly used antibiotics, most importantly to methicillin (MRSA) and vancomycin (VISA). Drug resistance is an increasingly important public health concern, and soon many infections caused by staphylococci may be untreatable by antibiotics. In addition to its adverse effect on public health, antimicrobial resistance contributes to higher health care costs, since treating resistant infections often requires the use of more toxic and more expensive drugs, and can result in longer hospital stays for infected patients. Moreover, even with the help of effective antibiotics, the most serious staphylococcal infections have 30-50% mortality.

Every human being is colonized with *S. epidermidis*. The normal habitats of *S. epidermidis* are the skin and the mucous membrane. Generally, the established flora of the nose prevents acquisition of new strains. However, colonization with other strains may occur when antibiotic treatment is given that leads to elimination of the susceptible carrier strain. Because this situation occurs in the hospitals, patients may become colonized with resistant nosocomial Staphylococci.

Staphylococci become potentially pathogenic as soon as the natural balance between microorganisms and the immune system gets disturbed, when natural barriers (skin, mucous membrane) are breached. The coagulase-positive *S. aureus* is the most pathogenic staphylococcal species, feared by surgeons for a long time. Most frequently it causes surgical wound infections, and induces the formation of abscesses. *S. epidermidis* causes diseases mostly related to the presence of foreign bodies and the use of devices, such as catheter related infections, cerebrospinal fluid shunt infections, peritonitis in dialysed patients (mainly CAPD), endocarditis in individuals with prosthetic valves. This is exemplified in immunocompromised individuals such as oncology patients and premature neonates in whom coagulase-negative staphylococcal infections frequently occur in association with the use of intravascular device. The increase in incidence is related to the increased used of these devices and increasing number of immuno-compromised patients.

The pathogenesis of staphylococci is multifactorial. In order to initiate infection the pathogen has to gain access to the cells and tissues of the host, that is adhere. Since adherence is obviously a crucial step in the initiation of foreign body infections, *S. epidermidis* is equipped with a number of cell surface molecules, which promote adherence to foreign material and through that mechanism establish infection in the host. A characteristic of many pathogenic strains of *S. epidermidis* is the production of a slime resulting in biofilm formation. The slime is predominantly a secreted teichoic acid, normally found in the cell wall of the staphylococci. This ability to form a biofilm on the surface of a prosthetic device is probably a significant determinant of virulence for these bacteria, since this prevents phagocytosis of the bacteria. A further means of staphylococci to cause damage to its host are the secreted products, such as enterotoxins, exotoxins, and tissue damaging enzymes. The toxins kill or misguide immune cells, which are important in the host defence. The several different types of toxins are responsible for most of the symptoms during infections.

For all the above-mentioned reasons there remains a need for an effective preventive and therapeutic treatment, but until today there is no effective preventive or therapeutic vaccine approved. It has been shown that an antibody deficiency state contributes to staphylococcal persistence, suggesting that anti-staphylococcal antibodies are important in host defence. Antibodies—added as passive immunisation or induced by active vaccination—directed towards surface components could both, prevent bacterial adherence, neutralize toxins and promote phagocytosis. An effective vaccine offers great potential for patients facing elective surgery in general, and those receiving endovascular devices, in particular. Moreover, patients suffering from chronic diseases, which decrease immune responses or undergoing continuous ambulatory peritoneal dialysis are likely to benefit from such a vaccine.

A vaccine can contain a whole variety of different antigens. Examples of antigens are whole-killed or attenuated organisms, subfractions of these organisms/tissues, proteins, or, in their most simple form, peptides. Antigens can also be recognized by the immune system in form of glycosylated proteins or peptides and may also be or contain polysaccharides or lipids. Short peptides can be used since for example cytotoxic T-cells (CTL) recognize antigens in form of short usually 8-11 amino acids long peptides in conjunction with major histocompatibility complex (MHC). B-cells can recognize linear epitopes as short as 4-5 amino acids, as well as three-dimensional structures (conformational epitopes). In order to obtain sustained, antigen-specific immune responses, adjuvants need to trigger immune cascades that involve all cells of the immune system necessary. Primarily, adjuvants are acting, but are not restricted in their mode of action, on so-called antigen presenting cells (APCs). These cells usually first encounter the antigen(s) followed by presentation of processed or unmodified antigen to immune effector cells. Intermediate cell types may also be involved. Only effector cells with the appropriate specificity are activated in a productive immune response. The adjuvant may also locally retain antigens and co-injected other factors. In addition the adjuvant may act as a chemoattractant for other immune cells or may act locally and/or systemically as a stimulating agent for the immune system.

Approaches to develop a vaccine have focused until today mainly on *S. aureus* {Shinefield, H. et al., 2002}. Therefore it would be of great value to develop a vaccine targeting *S. epidermidis* or preferentially both Staphylococci.

The present inventors have developed a method for identification, isolation and production of hyperimmune serum reactive antigens from a specific pathogen, especially from *Staphylococcus aureus* and *Staphylococcus epidermidis* (WO 02/059148). Importantly for the present invention, the selection of sera for the identification of antigens from *S. epidermidis* is different from that applied to the previous screens.

Individuals undergoing continuous peritoneal dialysis represent one of the most important groups of patients infected by *S. epidermidis*. Staphylococci preferentially infect patients with foreign bodies such as dialysis catheters. Peritoneal dialysis patients suffer from peritonitis mainly caused by *S. aureus* and coagulase negative staphylococci, especially *S. epidermidis*. In order to identify antigens expressed by *S. epidermidis* in humans during peritonitis, human serum samples were collected from patients undergoing peritoneal dialysis for an extended period of time and suffered from peritonitis caused by *S. epidermidis* within the previous 12 months, and thus considered to be in the late convalescent phase of the disease. It has been firmly established that patients with serious staphylococcal diseases—such as peritonitis—develop antibodies, which sustain for up to a year.

The problem underlying the present invention was to provide means for the development of medicaments such as vaccines against *S. epidermidis* infection. More particularly, the problem was to provide an efficient and relevant set of nucleic acid molecules or hyperimmune serum reactive antigens from *S. epidermidis* that can be used for the manufacture of said medicaments.

Therefore, the present invention provides an isolated nucleic acid molecule encoding a hyperimmune serum reactive antigen or a fragment thereof comprising a nucleic acid sequence, which is selected from the group consisting of:
a) a nucleic acid molecule having at least 70% sequence identity to a nucleic acid molecule selected from Seq ID No 1, 4, 6-9, 11-13, 15, 17, 19, 21, 25-26, 28-31.
b) a nucleic acid molecule which is complementary to the nucleic acid molecule of a),
c) a nucleic acid molecule comprising at least 15 sequential bases of the nucleic acid molecule of a) or b)
d) a nucleic acid molecule which anneals under stringent hybridisation conditions to the nucleic acid molecule of a), b), or c)
e) a nucleic acid molecule which, but for the degeneracy of the genetic code, would hybridise to the nucleic acid molecule defined in a), b), c) or d).

According to a preferred embodiment of the present invention the sequence identity is at least 80%, preferably at least 95%, especially 100%.

Furthermore, the present invention provides an isolated nucleic acid molecule encoding a hyperimmune serum reactive antigen or a fragment thereof comprising a nucleic acid sequence selected from the group consisting of
a) a nucleic acid molecule having at least 96% sequence identity to a nucleic acid molecule selected from Seq ID No 2-3, 5, 10, 14, 16, 18, 22-24, 27,
b) a nucleic acid molecule which is complementary to the nucleic acid molecule of a),
c) a nucleic acid molecule comprising at least 15 sequential bases of the nucleic acid molecule of a) or b)
d) a nucleic acid molecule which anneals under stringent hybridisation conditions to the nucleic acid molecule of a), b) or c),
e) a nucleic acid molecule which, but for the degeneracy of the genetic code, would hybridise to the nucleic acid defined in a), b), c) or d).

According to another aspect, the present invention provides an isolated nucleic acid molecule comprising a nucleic acid sequence selected from the group consisting of
a) a nucleic acid molecule selected from Seq ID No 20.
b) a nucleic acid molecule which is complementary to the nucleic acid of a),
c) a nucleic acid molecule which, but for the degeneracy of the genetic code, would hybridise to the nucleic acid defined in a), b), c) or d).

Preferably, the nucleic acid molecule is DNA or RNA.

According to a preferred embodiment of the present invention, the nucleic acid molecule is isolated from a genomic DNA, especially from a *S. epidermidis* genomic DNA.

According to the present invention a vector comprising a nucleic acid molecule according to any of the present invention is provided.

In a preferred embodiment the vector is adapted for recombinant expression of the hyperimmune serum reactive antigens or fragments thereof encoded by the nucleic acid molecule according to the present invention.

The present invention also provides a host cell comprising the vector according to the present invention.

According to another aspect the present invention further provides a hyperimmune serum-reactive antigen comprising an amino acid sequence being encoded by a nucleic acid molecule according to the present invention.

In a preferred embodiment the amino acid sequence (polypeptide) is selected from the group consisting of Seq ID No 32, 35, 37-40, 42-44, 46, 48, 50, 52, 56-57, 59-62.

In another preferred embodiment the amino acid sequence (polypeptide) is selected from the group consisting of Seq ID No 33-34, 36, 41, 45, 47, 49, 53-55, 58.

In a further preferred embodiment the amino acid sequence (polypeptide) is selected from the group consisting of Seq ID No 51.

According to a further aspect the present invention provides fragments of hyperimmune serum-reactive antigens selected from the group consisting of peptides comprising amino acid sequences of column "predicted immunogenic aa" and "location of identified immunogenic region" of Table 1; the serum reactive epitopes of Table 1, especially peptides comprising amino acids 6-28, 54-59, 135-147, 193-205, 274-279, 284-291, 298-308, 342-347, 360-366, 380-386, 408-425, 437-446, 457-464, 467-477, 504-510, 517-530, 535-543, 547-553, 562-569, 573-579, 592-600, 602-613, 626-631, 638-668 and 396-449 of Seq ID No 32; 5-24, 101-108, 111-117, 128-142, 170-184, 205-211, 252-267, 308-316, 329-337, 345-353, 360-371, 375-389, 393-399, 413-419, 429-439, 446-456, 471-485, 495-507, 541-556, 582-588, 592-602, 607-617, 622-628, 630-640 and 8-21 of Seq ID No 33; 10-20, 23-33, 40-45, 59-65, 72-107, 113-119, 127-136, 151-161 and 33-59 of Seq ID No 34; 4-16, 28-34, 39-61, 66-79, 100-113, 120-127, 130-137, 142-148, 150-157, 192-201, 203-210, 228-239, 245-250, 256-266, 268-278, 288-294, 312-322, 336-344, 346-358, 388-396, 399-413, 425-430, 445-461, 464-470, 476-482, 486-492, 503-511, 520-527, 531-541, 551-558, 566-572, 609-625, 635-642, 650-656, 683-689, 691-705, 734-741, 750-767, 782-789, 802-808, 812-818, 837-844, 878-885, 907-917, 930-936 and 913-933 of Seq ID No 35; 5-12, 20-27, 46-78, 85-92, 104-112, 121-132, 150-167, 179-185, 200-213, 221-227, 240-264, 271-279, 282-290, 311-317 and 177-206 of Seq ID No 36; 18-24, 31-40, 45-51, 89-97, 100-123, 127-132, 139-153, 164-170, 184-194, 200-205, 215-238, 244-255, 257-270, 272-280, 289-302, 312-318, 338-348, 356-367 and 132-152 of Seq ID No 37; 7-16, 39-45, 73-83, 90-98, 118-124, 130-136, 194-204, 269-280, 320-327, 373-381, 389-397, 403-408, 424-430, 436-441, 463-476, 487-499, 507-514, 527-534, 540-550, 571-577, 593-599, 620-629, 641-647, 650-664, 697-703, 708-717, 729-742, 773-790, 794-805, 821-828, 830-837, 839-851, 858-908, 910-917, 938-947, 965-980, 1025-1033, 1050-1056, 1073-1081, 1084-1098, 1106-1120, 1132-1140, 1164-1170, 1185-1194, 1201-1208, 1215-1224, 1226-1234, 1267-1279, 1325-1331, 1356-1364, 1394-1411, 1426-1439, 1445-1461, 1498-1504, 1556-1561, 1564-1573, 1613-1639, 1648-1655, 1694-1714, 1748-1755, 1778-1785, 1808-1813, 1821-1827, 1829-1837, 1846-1852, 1859-1865, 1874-1883, 1895-1900, 1908-1913, 1931-1937, 1964-1981, 1995-2005, 2020-2033, 2040-2047, 2103-2109, 2118-2127, 2138-2144, 2166-2175, 2180-2187, 2220-2225, 2237-2242, 2247-2253, 2273-2281, 2286-2306, 2314-2320, 2323-2345, 2350-2355, 2371-2384, 2415-2424, 2426-2431, 2452-2472, 2584-2589, 2610-2621, 2638-2655, 2664-2670, 2681-2690, 2692-2714, 2724-2730 and 687-730 of Seq ID No 38; 10-40, 53-59, 79-85, 98-104, 117-122, 130-136, 144-158, 169-175, 180-185, 203-223, 232-237, 243-254, 295-301 and 254-292 of Seq ID No 39; 28-50, 67-85, 93-115, 120-134, 144-179, 240-249, 328-340, 354-360, 368-400, 402-417, 419-427, 429-445, 447-455, 463-468, 472-480, 485-500, 502-510, 512-534, 537-546, 553-558, 582-594, 619-637, 645-654, 690-709, 735-745, 749-756, 786-792, 275-316 and 378-401 of Seq ID No 40; 5-16, 21-30, 33-40, 52-74, 101-108, 116-122, 164-182, 185-219, 256-261, 273-279, 285-291, 297-304, 312-328, 331-338, 355-362, 364-371, 373-401, 411-423 and 191-208 of Seq ID No 41; 34-55, 67-74, 85-93, 105-115, 138-152, 161-171, 182-189, 197-205, 213-219, 232-239, 241-248, 250-263, 272-277, 288-299 and 216-231 of Seq ID No 42; 21-27, 32-37, 43-51, 67-74, 82-92, 94-100, 106-112, 140-149, 153-159, 164-182, 193-215, 222-227, 260-267, 308-322, 330-340, 378-387, 396-403, 417-432, 435-441, 448-465, 476-482, 488-498, 500-510 and 214-280 of Seq ID No 43; 4-21, 29-52, 80-87, 104-123, 126-133, 141-157, 182-189, 194-202, 214-220, 227-235, 242-252 and 33-108 of Seq ID No 44; 12-18, 20-27, 29-59, 64-72, 84-90, 96-103, 109-121, 125-155, 164-177, 179-186, 188-201, 216-227, 235-253, 259-274, 276-294, 296-310, 322-339, 341-348, 369-379, 398-403, 409-421 and 76-96 of Seq ID No 45; 4-15, 24-41, 71-80, 104-111, 113-119, 123-130, 139-149, 168-178, 187-200 and 4-45 of Seq ID No 46; 13-19, 32-37, 44-56 and 1-14 of Seq ID No 47; 6-11, 16-35, 75-81, 95-100, 126-139, 206-214, 225-233, 241-259, 268-276, 319-325, 339-360, 371-401, 435-441, 452-459, 462-472, 491-503, 505-516, 549-556, 567-580, 590-595, 612-622, 624-630, 642-648, 656-662, 687-693, 698-704, 706-712, 736-750, 768-777, 784-789, 812-818, 847-858, 894-900, 922-931, 938-949, 967-984, 986-992, 1027-1032, 1041-1054, 1082-1088, 1091-1097, 1119-1124, 1234-1240, 1250-1258, 1274-1289, 1299-1305, 1392-1398, 1400-1405, 1429-1442, 1460-1474, 1505-1514, 1531-1537, 1540-1552, 1558-1571, 1582-1587, 1616-1623, 1659-1666, 1671-1677, 1680-1686, 1698-1704, 1706-1712, 1768-1774, 1783-1797, 1814-1819, 1849-1855, 1870-1876, 1890-1897, 1947-1953, 1972-1980, 1999-2013, 2044-2051, 2068-2084, 2093-2099, 2122-2131, 2142-2147, 2156-2163, 2170-2179, 2214-2220, 2235-2245, 2271-2281, 2287-2293, 2308-2317, 2352-2362, 2373-2378, 2387-2407, 2442-2448, 2458-2474, 2507-2516, 2531-2537, 2540-2551, 2555-2561, 2586-2599, 2617-2627, 2644-2649, 2661-2675, 2685-2692, 2695-2707, 2733-2739, 2741-2747, 2774-2783, 2788-2795, 2860-2870, 2891-2903, 2938-2947, 2973-2980, 2993-2999, 3004-3030, 3046-3059, 3066-3077, 3082-3088, 3120-3132, 3144-3149, 3153-3169, 3200-3212, 3232-3256, 3276-3290, 3308-3322, 3330-3338, 3353-3360, 3363-3371, 3390-3408, 3431-3447, 3454-3484, 3503-3515, 3524-3541, 3543-3550, 3560-3567, 3586-3599, 3616-3621, 3642-3647, 3663-3679, 213-276, 579-621 and 1516-1559 of Seq ID No 48; 19-41, 43-49, 55-62, 67-74, 114-121, 130-140, 188-197, 208-217, 226-232, 265-287, 292-299, 301-319, 372-394, 400-410, 421-427 and 12-56 of Seq ID No 49; 6-12, 44-51, 53-60, 67-88, 91-100, 104-123, 137-142, 148-158, 161-168, 175-201, 204-210, 222-231, 239-253, 258-264, 272-282 and 60-138 of Seq ID No 50; 4-63, 69-104, 110-121, 124-131, 134-152, 161-187, 204-221, 223-237, 239-296, 298-310, 331-365, 380-405, 423-451, 470-552, 554-562, 574-581, 592-649, 651-658, 661-671, 673-707, 713-734, 741-748, 758-765, 773-790 and 509-528 of Seq ID No 51; 89-94, 102-115, 123-129, 181-188, 200-206, 211-235, 239-249, 267-281, 295-310, 316-321, 331-341, 344-359, 365-386, 409-422, 443-453, 495-506, 514-521, 539-547, 553-560, 563-570, 586-596, 621-626, 633-638, 651-657, 666-683, 697-705, 731-739, 761-768, 865-883 and 213-265 of Seq ID No 52; 5-20, 24-34, 37-43, 92-102, 134-139, 156-162, 184-191, 193-205, 207-213, 225-231, 241-247, 259-267, 269-286, 337-350, 365-372, 378-386, 399-413, 415-421, 447-457, 467-481 and 145-183 of Seq ID No 53; 12-19, 29-41, 43-57, 80-98, 106-141, 143-156, 172-183, 185-210, 214-220, 226-234, 278-287 and 237-287 of Seq ID No 54; 5-12, 32-48, 50-72, 75-81, 88-94 and 16-40 of Seq ID No 55; 4-21, 29-42, 48-62, 65-80, 95-101, 103-118, 122-130, 134-140, 143-152, 155-165, 182-192, 198-208, 232-247, 260-268, 318-348, 364-369, 380-391, 403-411, 413-424 and 208-230 of Seq ID No 56; 4-18, 65-75, 82-92, 123-140, 144-159, 166-172, 188-194 and 174-195 of Seq ID No 57; 7-20, 58-71, 94-101, 110-119, 199-209, 231-242, 247-254, 267-277, 282-290, 297-306, 313-319, 333-342, 344-369, 390-402, 414-431, 436-448, 462-471 and 310-350 of Seq ID No 58; 4-25, 37-44, 53-59, 72-78, 86-99, 119-128, 197-203, 209-218, 220-226, 233-244, 246-254, 264-271, 277-289, 407-430, 437-445, 464-472, 482-488, 503-509 and 308-331 of Seq ID No 59; 4-12, 14-43, 52-58 and 43-58 of Seq ID No 60; 4-14, 21-29, 35-49 and 38-50 of Seq ID No 61; 4-19, 31-37, 58-72, 94-108 and 1-72 of Seq ID No 62.

The present invention also provides a process for producing a *S. epidermidis* hyperimmune serum reactive antigen or a fragment thereof according to the present invention comprising expressing one or more of the nucleic acid molecules according to the present invention in a suitable expression system.

Moreover, the present invention provides a process for producing a cell, which expresses a *S. epidermidis* hyperimmune serum reactive antigen or a fragment thereof according to the present invention comprising transforming or transfecting a suitable host cell with the vector according to the present invention.

According to the present invention a pharmaceutical composition, especially a vaccine, comprising a hyperimmune serum-reactive antigen or a fragment thereof as defined in the present invention or a nucleic acid molecule as defined in the present invention is provided.

In a preferred embodiment the pharmaceutical composition further comprises an immunostimulatory substance, preferably selected from the group comprising polycationic polymers, especially polycationic peptides, immunostimulatory deoxynucleotides (ODNs), peptides containing at least two LysLeuLys motifs, especially KLKL5KLK (SEQ ID NO:63), neuroactive compounds, especially human growth hormone, alumn, Freund's complete or incomplete adjuvants or combinations thereof.

In a more preferred embodiment the immunostimulatory substance is a combination of either a polycationic polymer and immunostimulatory deoxynucleotides or of a peptide containing at least two LysLeuLys motifs and immunostimulatory deoxynucleotides.

In a still more preferred embodiment the polycationic polymer is a polycationic peptide, especially polyarginine.

According to the present invention the use of a nucleic acid molecule according to the present invention or a hyperimmune serum-reactive antigen or fragment thereof according to the present invention for the manufacture of a pharmaceutical preparation, especially for the manufacture of a vaccine against S. epidermidis infection, is provided.

Also an antibody, or at least an effective part thereof, which binds at least to a selective part of the hyperimmune serum-reactive antigen or a fragment thereof according to the present invention is provided herewith.

In a preferred embodiment the antibody is a monoclonal antibody.

In another preferred embodiment the effective part of the antibody comprises Fab fragments.

In a further preferred embodiment the antibody is a chimeric antibody.

In a still preferred embodiment the antibody is a humanized antibody.

The present invention also provides a hybridoma cell line, which produces an antibody according to the present invention.

Moreover, the present invention provides a method for producing an antibody according to the present invention, characterized by the following steps:
  initiating an immune response in a non-human animal by administrating an hyperimmune serum-reactive antigen or a fragment thereof, as defined in the invention, to said animal,
  removing an antibody containing body fluid from said animal, and
  producing the antibody by subjecting said antibody containing body fluid to further purification steps.

Accordingly, the present invention also provides a method for producing an antibody according to the present invention, characterized by the following steps:
  initiating an immune response in a non-human animal by administrating an hyperimmune serum-reactive antigen or a fragment thereof, as defined in the present invention, to said animal,
  removing the spleen or spleen cells from said animal,
  producing hybridoma cells of said spleen or spleen cells,
  selecting and cloning hybridoma cells specific for said hyperimmune serum-reactive antigens or a fragment thereof,
  producing the antibody by cultivation of said cloned hybridoma cells and optionally further purification steps.

The antibodies provided or produced according to the above methods may be used for the preparation of a medicament for treating or preventing S. epidermidis infections.

According to another aspect the present invention provides an antagonist, which binds to a hyperimmune serum-reactive antigen or a fragment thereof according to the present invention.

Such an antagonist capable of binding to a hyperimmune serum-reactive antigen or fragment thereof according to the present invention may be identified by a method comprising the following steps:
  a) contacting an isolated or immobilized hyperimmune serum-reactive antigen or a fragment thereof according to the present invention with a candidate antagonist under conditions to permit binding of said candidate antagonist to said hyperimmune serum-reactive antigen or fragment, in the presence of a component capable of providing a detectable signal in response to the binding of the candidate antagonist to said hyperimmune serum reactive antigen or fragment thereof; and
  b) detecting the presence or absence of a signal generated in response to the binding of the antagonist to the hyperimmune serum reactive antigen or the fragment thereof.

An antagonist capable of reducing or inhibiting the interaction activity of a hyperimmune serum-reactive antigen or a fragment thereof according to the present invention to its interaction partner may be identified by a method comprising the following steps:
  a) providing a hyperimmune serum reactive antigen or a hyperimmune fragment thereof according to the present invention,
  b) providing an interaction partner to said hyperimmune serum reactive antigen or a fragment thereof, especially an antibody according to the present invention,
  c) allowing interaction of said hyperimmune serum reactive antigen or fragment thereof to said interaction partner to form an interaction complex,
  d) providing a candidate antagonist,
  e) allowing a competition reaction to occur between the candidate antagonist and the interaction complex,
  f) determining whether the candidate antagonist inhibits or reduces the interaction activities of the hyperimmune serum reactive antigen or the fragment thereof with the interaction partner.

The hyperimmune serum reactive antigens or fragments thereof according to the present invention may be used for the isolation and/or purification and/or identification of an interaction partner of said hyperimmune serum reactive antigen or fragment thereof.

The present invention also provides a process for in vitro diagnosing a disease related to expression of a hyperimmune serum-reactive antigen or a fragment thereof according to the present invention comprising determining the presence of a nucleic acid sequence encoding said hyperimmune serum reactive antigen or fragment thereof according to the present invention or the presence of the hyperimmune serum reactive antigen or fragment thereof according to the present invention.

The present invention also provides a process for in vitro diagnosis of a bacterial infection, especially a S. epidermidis infection, comprising analyzing for the presence of a nucleic acid sequence encoding said hyperimmune serum reactive antigen or fragment thereof according to the present invention or the presence of the hyperimmune serum reactive antigen or fragment thereof according to the present invention.

Moreover, the present invention provides the use of a hyperimmune serum reactive antigen or fragment thereof according to the present invention for the generation of a peptide binding to said hyperimmune serum reactive antigen or fragment thereof, wherein the peptide is an anticaline.

The present invention also provides the use of a hyperimmune serum-reactive antigen or fragment thereof according to the present invention for the manufacture of a functional nucleic acid, wherein the functional nucleic acid is selected from the group comprising aptamers and spiegelmers.

The nucleic acid molecule according to the present invention may also be used for the manufacture of a functional ribonucleic acid, wherein the functional ribonucleic acid is selected from the group comprising ribozymes, antisense nucleic acids and siRNA.

The present invention advantageously provides an efficient and relevant set of isolated nucleic acid molecules and their encoded hyperimmune serum reactive antigens or fragments thereof identified from S. epidermidis using an antibody preparation from a human plasma pool and surface expression libraries derived from the genome of S. epidermidis. Thus, the present invention fulfils a widely felt demand for S. epidermidis antigens, vaccines, diagnostics and products useful in procedures for preparing antibodies and for identifying compounds effective against S. epidermidis infection.

An effective vaccine should be composed of proteins or polypeptides, which are expressed by all strains and are able to induce high affinity, abundant antibodies against cell surface components of S. epidermidis. The antibodies should be IgG1 and/or IgG3 for opsonization, and any IgG sub-type and IgA for neutralisation of adherence and toxin action. A chemically defined vaccine must be definitely superior compared to a whole cell vaccine (attenuated or killed), since components of S. epidermidis, which might cross-react with human tissues or inhibit opsonization can be eliminated, and the individual proteins inducing protective antibodies and/or a protective immune response can be selected.

The approach, which has been employed for the present invention, is based on the interaction of staphylococcal proteins or peptides with the antibodies present in human sera. The antibodies produced against S. epidermidis by the human immune system and present in human sera are indicative of the in vivo expression of the antigenic proteins and their immunogenicity. In addition, the antigenic proteins as identified by the bacterial surface display expression libraries using pools of pre-selected sera, are processed in a second and third round of screening by individual selected or generated sera. Thus the present invention supplies an efficient and relevant set of staphyloococcal antigens as a pharmaceutical composition, especially a vaccine preventing infection by S. epidermidis.

In the antigen identification program for identifying a relevant and efficient set of antigens according to the present invention, three different bacterial surface expression libraries are screened with a serum pool derived from a serum collection, which has been tested against antigenic compounds of S. epidermidis, such as whole cell extracts and culture supernatant proteins in order to be considered hyperimmune and therefore relevant in the screening method applied for the present invention. The antibodies produced against staphylococci by the human immune system and present in human sera are indicative of the in vivo expression of the antigenic proteins and their immunogenicity.

The expression libraries as used in the present invention should allow expression of all potential antigens, e.g. derived from all surface proteins of S. epidermidis. Bacterial surface display libraries will be represented by a recombinant library of a bacterial host displaying a (total) set of expressed peptide sequences of staphylococci on a number of selected outer membrane proteins (LamB, FhuA) at the bacterial host membrane {Georgiou, G., 1997; Etz, H. et al., 2001}. One of the advantages of using recombinant expression libraries is that the identified hyperimmune serum-reactive antigens may be instantly produced by expression of the coding sequences of the screened and selected clones expressing the hyperimmune serum-reactive antigens without further recombinant DNA technology or cloning steps necessary.

The comprehensive set of antigens identified by the described program according to the present invention is analysed further by one or more additional rounds of screening. Therefore individual antibody preparations or antibodies generated against selected peptides, which were identified as immunogenic are used. According to a preferred embodiment the individual antibody preparations for the second round of screening are derived from patients who have suffered from an acute infection with staphylococci, especially from patients who show an antibody titer above a certain minimum level, for example an antibody titer being higher than 80 percentile, preferably higher than 90 percentile, especially higher than 95 percentile of the human (patient or healthy individual) sera tested. Using such high titer individual antibody preparations in the second screening round allows a very selective identification of the hyperimmune serum-reactive antigens and fragments thereof from S. epidermidis.

Following the screening procedure, the selected antigenic proteins, expressed as recombinant proteins or in vitro translated products, in case it can not be expressed in prokaryotic expression systems, or the identified antigenic peptides (produced synthetically) are tested in a second screening by a series of ELISA and Western blotting assays for the assessment of their immunogenicity with a large human serum collection (>100 uninfected, >50 patients sera).

It is important that the individual antibody preparations (which may also be the selected serum) allow a selective identification of the most promising candidates of all the hyperimmune serum-reactive antigens from all the promising candidates from the first round. Therefore, preferably at least 10 individual antibody preparations (i.e. antibody preparations (e.g. sera) from at least 10 different individuals having suffered from an infection to the chosen pathogen) should be used in identifying these antigens in the second screening round. Of course, it is possible to use also less than 10 individual preparations, however, selectivity of the step may not be optimal with a low number of individual antibody preparations. On the other hand, if a given hyperimmune serum-reactive antigen (or an antigenic fragment thereof) is recognized by at least 10 individual antibody preparations, preferably at least 30, especially at least 50 individual antibody preparations, identification of the hyperimmune serum-reactive antigen is also selective enough for a proper identification. Hyperimmune serum-reactivity may of course be tested with as many individual preparations as possible (e.g. with more than 100 or even with more than 1,000).

Therefore, the relevant portion of the hyperimmune serum-reactive antibody preparations according to the method of the present invention should preferably be at least 10, more preferred at least 30, especially at least 50 individual antibody preparations. Alternatively (or in combination) hyperimmune serum-reactive antigens may preferably be also identified with at least 20%, preferably at least 30%, especially at least 40% of all individual antibody preparations used in the second screening round.

According to a preferred embodiment of the present invention, the sera from which the individual antibody preparations for the second round of screening are prepared (or which are used as antibody preparations), are selected by their titer against S. epidermidis (e.g. against a preparation of this pathogen, such as a lysate, cell wall components and recombinant proteins). Preferably, some are selected with a total IgA titer above 4,000 U, especially above 6,000 U, and/or an IgG titer above 10,000 U, especially above 12,000 U (U=units, calculated from the OD405 nm reading at a given dilution) when the whole organism (total lysate or whole cells) is used as antigen in the ELISA.

The antibodies produced against staphylococci by the human immune system and present in human sera are indicative of the in vivo expression of the antigenic proteins and their immunogenicity. The recognition of linear epitopes by antibodies can be based on sequences as short as 4-5 amino acids. Of course it does not necessarily mean that these short peptides are capable of inducing the given antibody in vivo. For that reason the defined epitopes, polypeptides and proteins are further to be tested in animals (mainly in mice) for their capacity to induce antibodies against the selected proteins in vivo.

The preferred antigens are located on the cell surface or are secreted, and are therefore accessible extracellularly. Antibodies against cell wall proteins are expected to serve two purposes: to inhibit adhesion and to promote phagocytosis. Antibodies against secreted proteins are beneficial in neutralisation of their function as toxin or virulence component. It is also known that bacteria communicate with each other through secreted proteins. Neutralizing antibodies against these proteins will interrupt growth-promoting cross-talk between or within streptococcal species. Bioinformatic analyses (signal sequences, cell wall localisation signals, transmembrane domains) proved to be very useful in assessing cell surface localisation or secretion. The experimental approach includes the isolation of antibodies with the corresponding epitopes and proteins from human serum, and the generation of immune sera in mice against (poly)peptides selected by the bacterial surface display screens. These sera are then used in a third round of screening as reagents in the following assays: cell surface staining of staphylococci grown under different conditions (FACS, microscopy), determination of neutralizing capacity (toxin, adherence), and promotion of opsonization and phagocytosis (in vitro phagocytosis assay).

For that purpose, bacterial *E. coli* clones are directly injected into mice and immune sera are taken and tested in the relevant in vitro assay for functional opsonic or neutralizing antibodies. Alternatively, specific antibodies may be purified from human or mouse sera using peptides or proteins as substrate.

Host defence against *S. epidermidis* relies mainly on innate immunological mechanisms. Inducing high affinity antibodies of the opsonic and neutralizing type by vaccination helps the innate immune system to eliminate bacteria and toxins. This makes the method according to the present invention an optimal tool for the identification of staphylococcal antigenic proteins.

The skin and mucous membranes are formidable barriers against invasion by staphylococci. However, once the skin or the mucous membranes are breached the first line of non-adaptive cellular defence begins its co-ordinate action through complement and phagocytes, especially the polymorphonuclear leukocytes (PMNs). These cells can be regarded as the cornerstones in eliminating invading bacteria. As staphylococci are primarily extracellular pathogens, the major anti-staphylococcal adaptive response comes from the humoral arm of the immune system, and is mediated through three major mechanisms: promotion of opsonization, toxin neutralisation, and inhibition of adherence. It is believed that opsonization is especially important, because of its requirement for an effective phagocytosis. For efficient opsonization the microbial surface has to be coated with antibodies and complement factors for recognition by PMNs through receptors to the Fc fragment of the IgG molecule or to activated C3b. After opsonization, staphyloococci are phagocytosed and killed. Antibodies bound to specific antigens on the cell surface of bacteria serve as ligands for the attachment to PMNs and to promote phagocytosis. The very same antibodies bound to the adhesins and other cell surface proteins are expected to neutralize adhesion and prevent colonization. The selection of antigens as provided by the present invention is thus well suited to identify those that will lead to protection against infection in an animal model or in humans.

According to the antigen identification method used herein, the present invention can surprisingly provide a set of novel nucleic acids and novel hyperimmune serum reactive antigens and fragments thereof of *S. epidermidis*, among other things, as described below. According to one aspect, the invention particularly relates to the nucleotide sequences encoding hyperimmune serum reactive antigens which sequences are set forth in the Sequence listing Seq ID No: 1-31 and the corresponding encoded amino acid sequences representing hyperimmune serum reactive antigens are set forth in the Sequence Listing Seq ID No 32-62.

In a preferred embodiment of the present invention, a nucleic acid molecule is provided which exhibits 70% identity over their entire length to a nucleotide sequence set forth with Seq ID No 1, 4, 6-9, 11-13, 15, 17, 19, 21, 25-26, 28-31. Most highly preferred are nucleic acids that comprise a region that is at least 80% or at least 85% identical over their entire length to a nucleic acid molecule set forth with Seq ID No 1, 4, 6-9, 11-13, 15, 17, 19, 21, 25-26, 28-31. In this regard, nucleic acid molecules at least 90%, 91%, 92%, 93%, 94%, 95%, or 96% identical over their entire length to the same are particularly preferred. Furthermore, those with at least 97% are highly preferred, those with at least 98% and at least 99% are particularly highly preferred, with at least 99% or 99.5% being the more preferred, with 100% identity being especially preferred. Moreover, preferred embodiments in this respect are nucleic acids which encode hyperimmune serum reactive antigens or fragments thereof (polypeptides) which retain substantially the same biological function or activity as the mature polypeptide encoded by said nucleic acids set forth in the Seq ID No 1, 4, 6-9, 11-13, 15, 17, 19, 21, 25-26, 28-31.

Identity, as known in the art and used herein, is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Identity can be readily calculated. While there exist a number of methods to measure identity between two polynucleotide or two polypeptide sequences, the term is well known to skilled artisans (e.g. Sequence Analysis in Molecular Biology, von Heinje, G., Academic Press, 1987). Preferred methods to determine identity are designed to give the largest match between the sequences tested. Methods to determine identity are codified in computer programs. Preferred computer program methods to determine identity between two sequences include, but are not limited to, GCG program package {Devereux, J. et al., 1984}, BLASTP, BLASTN, and FASTA {Altschul, S. et al., 1990}.

According to another aspect of the invention, nucleic acid molecules are provided which exhibit at least 96% identity to the nucleic acid sequence set forth with Seq ID No 2-3, 5, 10, 14, 16, 18, 22-24, 27.

According to a further aspect of the present invention, nucleic acid molecules are provided which are identical to the nucleic acid sequences set forth with Seq ID No 20.

The nucleic acid molecules according to the present invention can as a second alternative also be a nucleic acid molecule which is at least essentially complementary to the nucleic acid described as the first alternative above. As used herein complementary means that a nucleic acid strand is base pairing via Watson-Crick base pairing with a second nucleic acid strand. Essentially complementary as used herein means that the base pairing is not occurring for all of the bases of the respective strands but leaves a certain number or percentage of the bases unpaired or wrongly paired. The percentage of correctly pairing bases is preferably at least 70%, more preferably 80%, even more preferably 90% and most preferably any percentage higher than 90%. It is to be noted that a percentage of 70% matching bases is considered as homology and the hybridization having this extent of matching base pairs is considered as stringent. Hybridization conditions for this kind of stringent hybridization may be taken from Current Protocols in Molecular Biology (John Wiley and Sons, Inc., 1987). More particularly, the hybridization conditions can be as follows:

Hybridization performed e.g. in 5×SSPE, 5×Denhardt's reagent, 0.1% SDS, 100 g/mL sheared DNA at 68° C.
Moderate stringency wash in 0.2×SSC, 0.1% SDS at 42° C.
High stringency wash in 0.1×SSC, 0.1% SDS at 68° C.

Genomic DNA with a GC content of 50% has an approximate TM of 96° C. For 1% mismatch, the TM is reduced by approximately 1° C.

In addition, any of the further hybridization conditions described herein are in principle applicable as well.

Of course, all nucleic acid sequence molecules which encode the same polypeptide molecule as those identified by the present invention are encompassed by any disclosure of a given coding sequence, since the degeneracy of the genetic code is directly applicable to unambiguously determine all possible nucleic acid molecules which encode a given polypeptide molecule, even if the number of such degenerated nucleic acid molecules may be high. This is also applicable for fragments of a given polypeptide, as long as the fragments encode a polypeptide being suitable to be used in a vaccination connection, e.g. as an active or passive vaccine.

The nucleic acid molecule according to the present invention can as a third alternative also be a nucleic acid which comprises a stretch of at least 15 bases of the nucleic acid molecule according to the first and second alternative of the nucleic acid molecules according to the present invention as outlined above. Preferably, the bases form a contiguous stretch of bases. However, it is also within the scope of the present invention that the stretch consists of two or more moieties, which are separated by a number of bases.

The present nucleic acids may preferably consist of at least 20, even more preferred at least 30, especially at least 50 contiguous bases from the sequences disclosed herein. The suitable length may easily be optimized due to the planned area of use (e.g. as (PCR) primers, probes, capture molecules (e.g. on a (DNA) chip), etc.). Preferred nucleic acid molecules contain at least a contiguous 15 base portion of one or more of the predicted immunogenic amino acid sequences listed in Table 1, especially the sequences of Table 1 with scores of more than 10, preferably more than 20, especially with a score of more than 25. Specifically preferred are nucleic acids containing a contiguous portion of a DNA sequence of any sequence in the sequence protocol of the present application which shows 1 or more, preferably more than 2, especially more than 5, non-identical nucleic acid residues compared to the published *Staphylococcus epidermidis* strain RP62A genome (http://www.tigr.org/tdb/mdb/mdbinprogress.html) and/or any other published *S. epidermidis* genome sequence or parts thereof. Specifically preferred non-identical nucleic acid residues are residues, which lead to a non-identical amino acid residue. Preferably, the nucleic acid sequences encode for polypeptides having at least 1, preferably at least 2, preferably at least three different amino acid residues compared to the published *S. epidermidis* counterparts mentioned above. Also such isolated polypeptides, being fragments of the proteins (or the whole protein) mentioned herein e.g. in the sequence listing, having at least 6, 7, or 8 amino acid residues and being encoded by these nucleic acids are preferred.

The nucleic acid molecule according to the present invention can as a fourth alternative also be a nucleic acid molecule which anneals under stringent hybridisation conditions to any of the nucleic acids of the present invention according to the above outlined first, second, and third alternative. Stringent hybridisation conditions are typically those described herein.

Finally, the nucleic acid molecule according to the present invention can as a fifth alternative also be a nucleic acid molecule which, but for the degeneracy of the genetic code, would hybridise to any of the nucleic acid molecules according to any nucleic acid molecule of the present invention according to the first, second, third, and fourth alternative as outlined above. This kind of nucleic acid molecule refers to the fact that preferably the nucleic acids according to the present invention code for the hyperimmune serum reactive antigens or fragments thereof according to the present invention. This kind of nucleic acid molecule is particularly useful in the detection of a nucleic acid molecule according to the present invention and thus the diagnosis of the respective microorganisms such as *S. epidermidis* and any disease or diseased condition where this kind of microorganism is involved. Preferably, the hybridisation would occur or be preformed under stringent conditions as described in connection with the fourth alternative described above.

Nucleic acid molecule as used herein generally refers to any ribonucleic acid molecule or deoxyribonucleic acid molecule, which may be unmodified RNA or DNA or modified RNA or DNA. Thus, for instance, nucleic acid molecule as used herein refers to, among other, single- and double-stranded DNA, DNA that is a mixture of single- and double-stranded RNA, and RNA that is a mixture of single- and double-stranded regions, hybrid molecules comprising DNA and RNA that may be single-stranded or, more typically, double-stranded, or triple-stranded, or a mixture of single- and double-stranded regions. In addition, nucleic acid molecule as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term nucleic acid molecule includes DNAs or RNAs as described above that contain one or more modified bases. Thus, DNAs or RNAs with backbones modified for stability or for other reasons are "nucleic acid molecule" as that term is intended herein. Moreover, DNAs or RNAs comprising unusual bases, such as inosine, or modified bases, such as tritylated bases, to name just two examples, are nucleic acid molecule as the term is used herein. It will be appreciated that a great variety of modifications have been made to DNA and RNA that serve many useful purposes known to those of skill in the art. The term nucleic acid molecule as it is employed herein embraces such chemically, enzymatically or metabolically modified forms of nucleic acid molecule, as well as the chemical forms of DNA and RNA characteristic of viruses and cells, including simple and complex cells, inter alia. The term nucleic acid molecule also embraces short nucleic acid molecules often referred to as oligonucleotide(s). "Polynucleotide" and "nucleic acid" or "nucleic acid molecule" are often used interchangeably herein.

Nucleic acid molecules provided in the present invention also encompass numerous unique fragments, both longer and shorter than the nucleic acid molecule sequences set forth in the sequencing listing of the *S. epidermidis* coding regions, which can be generated by standard cloning methods. To be unique, a fragment must be of sufficient size to distinguish it from other known nucleic acid sequences, most readily determined by comparing any selected *S. epidermidis* fragment to the nucleotide sequences in computer databases such as Gen-Bank.

Additionally, modifications can be made to the nucleic acid molecules and polypeptides that are encompassed by the present invention. For example, nucleotide substitutions can be made which do not affect the polypeptide encoded by the nucleic acid, and thus any nucleic acid molecule which encodes a hyperimmune serum reactive antigen or fragments thereof is encompassed by the present invention.

Furthermore, any of the nucleic acid molecules encoding hyperimmune serum reactive antigens or fragments thereof provided by the present invention can be functionally linked, using standard techniques such as standard cloning techniques, to any desired regulatory sequences, whether a *S. epidermidis* regulatory sequence or a heterologous regulatory sequence, heterologous leader sequence, heterologous marker sequence or a heterologous coding sequence to create a fusion protein.

Nucleic acid molecules of the present invention may be in the form of RNA, such as mRNA or cRNA, or in the form of DNA, including, for instance, cDNA and genomic DNA obtained by cloning or produced by chemical synthetic techniques or by a combination thereof. The DNA may be triple-stranded, double-stranded or single-stranded. Single-stranded DNA may be the coding strand, also known as the sense strand, or it may be the non-coding strand, also referred to as the anti-sense strand.

The present invention further relates to variants of the herein above described nucleic acid molecules which encode fragments, analogs and derivatives of the hyperimmune serum reactive antigens and fragments thereof having a deducted *S. epidermidis* amino acid sequence set forth in the Sequence Listing. A variant of the nucleic acid molecule may be a naturally occurring variant such as a naturally occurring allelic variant, or it may be a variant that is not known to occur naturally. Such non-naturally occurring variants of the nucleic acid molecule may be made by mutagenesis techniques, including those applied to nucleic acid molecules, cells or organisms.

Among variants in this regard are variants that differ from the aforementioned nucleic acid molecules by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions. Preferred are nucleic acid molecules encoding a variant, analog, derivative or fragment, or a variant, analogue or derivative of a fragment, which have a *S. epidermidis* sequence as set forth in the Sequence Listing, in which several, a few, 5 to 10, 1 to 5, 1 to 3, 2, 1 or no amino acid(s) is substituted, deleted or added, in any combination. Especially preferred among these are silent substitutions, additions and deletions, which do not alter the properties and activities of the *S. epidermidis* polypeptides set forth in the Sequence Listing. Also especially preferred in this regard are conservative substitutions.

The peptides and fragments according to the present invention also include modified epitopes wherein preferably one or two of the amino acids of a given epitope are modified or replaced according to the rules disclosed in e.g. {Tourdot, S. et al., 2000}, as well as the nucleic acid sequences encoding such modified epitopes.

It is clear that also epitopes derived from the present epitopes by amino acid exchanges improving, conserving or at least not significantly impeding the T cell activating capability of the epitopes are covered by the epitopes according to the present invention. Therefore the present epitopes also cover epitopes, which do not contain the original sequence as derived from *S. epidermidis*, but trigger the same or preferably an improved T cell response. These epitope are referred to as "heteroclitic"; they need to have a similar or preferably greater affinity to MHC/HLA molecules, and the need the ability to stimulate the T cell receptors (TCR) directed to the original epitope in a similar or preferably stronger manner.

Heteroclitic epitopes can be obtained by rational design i.e. taking into account the contribution of individual residues to binding to MHC/HLA as for instance described by {Rammensee, H. et al., 1999}, combined with a systematic exchange of residues potentially interacting with the TCR and testing the resulting sequences with T cells directed against the original epitope. Such a design is possible for a skilled man in the art without much experimentation.

Another possibility includes the screening of peptide libraries with T cells directed against the original epitope. A preferred way is the positional scanning of synthetic peptide libraries. Such approaches have been described in detail for instance by {Hemmer, B. et al., 1999} and the references given therein.

As an alternative to epitopes represented by the present derived amino acid sequences or heteroclitic epitopes, also substances mimicking these epitopes e.g. "peptidemimetica" or "retroinverso-peptides" can be applied.

Another aspect of the design of improved epitopes is their formulation or modification with substances increasing their capacity to stimulate T cells. These include T helper cell epitopes, lipids or liposomes or preferred modifications as described in WO 01/78767.

Another way to increase the T cell stimulating capacity of epitopes is their formulation with immune stimulating substances for instance cytokines or chemokines like interleukin-2, -7, -12, -18, class I and II interferons (IFN), especially IFN-gamma, GM-CSF, TNF-alpha, flt3-ligand and others.

As discussed additionally herein regarding nucleic acid molecule assays of the invention, for instance, nucleic acid molecules of the invention as discussed above, may be used as a hybridization probe for RNA, cDNA and genomic DNA to isolate full-length cDNAs and genomic clones encoding polypeptides of the present invention and to isolate cDNA and genomic clones of other genes that have a high sequence similarity to the nucleic acid molecules of the present invention. Such probes generally will comprise at least 15 bases. Preferably, such probes will have at least 20, at least 25 or at least 30 bases, and may have at least 50 bases. Particularly preferred probes will have at least 30 bases, and will have 50 bases or less, such as 30, 35, 40, 45, or 50 bases.

For example, the coding region of a nucleic acid molecule of the present invention may be isolated by screening a relevant library using the known DNA sequence to synthesize an oligonucleotide probe. A labeled oligonucleotide having a sequence complementary to that of a gene of the present invention is then used to screen a library of cDNA, genomic DNA or mRNA to determine to which members of the library the probe hybridizes.

The nucleic acid molecules and polypeptides of the present invention may be employed as reagents and materials for development of treatments of and diagnostics for disease, particularly human disease, as further discussed herein relating to nucleic acid molecule assays, inter alia.

The nucleic acid molecules of the present invention that are oligonucleotides can be used in the processes herein as described, but preferably for PCR, to determine whether or not the *S. epidermidis* genes identified herein in whole or in part are present and/or transcribed in infected tissue such as blood. It is recognized that such sequences will also have utility in diagnosis of the stage of infection and type of infection the pathogen has attained. For this and other purposes the arrays comprising at least one of the nucleic acids according to the present invention as described herein, may be used.

The nucleic acid molecules according to the present invention may be used for the detection of nucleic acid molecules and organisms or samples containing these nucleic acids. Preferably such detection is for diagnosis, more preferable for the diagnosis of a disease related or linked to the present or abundance of *S. epidermidis*.

Eukaryotes (herein also "individual(s)"), particularly mammals, and especially humans, infected with *S. epidermidis* may be identifiable by detecting any of the nucleic acid molecules according to the present invention detected at the DNA level by a variety of techniques. Preferred nucleic acid molecules candidates for distinguishing a *S. epidermidis* from other organisms can be obtained.

The different polypeptides described herein can have therapeutic and/or diagnostic utilities. The present application identifies different immunogenic polypeptides, and immunogenic polypeptide regions, characteristic of *S. epi*. An immunogenic polypeptide region can be present by itself or part of a longer length polypeptide. The polypeptides and polypeptide regions can be used in diagnostic applications to provide an indication as to whether a person is, or has been, infected with *S. epi*. For example, a polypeptide containing an *S. epi* immunogenic region can be used to generate *S. epi* antibodies, which can be used to detect the presence of *S. epi* in serum; and a polypeptide containing an *S. epi* immunogenic region can be used to detect the presence of *S. epi*. antibodies in serum.

The invention provides a process for diagnosing disease, arising from infection with *S. epidermidis*, comprising determining from a sample isolated or derived from an individual an increased level of expression of a nucleic acid molecule having the sequence of a nucleic acid molecule set forth in the Sequence Listing. Expression of nucleic acid molecules can be measured using any one of the methods well known in the art for the quantitation of nucleic acid molecules, such as, for example, PCR, RT-PCR, Rnase protection, Northern blotting, other hybridisation methods and the arrays described herein.

Isolated as used herein means separated "by the hand of man" from its natural state; i.e., that, if it occurs in nature, it has been changed or removed from its original environment, or both. For example, a naturally occurring nucleic acid molecule or a polypeptide naturally present in a living organism in its natural state is not "isolated," but the same nucleic acid molecule or polypeptide separated from the coexisting materials of its natural state is "isolated", as the term is employed herein. As part of or following isolation, such nucleic acid molecules can be joined to other nucleic acid molecules, such as DNAs, for mutagenesis, to form fusion proteins, and for propagation or expression in a host, for instance. The isolated nucleic acid molecules, alone or joined to other nucleic acid molecules such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the nucleic acid molecules and polypeptides may occur in a composition, such as a media formulations, solutions for introduction of nucleic acid molecules or polypeptides, for example, into cells, compositions or solutions for chemical or enzymatic reactions, for instance, which are not naturally occurring compositions, and, therein remain isolated nucleic acid molecules or polypeptides within the meaning of that term as it is employed herein.

The nucleic acids according to the present invention may be chemically synthesized. Alternatively, the nucleic acids can be isolated from *S. epidermidis* by methods known to the one skilled in the art.

According to another aspect of the present invention, a comprehensive set of novel hyperimmune serum reactive antigens and fragments thereof are provided by using the herein described antigen identification method. In a preferred embodiment of the invention, a hyperimmune serum-reactive antigen comprising an amino acid sequence being encoded by any one of the nucleic acids molecules herein described and fragments thereof are provided. In another preferred embodiment of the invention a novel set of hyperimmune serum-reactive antigens which comprises amino acid sequences selected from a group consisting of the polypeptide sequences as represented in Seq ID No 32, 35, 37-40, 42-44, 46, 48, 50, 52, 56-57, 59-62 and fragments thereof are provided. In a further preferred embodiment of the invention hyperimmune serum-reactive antigens, which comprise amino acid sequences selected from a group consisting of the polypeptide sequences as represented in Seq ID No 33-34, 36, 41, 45, 47, 49, 53-55, 58 and fragments thereof are provided. In a still preferred embodiment of the invention hyperimmune serum-reactive antigens which comprise amino acid sequences selected from a group consisting of the polypeptide sequences as represented in Seq ID No 51 and fragments thereof are provided.

The hyperimmune serum reactive antigens and fragments thereof as provided in the invention include any polypeptide set forth in the Sequence Listing as well as polypeptides which have at least 70% identity to a polypeptide set forth in the Sequence Listing, preferably at least 80% or 85% identity to a polypeptide set forth in the Sequence Listing, and more preferably at least 90% similarity (more preferably at least 90% identity) to a polypeptide set forth in the Sequence Listing and still more preferably at least 95%, 96%, 97%, 98%, 99% or 99.5% similarity (still more preferably at least 95%, 96%, 97%, 98%, 99%, or 99.5% identity) to a polypeptide set forth in the Sequence Listing and also include portions of such polypeptides with such portion of the polypeptide generally containing at least 4 amino acids and more preferably at least 8, still more preferably at least 30, still more preferably at least 50 amino acids, such as 4, 8, 10, 20, 30, 35, 40, 45 or 50 amino acids.

The invention also relates to fragments, analogs, and derivatives of these hyperimmune serum reactive antigens and fragments thereof. The terms "fragment", "derivative" and "analog" when referring to an antigen whose amino acid sequence is set forth in the Sequence Listing, means a polypeptide which retains essentially the same or a similar biological function or activity as such hyperimmune serum reactive antigen and fragment thereof.

The fragment, derivative or analog of a hyperimmune serum reactive antigen and fragment thereof may be 1) one in which one or more of the amino acid residues are substituted with a conserved or non-conserved amino acid residue (preferably a conserved amino acid residue) and such substituted amino acid residue may or may not be one encoded by the genetic code, or 2) one in which one or more of the amino acid residues includes a substituent group, or 3) one in which the mature hyperimmune serum reactive antigen or fragment thereof is fused with another compound, such as a compound to increase the half-life of the hyperimmune serum reactive antigen and fragment thereof (for example, polyethylene glycol), or 4) one in which the additional amino acids are fused to the mature hyperimmune serum reactive antigen or fragment thereof, such as a leader or secretory sequence or a sequence which is employed for purification of the mature hyperimmune serum reactive antigen or fragment thereof or a proprotein sequence. Such fragments, derivatives and analogs are deemed to be within the scope of those skilled in the art from the teachings herein.

Among the particularly preferred embodiments of the invention in this regard are the hyperimmune serum reactive antigens set forth in the Sequence Listing, variants, analogs, derivatives and fragments thereof, and variants, analogs and derivatives of fragments. Additionally, fusion polypeptides comprising such hyperimmune serum reactive antigens, variants, analogs, derivatives and fragments thereof, and variants, analogs and derivatives of the fragments are also encompassed by the present invention. Such fusion polypeptides and proteins, as well as nucleic acid molecules encoding them, can readily be made using standard techniques, including standard recombinant techniques for producing and expression of a recombinant polynucleic acid encoding a fusion protein.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

Further particularly preferred in this regard are variants, analogs, derivatives and fragments, and variants, analogs and derivatives of the fragments, having the amino acid sequence of any polypeptide set forth in the Sequence Listing, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the polypeptide of the present invention. Also especially preferred in this regard are conservative substitutions. Most highly preferred are polypeptides having an amino acid sequence set forth in the Sequence Listing without substitutions.

The hyperimmune serum reactive antigens and fragments thereof of the present invention are preferably provided in an isolated form, and preferably are purified to homogeneity.

Also among preferred embodiments of the present invention are polypeptides comprising fragments of the polypeptides having the amino acid sequence set forth in the Sequence Listing, and fragments of variants and derivatives of the polypeptides set forth in the Sequence Listing.

In this regard a fragment is a polypeptide having an amino acid sequence that entirely is the same as part but not all of the amino acid sequence of the afore mentioned hyperimmune serum reactive antigen and fragment thereof, and variants or derivative, analogs, fragments thereof. Such fragments may be "free-standing", i.e., not part of or fused to other amino acids or polypeptides, or they may be comprised within a larger polypeptide of which they form a part or region. Also preferred in this aspect of the invention are fragments characterised by structural or functional attributes of the polypeptide of the present invention, i.e. fragments that comprise alpha-helix and alpha-helix forming regions, beta-sheet and beta-sheet forming regions, turn and turn-forming regions, coil and coil-forming regions, hydrophilic regions, hydrophobic regions, alpha amphipathic regions, beta-amphipathic regions, flexible regions, surface-forming regions, substrate binding regions, and high antigenic index regions of the polypeptide of the present invention, and combinations of such fragments. Preferred regions are those that mediate activities of the hyperimmune serum reactive antigens and fragments thereof of the present invention. Most highly preferred in this regard are fragments that have a chemical, biological or other activity of the hyperimmune serum reactive antigen and fragments thereof of the present invention, including those with a similar activity or an improved activity, or with a decreased undesirable activity. Particularly preferred are fragments comprising receptors or domains of enzymes that confer a function essential for viability of *S. epidermidis* or the ability to cause disease in humans. Further preferred polypeptide fragments are those that comprise or contain antigenic or immunogenic determinants in an animal, especially in a human.

An antigenic fragment is defined as a fragment of the identified antigen, which is for itself antigenic or may be made antigenic when provided as a hapten. Therefore, also antigens or antigenic fragments showing one or (for longer fragments) only a few amino acid exchanges are enabled with the present invention, provided that the antigenic capacities of such fragments with amino acid exchanges are not severely deteriorated on the exchange(s), i.e., suited for eliciting an appropriate immune response in an individual vaccinated with this antigen and identified by individual antibody preparations from individual sera.

Preferred examples of such fragments of a hyperimmune serum-reactive antigen are selected from the group consisting of peptides comprising amino acid sequences of column "predicted immunogenic aa", and "Location of identified immunogenic region" of Table 1; the serum reactive epitopes of Table 1, especially peptides comprising amino acid 6-28, 54-59, 135-147, 193-205, 274-279, 284-291, 298-308, 342-347, 360-366, 380-386, 408-425, 437-446, 457-464, 467-477, 504-510, 517-530, 535-543, 547-553, 562-569, 573-579, 592-600, 602-613, 626-631, 638-668 and 396-449 of Seq ID No 32; 5-24, 101-108, 111-117, 128-142, 170-184, 205-211, 252-267, 308-316, 329-337, 345-353, 360-371, 375-389, 393-399, 413-419, 429-439, 446-456, 471-485, 495-507, 541-556, 582-588, 592-602, 607-617, 622-628, 630-640 and 8-21 of Seq ID No 33; 10-20, 23-33, 40-45, 59-65, 72-107, 113-119, 127-136, 151-161 and 33-59 of Seq ID No 34; 4-16, 28-34, 39-61, 66-79, 100-113, 120-127, 130-137, 142-148, 150-157, 192-201, 203-210, 228-239, 245-250, 256-266, 268-278, 288-294, 312-322, 336-344, 346-358, 388-396, 399-413, 425-430, 445-461, 464-470, 476-482, 486-492, 503-511, 520-527, 531-541, 551-558, 566-572, 609-625, 635-642, 650-656, 683-689, 691-705, 734-741, 750-767, 782-789, 802-808, 812-818, 837-844, 878-885, 907-917, 930-936 and 913-933 of Seq ID No 35;

5-12, 20-27, 46-78, 85-92, 104-112, 121-132, 150-167, 179-185, 200-213, 221-227, 240-264, 271-279, 282-290, 311-317 and 177-206 of Seq ID No 36; 18-24, 31-40, 45-51, 89-97, 100-123, 127-132, 139-153, 164-170, 184-194, 200-205, 215-238, 244-255, 257-270, 272-280, 289-302, 312-318, 338-348, 356-367 and 132-152 of Seq ID No 37; 7-16, 39-45, 73-83, 90-98, 118-124, 130-136, 194-204, 269-280, 320-327, 373-381, 389-397, 403-408, 424-430, 436-441, 463-476, 487-499, 507-514, 527-534, 540-550, 571-577, 593-599, 620-629, 641-647, 650-664, 697-703, 708-717, 729-742, 773-790, 794-805, 821-828, 830-837, 839-851, 858-908, 910-917, 938-947, 965-980, 1025-1033, 1050-1056, 1073-1081, 1084-1098, 1106-1120, 1132-1140, 1164-1170, 1185-1194, 1201-1208, 1215-1224, 1226-1234, 1267-1279, 1325-1331, 1356-1364, 1394-1411, 1426-1439, 1445-1461, 1498-1504, 1556-1561, 1564-1573, 1613-1639, 1648-1655, 1694-1714, 1748-1755, 1778-1785, 1808-1813, 1821-1827, 1829-1837, 1846-1852, 1859-1865, 1874-1883, 1895-1900, 1908-1913, 1931-1937, 1964-1981, 1995-2005, 2020-2033, 2040-2047, 2103-2109, 2118-2127, 2138-2144, 2166-2175, 2180-2187, 2220-2225, 2237-2242, 2247-2253, 2273-2281, 2286-2306, 2314-2320, 2323-2345, 2350-2355, 2371-2384, 2415-2424, 2426-2431, 2452-2472, 2584-2589, 2610-2621, 2638-2655, 2664-2670, 2681-2690, 2692-2714, 2724-2730 and 687-730 of Seq ID No 38; 10-40, 53-59, 79-85, 98-104, 117-122, 130-136, 144-158, 169-175, 180-185, 203-223, 232-237, 243-254, 295-301 and 254-292 of Seq ID No 39; 28-50, 67-85, 93-115, 120-134, 144-179, 240-249, 328-340, 354-360, 368-400, 402-417, 419-427, 429-445, 447-455, 463-468, 472-480, 485-500, 502-510, 512-534, 537-546, 553-558, 582-594, 619-637, 645-654, 690-709, 735-745, 749-756, 786-792, 275-316 and 378-401 of Seq ID No 40; 5-16, 21-30, 33-40, 52-74, 101-108, 116-122, 164-182, 185-219, 256-261, 273-279, 285-291, 297-304, 312-328, 331-338, 355-362, 364-371, 373-401, 411-423 and 191-208 of Seq ID No 41; 34-55, 67-74, 85-93, 105-115, 138-152, 161-171, 182-189, 197-205, 213-219, 232-239, 241-248, 250-263, 272-277, 288-299 and 216-231 of Seq ID No 42; 21-27, 32-37, 43-51, 67-74, 82-92, 94-100, 106-112, 140-149, 153-159, 164-182, 193-215, 222-227, 260-267, 308-322, 330-340, 378-387, 396-403, 417-432, 435-441, 448-465, 476-482, 488-498, 500-510 and 214-280 of Seq ID No 43; 4-21, 29-52, 80-87, 104-123, 126-133, 141-157, 182-189, 194-202, 214-220, 227-235, 242-252 and 33-108 of Seq ID No 44; 12-18, 20-27, 29-59, 64-72, 84-90, 96-103, 109-121, 125-155, 164-177, 179-186, 188-201, 216-227, 235-253, 259-274, 276-294, 296-310, 322-339, 341-348, 369-379, 398-403, 409-421 and 76-96 of Seq ID No 45; 4-15, 24-41, 71-80, 104-111, 113-119, 123-130, 139-149, 168-178, 187-200 and 4-45 of Seq ID No 46; 13-19, 32-37, 44-56 and 1-14 of Seq ID No 47; 6-11, 16-35, 75-81, 95-100, 126-139, 206-214, 225-233, 241-259, 268-276, 319-325, 339-360, 371-401, 435-441, 452-459, 462-472, 491-503, 505-516, 549-556, 567-580, 590-595, 612-622, 624-630, 642-648, 656-662, 687-693, 698-704, 706-712, 736-750, 768-777, 784-789, 812-818, 847-858, 894-900, 922-931, 938-949, 967-984, 986-992, 1027-1032, 1041-1054, 1082-1088, 1091-1097, 1119-1124, 1234-1240, 1250-1258, 1274-1289, 1299-1305, 1392-1398, 1400-1405, 1429-1442, 1460-1474, 1505-1514, 1531-1537, 1540-1552, 1558-1571, 1582-1587, 1616-1623, 1659-1666, 1671-1677, 1680-1686, 1698-1704, 1706-1712, 1768-1774, 1783-1797, 1814-1819, 1849-1855, 1870-1876, 1890-1897, 1947-1953, 1972-1980, 1999-2013, 2044-2051, 2068-2084, 2093-2099, 2122-2131, 2142-2147, 2156-2163, 2170-2179, 2214-2220, 2235-2245, 2271-2281, 2287-2293, 2308-2317, 2352-2362, 2373-2378, 2387-2407, 2442-2448, 2458-2474, 2507-2516, 2531-2537, 2540-2551, 2555-2561, 2586-2599, 2617-2627, 2644-2649, 2661-2675, 2685-2692, 2695-2707, 2733-2739, 2741-2747, 2774-2783, 2788-2795, 2860-2870, 2891-2903, 2938-2947, 2973-2980, 2993-2999, 3004-3030, 3046-3059, 3066-3077, 3082-3088, 3120-3132, 3144-3149, 3153-3169, 3200-3212, 3232-3256, 3276-3290, 3308-3322, 3330-3338, 3353-3360, 3363-3371, 3390-3408, 3431-3447, 3454-3484, 3503-3515, 3524-3541, 3543-3550, 3560-3567, 3586-3599, 3616-3621, 3642-3647, 3663-3679, 213-276, 579-621 and 1516-1559 of Seq ID No 48; 19-41, 43-49, 55-62, 67-74, 114-121, 130-140, 188-197, 208-217, 226-232, 265-287, 292-299, 301-319, 372-394, 400-410, 421-427 and 12-56 of Seq ID No 49; 6-12, 44-51, 53-60, 67-88, 91-100, 104-123, 137-142, 148-158, 161-168, 175-201, 204-210, 222-231, 239-253, 258-264, 272-282 and 60-138 of Seq ID No 50; 4-63, 69-104, 110-121, 124-131, 134-152, 161-187, 204-221, 223-237, 239-296, 298-310, 331-365, 380-405, 423-451, 470-552, 554-562, 574-581, 592-649, 651-658, 661-671, 673-707, 713-734, 741-748, 758-765, 773-790 and 509-528 of Seq ID No 51; 89-94, 102-115, 123-129, 181-188, 200-206, 211-235, 239-249, 267-281, 295-310, 316-321, 331-341, 344-359, 365-386, 409-422, 443-453, 495-506, 514-521, 539-547, 553-560, 563-570, 586-596, 621-626, 633-638, 651-657, 666-683, 697-705, 731-739, 761-768, 865-883 and 213-265 of Seq ID No 52; 5-20, 24-34, 37-43, 92-102, 134-139, 156-162, 184-191, 193-205, 207-213, 225-231, 241-247, 259-267, 269-286, 337-350, 365-372, 378-386, 399-413, 415-421, 447-457, 467-481 and 145-183 of Seq ID No 53; 12-19, 29-41, 43-57, 80-98, 106-141, 143-156, 172-183, 185-210, 214-220, 226-234, 278-287 and 237-287 of Seq ID No 54; 5-12, 32-48, 50-72, 75-81, 88-94 and 16-40 of Seq ID No 55; 4-21, 29-42, 48-62, 65-80, 95-101, 103-118, 122-130, 134-140, 143-152, 155-165, 182-192, 198-208, 232-247, 260-268, 318-348, 364-369, 380-391, 403-411, 413-424 and 208-230 of Seq ID No 56; 4-18, 65-75, 82-92, 123-140, 144-159, 166-172, 188-194 and 174-195 of Seq ID No 57; 7-20, 58-71, 94-101, 110-119, 199-209, 231-242, 247-254, 267-277, 282-290, 297-306, 313-319, 333-342, 344-369, 390-402, 414-431, 436-448, 462-471 and 310-350 of Seq ID No 58; 4-25, 37-44, 53-59, 72-78, 86-99, 119-128, 197-203, 209-218, 220-226, 233-244, 246-254, 264-271, 277-289, 407-430, 437-445, 464-472, 482-488, 503-509 and 308-331 of Seq ID No 59; 4-12, 14-43, 52-58 and 43-58 of Seq ID No 60; 4-14, 21-29, 35-49 and 38-50 of Seq ID No 61; 4-19, 31-37, 58-72, 94-108 and 1-72 of Seq ID No 62, and fragments comprising at least 6, preferably more than 8, especially more than 10 aa of said sequences. All these fragments individually and each independently form a preferred selected aspect of the present invention.

All linear hyperimmune serum reactive fragments of a particular antigen may be identified by analysing the entire sequence of the protein antigen by a set of peptides overlapping by 1 amino acid with a length of at least 10 amino acids. Subsequently, non-linear epitopes can be identified by analysis of the protein antigen with hyperimmune sera using the expressed full-length protein or domain polypeptides thereof. Assuming that a distinct domain of a protein is sufficient to form the 3D structure independent from the native protein, the analysis of the respective recombinant or synthetically produced domain polypeptide with hyperimmune serum would allow the identification of conformational epitopes within the individual domains of multi-domain proteins. For those antigens where a domain possesses linear as well as conformational epitopes, competition experiments with peptides corresponding to the linear epitopes may be used to confirm the presence of conformational epitopes.

It will be appreciated that the invention also relates to, among others, nucleic acid molecules encoding the aforementioned fragments, nucleic acid molecules that hybridise to nucleic acid molecules encoding the fragments, particularly those that hybridise under stringent conditions, and nucleic acid molecules, such as PCR primers, for amplifying nucleic acid molecules that encode the fragments. In these regards, preferred nucleic acid molecules are those that correspond to the preferred fragments, as discussed above.

The present invention also relates to vectors, which comprise a nucleic acid molecule or nucleic acid molecules of the present invention, host cells which are genetically engineered with vectors of the invention and the production of hyperimmune serum reactive antigens and fragments thereof by recombinant techniques.

A great variety of expression vectors can be used to express a hyperimmune serum reactive antigen or fragment thereof according to the present invention. Generally, any vector suitable to maintain, propagate or express nucleic acids to express a polypeptide in a host may be used for expression in this regard. In accordance with this aspect of the invention the vector may be, for example, a plasmid vector, a single or double-stranded phage vector, a single or double-stranded RNA or DNA viral vector. Starting plasmids disclosed herein are either commercially available, publicly available, or can be constructed from available plasmids by routine application of well-known, published procedures. Preferred among vectors, in certain respects, are those for expression of nucleic acid molecules and hyperimmune serum reactive antigens or fragments thereof of the present invention. Nucleic acid constructs in host cells can be used in a conventional manner to produce the gene product encoded by the recombinant sequence. Alternatively, the hyperimmune serum reactive antigens and fragments thereof of the invention can be synthetically produced by conventional peptide synthesizers. Mature proteins can be expressed in mammalian cells, yeast, bacteria, or other cells under the control of appropriate promoters. Cell-free translation systems can also be employed to produce such proteins using RNAs derived from the DNA construct of the present invention.

Host cells can be genetically engineered to incorporate nucleic acid molecules and express nucleic acid molecules of the present invention. Representative examples of appropriate hosts include bacterial cells, such as staphylococci, streptococci, *E. coli, Streptomyces* and *Bacillus subtillis* cells; fungal cells, such as yeast cells and *Aspergillus* cells; insect cells such as *Drosophila* S2 and *Spodoptera* Sf9 cells; animal cells such as CHO, COS, Hela, C127, 3T3, BHK, 293 and Bowes melanoma cells; and plant cells.

The invention also provides a process for producing a *S. epidermidis* hyperimmune serum reactive antigen and a fragment thereof comprising expressing from the host cell a hyperimmune serum reactive antigen or fragment thereof encoded by the nucleic acid molecules provided by the present invention. The invention further provides a process for producing a cell, which expresses a *S. epidermidis* hyperimmune serum reactive antigen or a fragment thereof comprising trans-forming or transfecting a suitable host cell with the vector according to the present invention such that the transformed or transfected cell expresses the polypeptide encoded by the nucleic acid contained in the vector.

The polypeptide may be expressed in a modified form, such as a fusion protein, and may include not only secretion signals but also additional heterologous functional regions. Thus, for instance, a region of additional amino acids, particularly charged amino acids, may be added to the N- or C-terminus of the polypeptide to improve stability and persistence in the host cell, during purification or during subsequent handling and storage. Also, regions may be added to the polypeptide to facilitate purification. Such regions may be removed prior to final preparation of the polypeptide. The addition of peptide moieties to polypeptides to engender secretion or excretion, to improve stability or to facilitate purification, among others, are familiar and routine techniques in the art. A preferred fusion protein comprises a heterologous region from immunoglobulin that is useful to solubilize or purify polypeptides. For example, EP-A-O 42-3, 5, 10, 14, 16, 18, 22-24, 27 533 (Canadian counterpart 2045869) discloses fusion proteins comprising various portions of constant region of immunoglobin molecules together with another protein or part thereof. In drug discovery, for example, proteins have been fused with antibody Fc portions for the purpose of high-throughput screening assays to identify antagonists. See for example, {Bennett, D. et al., 1995} and {Johanson, K. et al., 1995}.

The *S. epidermidis* hyperimmune serum reactive antigen or a fragment thereof can be recovered and purified from recombinant cell cultures by well-known methods including ammonium sulfate or ethanol precipitation, acid extraction, anion or cation exchange chromatography, phosphocellulose chromatography, hydrophobic interaction chromatography, hydroxylapatite chromatography and lectin chromatography.

The hyperimmune serum reactive antigens and fragments thereof according to the present invention can be produced by chemical synthesis as well as by biotechnological means. The latter comprise the transfection or transformation of a host cell with a vector containing a nucleic acid according to the present invention and the cultivation of the transfected or transformed host cell under conditions, which are known to the ones skilled in the art. The production method may also comprise a purification step in order to purify or isolate the polypeptide to be manufactured. In a preferred embodiment the vector is a vector according to the present invention.

The hyperimmune serum reactive antigens and fragments thereof according to the present invention may be used for the detection of the organism or organisms in a sample containing these organisms or polypeptides derived thereof. Preferably such detection is for diagnosis, more preferable for the diagnosis of a disease, most preferably for the diagnosis of a diseases related or linked to the presence or abundance of Gram-positive bacteria, especially bacteria selected from the group comprising staphylococci, streptococci and lactococci. More preferably, the microorganisms are selected from the group comprising *Staphylococcus aureus* and *Staphylococcus saprophyticus*, especially the microorganism is *Staphylococcus epidermidis*.

The present invention also relates to diagnostic assays such as quantitative and diagnostic assays for detecting levels of the hyperimmune serum reactive antigens and fragments thereof of the present invention in cells and tissues, including determination of normal and abnormal levels. Thus, for instance, a diagnostic assay in accordance with the invention for detecting overexpression of the polypeptide compared to normal control tissue samples may be used to detect the presence of an infection, for example, and to identify the infecting organism. Assay techniques that can be used to determine levels of a polypeptide, in a sample derived from a host are well known to those of skill in the art. Such assay methods include radioimmunoassays, competitive-binding assays, Western Blot analysis and ELISA assays. Among these, ELISAs frequently are preferred. An ELISA assay initially comprises preparing an antibody specific to the polypeptide, preferably a monoclonal antibody. In addition, a reporter antibody generally is prepared which binds to the monoclonal antibody. The reporter antibody is attached to a detectable reagent such as radioactive, fluorescent or enzymatic reagent, such as horseradish peroxidase enzyme.

The hyperimmune serum reactive antigens and fragments thereof according to the present invention may also be used for the purpose of or in connection with an array. More particularly, at least one of the hyperimmune serum reactive antigens and fragments thereof according to the present invention may be immobilized on a support. Said support typically comprises a variety of hyperimmune serum reactive antigens and fragments thereof whereby the variety may be created by using one or several of the hyperimmune serum reactive antigens and fragments thereof according to the present invention and/or hyperimmune serum reactive antigens and fragments thereof being different. The characterizing feature of such array as well as of any array in general is the fact that at a distinct or predefined region or position on said support or a surface thereof, a distinct polypeptide is immobilized. Because of this any activity at a distinct position or region of an array can be correlated with a specific polypeptide. The number of different hyperimmune serum reactive antigens and fragments thereof immobilized on a support may range from as little as 10 to several 1000 different hyperimmune serum reactive antigens and fragments thereof. The density of hyperimmune serum reactive antigens and fragments thereof per $cm^2$ is in a preferred embodiment as little as 10 peptides/polypeptides per $cm^2$ to at least 400 different peptides/polypeptides per $cm^2$ and more particularly at least 1000 different hyperimmune serum reactive antigens and fragments thereof per $cm^2$.

The manufacture of such arrays is known to the one skilled in the art and, for example, described in U.S. Pat. No. 5,744,309. The array preferably comprises a planar, porous or non-porous solid support having at least a first surface. The hyperimmune serum reactive antigens and fragments thereof as disclosed herein, are immobilized on said surface. Preferred support materials are, among others, glass or cellulose. It is also within the present invention that the array is used for any of the diagnostic applications described herein. Apart from the hyperimmune serum reactive antigens and fragments thereof according to the present invention also the nucleic acid molecules according to the present invention may be used for the generation of an array as described above. This applies as well to an array made of antibodies, preferably monoclonal antibodies as, among others, described herein.

In a further aspect the present invention relates to an antibody directed to any of the hyperimmune serum reactive antigens and fragments thereof, derivatives or fragments thereof according to the present invention. The present invention includes, for example, monoclonal and polyclonal antibodies, chimeric, single chain, and humanized antibodies, as well as Fab fragments, or the product of a Fab expression library. It is within the present invention that the antibody may be chimeric, i.e. that different parts thereof stem from different species or at least the respective sequences are taken from different species.

Antibodies generated against the hyperimmune serum reactive antigens and fragments thereof corresponding to a sequence of the present invention can be obtained by direct injection of the hyperimmune serum reactive antigens and fragments thereof into an animal or by administering the hyperimmune serum reactive antigens and fragments thereof to an animal, preferably a non-human. The antibody so obtained will then bind the hyperimmune serum reactive antigens and fragments thereof itself. In this manner, even a sequence encoding only a fragment of a hyperimmune serum reactive antigen and fragments thereof can be used to generate antibodies binding the whole native hyperimmune serum reactive antigen and fragments thereof. Such antibodies can then be used to isolate the hyperimmune serum reactive antigens and fragments thereof from tissue expressing those hyperimmune serum reactive antigens and fragments thereof.

For preparation of monoclonal antibodies, any technique known in the art, which provides antibodies produced by continuous cell line cultures can be used. (as described originally in {Kohler, G. et al., 1975}.

Techniques described for the production of single chain antibodies (U.S. Pat. No. 4,946,778) can be adapted to produce single chain antibodies to immunogenic hyperimmune serum reactive antigens and fragments thereof according to this invention. Also, transgenic mice, or other organisms such as other mammals, may be used to express humanized antibodies to immunogenic hyperimmune serum reactive antigens and fragments thereof according to this invention.

Alternatively, phage display technology or ribosomal display could be utilized to select antibody genes with binding activities towards the hyperimmune serum reactive antigens and fragments thereof either from repertoires of PCR amplified v-genes of lymphocytes from humans screened for possessing respective target antigens or from naïve libraries {McCafferty, J. et al., 1990}; {Marks, J. et al., 1992}. The affinity of these antibodies can also be improved by chain shuffling {Clackson, T. et al., 1991}.

If two antigen binding domains are present, each domain may be directed against a different epitope—termed 'bispecific' antibodies.

The above-described antibodies may be employed to isolate or to identify clones expressing the hyperimmune serum reactive antigens and fragments thereof or purify the hyperimmune serum reactive antigens and fragments thereof of the present invention by attachment of the antibody to a solid support for isolation and/or purification by affinity chromatography.

Thus, among others, antibodies against the hyperimmune serum reactive antigens and fragments thereof of the present invention may be employed to inhibit and/or treat infections, particularly bacterial infections and especially infections arising from *S. epidermidis*.

Hyperimmune serum reactive antigens and fragments thereof include antigenically, epitopically or immunologically equivalent derivatives, which form a particular aspect of this invention. The term "antigenically equivalent derivative" as used herein encompasses a hyperimmune serum reactive antigen and fragments thereof or its equivalent which will be specifically recognized by certain antibodies which, when raised to the protein or hyperimmune serum reactive antigen and fragments thereof according to the present invention, interfere with the interaction between pathogen and mammalian host. The term "immunologically equivalent derivative" as used herein encompasses a peptide or its equivalent which when used in a suitable formulation to raise antibodies in a vertebrate, the antibodies act to interfere with the interaction between pathogen and mammalian host.

The hyperimmune serum reactive antigens and fragments thereof, such as an antigenically or immunologically equivalent derivative or a fusion protein thereof can be used as an antigen to immunize a mouse or other animal such as a rat or chicken. The fusion protein may provide stability to the hyperimmune serum reactive antigens and fragments thereof. The antigen may be associated, for example by conjugation, with an immunogenic carrier protein, for example bovine serum albumin (BSA) or keyhole limpet haemocyanin (KLH). Alternatively, an antigenic peptide comprising multiple copies of the protein or hyperimmune serum reactive antigen and fragments thereof, or an antigenically or immunologically equivalent hyperimmune serum reactive antigen and fragments thereof, may be sufficiently antigenic to improve immunogenicity so as to obviate the use of a carrier.

Preferably the antibody or derivative thereof is modified to make it less immunogenic in the individual. For example, if the individual is human the antibody may most preferably be "humanized", wherein the complimentarity determining region(s) of the hybridoma-derived antibody has been transplanted into a human monoclonal antibody, for example as described in {Jones, P. et al., 1986} or {Tempest, P. et al., 1991}.

The use of a polynucleotide of the invention in genetic immunization will preferably employ a suitable delivery method such as direct injection of plasmid DNA into muscle, delivery of DNA complexed with specific protein carriers, coprecipitation of DNA with calcium phosphate, encapsulation of DNA in various forms of liposomes, particle bombardment {Tang, D. et al., 1992}, {Eisenbraun, M. et al., 1993} and in vivo infection using cloned retroviral vectors {Seeger, C. et al., 1984}.

In a further aspect the present invention relates to a peptide binding to any of the hyperimmune serum reactive antigens and fragments thereof according to the present invention, and a method for the manufacture of such peptides whereby the method is characterized by the use of the hyperimmune serum reactive antigens and fragments thereof according to the present invention and the basic steps are known to the one skilled in the art.

Such peptides may be generated by using methods according to the state of the art such as phage display or ribosome display. In case of phage display, basically a library of peptides is generated, in form of phages, and this kind of library is contacted with the target molecule, in the present case a hyperimmune serum reactive antigen and fragments thereof according to the present invention. Those peptides binding to the target molecule are subsequently removed, preferably as a complex with the target molecule, from the respective reaction. It is known to the one skilled in the art that the binding characteristics, at least to a certain extent, depend on the particularly realized experimental set-up such as the salt concentration and the like. After separating those peptides binding to the target molecule with a higher affinity or a bigger force, from the non-binding members of the library, and optionally also after removal of the target molecule from the complex of target molecule and peptide, the respective peptide(s) may subsequently be characterised. Prior to the characterisation optionally an amplification step is realized such as, e.g. by propagating the peptide encoding phages. The characterisation preferably comprises the sequencing of the target binding peptides. Basically, the peptides are not limited in their lengths, however, peptides having a length from about 8 to 20 amino acids are preferably obtained in the respective methods. The size of the libraries may be about 102 to 1018, preferably 108 to 1015 different peptides, however, is not limited thereto.

A particular form of target binding hyperimmune serum reactive antigens and fragments thereof are the so-called "anticalines" which are, among others, described in German patent application DE 197 42 706.

In a further aspect the present invention relates to functional nucleic acids interacting with any of the hyperimmune serum reactive antigens and fragments thereof according to the present invention, and a method for the manufacture of such functional nucleic acids whereby the method is characterized by the use of the hyperimmune serum reactive antigens and fragments thereof according to the present invention and the basic steps are known to the one skilled in the art. The functional nucleic acids are preferably aptamers and spiegelmers.

Aptamers are D-nucleic acids, which are either single stranded or double stranded and which specifically interact with a target molecule. The manufacture or selection of aptamers is, e.g., described in European patent EP 0 533 838. Basically the following steps are realized. First, a mixture of nucleic acids, i.e. potential aptamers, is provided whereby each nucleic acid typically comprises a segment of several, preferably at least eight subsequent randomised nucleotides. This mixture is subsequently contacted with the target molecule whereby the nucleic acid(s) bind to the target molecule, such as based on an increased affinity towards the target or with a bigger force thereto, compared to the candidate mixture. The binding nucleic acid(s) are/is subsequently separated from the remainder of the mixture. Optionally, the thus obtained nucleic acid(s) is amplified using, e.g. polymerase chain reaction. These steps may be repeated several times giving at the end a mixture having an increased ratio of nucleic acids specifically binding to the target from which the final binding nucleic acid is then optionally selected. These specifically binding nucleic acid(s) are referred to as aptamers. It is obvious that at any stage of the method for the generation or identification of the aptamers samples of the mixture of individual nucleic acids may be taken to determine the sequence thereof using standard techniques. It is within the present invention that the aptamers may be stabilized such as, e.g., by introducing defined chemical groups which are known to the one skilled in the art of generating aptamers. Such modification may for example reside in the introduction of an amino group at the 2'-position of the sugar moiety of the nucleotides. Aptamers are currently used as therapeutical agents. However, it is also within the present invention that the thus selected or generated aptamers may be used for target validation and/or as lead substance for the development of medicaments, preferably of medicaments based on small molecules. This is actually done by a competition assay whereby the specific interaction between the target molecule and the aptamer is inhibited by a candidate drug whereby upon replacement of the aptamer from the complex of target and aptamer it may be assumed that the respective drug candidate allows a specific inhibition of the interaction between target and aptamer, and if the interaction is specific, said candidate drug will, at least in principle, be suitable to block the target and thus decrease its biological availability or activity in a respective system comprising such target. The thus obtained small molecule may then be subject to further derivatisation and modification to optimise its physical, chemical, biological and/or medical characteristics such as toxicity, specificity, biodegradability and bioavailability.

Spiegelmers and their generation or manufacture is based on a similar principle. The manufacture of spiegelmers is described in international patent application WO 98/08856. Spiegelmers are L-nucleic acids, which means that they are composed of L-nucleotides rather than D-nucleotides as aptamers are. Spiegelmers are characterized by the fact that they have a very high stability in biological systems and, comparable to aptamers, specifically interact with the target molecule against which they are directed. In the process of generating spiegelmers, a heterogeonous population of D-nucleic acids is created and this population is contacted with the optical antipode of the target molecule, in the present case for example with the D-enantiomer of the naturally occurring L-enantiomer of the hyperimmune serum reactive antigens and fragments thereof according to the present invention. Subsequently, those D-nucleic acids are separated which do not interact with the optical antipode of the target molecule. But those D-nucleic acids interacting with the optical antipode of the target molecule are separated, optionally identified and/or sequenced and subsequently the corresponding L-nucleic acids are synthesized based on the nucleic acid sequence information obtained from the D-nucleic acids. These L-nucleic acids, which are identical in terms of sequence with the aforementioned D-nucleic acids interacting with the optical antipode of the target molecule, will specifically interact with the naturally occurring target molecule rather than with the optical antipode thereof. Similar to the method for the generation of aptamers it is also possible to repeat the various steps several times and thus to enrich those nucleic acids specifically interacting with the optical antipode of the target molecule.

In a further aspect the present invention relates to functional nucleic acids interacting with any of the nucleic acid molecules according to the present invention, and a method for the manufacture of such functional nucleic acids whereby the method is characterized by the use of the nucleic acid molecules and their respective sequences according to the present invention and the basic steps are known to the one skilled in the art. The functional nucleic acids are preferably ribozymes, antisense oligonucleotides and siRNA.

Ribozymes are catalytically active nucleic acids, which preferably consist of RNA, which basically comprises two moieties. The first moiety shows a catalytic activity whereas the second moiety is responsible for the specific interaction with the target nucleic acid, in the present case the nucleic acid coding for the hyperimmune serum reactive antigens and fragments thereof according to the present invention. Upon interaction between the target nucleic acid and the second moiety of the ribozyme, typically by hybridisation and Watson-Crick base pairing of essentially complementary stretches of bases on the two hybridising strands, the catalytically active moiety may become active which means that it catalyses, either intramolecularly or intermolecularly, the target nucleic acid in case the catalytic activity of the ribozyme is a phosphodiesterase activity. Subsequently, there may be a further degradation of the target nucleic acid, which in the end results in the degradation of the target nucleic acid as well as the protein derived from the said target nucleic acid. Ribozymes, their use and design principles are known to the one skilled in the art, and, for example described in {Doherty, E. et al., 2001} and {Lewin, A. et al., 2001}.

The activity and design of antisense oligonucleotides for the manufacture of a medicament and as a diagnostic agent, respectively, is based on a similar mode of action. Basically, antisense oligonucleotides hybridise based on base complementarity, with a target RNA, preferably with a mRNA, thereby activating RNase H. RNase H is activated by both phosphodiester and phosphorothioate-coupled DNA. Phosphodiester-coupled DNA, however, is rapidly degraded by cellular nucleases with the exception of phosphorothioate-coupled DNA. These resistant, non-naturally occurring DNA derivatives do not inhibit RNase H upon hybridisation with RNA. In other words, antisense polynucleotides are only effective as DNA RNA hybride complexes. Examples for this kind of antisense oligonucleotides are described, among others, in U.S. Pat. No. 5,849,902 and U.S. Pat. No. 5,989,912. In other words, based on the nucleic acid sequence of the target molecule which in the present case are the nucleic acid molecules for the hyperimmune serum reactive antigens and fragments thereof according to the present invention, either from the target protein from which a respective nucleic acid sequence may in principle be deduced, or by knowing the nucleic acid sequence as such, particularly the mRNA, suitable antisense oligonucleotides may be designed base on the principle of base complementarity.

Particularly preferred are antisense-oligonucleotides, which have a short stretch of phosphorothioate DNA (3 to 9 bases). A minimum of 3 DNA bases is required for activation of bacterial RNase H and a minimum of 5 bases is required for mammalian RNase H activation. In these chimeric oligonucleotides there is a central region that forms a substrate for RNase H that is flanked by hybridising "arms" comprised of modified nucleotides that do not form substrates for RNase H. The hybridising arms of the chimeric oligonucleotides may be modified such as by 2'-O-methyl or 2'-fluoro. Alternative approaches used methylphosphonate or phosphoramidate linkages in said arms. Further embodiments of the antisense oligonucleotide useful in the practice of the present invention are P-methoxyoligonucleotides, partial P-methoxyoligodeoxyribonucleotides or P-methoxyoligonucleotides.

Of particular relevance and usefulness for the present invention are those antisense oligonucleotides as more particularly described in the above two mentioned US patents. These oligonucleotides contain no naturally occurring 5' 3'-linked nucleotides. Rather the oligonucleotides have two types of nucleotides: 2'-deoxyphosphorothioate, which activate RNase H, and 2'-modified nucleotides, which do not. The linkages between the 2'-modified nucleotides can be phosphodiesters, phosphorothioate or P-ethoxyphosphodiester. Activation of RNase H is accomplished by a contiguous RNase H-activating region, which contains between 3 and 5 2'-deoxyphosphorothioate nucleotides to activate bacterial RNase H and between 5 and 10 2'-deoxyphosphorothioate nucleotides to activate eukaryotic and, particularly, mammalian RNase H. Protection from degradation is accomplished by making the 5' and 3' terminal bases highly nuclease resistant and, optionally, by placing a 3' terminal blocking group.

More particularly, the antisense oligonucleotide comprises a 5' terminus and a 3' terminus; and from position 11 to 59 5' 3'-linked nucleotides independently selected from the group consisting of 2'-modified phosphodiester nucleotides and 2'-modified P-alkyloxyphosphotriester nucleotides; and wherein the 5'-terminal nucleoside is attached to an RNase H-activating region of between three and ten contiguous phosphorothioate-linked deoxyribonucleotides, and wherein the 3'-terminus of said oligonucleotide is selected from the group consisting of an inverted deoxyribonucleotide, a contiguous stretch of one to three phosphorothioate 2'-modified ribonucleotides, a biotin group and a P-alkyloxyphosphotriester nucleotide.

Also an antisense oligonucleotide may be used wherein not the 5' terminal nucleoside is attached to an RNase H-activating region but the 3' terminal nucleoside as specified above. Also, the 5' terminus is selected from the particular group rather than the 3' terminus of said oligonucleotide.

The nucleic acids as well as the hyperimmune serum reactive antigens and fragments thereof according to the present invention may be used as or for the manufacture of pharmaceutical compositions, especially vaccines. Preferably such pharmaceutical composition, preferably vaccine is for the prevention or treatment of diseases caused by, related to or associated with *S. epidermidis*. In so far another aspect of the invention relates to a method for inducing an immunological response in an individual, particularly a mammal, which comprises inoculating the individual with the hyperimmune serum reactive antigens and fragments thereof of the invention, or a fragment or variant thereof, adequate to produce antibodies to protect said individual from infection, particularly *Staphylococcus* infection and most particularly *S. epidermidis* infections.

Yet another aspect of the invention relates to a method of inducing an immunological response in an individual which comprises, through gene therapy or otherwise, delivering a nucleic acid functionally encoding hyperimmune serum reactive antigens and fragments thereof, or a fragment or a variant thereof, for expressing the hyperimmune serum reactive antigens and fragments thereof, or a fragment or a variant thereof in vivo in order to induce an immunological response to produce antibodies or a cell mediated T cell response, either cytokine-producing T cells or cytotoxic T cells, to protect said individual from disease, whether that disease is already established within the individual or not. One way of administering the gene is by accelerating it into the desired cells as a coating on particles or otherwise.

A further aspect of the invention relates to an immunological composition which, when introduced into a host capable of having induced within it an immunological response, induces an immunological response in such host, wherein the composition comprises recombinant DNA which codes for and expresses an antigen of the hyperimmune serum reactive antigens and fragments thereof of the present invention. The immunological response may be used therapeutically or prophylactically and may take the form of antibody immunity or cellular immunity such as that arising from CTL or CD4+ T cells.

The hyperimmune serum reactive antigens and fragments thereof of the invention or a fragment thereof may be fused with a co-protein which may not by itself produce antibodies, but is capable of stabilizing the first protein and producing a fused protein which will have immunogenic and protective properties. This fused recombinant protein preferably further comprises an antigenic co-protein, such as Glutathione-S-transferase (GST) or beta-galactosidase, relatively large co-proteins which solubilise the protein and facilitate production and purification thereof. Moreover, the co-protein may act as an adjuvant in the sense of providing a generalized stimulation of the immune system. The co-protein may be attached to either the amino or carboxy terminus of the first protein.

Also, provided by this invention are methods using the described nucleic acid molecule or particular fragments thereof in such genetic immunization experiments in animal models of infection with *S. epidermidis*. Such fragments will be particularly useful for identifying protein epitopes able to provoke a prophylactic or therapeutic immune response. This approach can allow for the subsequent preparation of monoclonal antibodies of particular value from the requisite organ of the animal successfully resisting or clearing infection for the development of prophylactic agents or therapeutic treatments of *S. epidermidis* infection in mammals, particularly humans.

The hyperimmune serum reactive antigens and fragments thereof may be used as an antigen for vaccination of a host to produce specific antibodies which protect against invasion of bacteria, for example by blocking adherence of bacteria to damaged tissue. Examples of tissue damage include wounds in skin or connective tissue caused e.g. by mechanical, chemical or thermal damage or by implantation of indwelling devices, or wounds in the mucous membranes, such as the mouth, mammary glands, urethra or vagina.

The present invention also includes a vaccine formulation, which comprises the immunogenic recombinant protein together with a suitable carrier. Since the protein may be broken down in the stomach, it is preferably administered parenterally, including, for example, administration that is subcutaneous, intramuscular, intravenous, intradermal intranasal or transdermal. Formulations suitable for parenteral administration include aqueous and non-aqueous sterile injection solutions which may contain anti-oxidants, buffers, bacteriostats and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials, and may be stored in a freeze-dried condition requiring only the addition of the sterile liquid carrier immediately prior to use. The vaccine formulation may also include adjuvant systems for enhancing the immunogenicity of the formulation, such as oil-in-water systems and other systems known in the art. The dosage will depend on the specific activity of the vaccine and can be readily determined by routine experimentation.

According to another aspect, the present invention relates to a pharmaceutical composition comprising such a hyperimmune serum-reactive antigen or a fragment thereof as provided in the present invention for *S. epidermidis*. Such a pharmaceutical composition may comprise one or more hyperimmune serum reactive antigens or fragments thereof against *S. epidermidis*. Optionally, such *S. epidermidis* hyperimmune serum reactive antigens or fragments thereof may also be combined with antigens against other pathogens in a combination pharmaceutical composition. Preferably, said pharmaceutical composition is a vaccine for preventing or treating an infection caused by *S. epidermidis* and/or other pathogens against which the antigens have been included in the vaccine.

According to a further aspect, the present invention relates to a pharmaceutical composition comprising a nucleic acid molecule encoding a hyperimmune serum-reactive antigen or a fragment thereof as identified above for *S. epidermidis*. Such a pharmaceutical composition may comprise one or more nucleic acid molecules encoding hyperimmune serum reactive antigens or fragments thereof against *S. epidermidis*. Optionally, such *S. epidermidis* nucleic acid molecules encoding hyperimmune serum reactive antigens or fragments thereof may also be combined with nucleic acid molecules encoding antigens against other pathogens in a combination pharmaceutical composition. Preferably, said pharmaceutical composition is a vaccine for preventing or treating an infection caused by *S. epidermidis* and/or other pathogens against which the antigens have been included in the vaccine.

The pharmaceutical composition may contain any suitable auxiliary substances, such as buffer substances, stabilisers or further active ingredients, especially ingredients known in connection of pharmaceutical composition and/or vaccine production.

A preferable carrier/or excipient for the hyperimmune serum-reactive antigens, fragments thereof or a coding nucleic acid molecule thereof according to the present invention is an immunostimulatory compound for further stimulating the immune response to the given hyperimmune serum-reactive antigen, fragment thereof or a coding nucleic acid molecule thereof. Preferably the immunostimulatory compound in the pharmaceutical preparation according to the present invention is selected from the group of polycationic substances, especially polycationic peptides, immunostimulatory nucleic acids molecules, preferably immunostimulatory deoxynucleotides, alum, Freund's complete adjuvants, Freund's incomplete adjuvants, neuroactive compounds, especially human growth hormone, or combinations thereof.

It is also within the scope of the present invention that the pharmaceutical composition, especially vaccine, comprises apart from the hyperimmune serum reactive antigens, fragments thereof and/or coding nucleic acid molecules thereof according to the present invention other compounds which are biologically or pharmaceutically active. Preferably, the vaccine composition comprises at least one polycationic peptide. The polycationic compound(s) to be used according to the present invention may be any polycationic compound, which shows the characteristic effects according to the WO 97/30721. Preferred polycationic compounds are selected from basic polypeptides, organic polycations, basic polyamino acids or mixtures thereof. These polyamino acids should have a chain length of at least 4 amino acid residues (WO 97/30721). Especially preferred are substances like polylysine, polyarginine and polypeptides containing more than 20%, especially more than 50% of basic amino acids in a range of more than 8, especially more than 20, amino acid residues or mixtures thereof. Other preferred polycations and their pharmaceutical compositions are described in WO 97/30721 (e.g. polyethyleneimine) and WO 99/38528. Preferably these polypeptides contain between 20 and 500 amino acid residues, especially between 30 and 200 residues.

These polycationic compounds may be produced chemically or recombinantly or may be derived from natural sources.

Cationic (poly)peptides may also be anti-microbial with properties as reviewed in {Ganz, T., 1999}. These (poly) peptides may be of prokaryotic or animal or plant origin or may be produced chemically or recombinantly (WO 02/13857). Peptides may also belong to the class of defensins (WO 02/13857). Sequences of such peptides can be, for example, found in the Antimicrobial Sequences Database available on the World Wide Web under the following internet address:

bbcm.univ.trieste.it/~tossi/pag2.html

Such host defence peptides or defensives are also a preferred form of the polycationic polymer according to the present invention. Generally, a compound allowing as an end product activation (or down-regulation) of the adaptive immune system, preferably mediated by APCs (including dendritic cells) is used as polycationic polymer.

Especially preferred for use as polycationic substances in the present invention are cathelicidin derived antimicrobial peptides or derivatives thereof (International patent application WO 02/13857, incorporated herein by reference), especially antimicrobial peptides derived from mammalian cathelicidin, preferably from human, bovine or mouse.

Polycationic compounds derived from natural sources include HIV-REV or HIV-TAT (derived cationic peptides, antennapedia peptides, chitosan or other derivatives of chitin) or other peptides derived from these peptides or proteins by biochemical or recombinant production. Other preferred polycationic compounds are cathelin or related or derived substances from cathelin. For example, mouse cathelin is a peptide, which has the amino acid sequence NH$_2$-RLAGLL-RKGGEKIGEKLKKIGQKIKNFFQKLVPQPE-COOH (SEQ ID NO:64). Related or derived cathelin substances contain the whole or parts of the cathelin sequence with at least 15-20 amino acid residues. Derivations may include the substitution or modification of the natural amino acids by amino acids, which are not among the 20 standard amino acids. Moreover, further cationic residues may be introduced into such cathelin molecules. These cathelin molecules are preferred to be combined with the antigen. These cathelin molecules surprisingly have turned out to be also effective as an adjuvant for an antigen without the addition of further adjuvants. It is therefore possible to use such cathelin molecules as efficient adjuvants in vaccine formulations with or without further immunoactivating substances.

Another preferred polycationic substance to be used according to the present invention is a synthetic peptide containing at least 2 KLK-motifs separated by a linker of 3 to 7 hydrophobic amino acids (International patent application WO 02/32451, incorporated herein by reference).

The pharmaceutical composition of the present invention may further comprise immunostimulatory nucleic acid(s). Immunostimulatory nucleic acids are e.g. neutral or artificial CpG containing nucleic acids, short stretches of nucleic acids derived from non-vertebrates or in form of short oligonucleotides (ODNs) containing non-methylated cytosine-guanine di-nucleotides (CpG) in a certain base context (e.g. described in WO 96/02555). Alternatively, also nucleic acids based on inosine and cytidine as e.g. described in the WO 01/93903, or deoxynucleic acids containing deoxy-inosine and/or deoxyuridine residues (described in WO 01/93905 and PCT/EP 02/05448, incorporated herein by reference) may preferably be used as immunostimulatory nucleic acids for the present invention. Preferably, the mixtures of different immunostimulatory nucleic acids may be used according to the present invention.

It is also within the present invention that any of the aforementioned polycationic compounds is combined with any of the immunostimulatory nucleic acids as aforementioned. Preferably, such combinations are according to the ones as described in WO 01/93905, WO 02/32451, WO 01/54720, WO 01/93903, WO 02/13857 and PCT/EP 02/05448 and the Austrian patent application A 1924/2001, incorporated herein by reference.

In addition or alternatively such vaccine composition may comprise apart from the hyperimmune serum reactive antigens and fragments thereof, and the coding nucleic acid molecules thereof according to the present invention a neuroactive compound. Preferably, the neuroactive compound is human growth factor as, e.g. described in WO 01/24822. Also preferably, the neuroactive compound is combined with any of the polycationic compounds and/or immunostimulatory nucleic acids as afore-mentioned.

In a further aspect the present invention is related to a pharmaceutical composition. Such pharmaceutical composition is, for example, the vaccine described herein. Also a pharmaceutical composition is a pharmaceutical composition which comprises any of the following compounds or combinations thereof: the nucleic acid molecules according to the present invention, the hyperimmune serum reactive antigens and fragments thereof according to the present invention, the vector according to the present invention, the cells according to the present invention, the antibody according to the present invention, the functional nucleic acids according to the present invention and the binding peptides such as the anticalines according to the present invention, any agonists and antagonists screened as described herein. In connection therewith any of these compounds may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a hyperimmune serum reactive antigen and fragments thereof of the invention and a pharmaceutically acceptable carrier or excipient. Such carriers may include, but are not limited to, saline, buffered saline, dextrose, water, glycerol, ethanol and combinations thereof. The formulation should suit the mode of administration.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

A vaccine composition is conveniently in injectable form. Conventional adjuvants may be employed to enhance the immune response. A suitable unit dose for vaccination is 0.05-5 μg antigen/per kg of body weight, and such dose is preferably administered 1-3 times and with an interval of 1-3 weeks.

With the indicated dose range, no adverse toxicological effects should be observed with the compounds of the invention, which would preclude their administration to suitable individuals.

In a further embodiment the present invention relates to diagnostic and pharmaceutical packs and kits comprising one or more containers filled with one or more of the ingredients of the afore-mentioned compositions of the invention. The ingredient(s) can be present in a useful amount, dosage, formulation or combination. Associated with such container(s) can be a notice in the form prescribed by a governmental agency regulating the manufacture, use or sale of pharmaceuticals or biological products, reflecting approval by the agency of the manufacture, use or sale of the product for human administration.

In connection with the present invention any disease related use as disclosed herein such as, e.g. use of the pharmaceutical composition or vaccine, is particularly a disease or diseased condition which is caused by, linked or associated with Staphylococci, more preferably, *S. epidermidis*. In connection therewith it is to be noted that *S. epidermidis* comprises several strains including those disclosed herein. A disease related, caused or associated with the bacterial infection to be prevented and/or treated according to the present invention includes besides other diseases mostly those related to the presence of foreign bodies and the use of devices, such as catheters, cerebrospinal fluid shunt infections, peritonitis and endocarditis in humans.

In a still further embodiment the present invention is related to a screening method using any of the hyperimmune serum reactive antigens or nucleic acids according to the present invention. Screening methods as such are known to the one skilled in the art and can be designed such that an agonist or an antagonist is screened. Preferably an antagonist is screened which in the present case inhibits or prevents the binding of any hyperimmune serum reactive antigen and fragment thereof according to the present invention to an interaction partner. Such interaction partner can be a naturally occurring interaction partner or a non-naturally occurring interaction partner.

The invention also provides a method of screening compounds to identify those, which enhance (agonist) or block (antagonist) the function of hyperimmune serum reactive antigens and fragments thereof or nucleic acid molecules of the present invention, such as its interaction with a binding molecule. The method of screening may involve high-throughput.

For example, to screen for agonists or antagonists, the interaction partner of the nucleic acid molecule and nucleic acid, respectively, according to the present invention, maybe a synthetic reaction mix, a cellular compartment, such as a membrane, cell envelope or cell wall, or a preparation of any thereof, may be prepared from a cell that expresses a molecule that binds to the hyperimmune serum reactive antigens and fragments thereof of the present invention. The preparation is incubated with labelled hyperimmune serum reactive antigens and fragments thereof in the absence or the presence of a candidate molecule, which may be an agonist or antagonist. The ability of the candidate molecule to bind the binding molecule is reflected in decreased binding of the labelled ligand. Molecules which bind gratuitously, i.e., without inducing the functional effects of the hyperimmune serum reactive antigens and fragments thereof, are most likely to be good antagonists. Molecules that bind well and elicit functional effects that are the same as or closely related to the hyperimmune serum reactive antigens and fragments thereof are good agonists.

The functional effects of potential agonists and antagonists may be measured, for instance, by determining the activity of a reporter system following interaction of the candidate molecule with a cell or appropriate cell preparation, and comparing the effect with that of the hyperimmune serum reactive antigens and fragments thereof of the present invention or molecules that elicit the same effects as the hyperimmune serum reactive antigens and fragments thereof. Reporter systems that may be useful in this regard include but are not limited to colorimetric labelled substrate converted into product, a reporter gene that is responsive to changes in the functional activity of the hyperimmune serum reactive antigens and fragments thereof, and binding assays known in the art.

Another example of an assay for antagonists is a competitive assay that combines the hyperimmune serum reactive antigens and fragments thereof of the present invention and a potential antagonist with membrane-bound binding molecules, recombinant binding molecules, natural substrates or ligands, or substrate or ligand mimetics, under appropriate conditions for a competitive inhibition assay. The hyperimmune serum reactive antigens and fragments thereof can be labelled such as by radioactivity or a colorimetric compound, such that the molecule number of hyperimmune serum reactive antigens and fragments thereof bound to a binding molecule or converted to product can be determined accurately to assess the effectiveness of the potential antagonist.

Potential antagonists include small organic molecules, peptides, polypeptides and antibodies that bind to a hyperimmune serum reactive antigen and fragments thereof of the invention and thereby inhibit or extinguish its activity. Potential antagonists also may be small organic molecules, a peptide, a polypeptide such as a closely related protein or antibody that binds to the same sites on a binding molecule without inducing functional activity of the hyperimmune serum reactive antigens and fragments thereof of the invention.

Potential antagonists include a small molecule, which binds to and occupies the binding site of the hyperimmune serum reactive antigens and fragments thereof thereby preventing binding to cellular binding molecules, such that normal biological activity is prevented. Examples of small molecules include but are not limited to small organic molecules, peptides or peptide-like molecules.

Other potential antagonists include antisense molecules (see {Okano, H. et al., 1991}; OLIGODEOXYNUCLEOTIDES AS ANTISENSE INHIBITORS OF GENE EXPRESSION; CRC Press, Boca Ration, Fla. (1988), for a description of these molecules).

Preferred potential antagonists include derivatives of the hyperimmune serum reactive antigens and fragments thereof of the invention.

As used herein the activity of a hyperimmune serum reactive antigen and fragment thereof according to the present invention is its capability to bind to any of its interaction partner or the extent of such capability to bind to its or any interaction partner.

In a particular aspect, the invention provides the use of the hyperimmune serum reactive antigens and fragments thereof, nucleic acid molecules or inhibitors of the invention to interfere with the initial physical interaction between a pathogen and mammalian host responsible for sequelae of infection. In particular the molecules of the invention may be used: i) in the prevention of adhesion of S. epidermidis to mammalian extracellular matrix proteins on in-dwelling devices or to extracellular matrix proteins in wounds; ii) to block protein mediated mammalian cell invasion by, for example, initiating phosphorylation of mammalian tyrosine kinases {Rosenshine, I. et al., 1992} to block bacterial adhesion between mammalian extracellular matrix proteins and bacterial proteins which mediate tissue damage; iv) to block the normal progression of pathogenesis in infections initiated other than by the implantation of in-dwelling devices or by other surgical techniques.

Each of the DNA coding sequences provided herein may be used in the discovery and development of antibacterial compounds. The encoded protein upon expression can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The antagonists and agonists may be employed, for instance, to inhibit diseases arising from infection with Staphylococcus, especially S. epidermidis, such as sepsis.

In a still further aspect the present invention is related to an affinity device such affinity device comprises as least a support material and any of the hyperimmune serum reactive antigens and fragments thereof according to the present invention, which is attached to the support material. Because of the specificity of the hyperimmune serum reactive antigens and fragments thereof according to the present invention for their target cells or target molecules or their interaction partners, the hyperimmune serum reactive antigens and fragments thereof allow a selective removal of their interaction partner(s) from any kind of sample applied to the support material provided that the conditions for binding are met. The sample may be a biological or medical sample, including but not limited to, fermentation broth, cell debris, cell preparation, tissue preparation, organ preparation, blood, urine, lymph liquid, liquor and the like.

The hyperimmune serum reactive antigens and fragments thereof may be attached to the matrix in a covalent or non-covalent manner. Suitable support material is known to the one skilled in the art and can be selected from the group comprising cellulose, silicon, glass, aluminium, paramagnetic beads, starch and dextrane.

The present invention is further illustrated by the following figures, examples and the sequence listing from which further features, embodiments and advantages may be taken. It is to be understood that the present examples are given by way of illustration only and not by way of limitation of the disclosure.

In connection with the present invention

Table 1 shows the summary of the screens performed with genomic S. epidermidis libraries and human serum and the gene distribution data for selected antigens.

The figures to which it might be referred to in the specification are described in the following in more details.

Figure 1:
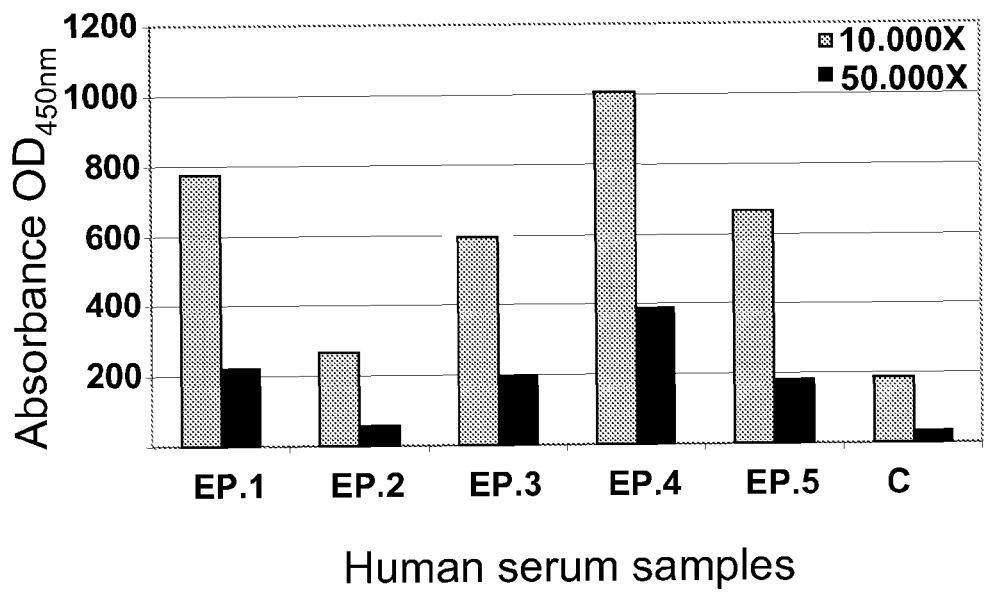
FIG. 1 shows the characterization of the selected human high titre sera specific for S. epidermidis.
Figure 1:
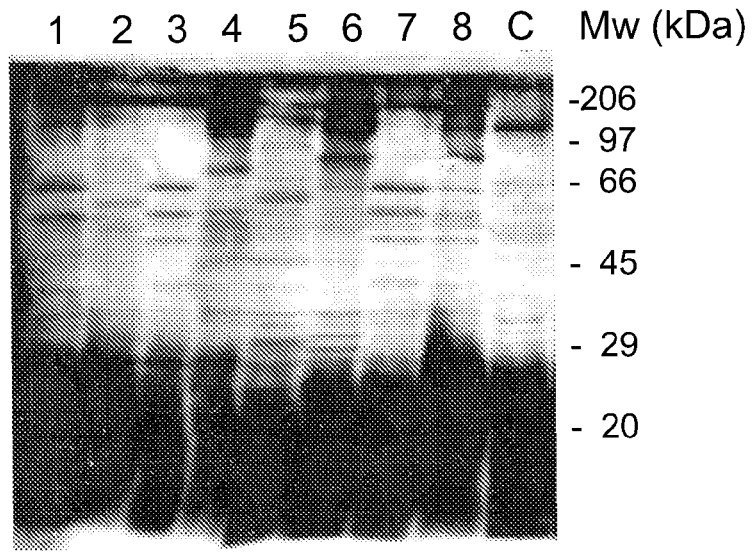

FIG. 1 shows the characterization and selection of human serum samples for identification of S. epidermidis antigens. (A) ELISA: Total anti-S. epidermidis IgGs were measured by standard ELISA using total bacterial lysate as coating antigen at two different serum dilutions. Five sera (EP.1-5) were selected from a serum collection obtained from patients with S. epidermidis peritonitis. C, control serum from a patient with unrelated infection. (B) Immunoblot analysis: Selected high titer sera were characterized by immunoblotting using total bacterial lysates prepared from eight different S. epidermidis clinical isolates (lanes 1-8), as well as from S. epidermidis strain RP62A (lane C). In each lane, ~20 µg total lysate proteins extracted from bacteria grown in BHI medium overnight were loaded. A representative immunoblot is shown for the EP.4 serum. The membrane was incubated with EP.4 serum at a dilution of 5,000 and developed with anti-human IgG secondary reagent. Mw, Protein standards (kDa).

FIG. 2A shows the fragment size distribution of the Staphylococcus epidermidis RP62A small fragment genomic library, LSE-70. After sequencing 572 randomly selected clones, sequences were trimmed to eliminate vector residues and the numbers of clones with various genomic fragment sizes were plotted. (B) Graphic illustration of the distribution of the same set of randomly sequenced clones of LSE-70 over the S. epidermidis chromosome. Circles indicate matching sequences to annotated ORFs in +/+ and +/− orientation. Rectangles represent fully matched clones to non-coding chromosomal sequences in +/+ and +/− orientation. Diamonds position the best match of all chimeric clone sequences. Numeric distances in base pairs are indicated over the circular genome for orientation. Partitioning of various clone sets within the library is given in numbers and percentage at the bottom of the figure.

Figure 3:
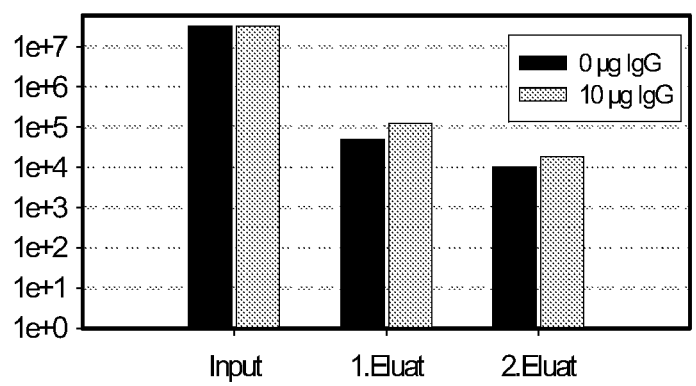
FIG. 3 shows the selection of bacterial cells by MACS using biotinylated human IgGs.
Figure 3:
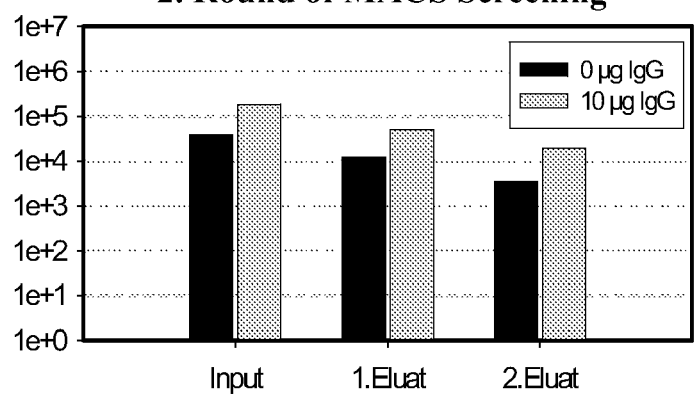
Figure 3:
Figure 3:

FIG. 3A shows the MACS selection with biotinylated human IgGs. The LSE-70 library in pMAL9.1 was screened with 10 µg biotinylated, human serum (P15-IgG) in the first and second selection round. As negative control, no serum was added to the library cells for screening. Number of cells selected after the 1st and 2nd elution are shown for each selection round. FIG. 3B shows the reactivity of specific clones (1-26) isolated by bacterial surface display as analysed by Western blot analysis with the human serum (P15-IgG) used for selection by MACS at a dilution of 1:3,000. As a loading control the same blot was also analysed with antibodies directed against the platform protein LamB at a dilution of 1:5,000. LB, Extract from a clone expressing LamB without foreign peptide insert.

Figure 4:
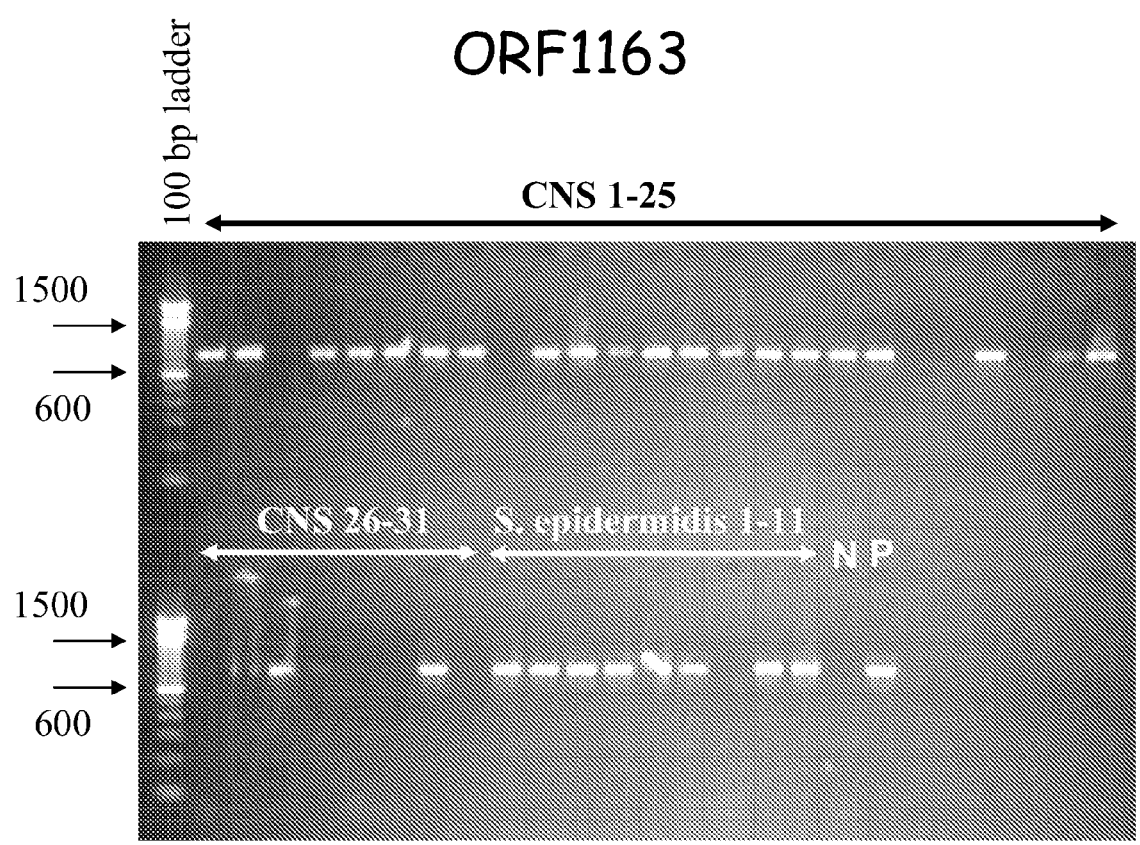
FIG. 4 shows an example for the gene distribution study with the identified antigens.

FIG. 4 shows the PCR analysis for the gene distribution of ORF1163 with the respective oligonucleotides. The predicted size of the PCR fragments is approximately 1,000 bp. The 31 coagulase negative *Staphylococcus* and 11 *S. epidermidis* strains used for analysis are marked in the figure; N, no genomic DNA added; P, genomic DNA from *S. epidermidis* RP62A, which served as template for library construction.

Table 1: Immunogenic proteins identified by bacterial surface display.

A, LSE-70 library in lamB with P15-IgG (804), B, LSE-150 library in fhuA with P15-IgG (826), C, LSA-300 library in fhuA with P15-IgG (729), *, prediction of antigenic sequences longer than 5 amino acids was performed with the program ANTIGENIC {Kolaskar, A. et al., 1990}. §, Forty-two coagulase negative *Staphylococcus* or *S. epidermidis* strains were tested by PCR with oligonucleotides specific for the genes encoding relevant antigens. Since 6 of the 31 CNS strains were negative for all genes analysed, we eliminated these data from the summary, because these strains are most likely not closely related to *S. epidermidis*.

EXAMPLES

Example 1

Preparation of Antibodies from Human Serum

Experimental Procedures
Peptide Synthesis

Peptides were synthesized in small scale (4 mg resin; up to 288 in parallel) using standard F-moc chemistry on a Rink amide resin (PepChem, Tübingen, Germany) using a SyroII synthesizer (Multisyntech, Witten, Germany). After the sequence was assembled, peptides were elongated with Fmoc-epsilon-aminohexanoic acid (as a linker) and biotin (Sigma, St. Louis, Mo.; activated like a normal amino acid). Peptides were cleaved off the resin with 93% TFA, 5% triethylsilane, and 2% water for one hour. Peptides were dried under vacuum and freeze dried three times from acetonitrile/water (1:1). The presence of the correct mass was verified by mass spectrometry on a Reflex III MALDI-TOF (Bruker, Bremen Germany). The peptides were used without further purification.

Enzyme Linked Immune Assay (ELISA).

For serum characterization: ELISA plates (Maxisorb, Millipore) were coated with 5-10 µg/ml total protein diluted in coating buffer (0.1M sodium carbonate pH 9.2). Three dilutions of sera (2,000×, 10,000×, 50,000×) were made in PBS-BSA.

For peptide serology: Biotin-labeled peptides were coating on Streptavidin ELISA plates (EXICON) at 10 µg/ml concentration according to the manufacturer's instructions. Sera were tested at two dilutions, 200× and 1,000×.

Highly specific Horse Radish Peroxidase (HRP)-conjugated anti-human IgG or anti-human IgA secondary antibodies (Southern Biotech) were used according to the manufacturers' recommendations (dilution: 1,000×). Antigen-antibody complexes were quantified by measuring the conversion of the substrate (ABTS) to colored product based on OD405 nm readings in an automated ELISA reader (TECAN SUNRISE). Following manual coating, peptide plates were processed and analyzed by the Gemini 160 ELISA robot (TECAN) with a built-in reader (GENIOS, TECAN).

Immunoblotting

Total bacterial lysate and culture supernatant samples were prepared from in vitro grown *S. epidermidis* RP62A. 10 to 25 µg total protein/lane was separated by SDS-PAGE using the BioRad Mini-Protean 3 Cell electrophoresis system and proteins transferred to nitrocellulose membrane (ECL, Amersham Pharmacia). After overnight blocking in 5% milk, antisera at 2,000× dilution were added, and HRPO labeled anti-mouse IgG was used for detection.

Preparation of Bacterial Antigen Extracts

Total bacterial lysate: Bacteria were lysed by repeated freeze-thaw cycles: incubation on dry ice/ethanol-mixture until frozen (1 min), then thawed at 370 C (5 min): repeated 3 times. This was followed by sonication and collection of supernatant by centrifugation (3,500 rpm, 15 min, 40 C).

Culture supernatant: After removal of bacteria, the supernatant of overnight grown bacterial cultures was precipitated with ice-cold ethanol (100%): 1 part supernatant/3 parts ethanol incubated o/n at −20° C. Precipitates were collected by centrifugation (2,600 g, for 15 min) and dried. Dry pellets were dissolved either in PBS for ELISA, or in urea and SDS-sample buffer for SDS-PAGE and immunoblotting. The protein concentration of samples was determined by Bradford assay.

Purification of antibodies for genomic screening. Five sera from the patient group were selected based on the overall anti-staphylococcal titers for a serum pool used in the screening procedure. Antibodies against *E. coli* proteins were removed by incubating the heat-inactivated sera with whole cell *E. coli* cells (DH5alpha, transformed with pHIE11, grown under the same condition as used for bacterial surface display). Highly enriched preparations of IgGs from the pooled, depleted sera were generated by protein G affinity chromatography, according to the manufacturer's instructions (UltraLink Immobilized Protein G, Pierce). IgA antibodies were purified also by affinity chromatography using biotin-labeled anti-human IgA (Southern Biotech) immobilized on Streptavidin-agarose (GIBCO BRL). The efficiency of depletion and purification was checked by SDS-PAGE, Western blotting, ELISA and protein concentration measurements.

The antibodies produced against *S. epidermidis* by the human immune system and present in human sera are indicative of the in vivo expression of the antigenic proteins and their immunogenicity. These molecules are essential for the identification of individual antigens in the approach as described in the present invention, which is based on the interaction of the specific anti-staphylococcal antibodies and the corresponding *S. epidermidis* peptides or proteins. To gain access to relevant antibody repertoires, human sera were collected from convalescent patients with *S. epidermidis* infections, namely peritonitis.

The sera were characterized for anti-*S. epidermidis* antibodies by a series of ELISA and immunoblotting assays. Bacterial lysate proteins prepared from *S. epidermidis* RP62A cultured overnight (stationary phase) in BHI (Brain Heart Infusion) growth medium have been used as staphylococcal antigens. Both IgG and IgA antibody levels were determined. Five sera having the highest antibody levels were pooled, and IgG prepared for use in bacterial surface display in order to identify antigenic proteins.

The titers were compared at given dilutions where the response was linear. Sera were ranked based on the reactivity against multiple staphylococcal components, and the highest ones were selected for further analysis by immunoblotting (FIG. 1). This extensive antibody characterization approach has led to the unambiguous identification of anti-staphylococcal hyperimmune sera.

Example 2

Generation of Highly Random, Frame-Selected, Small-Fragment, Genomic DNA Libraries of *Staphylococcus epidermidis*

Experimental Procedures

Preparation of staphylococcal genomic DNA. 50 ml BHI medium was inoculated with *S. epidermidis* RP62A bacteria from a frozen stab and grown with aeration and shaking for 18 h at 37° C. The culture was then harvested, centrifuged with 1,600×g for 15 min and the supernatant was removed. Bacterial pellets were washed 3× with PBS and carefully resuspended in 0.5 ml of Lysozyme solution (100 mg/ml). 0.1 ml of 10 mg/ml heat treated RNase A and 20 U of RNase T1 were added, mixed carefully and the solution was incubated for 1 h at 37° C. Following the addition of 0.2 ml of 20% SDS solution and 0.1 ml of Proteinase K (10 mg/ml) the tube was incubated overnight at 55° C. ⅓ volume of saturated NaCl was then added and the solution was incubated for 20 min at 4° C. The extract was pelleted in a microfuge (13,000 rpm) and the supernatant transferred into a new tube. The solution was extracted with PhOH/CHCl3/IAA (25:24:1) and with CHCl3/IAA (24:1). DNA was precipitated at room temperature by adding 0.6× volume of Isopropanol, spooled from the solution with a sterile Pasteur pipette and transferred into tubes containing 80% ice-cold ethanol. DNA was recovered by centrifuging the precipitates with 10-12,000×g, then dried on air and dissolved in ddH2O.

Preparation of small genomic DNA fragments. Genomic DNA fragments were mechanically sheared into fragments ranging in size between 150 and 300 bp using a cup-horn sonicator (Bandelin Sonoplus UV 2200 sonicator equipped with a BB5 cup horn, 10 sec. pulses at 100% power output) or into fragments of size between 50 and 70 bp by mild DNase I treatment (Novagen). It was observed that sonication yielded a much tighter fragment size distribution when breaking the DNA into fragments of the 150-300 bp size range. However, despite extensive exposure of the DNA to ultrasonic wave-induced hydromechanical shearing force, subsequent decrease in fragment size could not be efficiently and reproducibly achieved. Therefore, fragments of 50 to 70 bp in size were obtained by mild DNase I treatment using Novagen's shotgun cleavage kit. A 1:20 dilution of DNase I provided with the kit was prepared and the digestion was performed in the presence of $MnCl_2$ in a 60 µl volume at 20° C. for 5 min to ensure double-stranded cleavage by the enzyme. Reactions were stopped with 2 µl of 0.5 M EDTA and the fragmentation efficiency was evaluated on a 2% TAE-agarose gel. This treatment resulted in total fragmentation of genomic DNA into near 50-70 bp fragments. Fragments were then blunt-ended twice using T4 DNA Polymerase in the presence of 100 µM each of dNTPs to ensure efficient flushing of the ends. Fragments were used immediately in ligation reactions or frozen at −20° C. for subsequent use.

Description of the vectors. The vector pMAL4.31 was constructed on a pASK-IBA backbone {Skerra, A., 1994} with the beta-lactamase (bla) gene exchanged with the Kanamycin resistance gene. In addition the bla gene was cloned into the multiple cloning site. The sequence encoding mature beta-lactamase is preceded by the leader peptide sequence of ompA to allow efficient secretion across the cytoplasmic membrane. Furthermore a sequence encoding the first 12 amino acids (spacer sequence) of mature beta-lactamase follows the ompA leader peptide sequence to avoid fusion of sequences immediately after the leader peptidase cleavage site, since e.g. clusters of positive charged amino acids in this region would decrease or abolish translocation across the cytoplasmic membrane {Kajava, A. et al., 2000}. A SmaI restriction site serves for library insertion. An upstream FseI site and a downstream NotI site, which were used for recovery of the selected fragment, flank the SmaI site. The three restriction sites are inserted after the sequence encoding the 12 amino acid spacer sequence in such a way that the bla gene is transcribed in the −1 reading frame resulting in a stop codon 15 bp after the NotI site. A +1 bp insertion restores the bla ORF so that beta-lactamase protein is produced with a consequent gain of Ampicillin resistance.

The vector pMAL9.1 was constructed by cloning the lamB gene into the multiple cloning site of pEH1 {Hashemzadeh-Bonehi, L. et al., 1998}. Subsequently, a sequence was inserted in lamB after amino acid 154, containing the restriction sites FseI, SmaI and NotI. The reading frame for this insertion was constructed in such a way that transfer of frame-selected DNA fragments excised by digestion with FseI and NotI from plasmid pMAL4.31 yields a continuous reading frame of lamB and the respective insert.

The vector pHIE11 was constructed by cloning the fhuA gene into the multiple cloning site of pEH1. Thereafter, a sequence was inserted in fhuA after amino acid 405, containing the restriction site FseI, XbaI and NotI. The reading frame for this insertion was chosen in a way that transfer of frame-selected DNA fragments excised by digestion with FseI and NotI from plasmid pMAL4.31 yields a continuous reading frame of fhuA and the respective insert.

Cloning and evaluation of the library for frame selection. Genomic *S. epidermidis* DNA fragments were ligated into the SmaI site of the vector pMAL4.31. Recombinant DNA was electroporated into DH10B electrocompetent *E. coli* cells (GIBCO BRL) and transformants plated on LB-agar supplemented with Kanamycin (50 µg/ml) and Ampicillin (50 µg/ml). Plates were incubated over night at 37° C. and colonies collected for large scale DNA extraction. A representative plate was stored and saved for collecting colonies for colony PCR analysis and large-scale sequencing. A simple colony PCR assay was used to initially determine the rough fragment size distribution as well as insertion efficiency. From sequencing data the precise fragment size was evaluated, junction intactness at the insertion site as well as the frame selection accuracy (3n+1 rule).

Cloning and evaluation of the library for bacterial surface display. Genomic DNA fragments were excised from the pMAL4.31 vector, containing the *S. epidermidis* library with the restriction enzymes FseI and NotI. The entire population of fragments was then transferred into plasmids pMAL9.1 (LamB) or pHIE11 (FhuA), which have been digested with FseI and NotI. Using these two restriction enzymes, which recognise an 8 bp GC rich sequence, the reading frame that was selected in the pMAL4.31 vector is maintained in each of the platform vectors. The plasmid library was then transformed into *E. coli* DH5alpha cells by electroporation. Cells were plated onto large LB-agar plates supplemented with 50 µg/ml Kanamycin and grown over night at 37° C. at a density yielding clearly visible single colonies. Cells were then scraped off the surface of these plates, washed with fresh LB medium and stored in aliquots for library screening at −80° C.

Results

Figure 2:
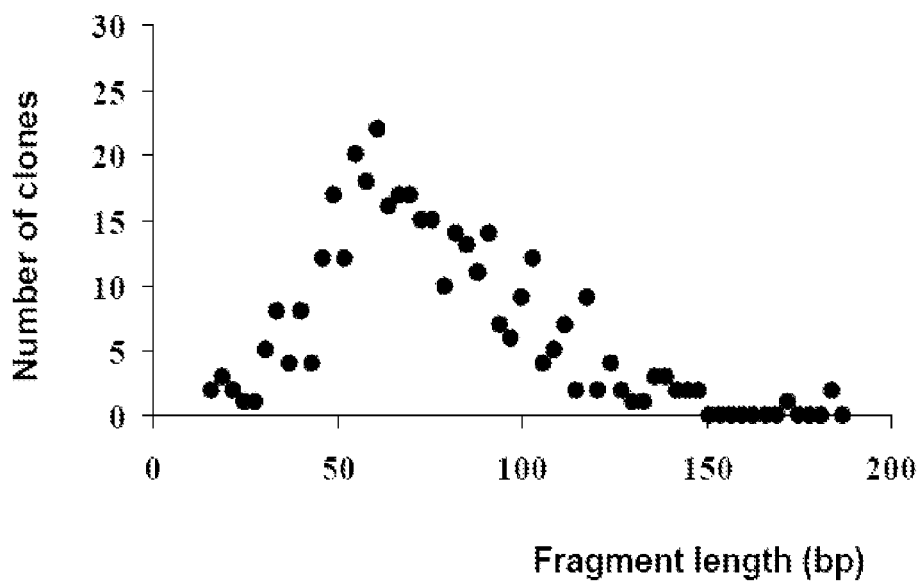
FIG. 2 shows the characterization of the small fragment genomic library, LSE-70, from Staphylococcus epidermidis RP62A.
Figure 2:
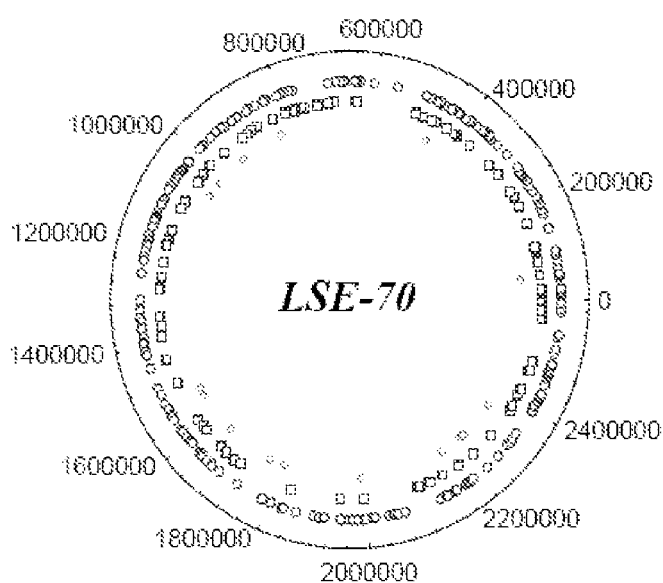

Libraries for frame selection. Two libraries (LSE-70 and LSE-150) were generated in the pMAL4.31 vector with sizes of approximately 70, 150 and 300 bp, respectively. For each library, ligation and subsequent transformation of approximately 1 µg of pMAL4.31 plasmid DNA and 50 ng of fragmented genomic *S. epidermidis* DNA yielded 4×105 to 2×106 clones after frame selection. To assess the randomness of the libraries, approximately 600 randomly chosen clones of LSE-70 were sequenced. The bioinformatic analysis showed that of these clones only very few were present more than once. Furthermore, it was shown that 90% of the clones fell in the size range between 16 and 61 bp with an average size of 34 bp (FIG. 2). Almost all sequences followed the 3n+1 rule, showing that all clones were properly frame selected.

Bacterial surface display libraries. The display of peptides on the surface of *E. coli* required the transfer of the inserts from the LSE libraries from the frame selection vector pMAL4.31 to the display plasmids pMAL9.1 (LamB) or pHIE11 (FhuA). Genomic DNA fragments were excised by FseI and NotI restriction and ligation of 5 ng inserts with 0.1 µg plasmid DNA and subsequent transformation into DH5alpha cells resulted in 2-5×106 clones. The clones were scraped off the LB plates and frozen without further amplification.

Example 3

Identification of Highly Immunogenic Peptide Sequences from *S. epidermidis* Using Bacterial Surface Displayed Genomic Libraries and Human Serum Experimental Procedures MACS screening. Approximately 2.5×108 cells from a given library were grown in 5 ml LB-medium supplemented with 50 µg/ml Kanamycin for 2 h at 37° C. Expression was induced by the addition of 1 mM IPTG for 30 min. Cells were washed twice with fresh LB medium and approximately 2×107 cells re-suspended in 100 µl LB medium and transferred to an Eppendorf tube.

10 µg of biotinylated, human IgGs purified from serum was added to the cells and the suspension incubated over night at 4° C. with gentle shaking. 900 µl of LB medium was added, the suspension mixed and subsequently centrifuged for 10 min at 6,000 rpm at 4° C. (For IgA screens, 10 µg of purified IgAs were used and these captured with biotinylated anti-human-IgG secondary antibodies). Cells were washed once with 1 ml LB and then re-suspended in 100 µl LB medium. 10 µl of MACS microbeads coupled to streptavidin (Miltenyi Biotech, Germany) were added and the incubation continued for 20 min at 4° C. Thereafter 900 µl of LB medium was added and the MACS microbead cell suspension was loaded onto the equilibrated MS column (Miltenyi Biotech, Germany) which was fixed to the magnet. (The MS columns were equilibrated by washing once with 1 ml 70% EtOH and twice with 2 ml LB medium.)

The column was then washed three times with 3 ml LB medium. After removal of the magnet, cells were eluted by washing with 2 ml LB medium. After washing the column with 3 ml LB medium, the 2 ml eluate was loaded a second time on the same column and the washing and elution process repeated. The loading, washing and elution process was performed a third time, resulting in a final eluate of 2 ml.

A second round of screening was performed as follows. The cells from the final eluate were collected by centrifugation and re-suspended in 1 ml LB medium supplemented with 50 µg/ml Kanamycin. The culture was incubated at 37° C. for 90 min and then induced with 1 mM IPTG for 30 min. Cells were subsequently collected, washed once with 1 ml LB medium and suspended in 10 µl LB medium. Since the volume was reduced, 10 µg of human, biotinylated IgGs was added and the suspension incubated over night at 4° C. with gentle shaking. All further steps were exactly the same as in the first selection round. Cells selected after two rounds of selection were plated onto LB-agar plates supplemented with 50 µg/ml Kanamycin and grown over night at 37° C.

Evaluation of selected clones by sequencing and Western blot analysis. Selected clones were grown over night at 37° C. in 3 ml LB medium supplemented with 50 µg/ml Kanamycin to prepare plasmid DNA using standard procedures. Sequencing was performed at MWG (Germany).

For Western blot analysis approximately 10 to 20 µg of total cellular protein was separated by 10% SDS-PAGE and blotted onto HybondC membrane (Amersham Pharmacia Biotech, England). The LamB or FhuA fusion proteins were detected using human serum as the primary antibody at a dilution of approximately 1:5,000 and anti-human IgG or IgA antibodies coupled to HRP at a dilution of 1:5,000 as secondary antibodies. Detection was performed using the ECL detection kit (Amersham Pharmacia Biotech, England). Alternatively, rabbit anti FhuA or mouse anti LamB antibodies were used as primary antibodies in combination with the respective secondary antibodies coupled to HRP for the detection of the fusion proteins.

Results

Screening of bacterial surface display libraries by magnetic activated cell sorting (MACS) using biotinylated Igs. The libraries LSE-70 in pMAL9.1 and LSE-150 in pHIE11 were screened with a pool of biotinylated, human IgG from patient sera (see Example 1: Preparation of antibodies from human serum). In addition, a *S. aureus* library (LSA-300 in pHIE11) was also screened with the same serum pool, P15-IgG. The selection procedure was performed as described under Experimental procedures. FIG. 3A shows a representative example of a screen with the LSE-70 library and P15-IgGs. As can be seen from the colony count after the first selection cycle from MACS screening, the total number of cells recovered at the end is drastically reduced from approximately 3×107 cells to app. 2×104 cells, whereas the selection without antibodies added showed a reduction to about 1×104 cells (FIG. 3A). After the second round, a similar number of cells was recovered with P15-IgG, while app. 8-fold fewer cells were recovered when no IgGs from human serum were added, clearly showing that selection was dependent on *S. epidermidis* specific antibodies. To evaluate the performance of the screen, 26 selected clones were picked randomly and subjected to Western blot analysis with the same, pooled serum (FIG. 3B). This analysis revealed that 70% of the selected clones showed reactivity with antibodies present in the relevant serum whereas the control strain expressing LamB without a *S. epidermidis* specific insert did not react with the same serum. In general, the rate of reactivity was observed to lie within the range of 35 to 75%. Colony PCR analysis showed that all selected clones contained an insert in the expected size range.

Subsequent sequencing of a larger number of randomly picked clones (600 to 1000 per screen) led to the identification of the gene and the corresponding peptide or protein sequence that was specifically recognized by the human serum used for screening. The frequency with which a specific clone is selected reflects at least in part the abundance and/or affinity of the specific antibodies in the serum used for selection and recognizing the epitope presented by this clone. Table 1 summarizes the data obtained for the three performed screens, but lists only those genes, which have not been identified by previous screens. All clones that are presented in Table 1 have been verified by Western blot analysis using whole cellular extracts from single clones to show the indicated reactivity with the pool of human serum used in the respective screen. As can be seen from Table 1, distinct regions of the identified ORF are identified as immunogenic, since variably sized fragments of the proteins are displayed on the surface by the platform proteins. The screen with the S. aureus library revealed one novel antigen, which had not been identified in previous screens.

It is further worth noticing that most of the genes identified by the bacterial surface display screen encode proteins that are either attached to the surface of S. epidermidis and/or are secreted. This is in accordance with the expected role of surface attached or secreted proteins in virulence of S. epidermidis.

Example 4

Gene Distribution Studies with Highly Immunogenic Proteins Identified from S. epidermidis Gene distribution of staphylococcal antigens by PCR. An ideal vaccine antigen would be an antigen that is present in all, or the vast majority of strains of the target organism to which the vaccine is directed. In order to establish whether the genes encoding the identified *Staphylococcus epidermidis* antigens occur ubiquitously in S. epidermidis and coagulase negative *Staphylococcus* strains, PCR was performed on a series of independent S. epidermidis and coagulase negative *Staphylococcus* isolates with primers specific for the gene of interest. Oligonucleotide sequences as primers were designed for all identified ORFs yielding products of approximately 1,000 bp, if possible covering all identified immunogenic epitopes. Genomic DNA of all *Staphylococcus* strains was prepared as described under Example 2. PCR was performed in a reaction volume of 25 µl using Taq polymerase (1 U), 200 nM dNTPs, 10 pMol of each oligonucleotide and the kit according to the manufacturers instructions (Invitrogen, The Netherlands). As standard, 30 cycles (1x: 5 min. 95° C., 30x: 30 sec. 95° C., 30 sec. 56° C., 30 sec. 72° C., 1x4 min. 72° C.) were performed, unless conditions had to be adapted for individual primer pairs.

Results

Exemplarily, a number of genes encoding immunogenic proteins were tested by PCR for their presence in 42 different coagulase negative *Staphylococcus* (CNS) or S. epidermidis strains. FIG. 4 shows the PCR reaction for ORF1163 with all indicated 42 strains. It was expected that not all of the CNS strains represent S. epidermidis isolates. Therefore it was not surprising that 6 of the 31 CNS strains were negative for all genes analysed. Some of the eight selected genes encoding identified antigens and analysed by PCR, were present in many strains tested (e.g. ORF0026, ORF0217 and ORF1163), rendering them as good candidates for further development. A few genes were present in only a smaller number of the tested 42 strains (e.g. ORF0742 and ORF2700). This result may indicate the absence of the gene in the analysed isolates, or it could be due to a variation in the sequence used for the oligonucleotide for the PCR analysis. Interestingly, none of the eight analysed genes showed any variation in size. Sequencing of the generated PCR fragment from one strain and subsequent comparison to the RP62A strain confirmed the amplification of the correct DNA fragment. Importantly, the identified antigens, which are well conserved in all strains in sequence and size constitute novel vaccine candidates to prevent infections by S. epidermidis. As can be seen in Table 1, 20 of the listed 30 S. epidermidis antigens have a homolog in S. aureus COL with at least 50% sequence identity at the amino acid level, 4 have homologs with an identity below 50% and 6 antigens do not possess a homologous sequence in S. aureus COL. This indicates that several of the antigens have also the potential to show cross-protection with other Staphylococcal strains such as S. aureus.

REFERENCES

Altschul, S., et al. (1990). Journal of Molecular Biology 215: 403-10.
Bennett, D., et al. (1995). J Mol Recognit 8: 52-8.
Clackson, T., et al. (1991). Nature 352: 624-8.
Crossley, K. B. and Archer G. L., eds (1997). The Staphylococci in Human Disease. Churchill Livingston Ing.
Devereux, J., et al. (1984). Nucleic acids research 12: 387-95.
Doherty, E., et al. (2001). Annu Rev Biophys Biomol Struct 30: 457-475.
Eisenbraun, M., et al. (1993). DNA Cell Biol 12: 791-7.
Etz, H., et al. (2001). J Bacteriol 183: 6924-35.
Ganz, T. (1999). Science 286: 420-421.
Georgiou, G. (1997). Nature Biotechnology 15: 29-34.
Hashemzadeh-Bonehi, L., et al. (1998). Mol Microbiol 30: 676-678.
Heinje, von G (1987) e.g. Sequence Analysis in Molecular Biology, Academic Press
Hemmer, B., et al. (1999). Nat Med 5: 1375-82.
Johanson, K., et al. (1995). J Biol Chem 270: 9459-71.
Jones, P., et al. (1986). Nature 321: 522-5.
Kajava, A., et al. (2000). J Bacteriol 182: 2163-9.
Kohler, G., et al. (1975). Nature 256: 495-7.
Kolaskar, A., et al. (1990). FEBS Lett 276: 172-4.
Lewin, A., et al. (2001). Trends Mol Med 7: 221-8.
Marks, J., et al. (1992). Biotechnology (NY) 10: 779-83.
McCafferty, J., et al. (1990). Nature 348: 552-4.
Okano, H., et al. (1991). J Neurochem 56: 560-7.
Oligodeoxynucleotides as antisense Inhibitors of Gene Expression; CRC Press, Boca Ration, Fla. (1988) for a description o these molecules
Rammensee, H., et al. (1999). Immunogenetics 50: 213-9.
Rosenshine, I., et al. (1992). Infect Immun 60: 2211-7.
Seeger, C., et al. (1984). Proc Natl Acad Sci USA 81: 5849-52.
Shinefield, H., et al. (2002). N Engl J Med 346: 491-6.
Skerra, A. (1994). Gene 151: 131-5.
Tang, D., et al. (1992). Nature 356: 152-4.
Tempest, P., et al. (1991). Biotechnology (NY) 9: 266-71.
Tourdot, S., et al. (2000). Eur J Immunol 30: 3411-21.
Wiley, J., et al. (1987) Current Protocols in Molecular Biology

TABLE 1

Immunogenic proteins identified by bacterial surface display.

| S. epidermidis or aureus antigenic protein | Putative function (by homology) | predicted immunogenic aa* | No. of selected clones per ORF and screen | Location of identified immunogenic region (aa) | Homology with S. aureus | Gene distribution§ | Seq. ID (DNA, Prot.) |
|---|---|---|---|---|---|---|---|
| ORF00026 | LPXTG-motif cell wall anchor domain protein | 6-28, 54-59, 135-147, 193-205, 274-279, 284-291, 298-308, 342-347, 360-366, 380-386, 408-425, 437-446, 457-464, 467-477, 504-510, 517-530, 535-543, 547-553, 562-569, 573-579, 592-600, 602-613, 626-631, 638-668 | A: 5 | 396-449 | 32% SA2668 | 26/36 | 1, 32 |
| ORF00027 | autolysin, putative | 5-24, 101-108, 111-117, 128-142, 170-184, 205-211, 252-267, 308-316, 329-337, 345-353, 360-371, 375-389, 393-399, 413-419, 429-439, 446-456, 471-485, 495-507, 541-556, 582-588, 592-602, 607-617, 622-628, 630-640 | A: 3 | 8-21 | 53% SA2666 | n.d. | 2, 33 |
| ORF00217 | toxin resistance protein, putative | 10-20, 23-33, 40-45, 59-65, 72-107, 113-119, 127-136, 151-161 | A: 2 | 33-59 | 66% SA2541 | 29/36 | 3, 34 |
| ORF00259 | helicase-related protein | 4-16, 28-34, 39-61, 66-79, 100-113, 120-127, 130-137, 142-148, 150-157, 192-201, 203-210, 228-239, 245-250, 256-266, 268-278, 288-294, 312-322, 336-344, 346-358, 388-396, 399-413, 425-430, 445-461, 464-470, 476-482, 486-492, 503-511, 520-527, 531-541, 551-558, 566-572, 609-625, 635-642, 650-656, 683-689, 691-705, 734-741, 750-767, 782-789, 802-808, 812-818, 837-844, 878-885, 907-917, 930-936 | A: 2 | 913-933 | 65% SA2499 | n.d. | 4, 35 |
| ORF00545 | tagatose 1,6-diphosphate aldolase (lacD) | 5-12, 20-27, 46-78, 85-92, 104-112, 121-132, 150-167, 179-185, 200-213, 221-227, 240-264, 271-279, 282-290, 311-317 | A: 10 | 177-206 | 90% SA2183 | n.d. | 5, 36 |
| ORF00646 | UDP-N-acetyl-glucosamine 2-epimerase | 18-24, 31-40, 45-51, 89-97, 100-123, 127-132, 139-153, 164-170, 184-194, 200-205, 215-238, 244-255, 257-270, 272-280, 289-302, 312-318, 338-348, 356-367 | A: 3 | 132-152 | 72% SA2103 62% SA0151 | n.d. | 6, 37 |
| ORF00742 | M23/M37 peptidase domain protein protein | 7-16, 39-45, 73-83, 90-98, 118-124, 130-136, 194-204, 269-280, 320-327, 373-381, 389-397, 403-408, 424-430, 436-441, 463-476, 487-499, 507-514, 527-534, 540-550, 571-577, 593-599, 620-629, 641-647, 650-664, 697-703, 708-717, 729-742, 773-790, 794-805, 821-828, 830-837, 839-851, 858-908, 910-917, 938-947, 965-980, 1025-1033, 1050-1056, 1073-1081, 1084-1098, 1106-1120, 1132-1140, 1164-1170, 1185-1194, 1201-1208, 1215-1224, 1226-1234, 1267-1279, 1325-1331, 1356-1364, 1394-1411, 1426-1439, 1445-1461, 1498-1504, 1556-1561, 1564-1573, 1613-1639, 1648-1655, 1694-1714, 1748-1755, 1778-1785, 1808-1813, 1821-1827, 1829-1837, 1846-1852, 1859-1865, 1874-1883, 1895-1900, 1908-1913, 1931-1937, 1964-1981, 1995-2005, 2020-2033, 2040-2047, 2103-2109, 2118-2127, 2138-2144, 2166-2175, 2180-2187, 2220-2225, 2237-2242, 2247-2253, 2273-2281, 2286-2306, 2314-2320, 2323-2345, 2350-2355, 2371-2384, 2415-2424, 2426-2431, 2452-2472, 2584-2589, 2610-2621, 2638-2655, 2664-2670, 2681-2690, 2692-2714, 2724-2730 | A: 14, B: 7 | 687-730 | 18% SA0379 | 5/36 | 7, 38 |
| ORF00788 | conserved hypothetical protein | 10-40, 53-59, 79-85, 98-104, 117-122, 130-136, 144-158, 169-175, 180-185, 203-223, 232-237, 243-254, 295-301 | B: 1 | 254-292 | none | 4/36 | 8, 39 |
| ORF00891 (42% | cell division protein | 28-50, 67-85, 93-115, 120-134, 144-179, 240-249, 328-340, 354-360, 368-400, | B: 5 | 275-316; 378-401 | 69% SA1295 | n.d. | 9, 40 |

TABLE 1-continued

Immunogenic proteins identified by bacterial surface display.

| S. epidermidis or aureus antigenic protein | Putative function (by homology) | predicted immunogenic aa* | No. of selected clones per ORF and screen | Location of identified immunogenic region (aa) | Homology with S. aureus | Gene distribution§ | Seq. ID (DNA, Prot.) |
|---|---|---|---|---|---|---|---|
| ORF01770) | FtsK (ftsK) | 402-417, 419-427, 429-445, 447-455, 463-468, 472-480, 485-500, 502-510, 512-534, 537-546, 553-558, 582-594, 619-637, 645-654, 690-709, 735-745, 749-756, 786-792 | | | 42% SA1791 | | |
| ORF00894 | metalloprotease, insulinase family, putative | 5-16, 21-30, 33-40, 52-74, 101-108, 116-122, 164-182, 185-219, 256-261, 273-279, 285-291, 297-304, 312-328, 331-338, 355-362, 364-371, 373-401, 411-423 | A: 1 | 191-208 | 76% SA1298 | n.d. | 10, 41 |
| ORF00988 | membrane-bound protein LytR | 34-55, 67-74, 85-93, 105-115, 138-152, 161-171, 182-189, 197-205, 213-219, 232-239, 241-248, 250-263, 272-277, 288-299 | A: 1 | 216-231 | 74% SA1398 | n.d. | 11, 42 |
| ORF01054 (31% ORF00724) | ABC transporter, ATP-binding protein | 21-27, 32-37, 43-51, 67-74, 82-92, 94-100, 106-112, 140-149, 153-159, 164-182, 193-215, 222-227, 260-267, 308-322, 330-340, 378-387, 396-403, 417-432, 435-441, 448-465, 476-482, 488-498, 500-510 | B: 4 | 214-280 | 75% SA0779 28% SA2036 | n.d. | 12, 43 |
| ORF01163 (38% ORF02440) | lipoprotein YaeC, putative | 4-21, 29-52, 80-87, 104-123, 126-133, 141-157, 182-189, 194-202, 214-220, 227-235, 242-252 | A: 3, B: 8 | 33-108 | 79% SA0884 35% SA0506 | 31/36 | 13, 44 |
| ORF01182 | UDP-sugar hydrolase, putative | 12-18, 20-27, 29-59, 64-72, 84-90, 96-103, 109-121, 125-155, 164-177, 179-186, 188-201, 216-227, 235-253, 259-274, 276-294, 296-310, 322-339, 341-348, 369-379, 398-403, 409-421 | A: 3 | 76-96 | 71% SA0926 | n.d. | 14, 45 |
| ORF01515 | hypothetical protein | 4-15, 24-41, 71-80, 104-111, 113-119, 123-130, 139-149, 168-178, 187-200 | A: 17 | 4-45 | none | 5/36 | 15, 46 |
| ORF01596 | conserved hypothetical protein | 13-19, 32-37, 44-56 | A: 3 | 1-14 | 60% SA1972 | n.d. | 16, 47 |
| ORF01755 | Mrp protein | 6-11, 16-35, 75-81, 95-100, 126-139, 206-214, 225-233, 241-259, 268-276, 319-325, 339-360, 371-401, 435-441, 452-459, 462-472, 491-503, 505-516, 549-556, 567-580, 590-595, 612-622, 624-630, 642-648, 656-662, 687-693, 698-704, 706-712, 736-750, 768-777, 784-789, 812-818, 847-858, 894-900, 922-931, 938-949, 967-984, 986-992, 1027-1032, 1041-1054, 1082-1088, 1091-1097, 1119-1124, 1234-1240, 1250-1258, 1274-1289, 1299-1305, 1392-1398, 1400-1405, 1429-1442, 1460-1474, 1505-1514, 1531-1537, 1540-1552, 1558-1571, 1582-1587, 1616-1623, 1659-1666, 1671-1677, 1680-1686, 1698-1704, 1706-1712, 1768-1774, 1783-1797, 1814-1819, 1849-1855, 1870-1876, 1890-1897, 1947-1953, 1972-1980, 1999-2013, 2044-2051, 2068-2084, 2093-2099, 2122-2131, 2142-2147, 2156-2163, 2170-2179, 2214-2220, 2235-2245, 2271-2281, 2287-2293, 2308-2317, 2352-2362, 2373-2378, 2387-2407, 2442-2448, 2458-2474, 2507-2516, 2531-2537, 2540-2551, 2555-2561, 2586-2599, 2617-2627, 2644-2649, 2661-2675, 2685-2692, 2695-2707, 2733-2739, 2741-2747, 2774-2783, 2788-2795, 2860-2870, 2891-2903, 2938-2947, 2973-2980, 2993-2999, 3004-3030, 3046-3059, 3066-3077, 3082-3088, 3120-3132, 3144-3149, 3153-3169, 3200-3212, 3232-3256, 3276-3290, 3308-3322, 3330-3338, 3353-3360, 3363-3371, 3390-3408, | A: 2, B: 8 | 213-276; 579-621; 1516-1559 | 31% SA1806 28% SA2150 | n.d. | 17, 48 |

TABLE 1-continued

Immunogenic proteins identified by bacterial surface display.

| S. epidermidis or aureus antigenic protein | Putative function (by homology) | predicted immunogenic aa* | No. of selected clones per ORF and screen | Location of identified immunogenic region (aa) | Homology with S. aureus | Gene distribution§ | Seq. ID (DNA, Prot.) |
|---|---|---|---|---|---|---|---|
| ORF02009 (32% ORF01373 & ORF01042) | 2-oxo acid dehydrogenase, E2 component, lipoamide | 3431-3447, 3454-3484, 3503-3515, 3524-3541, 3543-3550, 3560-3567, 3586-3599, 3616-3621, 3642-3647, 3663-3679 19-41, 43-49, 55-62, 67-74, 114-121, 130-140, 188-197, 208-217, 226-232, 265-287, 292-299, 301-319, 372-394, 400-410, 421-427 | B: 4 | 12-56 | 64% SA1560 32% SA1104 31% SA1448 | n.d. | 18, 49 |
| ORF02025 (35% ORF00861) | integrase/ recombinase XerD (xerD) | 6-12, 44-51, 53-60, 67-88, 91-100, 104-123, 137-142, 148-158, 161-168, 175-201, 204-210, 222-231, 239-253, 258-264, 272-282 | B: 3 | 60-138 | 85% SA1540 35% SA1269 | n.d. | 19, 50 |
| ORF02209 (37% ORF01212) | NADH dehydrogenase, putative | 4-63, 69-104, 110-121, 124-131, 134-152, 161-187, 204-221, 223-237, 239-296, 298-310, 331-365, 380-405, 423-451, 470-552, 554-562, 574-581, 592-649, 651-658, 661-671, 673-707, 713-734, 741-748, 758-765, 773-790 | A: 2 | 509-528 | 66% SA0679 38% SA0955 | n.d. | 20, 51 |
| ORF02289 | fibrinogen- binding protein SdrG | 89-94, 102-115, 123-129, 181-188, 200-206, 211-235, 239-249, 267-281, 295-310, 316-321, 331-341, 344-359, 365-386, 409-422, 443-453, 495-506, 514-521, 539-547, 553-560, 563-570, 586-596, 621-626, 633-638, 651-657, 666-683, 697-705, 731-739, 761-768, 865-883 | B: 2 | 213-265 | 41% SA0610 32% SA0608 30% SA0609 | n.d. | 21, 52 |
| ORF02329 | glutamyl-tRNA synthetase (gltX) | 5-20, 24-34, 37-43, 92-102, 134-139, 156-162, 184-191, 193-205, 207-213, 225-231, 241-247, 259-267, 269-286, 337-350, 365-372, 378-386, 399-413, 415-421, 447-457, 467-481 | A: 7 | 145-183 | 82% SA0574 | n.d. | 22, 53 |
| ORF02393 | dimethyl- adenosine transferase (ksgA) | 12-19, 29-41, 43-57, 80-98, 106-141, 143-156, 172-183, 185-210, 214-220, 226-234, 278-287 | A: 3, B: 2 | 237-287 | 85% SA0536 | n.d. | 23, 54 |
| ORF02412 (100% ORF02349 & ORF01658 & ORF00589 & ORF00701 | conserved hypothetical protein | 5-12, 32-48, 50-72, 75-81, 88-94 | A: 1, B: 1 | 16-40 | none | n.d. | 24, 55 |
| ORF02680 (74% ORF02594) | Metallo-beta- lactamase superfamily domain protein | 4-21, 29-42, 48-62, 65-80, 95-101, 103-118, 122-130, 134-140, 143-152, 155-165, 182-192, 198-208, 232-247, 260-268, 318-348, 364-369, 380-391, 403-411, 413-424 | A: 22 | 208-230 | 98% SA0046 73% SA0064 | 20/36 | 25, 56 |
| ORF02700 | hypothetical protein (lipoprotein) | 4-18, 65-75, 82-92, 123-140, 144-159, 166-172, 188-194 | A: 1 | 174-195 | none | 2/36 | 26, 57 |
| ORF02825 (83% ORF00132, 67% ORF02706, 51% ORF00369) | malate:quinone oxidoreductase | 7-20, 58-71, 94-101, 110-119, 199-209, 231-242, 247-254, 267-277, 282-290, 297-306, 313-319, 333-342, 344-369, 390-402, 414-431, 436-448, 462-471 | B: 2 | 310-350 | 83% SA2623 49% SA2362 | n.d. | 27, 58 |
| ORF02853 | hypothetical protein | 4-25, 37-44, 53-59, 72-78, 86-99, 119-128, 197-203, 209-218, 220-226, 233-244, 246-254, 264-271, 277-289, 407-430, 437-445, 464-472, 482-488, 503-509 | A: 1 | 308-331 | 61% SA0129 | n.d. | 28, 59 |
| CRF0299 | Hypothetical protein | 4-12, 14-43, 52-58 | A: 3, B: 4 | 43-58 | none | n.d. | 29, 60 |
| CRF1769 | Hypothetical protein | 4-14, 21-29, 35-49 | A: 6 | 38-50 | none | n.d. | 30, 61 |
| SA1169 | fibrinogen- binding protein precursor- related protein | 4-19, 31-37, 58-72, 94-108 | C: 2 | 1-72 | none | n.d. | 31, 62 |

The invention claimed is:

1. An isolated hyperimmune serum-reactive antigen consisting of a fragment of SEQ ID NO: 56, wherein said fragment comprises an amino acid sequence selected from the group consisting of amino acids 4-21, 29-42, 48-62, 65-80, 95-101, 103-118, 122-130, 134-140, 143-152, 155-165, 182-192, 198-208, 232-247, 260-268, 318-348, 364-369, 380-391, 403-411 and 413-424 of SEQ ID NO: 56, and wherein said fragment is less than 442 amino acids in length.

2. An immunogenic composition comprising the isolated hyperimmune serum-reactive antigen of claim 1.

3. The immunogenic composition of claim 2, comprising at least 2 different hyperimmune serum-reactive antigens.

4. The immunogenic composition of claim 2, further comprising an adjuvant.

5. The immunogenic composition of claim 3, further comprising an adjuvant.

6. A fusion protein comprising the hyperimmune serum-reactive antigen according to claim 1.

7. An immunogenic composition comprising the fusion protein of claim 6.

8. The immunogenic composition of claim 7, further comprising an adjuvant.

9. A method of inducing an immune response in a subject comprising:
   administering the immunogenic composition of claim 2 to a subject;
   wherein an immune response is induced in the subject.

10. The method of claim 9, wherein the subject is a human.

11. The method of claim 9, wherein the subject has an *S. epidermidis* infection.

12. A method of inducing an immune response in a subject comprising:
   administering the immunogenic composition of claim 7 to a subject;
   wherein an immune response is induced in the subject.

13. The method of claim 12, wherein the subject is a human.

14. The method of claim 12, wherein the subject has an *S. epidermidis* infection.

* * * * *

SEQUENCE LISTING

<160> NUMBER OF SEQ ID NOS: 64

<210> SEQ ID NO 1
<211> LENGTH: 2028
<212> TYPE: DNA
<213> ORGANISM: Staphylococcus epidermidis

<400> SEQUENCE: 1

| | | | | | |
|---|---|---|---|---|---|
| atgaagagaa | cagataaaat | tggtgtctac | ctcaagctgt | catgttctgc | gttgttactt | 60 |
| agtggttcgc | tggttggtta | tggcttcaca | aaagatgctt | ttgcagattc | agaaagtaca | 120 |
| tcatcaaatg | ttgaaaatac | ttctaatagt | aactccatcg | ctgacaaaat | ccaacaagct | 180 |
| aaagatgata | ttaaagattt | gaaagaactt | tctgacgcag | atatcaaaag | ttttgaagaa | 240 |
| cgtttagata | aagtcgataa | tcaatcaagt | attgaccgta | ttataaatga | tgcaaaagat | 300 |
| aaaaataatc | atttaaaatc | gacagactct | agtgccacat | catcaaaaac | tgaagatgac | 360 |
| gatacatctg | aaaaagataa | tgatgatatg | actaaagact | tagataaaat | actgtcggat | 420 |
| ttagattcaa | ttgctaaaaa | tgttgataac | cgtcaacaag | gtgaagagag | agcttctaaa | 480 |
| cctagtgact | caacaaccga | tgaaaaagat | gattcaaata | taaagtaca | cgatacaaat | 540 |
| gctagtacac | gtaatgcaac | tactgatgat | tctgaagagt | cggttattga | taaattagat | 600 |
| aaaatccaac | aagattttaa | atctgactct | aataataatc | cttctgaaca | aagcgatcag | 660 |
| caagcatcac | catctaataa | aaccgaaaat | aacaaagaag | aatctagtac | gacaacaaat | 720 |
| caatccgata | gtgatagtaa | agacgataaa | agtaatgatg | gtcatcgctc | aacattagaa | 780 |
| cgtatagcat | cagatactga | tcaaattagg | gattcaaaag | atcaacatgt | cacagatgaa | 840 |
| aaacaagata | tacaagcaat | tacacgttca | ttacaaggta | gtgataagat | tgaaaaagca | 900 |
| cttgctaagg | tacaatctga | caatcaatca | ctagattcta | attatataaa | taataaatta | 960 |
| atgaatttaa | gatcactaga | tacaaaagta | gaggataata | acactttatc | tgatgataag | 1020 |
| aaacaagcgc | ttaaacaaga | aattgataag | actaagcaaa | gtattgaccg | acaaagaaat | 1080 |
| attattatag | atcaactcaa | tggtgctagt | aataaaaaac | aagcaaccga | agatatctta | 1140 |
| aatagtgttt | ttagcaaaaa | tgaagtagaa | gacataatga | aacgtattaa | aacaaatggc | 1200 |
| cgaagtaatg | aagatatcgc | taatcaaatt | gccaagcaaa | ttgatggtct | tgcattaact | 1260 |
| tctagtgatg | atatttttaaa | atcaatgtta | gatcaatcta | aagataaaga | aagtttaatt | 1320 |
| aaacaattgt | tgacgacacg | acttggtaat | gatgaagcag | atcgtattgc | taaaaaattg | 1380 |
| ttaagccaaa | acttgtcgaa | ttctcaaatt | gtagaacaat | taaaacgtca | tttcaatagt | 1440 |
| caaggaacag | ctacagctga | tgatatattg | aatggtgtga | ttaatgatgc | taaagacaaa | 1500 |
| agacaagcga | ttgaaacaat | attacaaacc | cgtatcaata | aagacaaagc | taaaattatc | 1560 |
| gctgatgtta | ttgcgcgtgt | acaaaaggac | aaatcagata | tcatggatct | cattcactct | 1620 |
| gcgattgaag | gcaaggcaaa | tgatttatta | gatatagaaa | acgagcaaa | acaagctaag | 1680 |
| aaagatttag | aatatatttt | agatcctata | aagaatagac | catccttgtt | agatcgtatt | 1740 |
| aacaaaggtg | tcggtgattc | taattcaata | tttgatagac | caagtttact | tgataaactt | 1800 |
| cactcaagag | gatctattct | tgataaatta | gatcattcgg | caccggagaa | tggattatct | 1860 |
| ttagataata | aaggtggcct | tttaagtgat | ctatttgacg | acgatggtaa | tatctcatta | 1920 |
| ccagcgacag | gtgaagtcat | caaacaacat | tggataccag | tggctgttgt | actcatgtca | 1980 |
| ttaggtgggg | cgctcatctt | tatggcgcgt | agaaaaaaac | accaaaat | | 2028 |

<210> SEQ ID NO 2
<211> LENGTH: 1965
<212> TYPE: DNA
<213> ORGANISM: Staphylococcus epidermidis

<400> SEQUENCE: 2

```
atgaagaaaa ataaattttt agtatattta ctatcgacgg cgcttatcac gccaaccttc      60
gctacacaaa cagcttttgc tgaagattca tctaataaaa atacaaattc agataaaatg     120
gaacaacatc aatcacaaaa agaaacatca aaacaatctg aaaagatga atttaacaac     180
gatgattcta acacgattc tgatgataaa aaaagcactt ctgacagcaa ggacaaagac     240
tctaataaac cattatcagc tgattcaaca catcgtaact ataaaatgaa agatgataat     300
ttagttgatc aactttatga taattttaag tctcagtcag tagatttttc taaatactgg     360
gaaccgaata atacgaaga cagttttagt ttaacgtcac tcatccaaaa tttatttgat     420
tttgattctg atataacaga ttacgaacag ccacaaaaga caagccattc ttctaatgac     480
gaaaaagatc aagtagacca agcagatcag gcaaacaac catcacaaca tcaagaacca     540
tcacagtcgt ctgctaaaca agatcaagaa ccatcaaacg atgaaaaaga aaagacaact     600
aaccaccaag ccgattctga cgtcagtgat ttacttggag aaatggataa agaagatcaa     660
gaaggcgaaa acgtagatac aaacaaaaat caatcttctt ctgagcaaca acaaactcaa     720
gcgaatgatg atagctcaga acgtaacaaa aaatattcta gtattacaga ttcagcatta     780
gactctatat tagatgaata tagtcaggac gctaagaaaa cagaaaaaga ttacaataag     840
agcaagaata caagtcacac taaaacatct caaagtgata tgccgacaa aaatccacaa     900
ttaccaacag atgatgaatt aaaacatcaa tcaaaacctg cacaatcatt tgaggatgac     960
attaaacgct caaatacacg ttcaacaagt cttttccaac aactacctga attagacaat    1020
ggtgacttat cttctgattc atttaatgtt gttgacagtc aagacacacg tgatttcatt    1080
caatcaattg ctaaagatgc gcatcagatt ggaaaagacc aagatatata tgcatcagtt    1140
atgattgctc aagctatttt agaatctgac tctggaaaaa gttcacttgc acaatcacca    1200
aatcataact tgtttggaat caaggtgac tacaaaggac aatctgtaac ttttaatact    1260
ttagaagctg atagcagtaa tcatatgttt agtatccaag caggtttccg taaatacca    1320
agtactaaac aatctcttga agattatgca gatttaatca acatggtat cgatggtaat    1380
ccgtcaattt ataaaccaac ttggaagagt gaagctctat catataaaga tgctacttca    1440
catctgtcac gctcatacgc cacagatcct aattattcta aaaaattaaa tagtattatt    1500
aaacattatc atttaacatc ttttgacaaa gaaaaaatgc ctaacatgaa gaaatataat    1560
aaatcaatag gtacggatgt gtctggtaat gacttcaaac catttactga aacttccggt    1620
acatcacctt acccacatgg ccaatgtact tggtatgtgt accaccgtat gaatcaattt    1680
gatgcatcca tttctggtga cttaggtgat gctcataatt ggaataaccg tgctgaaagt    1740
gaaggctata cggtaacgca cacacctaaa aatcatactg cagttgtgtt tgaagctggg    1800
caattaggtg ctgatacaca gtatggtcat gttgccttcg ttgaaaaagt taatgacgac    1860
ggttcaattg ttatttctga atcaaatgtt aaaggattag gtgtcatttc attcagaact    1920
attgatgcag gagatgctca agatttagat tacattaaag gtaaa                    1965
```

<210> SEQ ID NO 3
<211> LENGTH: 492
<212> TYPE: DNA
<213> ORGANISM: Staphylococcus epidermidis

```
<400> SEQUENCE: 3
atgattagat ttgcacgact agaagatctt caagatattt tgacaattta taatgatgcc      60
atccttaata caacagctgt ttatacgtat aagccacaac aattagatga acgtcttcaa     120
tggtatcaat ctaaagcaaa aataaacgaa cctatatggg tttatgaaaa agaagggaaa     180
gtagttggtt ttgccactta tggttccttt agacaatggc cggcctattt atatactatt     240
gaacattcta tatatgttca tcaacagtac agaggactag gtatcgcttc tcaattatta     300
gagaatttaa ttcgttacgc taaagaacaa ggttatcgca ccattgttgc tgggattgat     360
gcatcgaaca tggatagtat cgcattgcat aagaagtttg acttctcaca tgcaggtaca     420
attaaaaatg taggttataa atttgatcga tggctcgatt tatcatttta tcaatatgat     480
ttatctgatt ca                                                         492

<210> SEQ ID NO 4
<211> LENGTH: 2856
<212> TYPE: DNA
<213> ORGANISM: Staphylococcus epidermidis

<400> SEQUENCE: 4
ttgagtaatt tgatacaaga tattaagcaa tctttatata agggatttat agataaagat      60
agttcccata aaggcaattt tgttccaaga ttactagtaa ataacaaaga agaaaatgta     120 cttctctacta ttatagatca gctgcataat tgccaatcat tttgtatttc ggttgcattt     180
ataaccgaga gtggtttagc aagtctaaaa tcacattttt atgatttaag taagaaaggc     240
gtaaaaggaa ggataataac atcaaattac ttaggtttta atagtccgaa atgtttgag      300 gaattattga aattagagaa tgtagaggtt aaattaacaa acattgaggg gttccatgct     360 aagggtaca tatttgaaca tcataaccac acttcttta ttatagggag ttcgaattta       420
acttctaatg cattgaaatt gaattatgaa cataatttat ttttatctac tcataaaaat    480
ggagatcttg ttaacaatat taaatataaa tttgatgaac tttgggattc tagcttttct    540
ttaactaatg aatggataaa tgaatataaa cagtcttttg aatatcaaac attgcaaaaa    600
gtatttgata acactgttgt tcaaaattca gatattaaaa agtttaatga atcaaaactt    660
ataaaaccca atttaatgca agaacacgca ttaaagtcat tagagtcttt gagaaatgtg    720
ggagaagaaa aggggttaat tatatctgcg acagggactg gaaaaactat tttatgcgca    780
cttgatgtaa gagcttattc tccagataaa tttctattta ttgttcataa tgaaggtata    840
ttaaatagag ctagagaaga atttaagaaa gtatttccat atgaggatga agtaatttt    900 ggattattaa caggaaaacg aaaggatcat gatgctaaat tccttttgc aacaattcaa      960 acactttcta aaaggaaaa ttataaattg tttaactcta atcatttga ctacatcgtt      1020 tttgacgagg ctcatcgaat tgctgcatct agttatcaga aaatatttaa ttattttaaa    1080
cctaactttt tgctaggaat gactgcaaca ccagaaagaa ctgatgaatt aaatattttt    1140
gaattgttta attataatat tgcttatgaa attcgtttac aagaggcttt agagagtaat    1200
attttatgtc cttttcatta ttttggagtt acagattata ttcaaaatga aatgagtcaa    1260
gaagatgcat ttaatctaaa atatttagca tctaatgaac gtgttgaaca catcataaaa    1320
aagactaatt attatggtta ttcaggtgac gttttaaagg gtttaatatt tgttagtagt    1380 agggggtgagg cgtatcaatt agcaaaccaa ttaagtaaac gtggtatatc atcggttggt    1440
ttgacaggaa aagattctat agcttataga gctgaaacaa ttcaacaact aaaagaagga    1500
tctattaatt atataattac tgtagatttg tttaacgaag gaattgatat tcctgaaata    1560
```

| | |
|---|---|
| aatcaagttg taatgttaag acctactaaa tcaagtatta tatttattca acagcttggt | 1620 |
| agaggattaa gaaaaagtac taataaagaa tttgttactg ttattgattt tatcggtaat | 1680 |
| tataaaacta actatatgat cccaatagcc ttatctggaa ataaatctca aaataaggat | 1740 |
| aattacagaa aattcttaac agatactacg gttttaaacg gtgtttcaac aataaattt | 1800 |
| gaagaagtag ctaaaaataa aatttataat tcactagatt ctgttaaatt aaatcaacca | 1860 |
| aaattaatta aagaagcttt taacaatgta aaagaccgta taggtaaatt acctttactt | 1920 |
| atggacttta taaataacga ttcgattgat ccaagtgtga ttttctcacg ttttaaaaat | 1980 |
| tattatgagt ttttaataaa aaataaaatt attgagaatg aattaagtat taatgaattt | 2040 |
| aaaaatttaa cattttatc aagacaatta acacctggac ttaaaaaagt agatattgat | 2100 |
| gtattgaaag aaattataca aatgacgta acttatgaaa atttaacaaa aaaaatgtta | 2160 |
| aacattaata acgatatttc ggaatatgat attaacactt cattaagcat tttagatttt | 2220 |
| acttttttca aaaagactat aggtaaaact tacggattac ctttaataca atataaggat | 2280 |
| aatcttattt gtctagcaaa tgaatttaaa gaggctttaa ataaaccact atttaacaca | 2340 |
| tttattcatg atttaattga tcttgctaat tataataatg acagatatca aaataagaaa | 2400 |
| aacagtttaa ttctatataa caaatattct agggaagatt ttgttaagtt attaaactgg | 2460 |
| gataaagatg aatctggaac aatcaatggt tatcgtatga acatcgtac acttcctta | 2520 |
| tttatcactt atgataaaca tgagaatatc agtgataata ctaagtacga cgatgaattt | 2580 |
| ttgagccaag acgaattgaa atggtacacg cggtccaatc gtaaattaac ttcaccagaa | 2640 |
| gtacaaaata ttttaaagca tgaagaaagt aatacagata tgtatatatt tgtgaaaaaa | 2700 |
| agagatgatg aagggaaata tttctactat ttaggtaaag ccaaatatat taaggaact | 2760 |
| gagaagcaag attatatgcc taatggaaat agcgtggtaa ctatgcatct atcaatgaat | 2820 |
| acgtccattc gagatgatat ttatagatac atcact | 2856 |

<210> SEQ ID NO 5
<211> LENGTH: 975
<212> TYPE: DNA
<213> ORGANISM: Staphylococcus epidermidis

<400> SEQUENCE: 5

| | |
|---|---|
| atgacaaaat cacaacaaaa agtgtcatca attgagaaat taagtaatca agaaggtatt | 60 |
| atttcagctt tagcatttga tcaacgtggt gcattaaaaa gaatgatggc agaacatcaa | 120 |
| tctgaaacac caacagttga acaaatagaa caattaaaag tacttgtttc tgaagaatta | 180 |
| actcaatatg cgtcttcaat tttattagat ccagaatatg gtttaccagc atcagatgct | 240 |
| cgaaataatg actgcggact attacttgca tacgaaaaaa ctggatatga tgtgaatgcg | 300 |
| aaaggtcgtt tgccagattg cttggtagaa tggtctgcga acgtttgaa agagcaaggg | 360 |
| gccaatgcag ttaaatttt actttattat gatgtagatg acacagaaga aattaacata | 420 |
| caaaagaaag catatattga acgaattggt tcagaatgtg ttgccgaaga tattcctttc | 480 |
| ttcttggaag ttttaacata tgacgacaat attcctgaca taaaagtgc agaattcgct | 540 |
| aaagttaagc cacgtaaagt taatgaagca atgaagttat tctctgaaga tcgtttttaat | 600 |
| gtggatgtac ttaaagttga agtacctgtg aaatatgaatt ttgtggaagg attttcagaa | 660 |
| ggagaagttg tttatactaa agaagaagct gcacaacatt tccgtgatca agatgcagct | 720 |
| actcacttac catatatttta tttaagtgca ggtgtatcag cagaattgtt ccaagataca | 780 |
| ttaaaatttg cgcatgattc tggtgcgcaa ttcaatggtt tttatgtgg acgtgccaca | 840 |

| | |
|---|---:|
| tggtcaggag cagttaaggt atacattgaa gaaggagagc aagctgccag agaatggttg | 900 |
| cgtacggtag gatttaagaa tattgatgat ttgaatacag tattgaaaac aacagctaca | 960 |
| tcatggaaaa acaaa | 975 |

<210> SEQ ID NO 6
<211> LENGTH: 1146
<212> TYPE: DNA
<213> ORGANISM: Staphylococcus epidermidis

<400> SEQUENCE: 6

| | |
|---|---:|
| ttgatgaaaa aagttatgac catatttgga actaggcctg aagctataaa aatggctccg | 60 |
| ttgattaaaa cgttagagaa agattctgac ctggaacccg ttgttgtagt caccgcccaa | 120 |
| catagagaga tgcttgattc agtgttgaat acttttaaca taagtgcaga ttatgatttg | 180 |
| aatattatga agctggtca aacattgtct gaagtaacat ctgaagcaat gaaaaagtta | 240 |
| gaagatatca tacaaaagga agtgcctgat atggtacttg ttcatggtga tacagtgaca | 300 |
| acctttctg gagcattagc cgcatttat agtcaaacac ctataggaca tgttgaagct | 360 |
| ggattaagga gttataataa atattcaccct tatcctgaag aaataaatag acaaatggtt | 420 |
| ggggtaatgg cagatttgca cttttgcccca acctataatg ctgcacagaa tttagtaaaa | 480 |
| gagggtaaat tagccaaaca tatagctatc actggtaata cagctattga cgcaatgaat | 540 |
| tatacaatcg atcaccaata ttcatcatct atcatacaaa aacataaaaa taaaaacttt | 600 |
| atttttactca cagcacatag acgtgaaaat ataggtaaac ctatgataaa cgtgtttaaa | 660 |
| gcgattagaa agttgattga tgaatatcag gatttagcgt tggtctatcc tatgcatatg | 720 |
| aatcccaaag taagagatat tgcgcaaaaa tatttaggaa atcatcctag gattgaattg | 780 |
| atagaaccac ttgatgtggt tgattttcat aattttgcta acaagcata tctcattatg | 840 |
| actgactctg gtggaataca agaggaggca ccatcattac acaaaccagt tttagtattg | 900 |
| agagatagta ctgaaagacc ggagggagta gatgctggaa cttttgagagt cattggtacg | 960 |
| aatgaagaag atgtctataa tgaaactaaa aaattaatag aaaacccaga cctttatcaa | 1020 |
| aaaatgagtc aagctgttaa tccatatggc gatggacaag ctagtgagag aattgtgcaa | 1080 |
| catataaaat attattttaa tttgacaaat gacagaccca atcatttga atttacaaaa | 1140 |
| gattta | 1146 |

<210> SEQ ID NO 7
<211> LENGTH: 8271
<212> TYPE: DNA
<213> ORGANISM: Staphylococcus epidermidis

<400> SEQUENCE: 7

| | |
|---|---:|
| gtggcaagtg attttaatat aggtatatta tctaccttag agatagactc tagctcctca | 60 |
| agaaagaaga ttaacgacac acttaaaaat attgaagcaa atattaatag cattaaagca | 120 |
| gacttagaag tttcagatac aaagaaatca gaaaataatg ctataaaaag tgcaaacaac | 180 |
| gtaatcagaa acatcaattc aaacggtaat ttaaagaaat taaatgttga actagatgta | 240 |
| aacttaacaa aaagtagaca aaacattcaa agagcattat ctactctatc aaaagatttt | 300 |
| aagaataaga aaattgatgt tgaagttaat gctaaagcta ataaaaattc aatcggacaa | 360 |
| gttaagaatt ctatttctaa aggtgcaagt cagccactag aaattaaaga gtcccctagt | 420 |
| agtgaaagca ctagtagaga tattaaagaa cagcagtctt taatgacagg tttagcaaat | 480 |
| tcttataaga acttagatga tttaacaaga gctttaaata caagtacatt tgaagggctt | 540 |

```
agaaaaactg taaagaaat  taagaacgca gataattctc ttaaaagtta tcaagttact    600
ttagaacgtg ttaccaaga  aggtaaaaaa ttaggctctc aaagatttga ttatacccct    660
tctgcaaatg gtttgaagtt aaacaaaact caattaactg atcaaacaga taaagctcgt    720
aaagaagaaa atgctgctat taataaaatta ttagaaaatg aagtttctaa gtatgatcgt   780
ttattgaata aggtaaaat  tgatattaaa caacatcaaa ctttacttca aactcttaga    840
caaattacta atgagaaatc aaaagctaac caatttaata gaactgattt caatagagta    900
gcaaaagctg ctgctgatga agcaaaagaa tatcaatatc aaaatgatat gcttcgaaag    960
aaattagctt taacttctca aattgagcgt attgaaaaca gaatggctgc tacaattgat   1020
aagcaacaaa caaatgcttt gaaaaatcaa ttgaattctt taggtaataa tagaacacca   1080
ttcggtaaag aagcagcttt ccatatgaac caaattcaag acaaggttcg tcaaatctct   1140
gctgaagctg aaagagcaac tagaactcag ttaagttttg ttgatcaatt cagagaagca   1200
atgacaaaat tcccagtttg gatgggtgct actaccctat tcttcggtgc cataaatggt   1260
gctaaagaaa tgcttgatgt aattactgaa attgatggaa aaatgattac tcttgcaaaa   1320
gttactggtg atgacaatgc acttcaacaa acatttattg acgcaaataa tgctgcttct   1380
caattcggac agacattagg aagcgtatta gatgtatatg cagaattcgc tagacaaggt   1440
gttaaaggta atgagttatc tcaattctca aatgcagcat taattgctgc taacgttggt   1500
gagattgacg ctaaacaagc ttctgaatat ttaacttcta tgtctgctca gtgggaaacg   1560
actggaaacc aagctatgag acaagttgac tcactcaacg aagtttccaa taaatatgct   1620
acaactgttg aaaagttagc acaaggtcaa gcaaaagctg gctctactgc taaatcaatg   1680
ggacttactt ttgatgaaac taatggtatt attggtgcat taacagctaa gactaagcaa   1740
tctggggacg aaattggtaa ctttatgaaa gccactttac ctaaacttta tagtggtaaa   1800
ggtaaatcaa ctattgaagg cttaggcatt agtatgaaag atgaaaatgg acaattaaaa   1860
tctgccattt ctcttttaga agaagtttct cagaaaacta aaaacttaga aaaagaccaa   1920
aaagccgctg ttataaatgg cttgggtgga acataccact accaacgtat gcaagtatta   1980
ttagatgatt tatctaaaac agatggctta tataaacaaa ttaaagaaag ttccgaaagt   2040
tcagctggct ctgcattaca agagaatgca aaatacatgg agtcaattga agctaaagtt   2100
aaccaagcaa aaacagcatt cgaacaattc gcattagctg ttggtgaaac atttgctaaa   2160
tcaggaatgc ttgatggtat cagaatggtt actcaacttt taactggttt aactcatgga   2220
attactgaat taggcacaac tgctccgatt ttcggcatgg ttggtggtgc tgcctcatta   2280
atgagtaaga atgttagaag tggttttgaa ggtgctagaa gtagtgttgc taattatatt   2340
actgaggtaa ataaattagc taaagttaac aatgctgctg gtcaagttgt ggacttcaa    2400 aaagttcaaa ctggtacagc ttcacaactt cagtttaata aaaatggtga atatgataaa   2460
gctgcttcac aagcaaaggc tgctgaacaa gcaacttacc aattctctaa agctcaaaaa   2520
gatgtatcag ctagtgctat gatcgcttca ggtgcaatca acaaaacaac tgtggctacc   2580
acagcaagca ctgttgccac tcgtgctgct acacttgcag ttaatggttt aaaattagcc   2640
tttagaggct tgttggctgc tactggtgtc gggttagcaa taactggtgt ttctttttgta   2700 ctggaaaaag ttgtaggtag ttttaatgct gcaagtcaag ctgctgaaca atataaacaa   2760
aaacaagagc aaacgaagca agcaatagct tctatgagta atggtgaaat taattcactt   2820
attagtagtt acgataaact acaacaaaaa atgaattctg gtagtgcatt taatacagcg   2880
gaagctgaga atataaaga  agtaacaagt caattagcta atatattccc cgatttagtt   2940
```

```
actggtgaaa accgttatgg taaggaaatg gccggtaata agaagtaat gaaacagaaa      3000 attgagttaa tcaagcaaga aatggagctt gaaagacaaa agaatgctat caaacaaaaa      3060
gaagagcaag acgcttacat caaagaacaa gatagcttag ctaagaaaaa cagaggtcaa      3120
aaatggtatc aacttggtca aacaccagag ttgaaacttc aggaacaagc acgtcctact      3180
actgtttctg ataatagtaa cattaacaaa attaatgcca ctatccaaaa agtgaagagt      3240
caagcccaag ctgaaaaagc attagaacaa gttgataagc aacttgctca atctcaaact      3300
aagaatagac aaaatgaagt tcagcactta caaaaagtta gacaagcttt acaagattat      3360
attactaaaa ctggtcaagc aaatcaggca acaagagctg cggtattaac tgcacagcaa      3420
caattcacta accagatagc aacaatgaaa aagcttggta ctactggtca acaagtgatg      3480
actactattt ctaactcagt tgcgaaaaca gcaaagtctg gtaaagctgc tcaagcaacc      3540
ttcaagtcgt ttgaaacctc attagttaaa agctcttcat tcaaaagcaa gatggctagt      3600
tatgaagctt ctgttaagaa atttaaaaat gctgctaacc aatctgctaa aattgctgct      3660
cttaaagacg tagaacgtga ttactctaaa gttgctaaag gtattatgca agcggcaaaa      3720
gcggcaaaca tgagtaaatc tcaaatgaaa gatttgaaaa aatctcttca acaaaatata      3780
caagcagaaa caggctttag agcttcagta agtaaagctg gtaaagttac tattgatcaa      3840
tctaagaaaa tcaaacagaa tactgctgaa acaagacgta actcaagtgc taaattacaa      3900
aatgctgacg cttcagacca agcttctgaa gaaaataaag agttagcaga ctcaatgcgt      3960
gctggtattg aaagttctca attacttgga aaagcgatgg gagaattaca atctcaagga      4020
acacttagta cagaaacttt aattgaatta actgagaagt atggagacga aattttagct      4080
gttgctggag atcaggaagc tttaagtaac ttcatcatgc aaaagcaaaa tgaagaaact      4140
gataactaca acaaaaacct taaaactaaa ttagaaaact cttcatcata ctataaggcg      4200
gtagctggag ctgactctgc cctatccaac tacttaatgg aaaactatgg tattgatact      4260
aaaaactata agagtttaac agaagtcaaa gctaaaatta cagacctttta ctacaatggt      4320 tcagctgaag aacaagctaa agtagtagac gctatcgcaa aagcttacca tattgactta      4380
tctaactatg gctctctgaa tgagaaaaaa gaagcattag agaaccaatt gatgaaaatc      4440
ttaggtagta agtggaaaaa atatattggt agcgtagcta aggatatgaa atctcttggt      4500
gttgacgctg tgaagttgg agcagatggt tttgatgaca gtaaaatgtt caatccgggt      4560
gctcttatcg gtgctaacaa tttccaaaac gtttctaacc taagtaatat cagtaatgta      4620
ttcaactcac ttaatggtgc atttaatgaa gctaagaatg aagctgctgg tgttagtaga      4680
ggcttagatg acgctgctag tggcttaaaa gatgttggtg acagtgctgg ctcagctggt      4740
agtggtttag gtaaaactgc taaaggcgcg gataaagcgt ctgacagttt agatggtact      4800
aataaagaat tagaaaaaac taaagaaaaa gctgaagaag ctggtgtcac agttaaacaa      4860
ctttataagc aatttacagt tactacttat gttgctgata aactaagtat ggctttagat      4920
aaaattaata ataagttaga gaaacaaaaa cttttaactg aaaaatacgc aacttggtca      4980
agcagttatc gtaactcact taaagcagaa aataaattgc tcgatgaaaa gaccgctaag      5040
attaaaaaac aaatcgagtc aatgaaagaa caaatcgctc aaggtaaagt tattgagtat      5100
ggtttagttg gtaaagatat taatgttcct tactatgaat atactgcaaa taatttagat      5160
gatggagaaa ctggtcgtat ttctcgatat accggtaatt caactcaagc taaggtttgg      5220
aatttcttta atctaaaagg ttatctgat catgctgttg cgggtatcat gggtaatatg      5280
gaacgtgagt ctagatttaa accgggagct caagaacaag gcggtactgg tattggttta      5340
```

```
gtacaacttt catttgggcg tgcaaataat ttaagaaatt atgctgctag aagaggaaaa   5400
agctggaaag acttaaatac tcaacttgac ttcatttgga aagaattaaa tactactgaa   5460
gttaatgctt tacgaggact taaatcagct acttcagtta ttggtgcagc aaactctttc   5520
caaagattat atgaacgtgc tggtgttgta gcacaaggag aacgtaatgc ggcagctaaa   5580
aagtattaca gacaatttaa aggtactaat ggttcatctg gcttcctaag tggtggcgtg   5640
gtcgctggaa caaatggtaa accacttact tcagatagaa acgcttatat cttagataga   5700
caattcggac gatataatgg tggtggtgtc catcacggaa gagatatcac gagtgctact   5760
attaacggat cacctattaa agctgcacgt tcaggtatag ttacttttaa aggatggact   5820
ggtggtggta atacactatc tatatttgat ggtaaaaata cttatacata catgcatatg   5880
aagaacccgg caagagtggt aaaaggacaa cgagttaaag ctggacaaat tgttggtaac   5940
gttggtacta cgcatgatag aagattaggt ggcttctcta ctggccctca ccttcacgta   6000
caagtaaact taggaaaaac tccttctggt acatttatga acactttcaa tggtgctcat   6060
agagcagtcg atcctgttaa atatggatat actagagttt ctggtggcgg tagtctaaac   6120
ttaggctcgc taacttctgg acattcagcg atgtctggtt ctatcagtgc tgcaatggct   6180
gaagacttaa atgaagctga acaagagcgt ttaaacaaaa ttgaacaagc aattaacgca   6240
cataataaag ctgaagaaat gaagcaaaaa gttgatgagc ttagaaaaac gttaatggat   6300
aaacagcttg aagaagttca aactgctaaa gaaaaaagtg aaaatcttta taacatccaa   6360
aaatctcacg tagaagaata tgatcattgg agaacattac aagaagcacg atctgctaaa   6420
ttagaatacg aattaaacaa aatcgaattc gaaaaaggta gaaatactaa agaatggcgt   6480
aataaaaata aacaacttca agcttctaga caacttgaag ttaatttcga agactcaaaa   6540
atacaatata ttaataaagc attgaagaag aatgcaaata aaatatttgg taaaaataca   6600
gtaaatcgtg atgagtttga acaatgaag cgagacgctc aacaaaatat aagagattta   6660
aaagctggta ttcaaactgc ttctggtgaa attgctactt caatgattga tcaaattctt   6720
gatgaatatg aagaccgtgt aggtaaagtt tcagctaaaa ttgaaaagat gggtaaacaa   6780
aaagaaaaac ttgatttagc cgataataaa caggcttttga aaagttcatc cctaagtaga   6840
caacaagcta aagactctaa gtcactagct agttacatta atttctatat caaacaatta   6900
gaacgccagt taaattaac gggtaaaaac catgaattac aacaaaaagt aaaagaacaa   6960 attaagaaa tgaaagttgc ttatgatgac gctaccctag ccgctcatca atatattact   7020
gaagctgctg aagttgatac agaaagacaa cttcaattaa acgctaatcg tttaagagac   7080
gcacaaaacg agttgtctaa agctgattat aaagctggtt tcatttcaca agaatatcaa   7140
attgacctat accgaaaaaa tcaagaagct aagttcaaag gttacttaaa agaaaaagaa   7200
gcacttgaac aaaataaatc agaacttcaa gacatgtatg agatttataa atctgtccct   7260
actcaagctc aaaaaatcaa agaagctcta attgaaacca aaaatgctat tagagataat   7320
aataaaggtc tctatgattt gaaatatgat atggctaaca gtgttataaa tcaaattaag   7380
gatatctatt caaacaaact agaggttgcc acgaaagcgt atgatgatga atacaaagca   7440
tacgaaaaaa tgatcaacaa aaagcttaaa cttattgatg atgaacaaac tcaagagtca   7500
ttcaataaag atgtccgtga tagaactgaa gcaatggata aaattagaga tgaaattgct   7560
caaagaagtg gtgacgatag tttagctaac caaaagaaac ttaaagattt aagagaacaa   7620
ttaaaacaac aagaagaaga ctatacgatt tcattaaca ataaaaatcg tgatgacaga   7680
agaaaagctt tacaagatga gctaaacgat aaaaacgaac aaatacaaga acaaaaagaa   7740
```

```
gatttaaata aagctttcca agacttaatt ggtgatacac gaagatttaa tgcgatccaa    7800
gagtcactta tggaaggtca aattgataaa tataaatctc taattgctga cttaactaaa    7860
tacgtcaacg ataatatgaa agaaattgga cgttctacta gtgaaggaat attagatggt    7920
cttgctgctt catttaaagg tttgtcttct ttatctaaag aacttcagaa acaagaaaaa    7980
aataatttga acccagtacc taattcaaaa ttaaaaccta ctaaggttga tgaagctaca    8040
atcgctgcca ttaagaaagt taatggttta tccctactac tatacttca aggtttagat     8100 atcaaacctg ttaaccttcc taaagatgta aaaccaagta aaacagttac taacaataat    8160
aaaacgactg ctaaagcatt agttaacatt gaaaacttca acggtacaaa agctgaagca    8220
gataaattag ctaataactt agcaactgcc atgagaaaac aaggcgtatt a             8271
```

<210> SEQ ID NO 8
<211> LENGTH: 957
<212> TYPE: DNA
<213> ORGANISM: Staphylococcus epidermidis

<400> SEQUENCE: 8

```
atggcagaaa ctaaaaaaca attcgaaaac aaagtaagcg tgacaggaac attaaaatca     60
ttagaggtaa cagatttagt aacagctaaa aaagtcccaa tgaaaattgc tacattaaga    120
attgaaactg gtaaaggtga aacacataca gctaaaatga tggcagttaa acattttgag    180
cgtgatggtg ttaaaactga aataaaagt tattctgcaa ttgaaacaat gcaaaaggaa    240
tatgtatcaa ttgaagacat ttcagaaaac aaagctggag aagacgcaga agcaacagtt    300
gttaacgtaa atggatcaat gtctattaat atgtataaaa ataaagcaga aaaagttgtt    360
gaaactaatc aaattgaagc tcgttttgtt atcgtgtaa aagatgttga aaatgctcaa     420
tttggtgcag aattcacatt acaaacttac ttaatttcaa aaggacaacg tgttattaag    480
aatgaagaag aaactgatga agtaacattc aaagcagcaa caattgatta tagaggacaa    540
gcacatccat ttgaattcac tgctaatgat gagtatggcg tagctgaatg gatcgaagat    600
gaagttgaat taggtcaatc acttatctta caaggtttaa ttattaataa atttatcgtt    660
gagcaagtag aacgctcatc atcagctggt atcggtaaag caattgttga tactagacgt    720
gaagtagaac gtaagttatt agttgaaggt attattccaa ttgaagatga ggatgatcca    780
aaatacatca ctgaagaaga aattaaagaa gcaaacaaaa aatacgaaga taagaaaaca    840
gaagtagaag cttctactaa tggaactaag aaaacagaag ttaaaaaagg tgtagcaact    900
agcaaaccta agctgctaa accaacaatc gaaattgatg atgacgattt accattc        957
```

<210> SEQ ID NO 9
<211> LENGTH: 2391
<212> TYPE: DNA
<213> ORGANISM: Staphylococcus epidermidis

<400> SEQUENCE: 9

```
ttgccacaag caaaaaaaag aacatcgacg aagagaaagg gtaataaaaa aacgaataaa      60
aaaaagcaaa atgaaacgcc tttaagatat atattctcaa taattgtagt aattcttatt    120
atactaggcg cttttcaatt aggaatcatt ggtagaatga ttgatagctt ttttaattat    180 cttttttggta tgagtcgata tttaacttat attttagtac ttattgcaac aattttttata  240 acatactcta agcaaatacc tagaactcga cgtagtatcg gtgcaatagt tttacaatta    300
gctttgttat ttatagcgca attgtatttt cattttttcac ataatatcac ttctcaaaga    360
gagcctgtac tgtcctttgt ttataaagct tatgaacaaa cacattttcc aaattttggg    420
```

-continued

```
ggaggcttaa taggttttta tttacttaaa ctatttatac ctctcatatc tattgtaggt    480
gtaataataa ttactatcct attactagct tcgagtttca ttttattact taatttaaga    540
catagagatg ttacaaaaag tttattcgac aacctcaagt catcaagtaa tcatgcatct    600
gagtcaataa aacaaaaaag agaacaaaat aagattaaaa aagaagaaaa agcccaatta    660
aaagaggcaa aaattgaacg aaaaaaacaa aaaaaatcac gtcagaataa taatgtcatt    720
aaagatgtta gtgattttcc agagatttct cagtcagacg atattccaat atatggtcat    780
aatgagcaag aagataaaag accaaatact gctaaccaac gtcaaaaacg tgttttggat    840
aatgaacaat ttcaacaatc attaccaagt accaaaaatc aatcaataaa taataatcag    900
ccatctacaa ccgctgaaaa caatcaacaa caaagtcagg ctgaaggctc aatatctgaa    960
gctggtgaag aagccaatat tgagtatacg gtgccaccct tatccttatt aaaacagcct   1020
actaaacaaa aaactacttc aaaagctgaa gtccaacgta aaggtcaggt tttagaatct   1080
acactaaaaa actttggagt taatgctaaa gtaacacaaa ttaaaatcgg tcctgcagtt   1140
acgcaatatg aaattcaacc agcgcaaggt gttaaagtaa gtaaaatagt caatctccat   1200
aatgacattg cattagcttt ggctgcgaaa gatgtacgaa tagaagcacc tattccaggt   1260
cgctctgcgg taggaattga ggttcccaat gataaaatct cacttgtcac tctaaaagaa   1320
gttttagaag ataagttccc atcaagtat aaattagaag tcggcattgg tagagatatt   1380
tctggtgatc caatatcaat tcaattaaat gaaatgcctc acttactcgt tgctggttca   1440
acaggaagcg gtaaatcagt ttgtattaat ggtattataa cgagtatatt actcaacaca   1500
aaaccgcacg aagttaaact tatgttaatc gatcctaaaa tggtagagtt aaatgtttac   1560
aatggtattc ctcatttact tataccggtt gtaacaaacc cacataaagc gtctcaagct   1620
ttagaaaaaa ttgtttcaga aatggaacgt cgttatgatt tgtttcaaca ttcatcgaca   1680
cgaaatattg aaggatataa ccaatatata cgcaaacaga atgaagaact tgatgaaaaa   1740
caacctgagt taccgtatat cgtcgtaata gtggatgaat tggctgattt aatgatggtt   1800
gcaggtaaag aagtagaaaa tgctatccaa cgtattactc aaatggctag agcagcgggt   1860
atacacttaa ttgtagctac tcaaagacct tccgttgatg ttattactgg tattattaaa   1920
aataacattc catcaagaat tgcgttcgct gtaagttctc aaactgactc tagaacaata   1980
attggtgctg gtggagctga aaagctactt ggtaaaggtg atatgctata tgttggtaac   2040
ggagaatcta ctacaacccg aattcaaggt gctttttta gtgatcaaga agtgcaagat   2100
gttgttaatt atgttgtaga gcaacagaaa gcaaattatg ttaaagaaat ggaaccagat   2160
gcacctgtag ataaatcaga atgaagagt gaggatgctt tatatgatga agcttattta   2220
tttgtaatag aaaagcaaaa agctagtact tctttattac aacgacaatt tagaatcggt   2280
tataatcgag cttcaaggct catggatgat ttggaacgta accaagttat tggtccacaa   2340
aaaggaagta aacctagaca aatattagtt gatttagaaa atgacgaggt g            2391
```

<210> SEQ ID NO 10
<211> LENGTH: 1287
<212> TYPE: DNA
<213> ORGANISM: Staphylococcus epidermidis

<400> SEQUENCE: 10

```
atgaaaacac atcaatatga acttatagat gagaaagttt tcgaacatga gtttgataat     60
ggattgaaat tatttatcat tcctaagcct ggttttcaaa aaacgtatgt gacctacaca    120
acacagtttg gttcattgga caatcatttt aagcccatag gtagtcagca atttgtaaaa    180
```

```
gttcctgacg gtgtggcaca ttttttagaa cataaattgt ttgaaaaaga agatgaagat    240
ttatttactg catttgccga agagaatgcg caagctaatg cttttacaag ctttgatcgt    300
acgagttatt tatttagcgc aacaagtaat attgaaagta acattaaacg tctcctcaat    360
atggtagaaa caccttattt tactgaagaa acagttaata agaaaaagg gattatagct     420 gaggaaatta aaatgtacca ggaacaacca ggatataaat taatgtttaa tactttaagg    480
gctatgtatt ccaagcaccc gatacggg tg gatatcgctg gtagtgttga aagcattta t   540 gaaataacaa agatgatttt atatctatgc tatgagacat tttatcatcc ctctaatatg    600
gtgttgtttg tggtaggcga tgttagtcct caatcgataa ttaaacttgt agaaaagcat    660
gaaaatcaaa gaaataaaac ttatcaacca cgtattgaac gtgcgcaaat tgatgagcct    720
agagagataa atcaacggtt tgtttctgag aaaatgaagt tacagtcacc acgattgatg    780
ctaggtttta aaaatgaacc attagatgaa agtgcaacta aatttgttca aagagatttg    840
gaaatgacat ttttctacga attggttttt ggagaggaaa cggagtttta tcaacaactt    900
ttaaataaag atttaataga tgaaacattc ggttatcaat ttgtattgga accgagctac    960 agttttttcaa ttattactag tgcaacacaa cagcctgatc tatttaaaca attaataatg   1020
gatgaattaa gaaaatataa aggaaaacctt aaagatcaag aagcatttga tttgttgaaa   1080 aagcaatttta ttggagaatt catatcaagt ttaaattctc cagaatatat tgctaatcaa   1140
tatgcaaaac tctatttcga gggagtgagt gtatttgata tgcttgatat cgtagaaaat   1200
attacgttag agagtgtaaa tgaaacttcc gaattattct tgaactttga ccaacttgtt   1260
gatagtcgtt tggagatgga aaataga                                      1287
```

<210> SEQ ID NO 11
<211> LENGTH: 987
<212> TYPE: DNA
<213> ORGANISM: Staphylococcus epidermidis

<400> SEQUENCE: 11

```
atgactgaac agaaggatat taaagaaaca gagtatcgac gacagaaagg aacaacttcg     60
acaccttcta ggcgaagaaa taaaaaaga atgcggaagt taccttttat cattttagtc    120
atccttatta ttttaatttc tatcattgtg tatattaccc atcagtataa cagtggtatg    180
aagtatgcta agaacatgc taaggatgtt aaggtgcata aatttaatgg aaatatgaaa    240
aatgatggga agatttcagt tcttgtcctt ggcgcggata aggctcaagg tggtaaatca    300
cgtactgact cgattatgat tgttcaatat gattacgtac ataaaaaaat gaaaatgatg    360
tctgtcatga gagatattta tgctgatatt cctggttatg ataaatataa aattaatgcc    420
gcatattcac ttggaggccc ggaattgtta agaaaaacac ttaacaaaaa tttaggtgtt    480
aatcctgagt attacgctgt agtagatttt actggatttg aaaaaatgat agatgaacta    540
cagcctaatg gtgtcccaat tgatgtggaa aaagacatgt ctgaaaatat aggtgtgtct    600
ttgaaaaaag gacatcataa gttaaatggt aaagaattac ttggttatgc tagattccgt    660
catgatccgg aaggcgattt tggtcgtgtg agaagacaac aacaagtgat gcaaacatta    720
aagcaagagt tagttaattt caatacagtt gcgaaactac caaaagttgc tggtattttta    780 agaggttatg ttaatacaaa tatgcctaac tctgcgattt ttcaaacagg tataagttttt   840 ggaattcgtg agataaaga tgtgcaatct ttgacagtcc ctattaaagg aagctatcaa    900
gatattaata caaataatga tggtagtgcg cttcaaatag actctgagaa aaataagcaa    960
gcaatcaaaa atttctttga agataat                                      987
```

<210> SEQ ID NO 12
<211> LENGTH: 1881
<212> TYPE: DNA
<213> ORGANISM: Staphylococcus epidermidis

<400> SEQUENCE: 12

```
atggaagcat acaaaattga acatttaaat aaatcctatg cagataaaga aattttaat      60
gatcttaacc tatctatatc tgagcatgaa agaattggat tagtaggtat caatggaaca    120
ggtaaaagta cactattaaa agtcattggt ggtctagatg aagattttac tgcagatatt    180
acccacccta atcaatatcg cattcgttat tcctctcaaa acaagacct caatggccat     240
atgactgtgt tcgaagctgt tttaagttcg gatactccta cattaagaat tataaaaaaa    300
tatgaagaag cagttaatcg ctatgcgtta gatcaaagtg actctaattt taataaaatg    360
atggaagcac aagaagaaat ggatcaaaag gatgcatggg actataatgc agaaattaaa    420
acgattttat ctaaactagg gattcacgat acaactaaga aatagttga actttcgggt     480
ggtcaacaaa aaagagttgt attggctaaa actctaatag aacaaccgga tttacttttg    540
ctagatgaac cgacgaacca tcttgactt gaatccatcc gttggctcat taattatgtc     600
aagcaatatc cacatacagt tttatttgta acacatgatc gctactttt aaatgaagta     660
tcgacgcgaa ttattgaact ggatagaggg aagttaaaaa catatccagg taattatgaa    720
gattacatag taatgcgtgc agaaaatgaa ttagtagaac aaaaacaaca agaaaaacaa    780
aaagcattgt ataaacaaga gttagcatgg atgcgagcag gagcaaaggc aagaactact    840
aaacaacagg cacgtatcaa tagatttaat caactagaat cagacgttaa gacgcaacat    900
acacaagata agggtgaact taatcttgca tattcaaggt taggtaaaca agtatatgaa    960
ttaaagaatt tatcaaaatc aattaataat aaagttttat ttgaagatgt cactgaaatt   1020
attcaaagtg gtagacgtat aggtattgta ggacctaatg gagcgggaaa acaacatta    1080
cttaatattt taagtaatga agatcaggac tatgagggtg agcttaaaat cggtcagact   1140
gttaaggtag cttatttaa gcaaacagaa aagacacttg accgtgatat tagagtgatt   1200
gactacctaa gagaagaaag tgaaatggct aaagaaaaag atggtacctc aatttcagtt   1260
acacaattgt tagaaagatt tttatttccg agcgctacac acggtaaaaa agtttataaa   1320
ctctcaggtg gagaacaaaa acgtctgtat ttattgcgtt tacttgttca taaacctaat   1380
gtactccttt tagatgaacc gactaatgat ttagatactg aaacacttac gatttagaa    1440
gattacattg atgatttcgg tggttctgtc attacggtca gtcatgatcg ttatttctta   1500
aataaagtgg tacaagaata ttggtttatt catgatggta aaatcgaaaa aattattgga   1560
tcatttgaag attatgaatc ttttaaaaag gaacatgaac gccaagccat gctatctaaa   1620
caaactgaac aacaaaataa acataagcat caaccaaaaa agaaaacagg actatcttat   1680
aaagagaagt tagaatacga acaattatg acgcgtatag aaatgactga acgcgttta     1740
gaagaccttg aacaagaaat gattaatgca agtgataatt atgcaagaat caaagaactt   1800
aatgaggaaa aagagcaact tgaagcaacc tatgaagcag acatcacgag atggagtgag   1860
cttgaggaaa ttaaagaaca a                                             1881
```

<210> SEQ ID NO 13
<211> LENGTH: 810
<212> TYPE: DNA
<213> ORGANISM: Staphylococcus epidermidis

<400> SEQUENCE: 13

```
atgaaaaaat tattcggaat tattttagta ttggctttaa cgattgcctt agctgcatgt    60
ggtggaggta aagataagga aaaactatc acagtaggtg catctccagc accacacgct    120
gaaattttag aaaaagcaaa accattattg aagaaaaag gttatgattt aaaaatcaaa    180
ccaattaacg attatacaac gcctaataaa ttattagaca aaggtgaaat cgatgcgaac    240
ttcttccaac atacaccata cttaaatact gaaagtaaag aaaaagggta taaaattgaa    300
tcggctggga atgttgaatt agaacctatg gctgtatact caaaaaaata taaaagctta    360
aaagatcttc ctaaaggtgc aacagtatat gtatcaaata cccagctga caaggacga    420
ttcttaaaat tctttgtaga tgaaggtctt attaaactta aaaaaggcgt taaaattgaa    480
aatgctaaat ttgatgacat aactgaaaac aaaaaagata ttaaatttaa caacaaacaa    540
tcagcagaat atttaccaaa aatctatcaa aatcaagacg ctgacgcagt aatcattaat    600
tctaactatg cgattgacca aaaattaagt cctaaaaaag attcgattgc tttagaatct    660
cctaaagata acccatatgc aaatttaatt gcagttaaaa aaggtcataa agatgataaa    720
aatatcaaag tattaatgga agtgctacaa tctaagaaaa ttcaagatta tattaaagat    780
aagtatgatg gagctgtcgt acctgctaag                                     810

<210> SEQ ID NO 14
<211> LENGTH: 1317
<212> TYPE: DNA
<213> ORGANISM: Staphylococcus epidermidis

<400> SEQUENCE: 14
atggaattaa caatatatca cacgaatgat attcatagtc atttaaatga atatgctcgt    60
attcaagctt atatggcaaa acatagaccg caacttgaac atccctcact ctatatagat    120
ataggtgacc atgttgattt atcagcacct gtgacagaag ctacggtagg acataaaaat    180
atagaacttt taaatgaagc acattgtgat attgcaacca ttggaaataa tgaaggaatg    240
acaatttctc atgatgcttt acaaaatcta tataacgacg cggattttaa agtgatttgc    300
acgaatgtca tagatgaaga gggacatctt ccacatcata ttacctcttc gtatatcaaa    360
gaaataaaag gaacacgtat tttatttgtt gcagcaacgg caccgttcac acctttttat    420
cgagcactgg attggattgt tactgaccca ttagcggcaa tcaaagatga aatcaatgca    480
catcaaggtg aatatgatct tttaatggtt atgagccatg tcggtatctt ttttgatgaa    540
aagttatgcc aagagattcc ggaaatagat gttatctttg gtagtcatac gcatcatcat    600
tttgaacatg gagaaataaa caatggtgtt ttgatgcag ctgccggaaa atatggctat    660
tatttaggtg aagttaatat tacgattgaa aatggaaaaa tcgttgataa aatcgccaaa    720
attcatccta ttgaaacact tcccttagtc gagacacatt ttgaagaaga aggaagagca    780
cttctaagta aaccagtagt taatcatcat gtgaacttag tcaaaagaac agatgttgtt    840
acaagaacat cgtatttact ggctgaaagt gtatatgagt tttcaaggc tgattgtgca    900
atcgtaaatg ctggacttat agttaatggc attgaagctg ataaagtgac ggaatatgat    960
atacatcgca tgttacccca tccaatcaat attgtaagag ttcgattaac cggtaaacaa   1020
ttaaagcaag tgattcaaaa aagccaaaag caagaatata tgcacgaaca tgcacaaggt   1080
cttggtttta gagggatat atttggagga tatattttat ataatctagg ctttattgag   1140
tcagaagacc gttattttat aggcgatgaa gagattcaaa atgataaaca atatacgtta   1200
ggtactgttg atatgtatac atttggaaga tatttcccat tgctaaaggg gttatctaca   1260
gattatatta tgcctgaatt tttacgtgat atttttaaag agaaattact aaaatta      1317
```

```
<210> SEQ ID NO 15
<211> LENGTH: 609
<212> TYPE: DNA
<213> ORGANISM: Staphylococcus epidermidis

<400> SEQUENCE: 15
atggagaaag taatttatct agctggccat attcttaatg aagcaatggt tgattataga      60
gaaaaacaac ataaccaagt tgaagcaatt gagggagtaa aaccttatag ccctcaccaa     120
gacaaatcta ttaatgataa gtctaatgca gttcaagaag gtttggccga gagaattta      180 aagaatgatt ttaccgcaat ggaaaaatca gatatctatg ttcttgatgt tttaaatgaa     240
ggtttaggaa caatttctga gctcggaatt attattggaa tgaagaaaca agctcaaaaa     300
acaattgata gattgagtgt cttatctgaa gaaataaaac atgatgtata tggagatcaa     360
acagaagctt atgatttaat tcaagacgaa atctacaagc aagaaaaaat cttaaataaa     420
acagttctat gttactgttc agatattaga caaggacacg gaaaaccta tactgatcca      480 gaccgtgctg aattctctac taaccaattt gtatatggaa tggtactgga agctactaat     540
ggtgaaggtt ttattacttg ggatcaagtt ttacatagat tagatttgtt tggaagtggc     600
ctaattgtt                                                             609

<210> SEQ ID NO 16
<211> LENGTH: 177
<212> TYPE: DNA
<213> ORGANISM: Staphylococcus epidermidis

<400> SEQUENCE: 16
atgagcaaaa agtttagagt tgaagataaa gaaacaattg cagattgtct cgacagaatg      60
aaaaaagaag ggtttatgcc aatacgtcgt attgagaaac cagtttataa agagaacaaa     120
gatggcagta tagagatttt aaaacaggat attatatttg taggtgcttt aatccaa        177

<210> SEQ ID NO 17
<211> LENGTH: 11076
<212> TYPE: DNA
<213> ORGANISM: Staphylococcus epidermidis

<400> SEQUENCE: 17
atgaatctat ttagaaaaca gaaatttagt attagaaaat ttaatatagg tattttttca      60
gcattaatag ctacagtcgc atttttagct catccggggc aagcaacagc atcagaactg     120
gaaccttctc aaaataatga cactacagct caatctgatg gagggttaga aaacacatct     180
cagtctaatc ctataagtga ggaaaccaca aatacattat ctgggcaaac agtaccttca     240
tctactgaaa ataagcaaac acaaaatgtt cctaatcata cgctcaacc aattgcaata      300 aatactgaag aagctgaatc tgctcaaaca gcatcttata ccaatatcaa tgaaaataat     360
gatacgagtg acgatgggtt acatgttaat cagccggcta acatcatat tgaagcccaa      420 tctgaagatg taacaaatca cacgaactca atcattcaa attcatcgat tccagaaaat      480
aaagctacaa cagaatcatc aagtaaacct aaaaaaagag ggaaaagatc attagataca     540
aataacggaa atgacacgac aagtacaact caaaatacgg atccaaattt aagtaataca     600
ggtccaaatg gcattaacac tgtaattaca tttgatgatt taggaattaa gacaagtact     660
aatcgctctc gacctgaggt aaaggtagtt gatagtctaa atggctttac aatggttaat     720
ggtggtaagg tcggttttatt aaatagtgtg ttagaacgta caagcgtgtt tgatagtgcc     780
gatccgaaaa attatcaagc aatagataat gtcgtagcct taggacgtat taaaggaaat     840
```

```
gatccgaatg atcatgatgg tttcaacggt atagaaaaag aattttcagt gaaccctaat      900
tctgagataa tattttcatt taatacaatg actgctaaaa acagaaaagg tggaactcaa      960
ttagttttaa gaaatgcaga aaataatcaa gaaattgctt caactgatat tcaaggaggc     1020
ggcgtatatc gtttattcaa gttacctgat aacgtacata ggttaaaagt tcaatttcta     1080
cctatgaacg aaatacactc agattttaaa agaattcaac agctacatga tgggtataga     1140
tactattctt ttatagatac aattggtgtt aattctggtt cacatctata tgtgaaatca     1200
agacaagtta acaaaaatgt aaagaatggt aaagaatttg aagttaatac tcgtatagag     1260
aataatggta acttcgctgc tgctataggt caaaatgaac ttacttataa agtaacacta     1320
ccagaaaatt tcgaatacgt tgataattca actgaagttt catttgttaa cgggaatgtg     1380
cctaattcta cggtaaatcc gttttcagtt aatttcgata gacaaaatca tactttaacg     1440
tttagtagta atggtttaaa tttaggaaga agtgctcagg atgttgctag attcttgccc     1500
aataaaatac taaatattag atacaagctt agacctgtca acatctcaac gccacgtgaa     1560
gtgactttca atgaagcaat taaatataag acattttctg aatattacat taacactaat     1620
gacaatactg ttactggtca acaaacacct ttcagtatta atgtcatcat gaataaagac     1680
gatttatcag aacaggtcaa taaggatatc atcccatcga actatacact tgcttcttat     1740
aataaatata ataagttgaa agaacgtgct cagactgttc tggatgaaga aacaaacaat     1800
acaccttttta accaaagata ctctcaaact caaattgatg atttgttaca cgaattacaa     1860
acaacactaa taaatcgtgt gagtgcttcg agagaaatta atgataaagc tcaagaaatg     1920
actgatgctg tatatgatag tacagaatta actactgaag aaaaagatac attagttgat     1980
caaattgaaa atcataaaaa tgaaatttct aataacattg atgatgaact tacagatgat     2040
ggtgttgaaa gagtcaaaga ggctggatta atactctag aaagtgatac tccacatcca     2100
gtaacaaaac caaatgcacg acaagttgtg ataacagag cagatcaaca aaagacgctt     2160
atacgtaaca atcatgaggc aactaccgaa gaacaaaatg aagcgattag acaagttgag     2220
gcacattcat ctgatgctat cgccaaaata ggtgaggcag aaacagatac cactgtaaat     2280
gaagctagag acaatggtac gaaattaata gctacagatg ttccaaatcc aactaaaaaa     2340
gcagaagcta gagcggcagt taccaacagt gcaaattcaa aaattaagga tatcaacaat     2400
aatacacaag caacattaga cgagagaaat gatgctatcg cacttgttaa tagatcaaaa     2460
gatgaagcaa ttcaaaatat taacactgca caaggtaatg atgatgtcac tgaagcacaa     2520
aataatggaa cgaatacgat acaacaagta ccattaactc cagtgaaaag acaaaatgca     2580
atagcaacta tcaatgctaa agcggatgaa caaaaacgtt taattcaagc aaacaataat     2640
gcaacgactg aagaaaaagc tgatgcagag cgtaaagtta atgaagcagt cataactgca     2700
aatcaaaata ttaccaatgc aactactaat agagatgttg atcaagcaca aacaactgga     2760
agtggtatca tatctgctat tagtcctgca acgaagatta aagaggatgc acgtgcagca     2820
gtagaagcta aagctattgc acaaaatcaa caaattaatt caaataatat ggcaacaact     2880
gaagaaaagg aggatgcatt aaatcaagta gaagcacata agcaggccgc aatagcaact     2940
atcaatcaag cgcagtcaac tcagcaagtt tctgaagcta agaataatgg cataaatact     3000
attaatcaag atcaacctaa cgcagttaag aaaaataata caaaataat attagaacaa     3060
aaaggaaacg agaaaaagtc agcaatagct caaacacctg atgctaccac tgaagagaaa     3120
caagaagctg tcagtgctgt ttcgcaagct gttaccaatg gcattaccca tatcaaccaa     3180
gcaaattcta atgatgatgt tgatcaagaa cttagtaatg cagaacaaat tattactcaa     3240
```

```
actaatgtca atgttcaaaa aaaacctcaa gccagacaag cattgattgc taaaacaaat    3300
gaaaggcaga gtacgattaa tactgacaat gaaggcacta tagaagaaaa acaaaaagca    3360
attcaaagtt tgaatgatgc taaaaattta gctgatgaac aaattacaca ggctgcttct    3420
aatcaaaatg tcgacaacgc cttaaatata ggtataagta atatcagtaa aatacagact    3480
aatttcacta aaaagcaaca agctagagac caagtaaatc aaagttcca agaaaaagaa    3540
gctgagttaa attcaacacc tcatgcaact caagatgaaa acaagatgc gttaactaga    3600
ttaacacaag caaggaaac tgcactcaac gacataaatc aagcacaaac aaatcaaaat    3660
gtggatacag cacttactag tggaattcaa aatattcaaa atacacaagt taatgttagg    3720
aaaaagcaag aagccaaaac tacgattaat gatattgttc aacaacataa acaaactata    3780
caaaataatg atgatgctac aactgaagag aaggaagtcg caaataattt agttaatgca    3840
tcacagcaaa atgtaattag taagattgat aatgctacaa cgaataatca aattgatggt    3900
attgtgagtg atggtagaca aagcataaat gcaattacac ctgatacatc aattaaaaga    3960
aatgctaaaa atgatattga tattaaagca gctgataaga aaataaaaat tcaaagaata    4020
aatgatgcta cagatgaaga aattcaagaa gcgaatcgta aaattgaaga agctaagatt    4080
gaagcaaaag ataatattca acgcaatagt actagagatc aagtaaatga agcgaaaact    4140
aatggaataa ataaaataga aaatataaca ccagcaacta ctgtgaaatc tgaagctaga    4200
caagcagtac agaataaagc aaatgaacag attaatcata ttcaaaacac gcctgatgca    4260
actaatgaag aaaaacaaga ggcaataaat agagtaagtg ctgaattagc aagagttcaa    4320
gcacaaataa atgcagaaca tacaacccaa ggtgtcaaaa ctatcaaaga cgacgcgata    4380
acttctttat ctcgaattaa tgcacaagtt gttgagaaaa agtctgcaag aaatgcaatc    4440
gaacaaaagg caacacaaca aacgcaattt attaataata atgataatgc tacagatgaa    4500
gaaaagagg tcgccaacaa tttagttatc gctacaaaac aaaaatcatt agataatatt    4560
aactccttat cttcaaataa tgatgttgaa aatgctaaag tagcaggaat aaatgaaata    4620
gctaacgttt taccagcaac cgctgttaag tcaaaagcaa aaaagatat tgatcaaaaa    4680
ctcgcgcaac agattaatca aattcaaacg catcaaactg ctacaactga ggaaaaagaa    4740
gcggctattc aattggcaaa tcaaaaatca aatgaagcaa gaacagcaat tcaaatgaa    4800
catagtaaca atggtgtcgc acaagctaaa tctaacggca ttcatgaaat tgaattagtt    4860
atgccagatg cgcacaaaaa atctgatgct aaacaaagta tcgataataa atataatgag    4920
caaagtaata ctatcaacac tacaccagat gcaacagatg aagaaaagca aaaagcatta    4980
gataaattaa aaatagctaa agatgcagga tacaacaaag ttgatcaagc gcaaacaaac    5040
caacaagtat ctgatgcaaa aactgaggct atagatacga taactaatat tcaagcaaat    5100
gttgcaaaaa accatccgc tcgagtggaa ttagattcaa agtttgagga tttaaagcgt    5160
caaatcaatg caacgcccaa tgctacagaa gaagaaaaac aagatgcaat tcaaagattg    5220
aatggtaaaa gagatgaagt taagaatcta ataaatcaag atagacgtga caatgaagtt    5280
gaacagcaca aaaatattgg acttcaagaa ttagaaacga ttcatgctaa tccaactaga    5340
aaatctgatg cgctccaaga gttacaaact aaatttatt cacaaacaga gttaattaat    5400
aataacaaag atgcaactaa tgaagaaaaa gatgaagcca acgacttct tgagattagt    5460
aaaaataaaa ctataacaaa tatcaatcaa gcgcaaacta ataatcaagt tgataatgct    5520
aaagataacg gcatgaatga gattgctacc ataataccag caacaacaat taaaacagat    5580
gcaaaaacgg ctattgataa aaaagctgag caacaagtta caatcatcaa tggtaacaac    5640
```

-continued

```
gatgcaacag atgaagaaaa agcagaggct agaaagctgg ttgaaaaagc gaaaattgaa    5700
gccaaatcta atattacaaa tagtgatact gaaagggaag tcaatggtgc taaaaccaat    5760
gggttagaaa aaataaacaa tattcaacca tcaactcaaa ctaaaacaaa tgctaagcaa    5820
gaaataaatg acaaagctca agaacaatta atccaaatta ataacacgcc tgatgcaacc    5880
gaagaagaaa agcaagaggc aacaaataga gtcaatgctg gattagcaca agcaatacaa    5940
aatattaata atgcacatag tactcaagaa gtaaatgaat ctaaaacaaa tagtattgct    6000
acaatcaaga gtgtacaacc caatgtgatc aaaaaaccga ctgctataaa tagtttgact    6060
caagaagcta ataatcaaaa gacgttaata ggtaatgatg gtaatgctac tgatgatgaa    6120
aaagaggctg caaagcaatt agtgacccaa aaattaaatg aacaaattca aaaaattcat    6180
gaaagtacac aagataatca agttgataac gtaaaagcac aagctatcac tgcaattaaa    6240
ttgattaatg caaatgcaca taaaagacaa gatgccatta atattttgac taatctagct    6300
gaaagtaaaa aatcagatat aagagccaat caagatgcaa ctactgaaga gaaaaatacg    6360
gcaatacaat ctatagatga tacgttagca caagcacgta acaatattaa tggtgcaaat    6420
acaaatgcgt tagtggatga gaatttagaa gatggtaagc aaaagttaca acgtattgtg    6480
ttgtcaactc aaactaaaac acaagctaaa gcagacattg ctcaagcaat aggtcaacaa    6540
aggtcgacaa tagaccagaa tcaaaatgct acaacagaag aaaaacaaga agcccttgag    6600
agacttaatc aagaaacaaa tggagtcaat gatagaatac aagcagcttt agcaaatcaa    6660
aatgttacag acgaaaaaaa taatatatta gaaacaataa gaaatgttga acctattgta    6720
attgtaaaac caaaggctaa tgaaataatt agaaaaaaag ctgcggaaca aacgactta     6780
ataaatcaaa atcaagatgc gacactagaa gaaaaacaaa tagcacttgg caaattagaa    6840
gaagtaaaga atgaagcgtt aaatcaagta tcacaggcac actcaaataa tgatgtgaaa    6900
attgtggaaa ataatggaat tgctaaaatt tctgaggtcc atcctgagac tataattaaa    6960
cgtaatgcta aacaagaaat tgaacaagat gcgcaaagtc aaattgatac tatcaatgca    7020
aataataaat caactaatga agaaaaatca gccgctatag atagagttaa tgtagctaaa    7080
attgatgcta ttaacaatat tactaatgct acaactacac aattagttaa tgatgctaaa    7140
aatagtggta acacgagtat tagccaaata ttaccaagta cagcagtcaa aactaatgca    7200
ttagcagctc tagctagcga agctaaaaat aaaaacgcta atagatca aacaccaaat     7260
gcgacagcag aagaaaaaga agaagcaaat aataaagttg atcgtcttca agaagaagca    7320
gatgctaata tcctaaaagc acacactact gatgaagtta ataatattaa aaatcaagct    7380
gttcaaaata ttaacgctgt tcaagttgaa gttatcaaga acaaaacgc taaaaaccaa     7440
ttaaatcaat tcattgataa tcaaaagaaa attattgaaa atacgcctga tgcaacacta    7500
gaagaaaaag ctgaagctaa tagattgctt caaaatgtac taacttccac atcagatgaa    7560
attgctaatg tagatcataa caacgaggtt gatcaagctt tagataaagc tagaccaaaa    7620
atcgaggcaa ttgtaccaca agttagtaag aaacgagatg ctttaaatgc aatccaagaa    7680
gcatttaatt cacaaactca agaaatacaa gagaaccaag aagctacgaa tgaagaaaaa    7740
actgaagcat taaataaaat aaaccaatta cttaatcagg ctaaagtaaa tattgatcaa    7800
gcacagtcaa ataaagatgt agatagtgcg aaaaacgta gtattcaaga tatagagcaa    7860
attcaaccac atccacaaac aaaagcaacc gggcgtcaca gattaaatga aaaagctaac    7920
caacaacaaa gtactattgc aactcatcct aattcaacaa ttgaagaaag acaggaagca    7980
agtgcaaaac tacaagaagt tcttaaaaaa gccatagcta aaatagataa aggtcaaacc    8040
```

```
aatgatgatg tagaaaagac tgtagtaaac ggaatagctg aaattgaaaa tatattacct   8100
gctactacag ttaaagataa agctaaagct gatgtaaatg ctgaaaaaga ggagaaaaac   8160
ctacaaatta atagtaatga tgaagcaacg actgaagaaa aattagttgc tagtgacaat   8220
ttaaatcacg ttgtcgagac aacaaatcaa gctattgagg atgcaccaga taccaaccaa   8280
gtgaatgtag aaaagaacaa aggtataggt acaattagag atattcaacc acttgtagtt   8340
aaaaaaccta ctgccaaatc taaaattgaa agcgcagtag aaaaaaagaa aactgaaatt   8400
aatcaaacac aaaatgcaac tcatgatgaa gtaagagagg gtttaaatca gttaaatcaa   8460
attcatgaaa aagccaaaaa tgatgtaaat caatctcaaa ctaatcagca agttgaaaat   8520
gctgagcaaa atagtttaga tcaaatcaat aacttcagac cagattttag taaaaaacgt   8580
aatgcagtag ctgaaattgt taaagcgcaa caaaacaaaa ttgatgaaat agagcaagaa   8640
tttagtgcta cacaagagga aaaagacaat gctttacaac atttagatga acaggttaaa   8700
gaaatcatta attctataaa tcaagctaat acagataatg aagtagataa tgctaaaact   8760 tctggggttga ataacataac tgaatacaga ccagaatata ataaaaagaa aaatgctata   8820
ttaaaattat atgatgtttc agatactcaa gaagctataa ttaatggtta tcctgatgca   8880
actgaagatg aacttcaaga agctaatagt aagttaaata aaatactttt agatgcaaaa   8940
aaacaaattg gtcttgcgca cacaaataat gaagttgatg atatttataa tgaagtttcc   9000
caaaaaatga aaactatttt accacgtgta gatacaaaag cggtagcacg ttctgtactt   9060
aatgcacttg ctaaacaatt gattaaaact tttgaaaata ctgcagatgt tactcacgag   9120
gaacgtaatg atgcgattaa tcatgtaaaa gaacaattat ctttagtatt caatgccatt   9180
gaaaaagacc gaaaagatat acaagttgcg caagatgaat tatttggatt aaatgaatta   9240
aatagtatat ttatcaacat aactcaaaag ccaactgcca gaaaagcaat tagtggtatg   9300
gcgagtcaat taacaactc tatcaataat acgccatatg ctacagaaga agaacgacaa   9360
attgcactga ataaagttaa ggcgattgtt gatgatgcaa atgaaaaaat acgagaagct   9420
aacactgata gcgaagtact tggaacaaaa tcaaacgcaa taacattgtt acaagcaatc   9480
agtgcggatg tacaagttaa accacaagca tttgaagaaa tcaatgcaca agctgaaatt   9540
caaagagaac gaattaatgg aaatagtgat gcgacaagag aagaaaaaga agaagcttta   9600
aaacaagttg atacattagt aaatcattca tttattacaa ttaataatgt taataaaaat   9660
caagaagttt atgatactaa agacaaaacg attgaagcta ttcataaaat caaaccaata   9720
tcaactatca aaccacaagc attaaatgaa atcactattc aactagacac tcaacgtgat   9780
ttaataaaga ataataaaga gtctacagtt gaagaaaaag cctcggctat cgataaatta   9840
attaaaactg cagcaagaat agccgaatca atagataaag ctcaaacaaa tgaagaagtt   9900 aaaatatta aaaacaaag tattgatgaa atttctaaaa tactacctgt tattgaaatt   9960
aaatcagctg caagaaatga aattcatcaa aaagcagaag ttattcgcgg attaattaat   10020
gataatgaag aagcgactaa agaagaaaaa gatatcgcat taaatcaatt agacacaact   10080
ctaacacaag caaatgtttc aattgaccaa gcattaacaa atgaagctgt taatagagct   10140
aaagaaatag caaattctga aattaataaa atttctgtca ttgccattaa aaagcctgaa   10200
gctatagcag aaaattcaaga actagcgat aaaaaattaa ataaatttaa acaaagtcaa   10260
gaagctacta ttgaagaaaa gcaatcagct atcaatgaat tagaacaagc tttaaaatca   10320
gctattaatc atattcatca atctcaaaat aatgaatcag tgagcgctgc attaaaagaa   10380
agtatatctt taatagactc gattgaaatt caagcacata aaaaattaga agctaaagca   10440
```

| tacattgatg gatatagtga cgataaaatt aatgacatat cttctagagc gactaacgaa | 10500 |
| gaaaacaaa tatttgtaag taaacttaaa gcattaatca atcgtacaca taaacagatt | 10560 |
| gacgaagctg aaacatttgt ttcagttgaa acaattgtcc gaaactttaa agttgaagcg | 10620 |
| gataaattaa actcaattgt acgtaaaaaa gctaaagcat cgaaggaaat tgaattagaa | 10680 |
| gcagaccatg taaagcaaat gataaatgca aatttaagtg ctagtactag agtgaaacaa | 10740 |
| aatgctcgta cattgataaa tgaaattgtt agtaacgctt taagtcaact taataaagta | 10800 |
| accacaaata aagaagttga tgaaatagtt aacgaaacga ttgaaaaact taagtcaata | 10860 |
| caaataagag aagataaaat attgagtagt caacgttcat caacatctat gacgaaaaaa | 10920 |
| tctaatcaat gttatagttc cgagaataat acaattaaat ctctaccaga ggcaggaaat | 10980 |
| gctgataaat cactaccatt agcaggagtt actttaatat ctggtttagc aatcatgtcc | 11040 |
| tcacgtaaaa agaaaaaaga taaaaagta aatgac | 11076 |

<210> SEQ ID NO 18
<211> LENGTH: 1317
<212> TYPE: DNA
<213> ORGANISM: Staphylococcus epidermidis

<400> SEQUENCE: 18

| ttggatataa aaatgcctaa gcttggtgaa agtgtgcatg aaggtacgat tgaacaatgg | 60 |
| ttagtatcag taggagatca tgtagatgag tatgaaccat tatgtgaagt tattacagat | 120 |
| aaagtaacag ctgaagtgcc ttcaacaatt tctggaacaa taacagaatt agtggttgaa | 180 |
| gaaggacaaa ctgtcaatat taacacggtg atttgtaaaa tcgattcgga aaatggtcaa | 240 |
| aatcaaacag aatcggcaaa tgagtttaag gaagaacaaa atcagcattc tcaatcaaat | 300 |
| ataaacgtgt cacaattcga aaataatcct aaaactcatg aaagtgaggt gcatacagcc | 360 |
| tctagtcgcg caaataacaa tggacgattt tcaccagttg tctttaaatt agcttctgaa | 420 |
| catgatattg atttaacaca agtcaaagga actggttttg aaggtcgtgt tactaagaaa | 480 |
| gatattcaaa atattattaa caatccaaac gatcaagaaa aagagaaaga atttaaacaa | 540 |
| acagataaaa aagatcattc aacgaaccat tgtgactttt tacatcaatc ctcaactaaa | 600 |
| aacgaacact caccattatc aaatgaacgt gtcgtaccag ttaaaggtat tagaaaagct | 660 |
| atcgcacaaa atatggttac tagtgtcagc gaaataccac acggttggat gatggttgaa | 720 |
| gctgatgcaa cgaatttggt tcagactaga aactatcata agctcaatt taaacagaat | 780 |
| gagggttaca atttaacttt ctttgcgttt tttgtaaaag ctgttgcaga ggcttttaaaa | 840 |
| gtaaatccat tactcaatag tacatggcaa ggagatgaaa ttgttatcca caagatatt | 900 |
| aatatctcta ttgctgttgc agacgatgat aagttgtatg tgccagtcat taaaaatgca | 960 |
| gatgaaaaat caattaaagg tatcgcgcgt gaaatcaatg atttagctac taaagcaaga | 1020 |
| ttaggaaaat tagcacaaag tgatatgcaa aacggtacat ttacggttaa taatactggt | 1080 |
| tcttttggtt ctgtttcttc aatgggaatc attaatcatc cacaagctgc cattttacaa | 1140 |
| gtagaatcag tcgttaagaa acctgtagtt atagatgata tgattgcaat tagaaatatg | 1200 |
| gttaatttgt gtatttcaat cgatcatcgt attctcgatg gtgttcaaac gggaaaattt | 1260 |
| atgaatcttg ttaagaaaaa aatagaacaa tattctattg aaaacacttc tatttat | 1317 |

<210> SEQ ID NO 19
<211> LENGTH: 885
<212> TYPE: DNA
<213> ORGANISM: Staphylococcus epidermidis

<400> SEQUENCE: 19

```
atgaatacta tcattgaaga atatttaaat ttcattcaaa ttgaaaaagg attaagtaac    60
aatactatag gagcgtatcg aagagattta aaaaaatata agattatct tgaagataac    120
aagatttcac atatcgattt tattgataga caaattatcc aagagtgtct tggacacctt   180
atagatatgg ggcaatcttc aaaatctctc gcaaggttta tttctacaat aagaagcttt   240
catcagtttg cattacgcga aaaatatgct gctaaagacc caactgtttt aattgaaaca   300
cccaaatatg aaagaaatt accagatgtg cttgaaatag acgaagtaat agcattactg    360
gaaacgcctg atttaactaa gaataatgga tatcgtgatc gtacgatgtt ggagctttta   420
tacgccacag gtatgcgtgt aactgaaatt attcaattag atgttgaaga cgtaaactta   480
atgatgggat ttgtaagagt tttcgggaaa gggaataagg aaagaatcgt tcccttagga   540
gataccgtca tcgaatattt aactacatat attgaaaccg taagacctca attactcaaa   600
caaaccacaa ctcaagcgct atttcttaac atgcatggaa agtctttatc aagacaaggc   660
atttggaaaa tcattaaaca atatggtttg aaagctaata tcaataaaac gcttacacca   720
catacattac ggcattcatt tgcaacacat ctcttagaaa atggtgctga tttaagagcc   780
gtacaagaaa tgttaggtca ctctgatatt tctacaactc aactttatac acatgtatct   840
aaatcacaaa ttagaaaaat gtatacgcag tttcatccaa gagct                   885
```

<210> SEQ ID NO 20
<211> LENGTH: 2400
<212> TYPE: DNA
<213> ORGANISM: Staphylococcus epidermidis

<400> SEQUENCE: 20

```
atgagtttag tatatcttat ggcgactaat ttattagtca tgctcatagt tttattcact    60
ctgagtcatc gtcaactaag aaaggttgcg ggctatgttg cattaatagc tcctattgtg   120
acatctacat attttattat gaaaatacca gatgtgattc gaaataagtt tattgctgtt   180
cgattaccat ggatgccttc aattgatatt aatttagatt taagattaga tggtttaagt   240
ttaatgttcg gcttaattat ttcgctaata ggtgtgggtg tatttttta tgctacgcaa   300
tatttatccc acagtacgga caatcttcct agattttca tctatttact attatttatg    360
ttcagtatga ttggcattgt aatagctaat aataccatct taatgtatgt atttggggaa   420
ctcacaagta tttcctcatt cttgcttata tcctattggt acaataatgg tgaaagtcaa   480
ttaggcgcca ttcaatcttt catgattaca gtgtttggtg ggctagcgtt attaacagga   540
tttatcattt tatatatcat tacaggaaca acacaatta ctgatatcct taatcaacgc    600
aatgcaattt cacgacatcc tttatttata ccaatgattt tgatgctatt attaggtgct   660
tttaccaaat ctgcacaatt tccgtttcat atttggttac caaaggccat ggcagcacct   720
acaccagtaa gtgcttatct tcattcggca acaatggtaa aggctggaat cttttttacta  780
tttagattta caccttttatt gggacttagt aatgtttata tttatacagt gacatttgtt   840
ggtctaataa ctatgttatt tggatctta actgctttac gacaatacga cttaaaaggt   900
atactcgctt attctacaat aagtcaatta ggtatgatta tgacaatggt aggtctaggt   960
ggcggttatg ctcagcacac atcagatgaa ttgtctaagt tttatatttt agttttattt   1020
gctggcttat tccatttaat gaatcatgcg gttttttaaat gtgcattatt tatgggcgtt   1080
ggtatcattg atcacgagtc cggaacacgt gatattcgtt tgctaaatgg tatgcgtaaa   1140
gtcttcccta aaatgcatat tgtcatgttg ctcgctgcat tatctatggc aggtgttcct   1200
```

-continued

```
tttttaaatg cttttttaag taaggaaatg tttttagatt cgttaactaa agcaaacgaa    1260
cttgatcaat atggcttcgt attaacgttt gtgattattt caataggtgt catcgcgagt    1320
atattgactt ttacttatgc actttacatg ataaaagaaa cattctgggg aaattacaat    1380
atagaaaaat ttaaacgtaa acaaatacat gaaccatggc tatttagttt accagctgtg    1440
attttaatgt tactcattcc agttatcttc tttgttccaa acgttttggg caactttgtt    1500
attttgcccg caaccagatc tgtatctggg ataggtgcgg aggttgatgc atttgtgcca    1560
catatttctc agtggcatgg tgtgaatctt ccattaattt taagtatagt tgttattatt    1620
attggactta ttttagctct agttgtgaat tggaaagagg ttacgcatca aataatcaaa    1680
agtgcttcga ttacagatgg ctatcggaaa atttatagag aatttgaatt atactcagcc    1740
cgtggtatac gtgcattgat gaataataaa ttgaattatt acatcatgat tacattattt    1800 attttttgtag ctattgtagt ttatggatat ttgactgtgg gttttcctca tgtacatcag    1860
cttcatatta gttctttcgg accgttggaa gttatcttat cagttgtaac attgattatc    1920
ggcatttcat taatctttat tcgtcaacga ctaacgatgg tggtattgaa tggaatgatt    1980
ggattcgcag ttacattata ttttattgca atgaaagctc cagatttagc tttaacacag    2040
ttagttgttg aaactattac gacaatctta tttattgtta gtttttcgag actacctaac    2100
atccctcgag ttaaggcaaa tttaaaaaaa gagaccttca aaatcattgt gtcacttgtt    2160
atggcattga cggtggtatc acttattttt gttgctcaac aagcagatgg tatgccttca    2220
attgctaaat tttatgaaga tgcatatgaa cttacaggtg gaaaaaatat tgtcaatgct    2280
atactaggtg acttcagagc tttagatact atgtttgaag gactagtgtt aatcatagct    2340
ggattaggta tttatacgtt acttaattac aaagataggga ggggcaaga tgaaagagaa    2400
```

<210> SEQ ID NO 21
<211> LENGTH: 2676
<212> TYPE: DNA
<213> ORGANISM: Staphylococcus epidermidis

<400> SEQUENCE: 21

```
ttgtttggtt taggtcataa tgaggccaaa gctgaggaga atacagtaca agacgttaaa      60
gattcgaata tggatgatga attatcagat agcaatgatc agtccagtaa tgaagaaaag     120
aatgatgtaa tcaataatag tcagtcaata acaccgatg atgataacca aataaaaaaa     180
gaagaaacga atagcaacga tgccatagaa aatcgctcta agatataac acagtcaaca     240 acaaatgtag atgaaaacga agcaacattt ttacaaaaga ccctcaaga taatactcag     300 cttaaagaag aagtggtaaa agaaccctca tcagtcgaat cctcaaattc atcaatggat     360
actgcccaac aaccatctca tacaacaata aatagtgaag catctattca aacaagtgat     420
aatgaagaaa attcccgcgt atcagatttt gctaactcta aaataataga gagtaacact     480
gaatccaata agaagagaa tactatagag caacctaaca agtaagaga agattcaata     540 acaagtcaac cgtctagcta taaaaatata gatgaaaaaa tttcaaatca agatgagtta     600
ttaaatttac caataaatga atatgaaaat aaggttagac cgttatctac aacatctgcc     660
caaccatcga gtaagcgtgt aaccgtaaat caattagcgg cagaacaagg ttcgaatgtt     720
aatcatttaa ttaaagttac tgatcaaagt attactgaag gatatgatga tagtgatggt     780
attattaaag cacatgatgc tgaaaactta atctatgatg taacttttga agtagatgat     840
aaggtgaaat ctggtgatac gatgacagtg aatatagata agaatacagt tccatcagat     900
ttaaccgata gttttgcaat accaaaaata aaagataatt ctggagaaat catcgctaca     960
```

-continued

```
ggtacttatg acaacacaaa taaacaaatt acctacactt ttacagatta tgtagataaa     1020
tatgaaaata ttaaagcgca ccttaaatta acatcataca ttgataaatc aaaggttcca     1080
aataataaca ctaagttaga tgtagaatat aagacggccc tttcatcagt aaataaaaca     1140
attacggttg aatatcaaaa acctaacgaa atcggactg ctaaccttca agtatgttc       1200 acaaacatag atacgaaaaa ccatacagtt gagcaaacga tttatattaa ccctcttcgt     1260
tattcagcca agaaacaaa tgtaaatatt tcagggaatg gcgatgaagg ttcaacaatt      1320
atcgacgata gtacaatcat taaagtttat aaggttggag ataatcaaaa tttaccagat     1380
agtaacagaa tttatgatta cagtgaatat gaagatgtca caaatgatga ttatgcccaa     1440
ttaggaaata taatgacgt gaatattaat tttggtaata tagattcacc atatattatt      1500
aaagttatta gtaaatatga ccctaataag gacgattaca cgacgataca gcaaactgtg     1560
acaatgcaaa cgactataaa tgagtatact ggtgagttta gaacagcatc ctatgataat     1620
acaattgctt tctctacaag ttcaggtcaa ggacaaggtg acttgcctcc tgaaaaaact     1680
tataaaatcg gagattacgt atgggaagat gtagataaag atggtattca aaatacaaat     1740
gataatgaaa aaccgcttag taatgtattg gtaactttga cgtatcctga tggaacttca     1800
aaatcagtca gaacagatga agaggggaaa tatcaatttg atgggttaaa aaacggattg     1860
acttataaaa ttcattcga aacaccggaa ggatatacgc cgacgcttaa acattcagga     1920
acaaatcctg cactagactc agaaggcaat tctgtatggg taactattaa cggacaagac     1980
gatatgacta ttgatagcgg atttatcaa acacctaaat atagcttagg gaactatgta     2040
tggtatgaca ctaataaaga tggtattcaa ggtgatgatg aaaaaggaat ctctggagta     2100
aaagtgacgt taaagatga aaacggaaat atcattagta caacaacaac tgatgaaaat     2160
ggaaagtatc aatttgataa tttaaatagt ggtaattata ttgttcattt tgataaacct     2220
tcaggtatga ctcaaacaac aacagattct ggtgatgatg acgaacagga tgctgatggg     2280
gaagaagtcc atgtaacaat tactgatcat gatgactta gtatagataa cggatactat      2340
gatgacgact cagattcaga tagtgattca gactcagata gcgacgactc agactccgat     2400
agcgattccg actcagacag cgactcagat tccgatagtg attcagattc agacagtgac     2460
tcagactcag atagtgattc agattcagac agcgattccg actcagacag tgactcagga     2520
ttagacaata gctcagataa gaatacaaaa gataaattac cggatacagg agctaatgaa     2580
gatcatgatt ctaaaggcac attacttgga gctttatttg caggtttagg agcgttatta     2640
ttagggaagc gtcgcaaaaa tagaaaaaat aaaaat                                2676
```

<210> SEQ ID NO 22
<211> LENGTH: 1452
<212> TYPE: DNA
<213> ORGANISM: Staphylococcus epidermidis

<400> SEQUENCE: 22

```
atgagtgaac gtatcagagt aagatatgcg ccaagtccaa caggatattt gcatattggt      60
aatgcaagaa cagcattatt caattattta tttgctaaac attataatgg tgattttgtt     120
gttcgcatcg aagatacaga tagtaaacgt aatttagaag atggtgaatc ttcacaattc     180
gataatctaa aatggttagg tttggattgg gatgaatctg tcgataaaga taaaggtttt     240
ggaccttatc gtcaatctga acgtgcagaa atctataatc cactaattca acagctatta     300
gaggaagaca agcatataa atgttatatg actgaagaag agttagaagc agagcgtgaa     360
gctcaaattg ctcgtggaga gatgccaaga tatggtggac aacatgcgca cttaacagaa     420
```

-continued

| | |
|---|---|
| gaacagcgtc aacagtacga agcggaaggg cgtaaaccat caattcgttt ccgtgtgcct | 480 |
| aaagatcaaa catatacttt caatgacatg gttaaaggag aaatttcctt tgaatctgac | 540 |
| aatatcggag actgggtaat tgtaaaaaaa gatggtgttc cgacttataa ttttgcagtt | 600 |
| gccgtagatg atcattatat gcaaatatca gatgttatac gtggtgatga ccatgtttca | 660 |
| aatacaccta agcagttaat gatatatgaa gcatttggat gggaagcacc tcgttttggt | 720 |
| catatgtcac tcattgttaa tgaagagcgt aaaaaattaa gcaagcgaga tggtcaaatc | 780 |
| ctacaatttta tcgagcaata tcgtgactta ggatatcttc cagaagcatt atttaacttt | 840 |
| attacattgt taggttggtc acctgaaggt gaagaggaaa tcttttctaa agaagaattt | 900 |
| ataaagattt ttgatgaaaa acgcttgtct aagtctccag ctatgttcga tagacaaaaa | 960 |
| cttgcttggg ttaacaatca gtatatgaaa acaaaagata cagaaacagt attcgaactt | 1020 |
| gcattacctc atttaatcaa ggctaatctt atacctgaaa acccatcaga aaggatagaa | 1080 |
| gaatggggac gtaaattaat agcgttgtat caaaaagaaa tgagttacgc tggtgaaatt | 1140 |
| gttccattat cagaaatgtt cttccatgaa atgccggaac ttggaaaaga tgaacaagag | 1200 |
| gtattacaag gagaacaagt gccagaacta atgaaccatt tatatggtaa attagaatct | 1260 |
| ttagaatcgt ttgaggcaac tgaaattaag aaaatgatta agaagttca aaaagaaact | 1320 |
| ggtattaaag gtaacaatt atttatgcct attcgtgttg ctgttactgg acaaatgcat | 1380 |
| ggtcctgaat tacctaacac aattgaagta ttaggcaaag ataaagtatt gtcacgctta | 1440 |
| aaaaaccttg tt | 1452 |

<210> SEQ ID NO 23
<211> LENGTH: 888
<212> TYPE: DNA
<213> ORGANISM: Staphylococcus epidermidis

<400> SEQUENCE: 23

| | |
|---|---|
| atggaatata aagatatagc aacaccatct cgaacacgtg ctttgcttga tcaatatggg | 60 |
| tttaattta agaaaagttt aggacaaaat tttctaatag atgtaaatat cattaataaa | 120 |
| attatcgaag cgagtcatat agattgtaca acgggtgtaa ttgaagttgg accaggtatg | 180 |
| ggatcattga ctgaacaact tgcaaagaat gctaagaagg tgatggcttt tgaaattgat | 240 |
| caaagattaa tacctgtgct taaagataca ctttcaccat acgataatgt aacaattatc | 300 |
| aatgaagata tacttaaagc tgatattgct aaagctgtag atacacatct acaagattgt | 360 |
| gacaagatta tggttgttgc taatttaccg tattatatta ccacacctat tttacttaat | 420 |
| ttgatgcaac aggatgtacc tattgatggt tttgtcgtaa tgatgcaaaa agaggtagga | 480 |
| gaacgtttga acgctcaagt aggtaccaaa gcatacggtt cgttatcgat tgttgctcaa | 540 |
| tactatacgg agacaagtaa agttttaaca gttcctaaaa ctgtatttat gcctcctcca | 600 |
| aacgttgatt ctatcgttgt aaaattgatg caacgccaag aaccacttgt acaggttgat | 660 |
| gatgaggaag gcttttttaa gttagcaaag gccgcttttg cacaacgacg taaaacaatt | 720 |
| aataataact accaaaactt ctttaaagat ggtaagaaga ataagaaac tatacgacag | 780 |
| tggctagaaa gcgctggtat tgatcctaaa agacgtggag aaacactcac gattcaagat | 840 |
| ttcgccacat tatatgaaca aagaaaaaa ttctccgaat taacaaat | 888 |

<210> SEQ ID NO 24
<211> LENGTH: 318
<212> TYPE: DNA
<213> ORGANISM: Staphylococcus epidermidis

```
<400> SEQUENCE: 24
atgacgtcaa atcatcatgc cccttatgat ttgggctaca cacgtgctac aatggacaat      60
acaaagggca gcgaaaccgc gaggtcaagc aaatcccata agttgttct cagttcggat       120 tgtagtctgc aactcgacta tatgaagctg aatcgctag taatcgtaga tcagcatgct       180
acggtgaata cgttcccggg tcttgtacac accgcccgtc acaccacgag agtttgtaac      240
acccgaagcc ggtggagtaa ccatttggag ctagccgtcg aaggtgggac aaatgattgg      300
ggtgaagtcg taacaagg                                                    318

<210> SEQ ID NO 25
<211> LENGTH: 1326
<212> TYPE: DNA
<213> ORGANISM: Staphylococcus epidermidis

<400> SEQUENCE: 25 atgttttta aacaatttta tgataaacac ttatctcaag catcttattt aatcggttgt       60 caaaaactg gagaagccat gattattgat cctattcgtg acttatcttc atatattcga       120
gttgctgatg aagaaggttt aaccattact catgcagctg aaacacatat acatgcagat      180
tttgcttcag gaattagaga tgttgctata agttaaatg ctagtattta tgtatcgggt       240
gaaagtgatg acacgttagg ttataaaaat atgcctaacc agactcattt tgttcaacat      300
aatgatgata tttatgtagg aaatataaaa ttaaagtgc ttcatacacc tggtcacacg       360
ccagaaagta taagtttttt acttactgat gaaggtgctg gagcacaagt tccaatggga      420
ctattcagtg gtgatttat ttttgtagga gatatcggta gacctgattt actagaaaaa       480
gctgttaaag tagaaggatc atctgaaata ggcgctaaac aaatgtttaa atctattgaa      540
agtattaaag acttgccaaa ctacattcaa atttggcctg gccatggagc tggtagtcct       600
tgtggtaaat ctttaggtgc tattccaaca tctactcttg gctatgaaaa acaaacaaac      660
tgggcttttt ctgaaaataa cgaagctacc tttatcgata aactaatttc tgaccaacct      720
gcaccaccac atcattttgc acaaatgaaa aaaattaatc aattcggtat gaattttatat      780 caaccttata cggtttatcc agctacaaat acaaacagat taacttttga tctccgcagt      840
aaggaggctt atcatggtgg acatattgaa ggtacaatca atattccata tgataaaaat      900
ttcatcaatc aaattggctg gtatctaaac tatgatcaag aaattaactt gattggagaa      960
tatcaccttg tttcaaaagc aacacacacc ttacaactca ttggatatga tgatgttgct     1020
ggatatcaat tacctcaatc taagattcaa acacgttcca ttcatagtga agatattaca     1080
ggtaacgaat cacatatatt agatgtacgt aatgataatg aatggaataa tggccactta     1140
tctcaagcgg ttcatgtacc acacggcaaa cttttagaaa cagatttacc tttcaataga     1200
aacgatgtta tttatgtaca ctgtcagtct ggcattagaa gttcgatagc tattggtatt     1260
ttagaacata aaggttatca caacattatt aatgtaaatg aaggttacaa agatatacac     1320
ctttct                                                                1326

<210> SEQ ID NO 26
<211> LENGTH: 855
<212> TYPE: DNA
<213> ORGANISM: Staphylococcus epidermidis

<400> SEQUENCE: 26
ttgaaaaaaa ttctggtgtt aagtttaacg gcatttttag ttttggctgg ttgtaattca      60
ggtgataaga ctgatactaa agataagaaa gaagaaacaa agcaaacttc aaaggcaaat     120
```

-continued

| | |
|---|---|
| aaagagaaca aagaacaaca tcataagcaa gagaatgata ataaggcttc aactcaattg | 180 |
| tcagaaaaag aaaggttagc attagcattt tatgcggatg gagtagaaaa atatatgtta | 240 |
| actaaaaacg aagtgttgac aggcgtgtat gattatcaaa aaggaaatga aacagagaag | 300 |
| aaacaaatgg aacaattgat gttagaaaaa gctgattcga tgaaaaatgc gccaaaggat | 360 |
| atgaaatttt atcaagttta tccgtctaaa ggacagttcg cttcaattgt tggtgtaaat | 420 |
| aaaaataaaa tatttatagg tagtacgcaa ggcgcactga ttgattatca acattatta | 480 |
| aataatggca aggagttaga tattagtcaa ttgtatgaag ataataaaga caatcgctca | 540 |
| ttggaagaaa tgaagaataa aatagagatt gttgatagtg gagcagctca aaaagctgat | 600 |
| gatcctgata aaaattctgc aaatacgatg gcacatatga aagtcaaat ttatgaaaaa | 660 |
| ataagtgact tgatggtaa gttagataat aaaacttatc tatgggacaa tattagaatc | 720 |
| aatgacgatg gtaattggac agttcattac cgtaatcatg atggtgaaat tatgggtact | 780 |
| tataagagtg agaaaaataa aattattaaa cttgatcaaa atggaaataa aattaaagaa | 840 |
| caacaaatgt ctaat | 855 |

<210> SEQ ID NO 27
<211> LENGTH: 1494
<212> TYPE: DNA
<213> ORGANISM: Staphylococcus epidermidis

<400> SEQUENCE: 27

| | |
|---|---|
| atggctaata aagagtcaaa aaatgttgtt attattggcg ctggtgtctt aagtacgaca | 60 |
| tttggttcta tgattaaaga attagaacct gattggaaca tcaaactcta tgaacgctta | 120 |
| gatcgtccag gtattgaaag ttctaacgaa agaaacaatg ccggtacagg acatgcggcg | 180 |
| ttatgtgaat tgaactatac agtacaacaa cctgatggtt caattgatat agaaaaagcc | 240 |
| aaagaaatca cgaacaatt cgagatttca aacaattct ggggtcactt agtaaaaagt | 300 |
| ggtaacatca gtaaccctag agatttcatt aatccactc ctcacattag tttcgtaaga | 360 |
| ggtaaaaata cgttaaatt cttaaaaaac cgttacgaag caatgcgtaa cttccctatg | 420 |
| ttcgataaca tcgaatatac agaagatatc gaagaaatga aaaatggat gccattaatg | 480 |
| atgacaggtc gtactggtaa cgaaatcatg gcggctagta aaatcgacga aggtacagat | 540 |
| gttaactacg tgaattaac tcgtaaatg gcaaaagta ttgaaaaaca tccaaatgct | 600 |
| gatgttcaat acaaccacga agtaattaat ttcaatcgtc gtaaagacgg tatttgggaa | 660 |
| gttaaagtta aaaaccgtaa ttctggagac gttgaaactg ttctagctga ttatgtattt | 720 |
| atcggtgcag gcggtggcgc tattccacta ttacaaaaaa ctggtatccc agaaagtaaa | 780 |
| catcttggtg gattccctat cagtggtcag ttcttaattt gtacaaaccc tgatgtaatt | 840 |
| aatgaacatg acgtcaaagt atatggtaaa gaaccaccag gcacacctcc aatgactgta | 900 |
| ccacatttag atacacgtta tatcgatggt gaaagaacat tattatttgg accatttgca | 960 |
| aatattggcc ctaaattctt aagaaacggt tctaacttag acttattcaa atcagttaaa | 1020 |
| ccttataaca tcacaacatt actagcatct gcagttaaaa acttaccttt aatcaaatac | 1080 |
| tctatcgacc aagtattaat gactaaagaa ggttgtatga accatctacg cacgttctac | 1140 |
| cctgaagctc gtgacgaaga ttggcaatta tacactgcag gtaaacgtgt tcaagttatc | 1200 |
| aaagatacta agaacacgg taaggattc attcaatttg gtacagaagt tgttaactct | 1260 |
| aaagaccact ctgttatcgc actattgggt gaatcacctg gagcatcaac ttcagtatca | 1320 |
| gtagccctag aagtttttaga gaaaaacttt gctgagtatg aaaaagattg gactccaaaa | 1380 |

```
ttacaaaaaa tgatcccatc atatggtaaa tctcttatcg atgatgttaa gttaatgaga   1440
gcaactcgta aacaaacatc taaagattta gaattaaatt attacgaatc taaa          1494

<210> SEQ ID NO 28
<211> LENGTH: 1548
<212> TYPE: DNA
<213> ORGANISM: Staphylococcus epidermidis

<400> SEQUENCE: 28
atgaaaatat ttaaaacttt aagttctata ctagttacat ctgttctttc tgtgactgtg     60
attccctcaa catttgcatc aacagaatct actgctacaa atcagacaca acaaacagta    120 cttttgata attctcatgc tcaaactgcg ggcgctgccg attgggtgat tgatggcgct     180
ttctcagatt atgcagattc aatgagaaag caaggttacc aagttaaaga actgaaggaa    240
gaatcaaaca tttctgatca atctttacag caggcgcatg tattagttat tcccgaagct    300
aacaatccat ttaaagaaaa tgagcagaaa gcaatcatta ttttgttaa aaatggtggt     360 agcgtcattt tcatctcaga ccattataat gccgatcgta atttaaatcg tattgattct    420
tcagaatcaa tgaatggtta tcgacgtggc gcatacgaaa atatgactaa agatatgaat    480
aatgaagaaa agaattctaa cgttatgcat aacgttaaga gttctgattg gctctcacaa    540
aacttcggtg ttcgctttag atataatgca cttggagata tcaatactca aaatatcgtt    600
tcaagcaaag atagttttgg tattactaaa ggtgtacaat cagtttcgat gcacgcaggt    660
tcaacattag caataactga tcctaataaa gctaaaggca tatttatat gccggaacat     720 ttaacgcata gtcaaaaatg gcctcacgca gttgatcaag gtatttacaa tgggggtggc    780
atcaacgaag gaccttatgt agccatttca aaaatcggca aggtaaagc tgcatttatt     840 ggcgatagct ccctcgtaga agatcgttca cctaaatatc ttcgtgaaga taatgggaaa    900
cctaaaaaaa cgtacgatgg ttttaaagaa caagataatg gaaagttatt aaataattta    960
acaacatggc taggcaaaaa agaatctcaa tcttctatga agacatggg gattaaactt    1020 gataataaaa caccgctact taactttgag caacctgaga attcaattga acctcaaaaa    1080
gaaccgtgga ctaacccaat agaaggttac aaatggtatg atcgttcaac atttaaaaca    1140
ggtagttatg aagtaatca acggggtgct gacgatggag tagatgacaa aagctcttct    1200
catcaaaatc aaaatgccaa agttgaatta actttacctc aaaatatcca accgcatcat    1260
ccatttcaat ttacaatcaa actcacggga tatgagccta atagcacaat tagcgatgta    1320
agagttggac tttataaaga tggaggtaag caaatcggta gcttttcttc taaccgtaac    1380
caattcaata ctctcggcta tagtcctggc caatcaatta aagcaaatgg tgcgggtgaa    1440
gcttcattca cactcacagc taaagtgaca gatgaaatta aagatgctaa tattcgtgtt    1500
aaacaaggga aaaaaattct attaactcaa aaaatgaatg aaaattttt                1548

<210> SEQ ID NO 29
<211> LENGTH: 252
<212> TYPE: DNA
<213> ORGANISM: Staphylococcus epidermidis

<400> SEQUENCE: 29
ggtacaccat tagaattagt ttttgtcaat actttaggac ctaaaccttg tttcgctaaa     60
ccaaataaaa ttctactatt agaatatatt ccgctatttg ttgcagatgc tgctgctgtt    120 aaacaacaa aattaactat gccagcagca aagggaacac caattagtgt gaataattta    180
acaaacggac tactatcagg atcaacttta aaccatggaa tgacagacat gattacaagt    240
```

```
aaaccaccta ta                                                          252
```

<210> SEQ ID NO 30
<211> LENGTH: 162
<212> TYPE: DNA
<213> ORGANISM: Staphylococcus epidermidis

<400> SEQUENCE: 30

```
tcatcgttaa gtaccataat tcctttttct ttaggagcat taggcaaatt taattctttc      60
attgagcaaa tcataccact agaatctacc ccacgtaatt gggcatcttt aattaccatt     120
ccgcttggca taacggcccc aacttttgca acaacgacct tc                        162
```

<210> SEQ ID NO 31
<211> LENGTH: 348
<212> TYPE: DNA
<213> ORGANISM: Staphylococcus aureus

<400> SEQUENCE: 31

```
atgaaattta aaaatatat attaacagga acattagcat tactttatc atcaactggg       60 atagcaacta tagaagggaa taaagcagat gcaagtagtc tggacaaata tttaactgaa    120
agtcagtttc atgataaacg catagcagaa gaattaagaa ctttacttaa caaatcgaat    180
gtatatgcat tagctgcagg aagcttaaat ccatattata aacgtacgat tatgatgaat    240
gaatatagag ctaaagcggc acttaagaaa aatgatttcg tatcaatggc tgatgctaaa    300
gttgcattag aaaaaatata caagaaaatt gatgaaatta taaataga                 348
```

<210> SEQ ID NO 32
<211> LENGTH: 676
<212> TYPE: PRT
<213> ORGANISM: Staphylococcus epidermidis

<400> SEQUENCE: 32

```
Met Lys Arg Thr Asp Lys Ile Gly Val Tyr Leu Lys Leu Ser Cys Ser
1               5                   10                  15

Ala Leu Leu Leu Ser Gly Ser Leu Val Gly Tyr Gly Phe Thr Lys Asp
            20                  25                  30

Ala Phe Ala Asp Ser Glu Ser Thr Ser Ser Asn Val Glu Asn Thr Ser
        35                  40                  45

Asn Ser Asn Ser Ile Ala Asp Lys Ile Gln Gln Ala Lys Asp Asp Ile
    50                  55                  60

Lys Asp Leu Lys Glu Leu Ser Asp Ala Asp Ile Lys Ser Phe Glu Glu
65                  70                  75                  80

Arg Leu Asp Lys Val Asp Asn Gln Ser Ser Ile Asp Arg Ile Ile Asn
                85                  90                  95

Asp Ala Lys Asp Lys Asn Asn His Leu Lys Ser Thr Asp Ser Ser Ala
            100                 105                 110

Thr Ser Ser Lys Thr Glu Asp Asp Thr Ser Glu Lys Asp Asn Asn Asp
        115                 120                 125

Asp Met Thr Lys Asp Leu Asp Lys Ile Leu Ser Asp Leu Asp Ser Ile
    130                 135                 140

Ala Lys Asn Val Asp Asn Arg Gln Gln Gly Glu Glu Arg Ala Ser Lys
145                 150                 155                 160

Pro Ser Asp Ser Thr Thr Asp Glu Lys Asp Asp Ser Asn Asn Lys Val
                165                 170                 175

His Asp Thr Asn Ala Ser Thr Arg Asn Ala Thr Thr Asp Ser Glu
            180                 185                 190
```

-continued

```
Glu Ser Val Ile Asp Lys Leu Asp Lys Ile Gln Gln Asp Phe Lys Ser
            195                 200                 205

Asp Ser Asn Asn Asn Pro Ser Glu Gln Ser Asp Gln Gln Ala Ser Pro
    210                 215                 220

Ser Asn Lys Thr Glu Asn Asn Lys Glu Ser Ser Thr Thr Thr Asn
225                 230                 235                 240

Gln Ser Asp Ser Asp Ser Lys Asp Asp Lys Ser Asn Asp Gly His Arg
                245                 250                 255

Ser Thr Leu Glu Arg Ile Ala Ser Asp Thr Asp Gln Ile Arg Asp Ser
            260                 265                 270

Lys Asp Gln His Val Thr Asp Glu Lys Gln Asp Ile Gln Ala Ile Thr
            275                 280                 285

Arg Ser Leu Gln Gly Ser Asp Lys Ile Glu Lys Ala Leu Ala Lys Val
            290                 295                 300

Gln Ser Asp Asn Gln Ser Leu Asp Ser Asn Tyr Ile Asn Asn Lys Leu
305                 310                 315                 320

Met Asn Leu Arg Ser Leu Asp Thr Lys Val Glu Asp Asn Asn Thr Leu
                325                 330                 335

Ser Asp Asp Lys Lys Gln Ala Leu Lys Gln Glu Ile Asp Lys Thr Lys
            340                 345                 350

Gln Ser Ile Asp Arg Gln Arg Asn Ile Ile Ile Asp Gln Leu Asn Gly
            355                 360                 365

Ala Ser Asn Lys Lys Gln Ala Thr Glu Asp Ile Leu Asn Ser Val Phe
    370                 375                 380

Ser Lys Asn Glu Val Glu Asp Ile Met Lys Arg Ile Lys Thr Asn Gly
385                 390                 395                 400

Arg Ser Asn Glu Asp Ile Ala Asn Gln Ile Ala Lys Gln Ile Asp Gly
                405                 410                 415

Leu Ala Leu Thr Ser Ser Asp Ile Leu Lys Ser Met Leu Asp Gln
            420                 425                 430

Ser Lys Asp Lys Glu Ser Leu Ile Lys Gln Leu Leu Thr Thr Arg Leu
    435                 440                 445

Gly Asn Asp Glu Ala Asp Arg Ile Ala Lys Lys Leu Leu Ser Gln Asn
    450                 455                 460

Leu Ser Asn Ser Gln Ile Val Glu Gln Leu Lys Arg His Phe Asn Ser
465                 470                 475                 480

Gln Gly Thr Ala Thr Ala Asp Asp Ile Leu Asn Gly Val Ile Asn Asp
                485                 490                 495

Ala Lys Asp Lys Arg Gln Ala Ile Glu Thr Ile Leu Gln Thr Arg Ile
            500                 505                 510

Asn Lys Asp Lys Ala Lys Ile Ile Ala Asp Val Ile Ala Arg Val Gln
            515                 520                 525

Lys Asp Lys Ser Asp Ile Met Asp Leu Ile His Ser Ala Ile Glu Gly
            530                 535                 540

Lys Ala Asn Asp Leu Leu Asp Ile Glu Lys Arg Ala Lys Gln Ala Lys
545                 550                 555                 560

Lys Asp Leu Glu Tyr Ile Leu Asp Pro Ile Lys Asn Arg Pro Ser Leu
                565                 570                 575

Leu Asp Arg Ile Asn Lys Gly Val Gly Asp Ser Asn Ser Ile Phe Asp
            580                 585                 590

Arg Pro Ser Leu Leu Asp Lys Leu His Ser Arg Gly Ser Ile Leu Asp
            595                 600                 605

Lys Leu Asp His Ser Ala Pro Glu Asn Gly Leu Ser Leu Asp Asn Lys
            610                 615                 620
```

```
Gly Gly Leu Leu Ser Asp Leu Phe Asp Asp Gly Asn Ile Ser Leu
625                 630                 635                 640

Pro Ala Thr Gly Glu Val Ile Lys Gln His Trp Ile Pro Val Ala Val
            645                 650                 655

Val Leu Met Ser Leu Gly Gly Ala Leu Ile Phe Met Ala Arg Arg Lys
            660                 665                 670

Lys His Gln Asn
        675

<210> SEQ ID NO 33
<211> LENGTH: 655
<212> TYPE: PRT
<213> ORGANISM: Staphylococcus epidermidis

<400> SEQUENCE: 33

Met Lys Lys Asn Lys Phe Leu Val Tyr Leu Leu Ser Thr Ala Leu Ile
1               5                   10                  15

Thr Pro Thr Phe Ala Thr Gln Thr Ala Phe Ala Glu Asp Ser Ser Asn
            20                  25                  30

Lys Asn Thr Asn Ser Asp Lys Met Glu Gln His Gln Ser Gln Lys Glu
        35                  40                  45

Thr Ser Lys Gln Ser Glu Lys Asp Glu Phe Asn Asn Asp Asp Ser Lys
50                  55                  60

His Asp Ser Asp Asp Lys Lys Ser Thr Ser Asp Ser Lys Asp Lys Asp
65                  70                  75                  80

Ser Asn Lys Pro Leu Ser Ala Asp Ser Thr His Arg Asn Tyr Lys Met
                85                  90                  95

Lys Asp Asp Asn Leu Val Asp Gln Leu Tyr Asp Asn Phe Lys Ser Gln
            100                 105                 110

Ser Val Asp Phe Ser Lys Tyr Trp Glu Pro Asn Lys Tyr Glu Asp Ser
        115                 120                 125

Phe Ser Leu Thr Ser Leu Ile Gln Asn Leu Phe Asp Phe Asp Ser Asp
    130                 135                 140

Ile Thr Asp Tyr Glu Gln Pro Gln Lys Thr Ser His Ser Ser Asn Asp
145                 150                 155                 160

Glu Lys Asp Gln Val Asp Gln Ala Asp Gln Ala Lys Gln Pro Ser Gln
                165                 170                 175

His Gln Glu Pro Ser Gln Ser Ser Ala Lys Gln Asp Gln Glu Pro Ser
            180                 185                 190

Asn Asp Glu Lys Glu Lys Thr Thr Asn His Gln Ala Asp Ser Asp Val
        195                 200                 205

Ser Asp Leu Leu Gly Glu Met Asp Lys Glu Asp Gln Glu Gly Glu Asn
    210                 215                 220

Val Asp Thr Asn Lys Asn Gln Ser Ser Glu Gln Gln Gln Thr Gln
225                 230                 235                 240

Ala Asn Asp Asp Ser Ser Glu Arg Asn Lys Lys Tyr Ser Ser Ile Thr
                245                 250                 255

Asp Ser Ala Leu Asp Ser Ile Leu Asp Glu Tyr Ser Gln Asp Ala Lys
            260                 265                 270

Lys Thr Glu Lys Asp Tyr Asn Lys Ser Lys Asn Thr Ser His Thr Lys
        275                 280                 285

Thr Ser Gln Ser Asp Asn Ala Asp Lys Asn Pro Gln Leu Pro Thr Asp
    290                 295                 300

Asp Glu Leu Lys His Gln Ser Lys Pro Ala Gln Ser Phe Glu Asp Asp
305                 310                 315                 320
```

```
Ile Lys Arg Ser Asn Thr Arg Ser Thr Ser Leu Phe Gln Gln Leu Pro
                325                 330                 335

Glu Leu Asp Asn Gly Asp Leu Ser Ser Asp Ser Phe Asn Val Val Asp
                340                 345                 350

Ser Gln Asp Thr Arg Asp Phe Ile Gln Ser Ile Ala Lys Asp Ala His
                355                 360                 365

Gln Ile Gly Lys Asp Gln Asp Ile Tyr Ala Ser Val Met Ile Ala Gln
                370                 375                 380

Ala Ile Leu Glu Ser Asp Ser Gly Lys Ser Ser Leu Ala Gln Ser Pro
385                 390                 395                 400

Asn His Asn Leu Phe Gly Ile Lys Gly Asp Tyr Lys Gly Gln Ser Val
                405                 410                 415

Thr Phe Asn Thr Leu Glu Ala Asp Ser Ser Asn His Met Phe Ser Ile
                420                 425                 430

Gln Ala Gly Phe Arg Lys Tyr Pro Ser Thr Lys Gln Ser Leu Glu Asp
                435                 440                 445

Tyr Ala Asp Leu Ile Lys His Gly Ile Asp Gly Asn Pro Ser Ile Tyr
                450                 455                 460

Lys Pro Thr Trp Lys Ser Glu Ala Leu Ser Tyr Lys Asp Ala Thr Ser
465                 470                 475                 480

His Leu Ser Arg Ser Tyr Ala Thr Asp Pro Asn Tyr Ser Lys Lys Leu
                485                 490                 495

Asn Ser Ile Ile Lys His Tyr His Leu Thr Ser Phe Asp Lys Glu Lys
                500                 505                 510

Met Pro Asn Met Lys Lys Tyr Asn Lys Ser Ile Gly Thr Asp Val Ser
                515                 520                 525

Gly Asn Asp Phe Lys Pro Phe Thr Glu Thr Ser Gly Thr Ser Pro Tyr
                530                 535                 540

Pro His Gly Gln Cys Thr Trp Tyr Val Tyr His Arg Met Asn Gln Phe
545                 550                 555                 560

Asp Ala Ser Ile Ser Gly Asp Leu Gly Asp Ala His Asn Trp Asn Asn
                565                 570                 575

Arg Ala Glu Ser Glu Gly Tyr Thr Val Thr His Thr Pro Lys Asn His
                580                 585                 590

Thr Ala Val Val Phe Glu Ala Gly Gln Leu Gly Ala Asp Thr Gln Tyr
                595                 600                 605

Gly His Val Ala Phe Val Glu Lys Val Asn Asp Asp Gly Ser Ile Val
                610                 615                 620

Ile Ser Glu Ser Asn Val Lys Gly Leu Gly Val Ile Ser Phe Arg Thr
625                 630                 635                 640

Ile Asp Ala Gly Asp Ala Gln Asp Leu Asp Tyr Ile Lys Gly Lys
                645                 650                 655

<210> SEQ ID NO 34
<211> LENGTH: 164
<212> TYPE: PRT
<213> ORGANISM: Staphylococcus epidermidis

<400> SEQUENCE: 34

Met Ile Arg Phe Ala Arg Leu Glu Asp Leu Gln Asp Ile Leu Thr Ile
1               5                   10                  15

Tyr Asn Asp Ala Ile Leu Asn Thr Thr Ala Val Tyr Thr Tyr Lys Pro
                20                  25                  30

Gln Gln Leu Asp Glu Arg Leu Gly Trp Tyr Gln Ser Lys Ala Lys Ile
                35                  40                  45
```

```
Asn Glu Pro Ile Trp Val Tyr Glu Lys Glu Gly Lys Val Val Gly Phe
        50                  55                  60

Ala Thr Tyr Gly Ser Phe Arg Gln Trp Pro Ala Tyr Leu Tyr Thr Ile
 65                  70                  75                  80

Glu His Ser Ile Tyr Val His Gln Gln Tyr Arg Gly Leu Gly Ile Ala
                     85                  90                  95

Ser Gln Leu Leu Glu Asn Leu Ile Arg Tyr Ala Lys Glu Gln Gly Tyr
                100                 105                 110

Arg Thr Ile Val Ala Gly Ile Asp Ala Ser Asn Met Asp Ser Ile Ala
                115                 120                 125

Leu His Lys Lys Phe Asp Phe Ser His Ala Gly Thr Ile Lys Asn Val
        130                 135                 140

Gly Tyr Lys Phe Asp Arg Trp Leu Asp Leu Ser Phe Tyr Gln Tyr Asp
145                 150                 155                 160

Leu Ser Asp Ser

<210> SEQ ID NO 35
<211> LENGTH: 952
<212> TYPE: PRT
<213> ORGANISM: Staphylococcus epidermidis

<400> SEQUENCE: 35

Leu Ser Asn Leu Ile Gln Asp Ile Lys Gln Ser Leu Tyr Lys Gly Phe
 1               5                  10                  15

Ile Asp Lys Asp Ser Ser His Lys Gly Asn Phe Val Pro Arg Leu Leu
                20                  25                  30

Val Asn Asn Lys Glu Glu Asn Val Leu Ser Thr Ile Ile Asp Gln Leu
                35                  40                  45

His Asn Cys Gln Ser Phe Cys Ile Ser Val Ala Phe Ile Thr Glu Ser
        50                  55                  60

Gly Leu Ala Ser Leu Lys Ser His Phe Tyr Asp Leu Ser Lys Lys Gly
 65                  70                  75                  80

Val Lys Gly Arg Ile Ile Thr Ser Asn Tyr Leu Gly Phe Asn Ser Pro
                 85                  90                  95

Lys Met Phe Glu Glu Leu Leu Lys Leu Glu Asn Val Glu Val Lys Leu
                100                 105                 110

Thr Asn Ile Glu Gly Phe His Ala Lys Gly Tyr Ile Phe Glu His His
                115                 120                 125

Asn His Thr Ser Phe Ile Ile Gly Ser Ser Asn Leu Thr Ser Asn Ala
        130                 135                 140

Leu Lys Leu Asn Tyr Glu His Asn Leu Phe Leu Ser Thr His Lys Asn
145                 150                 155                 160

Gly Asp Leu Val Asn Asn Ile Lys Tyr Lys Phe Asp Glu Leu Trp Asp
                165                 170                 175

Ser Ser Phe Ser Leu Thr Asn Glu Trp Ile Asn Glu Tyr Lys Gln Ser
                180                 185                 190

Phe Glu Tyr Gln Thr Leu Gln Lys Val Phe Asp Asn Thr Val Val Gln
                195                 200                 205

Asn Ser Asp Ile Lys Lys Phe Asn Glu Ser Lys Leu Ile Lys Pro Asn
        210                 215                 220

Leu Met Gln Glu His Ala Leu Lys Ser Leu Glu Ser Leu Arg Asn Val
225                 230                 235                 240

Gly Glu Glu Lys Gly Leu Ile Ile Ser Ala Thr Gly Thr Gly Lys Thr
                245                 250                 255
```

```
Ile Leu Cys Ala Leu Asp Val Arg Ala Tyr Ser Pro Asp Lys Phe Leu
                260                 265                 270

Phe Ile Val His Asn Glu Gly Ile Leu Asn Arg Ala Ile Glu Glu Phe
                275                 280                 285

Lys Lys Val Phe Pro Tyr Glu Asp Ser Asn Phe Gly Leu Leu Thr
            290                 295                 300

Gly Lys Arg Lys Asp His Asp Ala Lys Phe Leu Phe Ala Thr Ile Gln
305                 310                 315                 320

Thr Leu Ser Lys Lys Glu Asn Tyr Lys Leu Phe Asn Ser Asn His Phe
                325                 330                 335

Asp Tyr Ile Val Phe Asp Glu Ala His Arg Ile Ala Ala Ser Ser Tyr
                340                 345                 350

Gln Lys Ile Phe Asn Tyr Phe Lys Pro Asn Phe Leu Leu Gly Met Thr
                355                 360                 365

Ala Thr Pro Glu Arg Thr Asp Glu Leu Asn Ile Phe Glu Leu Phe Asn
            370                 375                 380

Tyr Asn Ile Ala Tyr Glu Ile Arg Leu Gln Glu Ala Leu Glu Ser Asn
385                 390                 395                 400

Ile Leu Cys Pro Phe His Tyr Phe Gly Val Thr Asp Tyr Ile Gln Asn
                405                 410                 415

Glu Met Ser Gln Glu Asp Ala Phe Asn Leu Lys Tyr Leu Ala Ser Asn
                420                 425                 430

Glu Arg Val Glu His Ile Ile Lys Lys Thr Asn Tyr Tyr Gly Tyr Ser
            435                 440                 445

Gly Asp Val Leu Lys Gly Leu Ile Phe Val Ser Arg Gly Glu Ala
450                 455                 460

Tyr Gln Leu Ala Asn Gln Leu Ser Lys Arg Gly Ile Ser Ser Val Gly
465                 470                 475                 480

Leu Thr Gly Lys Asp Ser Ile Ala Tyr Arg Ala Glu Thr Ile Gln Gln
            485                 490                 495

Leu Lys Glu Gly Ser Ile Asn Tyr Ile Ile Thr Val Asp Leu Phe Asn
                500                 505                 510

Glu Gly Ile Asp Ile Pro Glu Ile Asn Gln Val Val Met Leu Arg Pro
            515                 520                 525

Thr Lys Ser Ser Ile Ile Phe Ile Gln Gln Leu Gly Arg Gly Leu Arg
            530                 535                 540

Lys Ser Thr Asn Lys Glu Phe Val Thr Val Ile Asp Phe Ile Gly Asn
545                 550                 555                 560

Tyr Lys Thr Asn Tyr Met Ile Pro Ile Ala Leu Ser Gly Asn Lys Ser
                565                 570                 575

Gln Asn Lys Asp Asn Tyr Arg Lys Phe Leu Thr Asp Thr Thr Val Leu
            580                 585                 590

Asn Gly Val Ser Thr Ile Asn Phe Glu Glu Val Ala Lys Asn Lys Ile
            595                 600                 605

Tyr Asn Ser Leu Asp Ser Val Lys Leu Asn Gln Pro Lys Leu Ile Lys
            610                 615                 620

Glu Ala Phe Asn Asn Val Lys Asp Arg Ile Gly Lys Leu Pro Leu Leu
625                 630                 635                 640

Met Asp Phe Ile Asn Asn Asp Ser Ile Asp Pro Ser Val Ile Phe Ser
                645                 650                 655

Arg Phe Lys Asn Tyr Tyr Glu Phe Leu Ile Lys Asn Lys Ile Ile Glu
                660                 665                 670

Asn Glu Leu Ser Ile Asn Glu Phe Lys Asn Leu Thr Phe Leu Ser Arg
                675                 680                 685
```

```
Gln Leu Thr Pro Gly Leu Lys Lys Val Asp Ile Asp Val Leu Lys Glu
    690                 695                 700

Ile Ile Gln Asn Asp Val Thr Tyr Glu Asn Leu Thr Lys Lys Met Leu
705                 710                 715                 720

Asn Ile Asn Asn Asp Ile Ser Glu Tyr Asp Ile Asn Thr Ser Leu Ser
                725                 730                 735

Ile Leu Asp Phe Thr Phe Phe Lys Lys Thr Ile Gly Lys Thr Tyr Gly
            740                 745                 750

Leu Pro Leu Ile Gln Tyr Lys Asp Asn Leu Ile Cys Leu Ala Asn Glu
        755                 760                 765

Phe Lys Glu Ala Leu Asn Lys Pro Leu Phe Asn Thr Phe Ile His Asp
770                 775                 780

Leu Ile Asp Leu Ala Asn Tyr Asn Asn Asp Arg Tyr Gln Asn Lys Lys
785                 790                 795                 800

Asn Ser Leu Ile Leu Tyr Asn Lys Tyr Ser Arg Glu Asp Phe Val Lys
                805                 810                 815

Leu Leu Asn Trp Asp Lys Asp Glu Ser Gly Thr Ile Asn Gly Tyr Arg
            820                 825                 830

Met Lys His Arg Thr Leu Pro Leu Phe Ile Thr Tyr Asp Lys His Glu
        835                 840                 845

Asn Ile Ser Asp Asn Thr Lys Tyr Asp Asp Glu Phe Leu Ser Gln Asp
850                 855                 860

Glu Leu Lys Trp Tyr Thr Arg Ser Asn Arg Lys Leu Thr Ser Pro Glu
865                 870                 875                 880

Val Gln Asn Ile Leu Lys His Glu Glu Ser Asn Thr Asp Met Tyr Ile
                885                 890                 895

Phe Val Lys Lys Arg Asp Asp Glu Gly Lys Tyr Phe Tyr Tyr Leu Gly
            900                 905                 910

Lys Ala Lys Tyr Ile Lys Gly Thr Glu Lys Gln Asp Tyr Met Pro Asn
        915                 920                 925

Gly Asn Ser Val Val Thr Met His Leu Ser Met Asn Thr Ser Ile Arg
930                 935                 940

Asp Asp Ile Tyr Arg Tyr Ile Thr
945                 950

<210> SEQ ID NO 36
<211> LENGTH: 325
<212> TYPE: PRT
<213> ORGANISM: Staphylococcus epidermidis

<400> SEQUENCE: 36

Met Thr Lys Ser Gln Gln Lys Val Ser Ser Ile Glu Lys Leu Ser Asn
1               5                   10                  15

Gln Glu Gly Ile Ile Ser Ala Leu Ala Phe Asp Gln Arg Gly Ala Leu
                20                  25                  30

Lys Arg Met Met Ala Glu His Gln Ser Glu Thr Pro Thr Val Glu Gln
            35                  40                  45

Ile Glu Gln Leu Lys Val Leu Val Ser Glu Glu Leu Thr Gln Tyr Ala
        50                  55                  60

Ser Ser Ile Leu Leu Asp Pro Glu Tyr Gly Leu Pro Ala Ser Asp Ala
65                  70                  75                  80

Arg Asn Asn Asp Cys Gly Leu Leu Ala Tyr Glu Lys Thr Gly Tyr
                85                  90                  95

Asp Val Asn Ala Lys Gly Arg Leu Pro Asp Cys Leu Val Glu Trp Ser
            100                 105                 110
```

```
Ala Lys Arg Leu Lys Glu Gln Gly Ala Asn Ala Val Lys Phe Leu Leu
        115                 120                 125

Tyr Tyr Asp Val Asp Asp Thr Glu Glu Ile Asn Ile Gln Lys Lys Ala
130                 135                 140

Tyr Ile Glu Arg Ile Gly Ser Glu Cys Val Ala Glu Asp Ile Pro Phe
145                 150                 155                 160

Phe Leu Glu Val Leu Thr Tyr Asp Asp Asn Ile Pro Asp Asn Lys Ser
                165                 170                 175

Ala Glu Phe Ala Lys Val Lys Pro Arg Lys Val Asn Glu Ala Met Lys
            180                 185                 190

Leu Phe Ser Glu Asp Arg Phe Asn Val Asp Val Leu Lys Val Glu Val
        195                 200                 205

Pro Val Asn Met Asn Phe Val Glu Gly Phe Ser Glu Gly Val Val
    210                 215                 220

Tyr Thr Lys Glu Glu Ala Ala Gln His Phe Arg Asp Gln Asp Ala Ala
225                 230                 235                 240

Thr His Leu Pro Tyr Ile Tyr Leu Ser Ala Gly Val Ser Ala Glu Leu
                245                 250                 255

Phe Gln Asp Thr Leu Lys Phe Ala His Asp Ser Gly Ala Gln Phe Asn
            260                 265                 270

Gly Val Leu Cys Gly Arg Ala Thr Trp Ser Gly Ala Val Lys Val Tyr
        275                 280                 285

Ile Glu Glu Gly Glu Gln Ala Ala Arg Glu Trp Leu Arg Thr Val Gly
    290                 295                 300

Phe Lys Asn Ile Asp Asp Leu Asn Thr Val Leu Lys Thr Thr Ala Thr
305                 310                 315                 320

Ser Trp Lys Asn Lys
                325

<210> SEQ ID NO 37
<211> LENGTH: 382
<212> TYPE: PRT
<213> ORGANISM: Staphylococcus epidermidis

<400> SEQUENCE: 37

Leu Met Lys Lys Val Met Thr Ile Phe Gly Thr Arg Pro Glu Ala Ile
1               5                   10                  15

Lys Met Ala Pro Leu Ile Lys Thr Leu Glu Lys Asp Ser Asp Leu Glu
            20                  25                  30

Pro Val Val Val Thr Ala Gln His Arg Glu Met Leu Asp Ser Val
        35                  40                  45

Leu Asn Thr Phe Asn Ile Ser Ala Asp Tyr Asp Leu Asn Ile Met Lys
    50                  55                  60

Ala Gly Gln Thr Leu Ser Glu Val Thr Ser Glu Ala Met Lys Lys Leu
65                  70                  75                  80

Glu Asp Ile Ile Gln Lys Glu Val Pro Asp Met Val Leu Val His Gly
                85                  90                  95

Asp Thr Val Thr Thr Phe Ser Gly Ala Leu Ala Ala Phe Tyr Ser Gln
            100                 105                 110

Thr Pro Ile Gly His Val Glu Ala Gly Leu Arg Ser Tyr Asn Lys Tyr
        115                 120                 125

Ser Pro Tyr Pro Glu Glu Ile Asn Arg Gln Met Val Gly Val Met Ala
    130                 135                 140

Asp Leu His Phe Ala Pro Thr Tyr Asn Ala Ala Gln Asn Leu Val Lys
145                 150                 155                 160
```

```
Glu Gly Lys Leu Ala Lys His Ile Ala Ile Thr Gly Asn Thr Ala Ile
            165                 170                 175

Asp Ala Met Asn Tyr Thr Ile Asp His Gln Tyr Ser Ser Ile Ile
        180                 185                 190

Gln Lys His Lys Asn Lys Asn Phe Ile Leu Thr Ala His Arg Arg
        195                 200                 205

Glu Asn Ile Gly Lys Pro Met Ile Asn Val Phe Lys Ala Ile Arg Lys
210                 215                 220

Leu Ile Asp Glu Tyr Gln Asp Leu Ala Leu Val Tyr Pro Met His Met
225                 230                 235                 240

Asn Pro Lys Val Arg Asp Ile Ala Gln Lys Tyr Leu Gly Asn His Pro
                245                 250                 255

Arg Ile Glu Leu Ile Glu Pro Leu Asp Val Val Asp Phe His Asn Phe
            260                 265                 270

Ala Lys Gln Ala Tyr Leu Ile Met Thr Asp Ser Gly Gly Ile Gln Glu
        275                 280                 285

Glu Ala Pro Ser Leu His Lys Pro Val Leu Val Leu Arg Asp Ser Thr
    290                 295                 300

Glu Arg Pro Glu Gly Val Asp Ala Gly Thr Leu Arg Val Ile Gly Thr
305                 310                 315                 320

Asn Glu Glu Asp Val Tyr Asn Glu Thr Lys Lys Leu Ile Glu Asn Pro
                325                 330                 335

Asp Leu Tyr Gln Lys Met Ser Gln Ala Val Asn Pro Tyr Gly Asp Gly
            340                 345                 350

Gln Ala Ser Glu Arg Ile Val Gln His Ile Lys Tyr Tyr Phe Asn Leu
        355                 360                 365

Thr Asn Asp Arg Pro Asn His Phe Glu Phe Thr Lys Asp Leu
    370                 375                 380

<210> SEQ ID NO 38
<211> LENGTH: 2757
<212> TYPE: PRT
<213> ORGANISM: Staphylococcus epidermidis

<400> SEQUENCE: 38

Val Ala Ser Asp Phe Asn Ile Gly Ile Leu Ser Thr Leu Glu Ile Asp
1               5                   10                  15

Ser Ser Ser Ser Arg Lys Lys Ile Asn Asp Thr Leu Lys Asn Ile Glu
                20                  25                  30

Ala Asn Ile Asn Ser Ile Lys Ala Asp Leu Glu Val Ser Asp Thr Lys
            35                  40                  45

Lys Ser Glu Asn Asn Ala Ile Lys Ser Ala Asn Val Ile Arg Asn
        50                  55                  60

Ile Asn Ser Asn Gly Asn Leu Lys Lys Leu Asn Val Glu Leu Asp Val
65                  70                  75                  80

Asn Leu Thr Lys Ser Arg Gln Asn Ile Gln Arg Ala Leu Ser Thr Leu
                85                  90                  95

Ser Lys Asp Phe Lys Asn Lys Lys Ile Asp Val Glu Val Asn Ala Lys
            100                 105                 110

Ala Asn Lys Asn Ser Ile Gly Gln Val Lys Asn Ser Ile Ser Lys Gly
        115                 120                 125

Ala Ser Gln Pro Leu Glu Ile Lys Glu Ser Pro Ser Arg Ser Thr
    130                 135                 140

Ser Arg Asp Ile Lys Glu Gln Gln Ser Leu Met Thr Gly Leu Ala Asn
145                 150                 155                 160
```

-continued

Ser Tyr Lys Asn Leu Asp Asp Leu Thr Arg Ala Leu Asn Thr Ser Thr
                    165                 170                 175

Phe Glu Gly Leu Arg Lys Thr Val Lys Glu Ile Lys Asn Ala Asp Asn
            180                 185                 190

Ser Leu Lys Ser Tyr Gln Val Thr Leu Glu Arg Val Asn Gln Glu Gly
        195                 200                 205

Lys Lys Leu Gly Ser Gln Arg Phe Asp Tyr Thr Pro Ser Ala Asn Gly
    210                 215                 220

Leu Lys Leu Asn Lys Thr Gln Leu Thr Asp Gln Thr Asp Lys Ala Arg
225                 230                 235                 240

Lys Glu Glu Asn Ala Ala Ile Asn Lys Leu Leu Glu Asn Glu Val Ser
                245                 250                 255

Lys Tyr Asp Arg Leu Leu Asn Lys Gly Lys Ile Asp Ile Lys Gln His
            260                 265                 270

Gln Thr Leu Leu Gln Thr Leu Arg Gln Ile Thr Asn Glu Lys Ser Lys
        275                 280                 285

Ala Asn Gln Phe Asn Arg Thr Asp Phe Asn Arg Val Ala Lys Ala Ala
    290                 295                 300

Ala Asp Glu Ala Lys Glu Tyr Gln Tyr Gln Asn Asp Met Leu Arg Lys
305                 310                 315                 320

Lys Leu Ala Leu Thr Ser Gln Ile Glu Arg Ile Glu Asn Arg Met Ala
                325                 330                 335

Ala Thr Ile Asp Lys Gln Gln Thr Asn Ala Leu Lys Asn Gln Leu Asn
            340                 345                 350

Ser Leu Gly Asn Asn Arg Thr Pro Phe Gly Lys Glu Ala Ala Phe His
        355                 360                 365

Met Asn Gln Ile Gln Asp Lys Val Arg Gln Ile Ser Ala Glu Ala Glu
    370                 375                 380

Arg Ala Thr Arg Thr Gln Leu Ser Phe Val Asp Gln Phe Arg Glu Ala
385                 390                 395                 400

Met Thr Lys Phe Pro Val Trp Met Gly Ala Thr Thr Leu Phe Phe Gly
                405                 410                 415

Ala Ile Asn Gly Ala Lys Glu Met Leu Asp Val Ile Thr Glu Ile Asp
            420                 425                 430

Gly Lys Met Ile Thr Leu Ala Lys Val Thr Gly Asp Asp Asn Ala Leu
        435                 440                 445

Gln Gln Thr Phe Ile Asp Ala Asn Asn Ala Ser Gln Phe Gly Gln
    450                 455                 460

Thr Leu Gly Ser Val Leu Asp Val Tyr Ala Glu Phe Ala Arg Gln Gly
465                 470                 475                 480

Val Lys Gly Asn Glu Leu Ser Gln Phe Ser Asn Ala Ala Leu Ile Ala
                485                 490                 495

Ala Asn Val Gly Glu Ile Asp Ala Lys Gln Ala Ser Glu Tyr Leu Thr
            500                 505                 510

Ser Met Ser Ala Gln Trp Glu Thr Thr Gly Asn Gln Ala Met Arg Gln
        515                 520                 525

Val Asp Ser Leu Asn Glu Val Ser Asn Lys Tyr Ala Thr Thr Val Glu
    530                 535                 540

Lys Leu Ala Gln Gly Gln Ala Lys Ala Gly Ser Thr Ala Lys Ser Met
545                 550                 555                 560

Gly Leu Thr Phe Asp Glu Thr Asn Gly Ile Ile Gly Ala Leu Thr Ala
                565                 570                 575

Lys Thr Lys Gln Ser Gly Asp Glu Ile Gly Asn Phe Met Lys Ala Thr

-continued

```
                580                 585                 590
Leu Pro Lys Leu Tyr Ser Gly Lys Gly Lys Ser Thr Ile Glu Gly Leu
                595                 600                 605

Gly Ile Ser Met Lys Asp Glu Asn Gly Gln Leu Lys Ser Ala Ile Ser
            610                 615                 620

Leu Leu Glu Glu Val Ser Gln Lys Thr Lys Asn Leu Glu Lys Asp Gln
625                 630                 635                 640

Lys Ala Ala Val Ile Asn Gly Leu Gly Gly Thr Tyr His Tyr Gln Arg
                645                 650                 655

Met Gln Val Leu Leu Asp Asp Leu Ser Lys Thr Asp Gly Leu Tyr Lys
            660                 665                 670

Gln Ile Lys Glu Ser Ser Glu Ser Ser Ala Gly Ser Ala Leu Gln Glu
            675                 680                 685

Asn Ala Lys Tyr Met Glu Ser Ile Glu Ala Lys Val Asn Gln Ala Lys
            690                 695                 700

Thr Ala Phe Glu Gln Phe Ala Leu Ala Val Gly Glu Thr Phe Ala Lys
705                 710                 715                 720

Ser Gly Met Leu Asp Gly Ile Arg Met Val Thr Gln Leu Leu Thr Gly
                725                 730                 735

Leu Thr His Gly Ile Thr Glu Leu Gly Thr Thr Ala Pro Ile Phe Gly
                740                 745                 750

Met Val Gly Gly Ala Ala Ser Leu Met Ser Lys Asn Val Arg Ser Gly
                755                 760                 765

Phe Glu Gly Ala Arg Ser Ser Val Ala Asn Tyr Ile Thr Glu Val Asn
            770                 775                 780

Lys Leu Ala Lys Val Asn Asn Ala Ala Gly Gln Val Val Gly Leu Gln
785                 790                 795                 800

Lys Val Gln Thr Gly Thr Ala Ser Gln Leu Gln Phe Asn Lys Asn Gly
                805                 810                 815

Glu Tyr Asp Lys Ala Ala Ser Gln Ala Lys Ala Ala Glu Gln Ala Thr
            820                 825                 830

Tyr Gln Phe Ser Lys Ala Gln Lys Asp Val Ser Ala Ser Ala Met Ile
            835                 840                 845

Ala Ser Gly Ala Ile Asn Lys Thr Thr Val Ala Thr Thr Ala Ser Thr
850                 855                 860

Val Ala Thr Arg Ala Ala Thr Leu Ala Val Asn Gly Leu Lys Leu Ala
865                 870                 875                 880

Phe Arg Gly Leu Leu Ala Ala Thr Gly Val Gly Leu Ala Ile Thr Gly
                885                 890                 895

Val Ser Phe Val Leu Glu Lys Val Val Gly Ser Phe Asn Ala Ala Ser
                900                 905                 910

Gln Ala Ala Glu Gln Tyr Lys Gln Lys Gln Glu Gln Thr Lys Gln Ala
            915                 920                 925

Ile Ala Ser Met Ser Asn Gly Glu Ile Asn Ser Leu Ile Ser Ser Tyr
            930                 935                 940

Asp Lys Leu Gln Gln Lys Met Asn Ser Gly Ser Ala Phe Asn Thr Ala
945                 950                 955                 960

Glu Ala Glu Lys Tyr Lys Glu Val Thr Ser Gln Leu Ala Asn Ile Phe
                965                 970                 975

Pro Asp Leu Val Thr Gly Glu Asn Arg Tyr Gly Lys Glu Met Ala Gly
                980                 985                 990

Asn Lys Glu Val Met Lys Gln Lys  Ile Glu Leu Ile Lys  Gln Glu Met
            995                 1000                1005
```

```
Glu Leu Glu Arg Gln Lys Asn Ala Ile Lys Gln Lys Glu Glu Gln
1010                1015                1020

Asp Ala Tyr Ile Lys Glu Gln Asp Ser Leu Ala Lys Lys Asn Arg
1025                1030                1035

Gly Gln Lys Trp Tyr Gln Leu Gly Gln Thr Pro Glu Leu Lys Leu
1040                1045                1050

Gln Glu Gln Ala Arg Pro Thr Thr Val Ser Asp Asn Ser Asn Ile
1055                1060                1065

Asn Lys Ile Asn Ala Thr Ile Gln Lys Val Lys Ser Gln Ala Gln
1070                1075                1080

Ala Glu Lys Ala Leu Glu Gln Val Asp Lys Gln Leu Ala Gln Ser
1085                1090                1095

Gln Thr Lys Asn Arg Gln Asn Glu Val Gln His Leu Gln Lys Val
1100                1105                1110

Arg Gln Ala Leu Gln Asp Tyr Ile Thr Lys Thr Gly Gln Ala Asn
1115                1120                1125

Gln Ala Thr Arg Ala Ala Val Leu Thr Ala Gln Gln Gln Phe Thr
1130                1135                1140

Asn Gln Ile Ala Thr Met Lys Lys Leu Gly Thr Thr Gly Gln Gln
1145                1150                1155

Val Met Thr Thr Ile Ser Asn Ser Val Ala Lys Thr Ala Lys Ser
1160                1165                1170

Gly Lys Ala Ala Gln Ala Thr Phe Lys Ser Phe Glu Thr Ser Leu
1175                1180                1185

Val Lys Ser Ser Ser Phe Lys Ser Lys Met Ala Ser Tyr Glu Ala
1190                1195                1200

Ser Val Lys Lys Phe Lys Asn Ala Ala Asn Gln Ser Ala Lys Ile
1205                1210                1215

Ala Ala Leu Lys Asp Val Glu Arg Asp Tyr Ser Lys Val Ala Lys
1220                1225                1230

Gly Ile Met Gln Ala Ala Lys Ala Ala Asn Met Ser Lys Ser Gln
1235                1240                1245

Met Lys Asp Leu Lys Lys Ser Leu Gln Gln Asn Ile Gln Ala Glu
1250                1255                1260

Thr Gly Phe Arg Ala Ser Val Ser Lys Ala Gly Lys Val Thr Ile
1265                1270                1275

Asp Gln Ser Lys Lys Ile Lys Gln Asn Thr Ala Glu Thr Arg Arg
1280                1285                1290

Asn Ser Ser Ala Lys Leu Gln Asn Ala Asp Ala Ser Asp Gln Ala
1295                1300                1305

Ser Glu Glu Asn Lys Glu Leu Ala Asp Ser Met Arg Ala Gly Ile
1310                1315                1320

Glu Ser Ser Gln Leu Leu Gly Lys Ala Met Gly Glu Leu Gln Ser
1325                1330                1335

Gln Gly Thr Leu Ser Thr Glu Thr Leu Ile Glu Leu Thr Glu Lys
1340                1345                1350

Tyr Gly Asp Glu Ile Leu Ala Val Ala Gly Asp Gln Glu Ala Leu
1355                1360                1365

Ser Asn Phe Ile Met Gln Lys Gln Asn Glu Glu Thr Asp Asn Tyr
1370                1375                1380

Asn Lys Asn Leu Lys Thr Lys Leu Glu Asn Ser Ser Ser Tyr Tyr
1385                1390                1395

Lys Ala Val Ala Gly Ala Asp Ser Ala Leu Ser Asn Tyr Leu Met
1400                1405                1410
```

```
Glu Asn Tyr Gly Ile Asp Thr Lys Asn Tyr Lys Ser Leu Thr Glu
    1415                1420                1425

Val Lys Ala Lys Ile Thr Asp Leu Tyr Tyr Asn Gly Ser Ala Glu
    1430                1435                1440

Glu Gln Ala Lys Val Val Asp Ala Ile Ala Lys Ala Tyr His Ile
    1445                1450                1455

Asp Leu Ser Asn Tyr Gly Ser Leu Asn Glu Lys Glu Ala Leu
    1460                1465                1470

Glu Asn Gln Leu Met Lys Ile Leu Gly Ser Lys Trp Lys Lys Tyr
    1475                1480                1485

Ile Gly Ser Val Ala Lys Asp Met Lys Ser Leu Gly Val Asp Ala
    1490                1495                1500

Gly Glu Val Gly Ala Asp Gly Phe Asp Asp Ser Lys Met Phe Asn
    1505                1510                1515

Pro Gly Ala Leu Ile Gly Ala Asn Asn Phe Gln Asn Val Ser Asn
    1520                1525                1530

Leu Ser Asn Ile Ser Asn Val Phe Asn Ser Leu Asn Gly Ala Phe
    1535                1540                1545

Asn Glu Ala Lys Asn Glu Ala Ala Gly Val Ser Arg Gly Leu Asp
    1550                1555                1560

Asp Ala Ala Ser Gly Leu Lys Asp Val Gly Asp Ser Ala Gly Ser
    1565                1570                1575

Ala Gly Ser Gly Leu Gly Lys Thr Ala Lys Gly Ala Asp Lys Ala
    1580                1585                1590

Ser Asp Ser Leu Asp Gly Thr Asn Lys Glu Leu Glu Lys Thr Lys
    1595                1600                1605

Glu Lys Ala Glu Glu Ala Gly Val Thr Val Lys Gln Leu Tyr Lys
    1610                1615                1620

Gln Phe Thr Val Thr Thr Tyr Val Ala Asp Lys Leu Ser Met Ala
    1625                1630                1635

Leu Asp Lys Ile Asn Asn Lys Leu Glu Lys Gln Lys Leu Leu Thr
    1640                1645                1650

Glu Lys Tyr Ala Thr Trp Ser Ser Ser Tyr Arg Asn Ser Leu Lys
    1655                1660                1665

Ala Glu Asn Lys Leu Leu Asp Glu Lys Thr Ala Lys Ile Lys Lys
    1670                1675                1680

Gln Ile Glu Ser Met Lys Glu Gln Ile Ala Gln Gly Lys Val Ile
    1685                1690                1695

Glu Tyr Gly Leu Val Gly Lys Asp Ile Asn Val Pro Tyr Tyr Glu
    1700                1705                1710

Tyr Thr Ala Asn Asn Leu Asp Asp Gly Glu Thr Gly Arg Ile Ser
    1715                1720                1725

Arg Tyr Thr Gly Asn Ser Thr Gln Ala Lys Val Trp Asn Phe Phe
    1730                1735                1740

Lys Ser Lys Gly Leu Ser Asp His Ala Val Ala Gly Ile Met Gly
    1745                1750                1755

Asn Met Glu Arg Glu Ser Arg Phe Lys Pro Gly Ala Gln Glu Gln
    1760                1765                1770

Gly Gly Thr Gly Ile Gly Leu Val Gln Leu Ser Phe Gly Arg Ala
    1775                1780                1785

Asn Asn Leu Arg Asn Tyr Ala Ala Arg Arg Gly Lys Ser Trp Lys
    1790                1795                1800

Asp Leu Asn Thr Gln Leu Asp Phe Ile Trp Lys Glu Leu Asn Thr
```

```
              1805                1810                1815

Thr Glu  Val Asn Ala Leu  Arg Gly Leu Lys  Ser Ala  Thr Ser Val
    1820               1825              1830

Ile Gly  Ala Ala Asn Ser  Phe Gln Arg Leu  Tyr Glu  Arg Ala Gly
    1835               1840              1845

Val Val  Ala Gln Gly Glu  Arg Asn Ala Ala  Lys Lys  Tyr Tyr
    1850               1855              1860

Arg Gln  Phe Lys Gly Thr  Asn Gly Ser Ser  Gly Phe  Leu Ser Gly
    1865               1870              1875

Gly Val  Val Ala Gly Thr  Asn Gly Lys Pro  Leu Thr  Ser Asp Arg
    1880               1885              1890

Asn Ala  Tyr Ile Leu Asp  Arg Gln Phe Gly  Arg Tyr  Asn Gly Gly
    1895               1900              1905

Gly Val  His His Gly Arg  Asp Ile Thr Ser  Ala Thr  Ile Asn Gly
    1910               1915              1920

Ser Pro  Ile Lys Ala Ala  Arg Ser Gly Ile  Val Thr  Phe Lys Gly
    1925               1930              1935

Trp Thr  Gly Gly Gly Asn  Thr Leu Ser Ile  Phe Asp  Gly Lys Asn
    1940               1945              1950

Thr Tyr  Thr Tyr Met His  Met Lys Asn Pro  Ala Arg  Val Val Lys
    1955               1960              1965

Gly Gln  Arg Val Lys Ala  Gly Gln Ile Val  Gly Asn  Val Gly Thr
    1970               1975              1980

Thr His  Asp Arg Arg Leu  Gly Gly Phe Ser  Thr Gly  Pro His Leu
    1985               1990              1995

His Val  Gln Val Asn Leu  Gly Lys Thr Pro  Ser Gly  Thr Phe Met
    2000               2005              2010

Asn Thr  Phe Asn Gly Ala  His Arg Ala Val  Asp Pro  Val Lys Tyr
    2015               2020              2025

Gly Tyr  Thr Arg Val Ser  Gly Gly Gly Ser  Leu Asn  Leu Gly Ser
    2030               2035              2040

Leu Thr  Ser Gly His Ser  Ala Met Ser Gly  Ser Ile  Ser Ala Ala
    2045               2050              2055

Met Ala  Glu Asp Leu Asn  Glu Ala Glu Gln  Glu Arg  Leu Asn Lys
    2060               2065              2070

Ile Glu  Gln Ala Ile Asn  Ala His Asn Lys  Ala Glu  Glu Met Lys
    2075               2080              2085

Gln Lys  Val Asp Glu Leu  Arg Lys Thr Leu  Met Asp  Lys Gln Leu
    2090               2095              2100

Glu Glu  Val Gln Thr Ala  Lys Glu Lys Ser  Glu Asn  Leu Tyr Asn
    2105               2110              2115

Ile Gln  Lys Ser His Val  Glu Glu Tyr Asp  His Trp  Arg Thr Leu
    2120               2125              2130

Gln Glu  Ala Arg Ser Ala  Lys Leu Glu Tyr  Glu Leu  Asn Lys Ile
    2135               2140              2145

Glu Phe  Glu Lys Gly Arg  Asn Thr Lys Glu  Trp Arg  Asn Lys Asn
    2150               2155              2160

Lys Gln  Leu Gln Ala Ser  Arg Gln Leu Glu  Val Asn  Phe Glu Asp
    2165               2170              2175

Ser Lys  Ile Gln Tyr Ile  Asn Lys Ala Leu  Lys Lys  Asn Ala Asn
    2180               2185              2190

Lys Ile  Phe Gly Lys Asn  Thr Val Asn Arg  Asp Glu  Phe Glu Thr
    2195               2200              2205
```

-continued

```
Met Lys Arg Asp Ala Gln Gln Asn Ile Arg Asp Leu Lys Ala Gly
    2210                2215                2220
Ile Gln Thr Ala Ser Gly Glu Ile Ala Thr Ser Met Ile Asp Gln
2225                2230                2235
Ile Leu Asp Glu Tyr Glu Asp Arg Val Gly Lys Val Ser Ala Lys
2240                2245                2250
Ile Glu Lys Met Gly Lys Gln Lys Glu Lys Leu Asp Leu Ala Asp
2255                2260                2265
Asn Lys Gln Ala Leu Lys Ser Ser Ser Leu Ser Arg Gln Gln Ala
2270                2275                2280
Lys Asp Ser Lys Ser Leu Ala Ser Tyr Ile Asn Phe Tyr Ile Lys
2285                2290                2295
Gln Leu Glu Arg Gln Leu Lys Leu Thr Gly Lys Asn His Glu Leu
2300                2305                2310
Gln Gln Lys Val Lys Glu Gln Ile Lys Glu Met Lys Val Ala Tyr
2315                2320                2325
Asp Asp Ala Thr Leu Ala Ala His Gln Tyr Ile Thr Glu Ala Ala
2330                2335                2340
Glu Val Asp Thr Glu Arg Gln Leu Gln Leu Asn Ala Asn Arg Leu
2345                2350                2355
Arg Asp Ala Gln Asn Glu Leu Ser Lys Ala Asp Tyr Lys Ala Gly
2360                2365                2370
Phe Ile Ser Gln Glu Tyr Gln Ile Asp Leu Tyr Arg Lys Asn Gln
2375                2380                2385
Glu Ala Lys Phe Lys Gly Tyr Leu Lys Glu Lys Glu Ala Leu Glu
2390                2395                2400
Gln Asn Lys Ser Glu Leu Gln Asp Met Tyr Glu Ile Tyr Lys Ser
2405                2410                2415
Val Pro Thr Gln Ala Gln Lys Ile Lys Glu Ala Leu Ile Glu Thr
2420                2425                2430
Lys Asn Ala Ile Arg Asp Asn Asn Lys Gly Leu Tyr Asp Leu Lys
2435                2440                2445
Tyr Asp Met Ala Asn Ser Val Ile Asn Gln Ile Lys Asp Ile Tyr
2450                2455                2460
Ser Lys Gln Leu Glu Val Ala Thr Lys Ala Tyr Asp Asp Glu Tyr
2465                2470                2475
Lys Ala Tyr Glu Lys Met Ile Asn Lys Lys Leu Lys Leu Ile Asp
2480                2485                2490
Asp Glu Gln Thr Gln Glu Ser Phe Asn Lys Asp Val Arg Asp Arg
2495                2500                2505
Thr Glu Ala Met Asp Lys Ile Arg Asp Glu Ile Ala Gln Arg Ser
2510                2515                2520
Gly Asp Asp Ser Leu Ala Asn Gln Lys Lys Leu Lys Asp Leu Arg
2525                2530                2535
Glu Gln Leu Lys Gln Gln Glu Glu Asp Tyr Thr Met Phe Ile Asn
2540                2545                2550
Asn Lys Asn Arg Asp Asp Arg Arg Lys Ala Leu Gln Asp Glu Leu
2555                2560                2565
Asn Asp Lys Asn Glu Gln Ile Gln Glu Gln Lys Glu Asp Leu Asn
2570                2575                2580
Lys Ala Phe Gln Asp Leu Ile Gly Asp Thr Arg Arg Phe Asn Ala
2585                2590                2595
Ile Gln Glu Ser Leu Met Glu Gly Gln Ile Asp Lys Tyr Lys Ser
2600                2605                2610
```

```
Leu Ile Ala Asp Leu Thr Lys Tyr Val Asn Asp Asn Met Lys Glu
    2615                2620                2625

Ile Gly Arg Ser Thr Ser Glu Gly Ile Leu Asp Gly Leu Ala Ala
    2630                2635                2640

Ser Phe Lys Gly Leu Ser Ser Leu Ser Lys Glu Leu Gln Lys Gln
    2645                2650                2655

Glu Lys Asn Asn Leu Asn Pro Val Pro Asn Ser Lys Leu Lys Pro
    2660                2665                2670

Thr Lys Val Asp Glu Ala Thr Ile Ala Ala Ile Lys Lys Val Asn
    2675                2680                2685

Gly Leu Ser Pro Thr Thr Ile Leu Gln Gly Leu Asp Ile Lys Pro
    2690                2695                2700

Val Asn Leu Pro Lys Asp Val Lys Pro Ser Lys Thr Val Thr Asn
    2705                2710                2715

Asn Asn Lys Thr Thr Ala Lys Ala Leu Val Asn Ile Glu Asn Phe
    2720                2725                2730

Asn Gly Thr Lys Ala Glu Ala Asp Lys Leu Ala Asn Asn Leu Ala
    2735                2740                2745

Thr Ala Met Arg Lys Gln Gly Val Leu
    2750                2755

<210> SEQ ID NO 39
<211> LENGTH: 319
<212> TYPE: PRT
<213> ORGANISM: Staphylococcus epidermidis

<400> SEQUENCE: 39

Met Ala Glu Thr Lys Lys Gln Phe Glu Asn Lys Val Ser Val Thr Gly
1               5                   10                  15

Thr Leu Lys Ser Leu Glu Val Thr Asp Leu Val Thr Ala Lys Lys Val
                20                  25                  30

Pro Met Lys Ile Ala Thr Leu Arg Ile Glu Thr Gly Lys Gly Glu Thr
            35                  40                  45

His Thr Ala Lys Met Met Ala Val Lys His Phe Glu Arg Asp Gly Val
        50                  55                  60

Lys Thr Glu Asn Lys Ser Tyr Ser Ala Ile Glu Thr Met Gln Lys Glu
65                  70                  75                  80

Tyr Val Ser Ile Glu Asp Ile Ser Glu Asn Lys Ala Gly Glu Asp Ala
                85                  90                  95

Glu Ala Thr Val Val Asn Val Asn Gly Ser Met Ser Ile Asn Met Tyr
            100                 105                 110

Lys Asn Lys Ala Glu Lys Val Val Glu Thr Asn Gln Ile Glu Ala Arg
        115                 120                 125

Phe Val Asn Arg Val Lys Asp Val Glu Asn Ala Gln Phe Gly Ala Glu
    130                 135                 140

Phe Thr Leu Gln Thr Tyr Leu Ile Ser Lys Gly Gln Arg Val Ile Lys
145                 150                 155                 160

Asn Glu Glu Glu Thr Asp Glu Val Thr Phe Lys Ala Ala Thr Ile Asp
                165                 170                 175

Tyr Arg Gly Gln Ala His Pro Phe Glu Phe Thr Ala Asn Asp Glu Tyr
            180                 185                 190

Gly Val Ala Glu Trp Ile Glu Asp Glu Val Glu Leu Gly Gln Ser Leu
        195                 200                 205

Ile Leu Gln Gly Leu Ile Ile Asn Lys Phe Ile Val Glu Gln Val Glu
    210                 215                 220
```

```
Arg Ser Ser Ser Ala Gly Ile Gly Lys Ala Ile Val Asp Thr Arg Arg
225                 230                 235                 240

Glu Val Glu Arg Lys Leu Leu Val Glu Gly Ile Ile Pro Ile Glu Asp
                245                 250                 255

Glu Asp Asp Pro Lys Tyr Ile Thr Glu Glu Ile Lys Glu Ala Asn
                260                 265                 270

Lys Lys Tyr Glu Asp Lys Lys Thr Glu Val Glu Ala Ser Thr Asn Gly
                275                 280                 285

Thr Lys Lys Thr Glu Val Lys Lys Gly Val Ala Thr Ser Lys Pro Lys
            290                 295                 300

Ala Ala Lys Pro Thr Ile Glu Ile Asp Asp Asp Leu Pro Phe
305                 310                 315

<210> SEQ ID NO 40
<211> LENGTH: 797
<212> TYPE: PRT
<213> ORGANISM: Staphylococcus epidermidis

<400> SEQUENCE: 40

Leu Pro Gln Ala Lys Lys Arg Thr Ser Thr Lys Arg Lys Gly Asn Lys
1               5                   10                  15

Lys Thr Asn Lys Lys Lys Gln Asn Glu Thr Pro Leu Arg Tyr Ile Phe
                20                  25                  30

Ser Ile Ile Val Val Ile Leu Ile Leu Gly Ala Phe Gln Leu Gly
            35                  40                  45

Ile Ile Gly Arg Met Ile Asp Ser Phe Phe Asn Tyr Leu Phe Gly Met
50                  55                  60

Ser Arg Tyr Leu Thr Tyr Ile Leu Val Leu Ile Ala Thr Ile Phe Ile
65                  70                  75                  80

Thr Tyr Ser Lys Gln Ile Pro Arg Thr Arg Arg Ser Ile Gly Ala Ile
                85                  90                  95

Val Leu Gln Leu Ala Leu Leu Phe Ile Ala Gln Leu Tyr Phe His Phe
            100                 105                 110

Ser His Asn Ile Thr Ser Gln Arg Glu Pro Val Leu Ser Phe Val Tyr
        115                 120                 125

Lys Ala Tyr Glu Gln Thr His Phe Pro Asn Phe Gly Gly Gly Leu Ile
130                 135                 140

Gly Phe Tyr Leu Leu Lys Leu Phe Ile Pro Leu Ile Ser Ile Val Gly
145                 150                 155                 160

Val Ile Ile Ile Thr Ile Leu Leu Leu Ala Ser Ser Phe Ile Leu Leu
                165                 170                 175

Leu Asn Leu Arg His Arg Asp Val Thr Lys Ser Leu Phe Asp Asn Leu
            180                 185                 190

Lys Ser Ser Ser Asn His Ala Ser Glu Ser Ile Lys Gln Lys Arg Glu
        195                 200                 205

Gln Asn Lys Ile Lys Lys Glu Glu Lys Ala Gln Leu Lys Glu Ala Lys
    210                 215                 220

Ile Glu Arg Lys Lys Gln Lys Lys Ser Arg Gln Asn Asn Asn Val Ile
225                 230                 235                 240

Lys Asp Val Ser Asp Phe Pro Glu Ile Ser Gln Ser Asp Asp Ile Pro
                245                 250                 255

Ile Tyr Gly His Asn Glu Gln Glu Asp Lys Arg Pro Asn Thr Ala Asn
            260                 265                 270

Gln Arg Gln Lys Arg Val Leu Asp Asn Glu Gln Phe Gln Gln Ser Leu
        275                 280                 285
```

```
Pro Ser Thr Lys Asn Gln Ser Ile Asn Asn Gln Pro Ser Thr Thr
    290                 295                 300
Ala Glu Asn Asn Gln Gln Gln Ser Gln Ala Glu Gly Ser Ile Ser Glu
305                 310                 315                 320
Ala Gly Glu Glu Ala Asn Ile Glu Tyr Thr Val Pro Pro Leu Ser Leu
                325                 330                 335
Leu Lys Gln Pro Thr Lys Gln Lys Thr Thr Ser Lys Ala Glu Val Gln
            340                 345                 350
Arg Lys Gly Gln Val Leu Glu Ser Thr Leu Lys Asn Phe Gly Val Asn
            355                 360                 365
Ala Lys Val Thr Gln Ile Lys Ile Gly Pro Ala Val Thr Gln Tyr Glu
370                 375                 380
Ile Gln Pro Ala Gln Gly Val Lys Val Ser Lys Ile Val Asn Leu His
385                 390                 395                 400
Asn Asp Ile Ala Leu Ala Leu Ala Ala Lys Asp Val Arg Ile Glu Ala
                405                 410                 415
Pro Ile Pro Gly Arg Ser Ala Val Gly Ile Glu Val Pro Asn Asp Lys
            420                 425                 430
Ile Ser Leu Val Thr Leu Lys Glu Val Leu Glu Asp Lys Phe Pro Ser
            435                 440                 445
Lys Tyr Lys Leu Glu Val Gly Ile Gly Arg Asp Ile Ser Gly Asp Pro
450                 455                 460
Ile Ser Ile Gln Leu Asn Glu Met Pro His Leu Leu Val Ala Gly Ser
465                 470                 475                 480
Thr Gly Ser Gly Lys Ser Val Cys Ile Asn Gly Ile Ile Thr Ser Ile
                485                 490                 495
Leu Leu Asn Thr Lys Pro His Glu Val Lys Leu Met Leu Ile Asp Pro
            500                 505                 510
Lys Met Val Glu Leu Asn Val Tyr Asn Gly Ile Pro His Leu Leu Ile
            515                 520                 525
Pro Val Val Thr Asn Pro His Lys Ala Ser Gln Ala Leu Glu Lys Ile
530                 535                 540
Val Ser Glu Met Glu Arg Arg Tyr Asp Leu Phe Gln His Ser Ser Thr
545                 550                 555                 560
Arg Asn Ile Glu Gly Tyr Asn Gln Tyr Ile Arg Lys Gln Asn Glu Glu
                565                 570                 575
Leu Asp Glu Lys Gln Pro Glu Leu Pro Tyr Ile Val Ile Val Asp
            580                 585                 590
Glu Leu Ala Asp Leu Met Met Val Ala Gly Lys Glu Val Glu Asn Ala
            595                 600                 605
Ile Gln Arg Ile Thr Gln Met Ala Arg Ala Ala Gly Ile His Leu Ile
610                 615                 620
Val Ala Thr Gln Arg Pro Ser Val Asp Val Ile Thr Gly Ile Ile Lys
625                 630                 635                 640
Asn Asn Ile Pro Ser Arg Ile Ala Phe Ala Val Ser Ser Gln Thr Asp
                645                 650                 655
Ser Arg Thr Ile Ile Gly Ala Gly Gly Ala Glu Lys Leu Leu Gly Lys
            660                 665                 670
Gly Asp Met Leu Tyr Val Gly Asn Gly Glu Ser Thr Thr Thr Arg Ile
            675                 680                 685
Gln Gly Ala Phe Leu Ser Asp Gln Glu Val Gln Asp Val Val Asn Tyr
690                 695                 700
Val Val Glu Gln Gln Lys Ala Asn Tyr Val Lys Glu Met Glu Pro Asp
```

```
                705                 710                 715                 720
Ala Pro Val Asp Lys Ser Glu Met Lys Ser Glu Asp Ala Leu Tyr Asp
                    725                 730                 735

Glu Ala Tyr Leu Phe Val Ile Glu Lys Gln Lys Ala Ser Thr Ser Leu
                740                 745                 750

Leu Gln Arg Gln Phe Arg Ile Gly Tyr Asn Arg Ala Ser Arg Leu Met
            755                 760                 765

Asp Asp Leu Glu Arg Asn Gln Val Ile Gly Pro Gln Lys Gly Ser Lys
        770                 775                 780

Pro Arg Gln Ile Leu Val Asp Leu Glu Asn Asp Glu Val
785                 790                 795

<210> SEQ ID NO 41
<211> LENGTH: 429
<212> TYPE: PRT
<213> ORGANISM: Staphylococcus epidermidis

<400> SEQUENCE: 41

Met Lys Thr His Gln Tyr Glu Leu Ile Asp Glu Lys Val Phe Glu His
1               5                   10                  15

Glu Phe Asp Asn Gly Leu Lys Leu Phe Ile Ile Pro Lys Pro Gly Phe
                20                  25                  30

Gln Lys Thr Tyr Val Thr Tyr Thr Thr Gln Phe Gly Ser Leu Asp Asn
            35                  40                  45

His Phe Lys Pro Ile Gly Ser Gln Gln Phe Val Lys Val Pro Asp Gly
        50                  55                  60

Val Ala His Phe Leu Glu His Lys Leu Phe Glu Lys Glu Asp Glu Asp
65                  70                  75                  80

Leu Phe Thr Ala Phe Ala Glu Glu Asn Ala Gln Ala Asn Ala Phe Thr
                85                  90                  95

Ser Phe Asp Arg Thr Ser Tyr Leu Phe Ser Ala Thr Ser Asn Ile Glu
                100                 105                 110

Ser Asn Ile Lys Arg Leu Leu Asn Met Val Glu Thr Pro Tyr Phe Thr
            115                 120                 125

Glu Glu Thr Val Asn Lys Glu Lys Gly Ile Ile Ala Glu Glu Ile Lys
        130                 135                 140

Met Tyr Gln Glu Gln Pro Gly Tyr Lys Leu Met Phe Asn Thr Leu Arg
145                 150                 155                 160

Ala Met Tyr Ser Lys His Pro Ile Arg Val Asp Ile Ala Gly Ser Val
                165                 170                 175

Glu Ser Ile Tyr Glu Ile Thr Lys Asp Asp Leu Tyr Leu Cys Tyr Glu
                180                 185                 190

Thr Phe Tyr His Pro Ser Asn Met Val Leu Phe Val Val Gly Asp Val
            195                 200                 205

Ser Pro Gln Ser Ile Ile Lys Leu Val Glu Lys His Glu Asn Gln Arg
        210                 215                 220

Asn Lys Thr Tyr Gln Pro Arg Ile Glu Arg Ala Gln Ile Asp Glu Pro
225                 230                 235                 240

Arg Glu Ile Asn Gln Arg Phe Val Ser Glu Lys Met Lys Leu Gln Ser
                245                 250                 255

Pro Arg Leu Met Leu Gly Phe Lys Asn Glu Pro Leu Asp Glu Ser Ala
                260                 265                 270

Thr Lys Phe Val Gln Arg Asp Leu Glu Met Thr Phe Phe Tyr Glu Leu
            275                 280                 285

Val Phe Gly Glu Glu Thr Glu Phe Tyr Gln Gln Leu Leu Asn Lys Asp
```

```
                     290                 295                 300
Leu Ile Asp Glu Thr Phe Gly Tyr Gln Phe Val Leu Glu Pro Ser Tyr
305                 310                 315                 320

Ser Phe Ser Ile Ile Thr Ser Ala Thr Gln Gln Pro Asp Leu Phe Lys
                325                 330                 335

Gln Leu Ile Met Asp Glu Leu Arg Lys Tyr Lys Gly Asn Leu Lys Asp
                340                 345                 350

Gln Glu Ala Phe Asp Leu Leu Lys Lys Gln Phe Ile Gly Glu Phe Ile
                355                 360                 365

Ser Ser Leu Asn Ser Pro Glu Tyr Ile Ala Asn Gln Tyr Ala Lys Leu
370                 375                 380

Tyr Phe Glu Gly Val Ser Val Phe Asp Met Leu Asp Ile Val Glu Asn
385                 390                 395                 400

Ile Thr Leu Glu Ser Val Asn Glu Thr Ser Glu Leu Phe Leu Asn Phe
                405                 410                 415

Asp Gln Leu Val Asp Ser Arg Leu Glu Met Glu Asn Arg
                420                 425

<210> SEQ ID NO 42
<211> LENGTH: 329
<212> TYPE: PRT
<213> ORGANISM: Staphylococcus epidermidis

<400> SEQUENCE: 42

Met Thr Glu Gln Lys Asp Ile Lys Glu Thr Glu Tyr Arg Arg Gln Lys
1               5                   10                  15

Gly Thr Thr Ser Thr Pro Ser Arg Arg Arg Asn Lys Lys Arg Met Arg
                20                  25                  30

Lys Leu Pro Phe Ile Ile Leu Val Ile Leu Ile Leu Ile Ser Ile
                35                  40                  45

Ile Val Tyr Ile Thr His Gln Tyr Asn Ser Gly Met Lys Tyr Ala Lys
    50                  55                  60

Glu His Ala Lys Asp Val Lys Val His Lys Phe Asn Gly Asn Met Lys
65                  70                  75                  80

Asn Asp Gly Lys Ile Ser Val Leu Val Leu Gly Ala Asp Lys Ala Gln
                85                  90                  95

Gly Gly Lys Ser Arg Thr Asp Ser Ile Met Ile Val Gln Tyr Asp Tyr
                100                 105                 110

Val His Lys Lys Met Lys Met Met Ser Val Met Arg Asp Ile Tyr Ala
    115                 120                 125

Asp Ile Pro Gly Tyr Asp Lys Tyr Lys Ile Asn Ala Ala Tyr Ser Leu
    130                 135                 140

Gly Gly Pro Glu Leu Leu Arg Lys Thr Leu Asn Lys Asn Leu Gly Val
145                 150                 155                 160

Asn Pro Glu Tyr Tyr Ala Val Val Asp Phe Thr Gly Phe Glu Lys Met
                165                 170                 175

Ile Asp Glu Leu Gln Pro Asn Gly Val Pro Ile Asp Val Glu Lys Asp
                180                 185                 190

Met Ser Glu Asn Ile Gly Val Ser Leu Lys Lys Gly His His Lys Leu
    195                 200                 205

Asn Gly Lys Glu Leu Leu Gly Tyr Ala Arg Phe Arg His Asp Pro Glu
    210                 215                 220

Gly Asp Phe Gly Arg Val Arg Arg Gln Gln Val Met Gln Thr Leu
225                 230                 235                 240

Lys Gln Glu Leu Val Asn Phe Asn Thr Val Ala Lys Leu Pro Lys Val
```

```
              245                 250                 255
Ala Gly Ile Leu Arg Gly Tyr Val Asn Thr Asn Met Pro Asn Ser Ala
            260                 265                 270

Ile Phe Gln Thr Gly Ile Ser Phe Gly Ile Arg Gly Asp Lys Asp Val
            275                 280                 285

Gln Ser Leu Thr Val Pro Ile Lys Gly Ser Tyr Gln Asp Ile Asn Thr
            290                 295                 300

Asn Asn Asp Gly Ser Ala Leu Gln Ile Asp Ser Glu Lys Asn Lys Gln
305                 310                 315                 320

Ala Ile Lys Asn Phe Phe Glu Asp Asn
            325

<210> SEQ ID NO 43
<211> LENGTH: 627
<212> TYPE: PRT
<213> ORGANISM: Staphylococcus epidermidis

<400> SEQUENCE: 43

Met Glu Ala Tyr Lys Ile Glu His Leu Asn Lys Ser Tyr Ala Asp Lys
1               5                   10                  15

Glu Ile Phe Asn Asp Leu Asn Leu Ser Ile Ser Glu His Glu Arg Ile
            20                  25                  30

Gly Leu Val Gly Ile Asn Gly Thr Gly Lys Ser Thr Leu Leu Lys Val
            35                  40                  45

Ile Gly Gly Leu Asp Glu Asp Phe Thr Ala Asp Ile Thr His Pro Asn
        50                  55                  60

Gln Tyr Arg Ile Arg Tyr Ser Ser Gln Lys Gln Asp Leu Asn Gly His
65                  70                  75                  80

Met Thr Val Phe Glu Ala Val Leu Ser Ser Asp Thr Pro Thr Leu Arg
                85                  90                  95

Ile Ile Lys Lys Tyr Glu Glu Ala Val Asn Arg Tyr Ala Leu Asp Gln
            100                 105                 110

Ser Asp Ser Asn Phe Asn Lys Met Met Glu Ala Gln Glu Glu Met Asp
        115                 120                 125

Gln Lys Asp Ala Trp Asp Tyr Asn Ala Glu Ile Lys Thr Ile Leu Ser
130                 135                 140

Lys Leu Gly Ile His Asp Thr Thr Lys Lys Ile Val Glu Leu Ser Gly
145                 150                 155                 160

Gly Gln Gln Lys Arg Val Val Leu Ala Lys Thr Leu Ile Glu Gln Pro
                165                 170                 175

Asp Leu Leu Leu Leu Asp Glu Pro Thr Asn His Leu Asp Phe Glu Ser
            180                 185                 190

Ile Arg Trp Leu Ile Asn Tyr Val Lys Gln Tyr Pro His Thr Val Leu
        195                 200                 205

Phe Val Thr His Asp Arg Tyr Phe Leu Asn Glu Val Ser Thr Arg Ile
    210                 215                 220

Ile Glu Leu Asp Arg Gly Lys Leu Lys Thr Tyr Pro Gly Asn Tyr Glu
225                 230                 235                 240

Asp Tyr Ile Val Met Arg Ala Glu Asn Glu Leu Val Glu Gln Lys Gln
                245                 250                 255

Gln Glu Lys Gln Lys Ala Leu Tyr Lys Gln Glu Leu Ala Trp Met Arg
            260                 265                 270

Ala Gly Ala Lys Ala Arg Thr Thr Lys Gln Gln Ala Arg Ile Asn Arg
        275                 280                 285

Phe Asn Gln Leu Glu Ser Asp Val Lys Thr Gln His Thr Gln Asp Lys
```

```
            290                 295                 300
Gly Glu Leu Asn Leu Ala Tyr Ser Arg Leu Gly Lys Gln Val Tyr Glu
305                 310                 315                 320

Leu Lys Asn Leu Ser Lys Ser Ile Asn Asn Lys Val Leu Phe Glu Asp
                325                 330                 335

Val Thr Glu Ile Ile Gln Ser Arg Arg Ile Gly Ile Val Gly Pro
            340                 345                 350

Asn Gly Ala Gly Lys Thr Thr Leu Leu Asn Ile Leu Ser Asn Glu Asp
                355                 360                 365

Gln Asp Tyr Glu Gly Glu Leu Lys Ile Gly Gln Thr Val Lys Val Ala
            370                 375                 380

Tyr Phe Lys Gln Thr Glu Lys Thr Leu Asp Arg Asp Ile Arg Val Ile
385                 390                 395                 400

Asp Tyr Leu Arg Glu Glu Ser Glu Met Ala Lys Glu Lys Asp Gly Thr
                405                 410                 415

Ser Ile Ser Val Thr Gln Leu Leu Glu Arg Phe Leu Phe Pro Ser Ala
            420                 425                 430

Thr His Gly Lys Lys Val Tyr Lys Leu Ser Gly Gly Glu Gln Lys Arg
            435                 440                 445

Leu Tyr Leu Leu Arg Leu Leu Val His Lys Pro Asn Val Leu Leu Leu
450                 455                 460

Asp Glu Pro Thr Asn Asp Leu Asp Thr Glu Thr Leu Thr Ile Leu Glu
465                 470                 475                 480

Asp Tyr Ile Asp Asp Phe Gly Gly Ser Val Ile Thr Val Ser His Asp
                485                 490                 495

Arg Tyr Phe Leu Asn Lys Val Val Gln Glu Tyr Trp Phe Ile His Asp
            500                 505                 510

Gly Lys Ile Glu Lys Ile Ile Gly Ser Phe Glu Asp Tyr Glu Ser Phe
            515                 520                 525

Lys Lys Glu His Glu Arg Gln Ala Met Leu Ser Lys Gln Thr Glu Gln
            530                 535                 540

Gln Asn Lys His Lys His Gln Pro Lys Lys Lys Thr Gly Leu Ser Tyr
545                 550                 555                 560

Lys Glu Lys Leu Glu Tyr Glu Thr Ile Met Thr Arg Ile Glu Met Thr
                565                 570                 575

Glu Thr Arg Leu Glu Asp Leu Glu Gln Glu Met Ile Asn Ala Ser Asp
            580                 585                 590

Asn Tyr Ala Arg Ile Lys Glu Leu Asn Glu Glu Lys Glu Gln Leu Glu
            595                 600                 605

Ala Thr Tyr Glu Ala Asp Ile Thr Arg Trp Ser Glu Leu Glu Glu Ile
    610                 615                 620

Lys Glu Gln
625

<210> SEQ ID NO 44
<211> LENGTH: 270
<212> TYPE: PRT
<213> ORGANISM: Staphylococcus epidermidis

<400> SEQUENCE: 44

Met Lys Lys Leu Phe Gly Ile Ile Leu Val Leu Ala Leu Thr Ile Ala
1               5                   10                  15

Leu Ala Ala Cys Gly Gly Gly Lys Asp Lys Glu Lys Thr Ile Thr Val
                20                  25                  30

Gly Ala Ser Pro Ala Pro His Ala Glu Ile Leu Glu Lys Ala Lys Pro
```

```
                35                  40                  45
Leu Leu Lys Lys Lys Gly Tyr Asp Leu Lys Ile Lys Pro Ile Asn Asp
 50                  55                  60

Tyr Thr Thr Pro Asn Lys Leu Leu Asp Lys Gly Glu Ile Asp Ala Asn
 65                  70                  75                  80

Phe Phe Gln His Thr Pro Tyr Leu Asn Thr Glu Ser Lys Glu Lys Gly
                 85                  90                  95

Tyr Lys Ile Glu Ser Ala Gly Asn Val Glu Leu Glu Pro Met Ala Val
                100                 105                 110

Tyr Ser Lys Lys Tyr Lys Ser Leu Lys Asp Leu Pro Lys Gly Ala Thr
                115                 120                 125

Val Tyr Val Ser Asn Asn Pro Ala Glu Gln Gly Arg Phe Leu Lys Phe
                130                 135                 140

Phe Val Asp Glu Gly Leu Ile Lys Leu Lys Lys Gly Val Lys Ile Glu
145                 150                 155                 160

Asn Ala Lys Phe Asp Asp Ile Thr Glu Asn Lys Lys Asp Ile Lys Phe
                165                 170                 175

Asn Asn Lys Gln Ser Ala Glu Tyr Leu Pro Lys Ile Tyr Gln Asn Gln
                180                 185                 190

Asp Ala Asp Ala Val Ile Ile Asn Ser Asn Tyr Ala Ile Asp Gln Lys
                195                 200                 205

Leu Ser Pro Lys Lys Asp Ser Ile Ala Leu Glu Ser Pro Lys Asp Asn
210                 215                 220

Pro Tyr Ala Asn Leu Ile Ala Val Lys Lys Gly His Lys Asp Asp Lys
225                 230                 235                 240

Asn Ile Lys Val Leu Met Glu Val Leu Gln Ser Lys Glu Ile Gln Asp
                245                 250                 255

Tyr Ile Lys Asp Lys Tyr Asp Gly Ala Val Val Pro Ala Lys
                260                 265                 270

<210> SEQ ID NO 45
<211> LENGTH: 439
<212> TYPE: PRT
<213> ORGANISM: Staphylococcus epidermidis

<400> SEQUENCE: 45

Met Glu Leu Thr Ile Tyr His Thr Asn Asp Ile His Ser His Leu Asn
 1               5                  10                  15

Glu Tyr Ala Arg Ile Gln Ala Tyr Met Ala Lys His Arg Pro Gln Leu
                20                  25                  30

Glu His Pro Ser Leu Tyr Ile Asp Ile Gly Asp His Val Asp Leu Ser
                35                  40                  45

Ala Pro Val Thr Glu Ala Thr Val Gly His Lys Asn Ile Glu Leu Leu
 50                  55                  60

Asn Glu Ala His Cys Asp Ile Ala Thr Ile Gly Asn Asn Glu Gly Met
 65                  70                  75                  80

Thr Ile Ser His Asp Ala Leu Gln Asn Leu Tyr Asn Asp Ala Asp Phe
                 85                  90                  95

Lys Val Ile Cys Thr Asn Val Ile Asp Glu Glu Gly His Leu Pro His
                100                 105                 110

His Ile Thr Ser Ser Tyr Ile Lys Glu Ile Lys Gly Thr Arg Ile Leu
                115                 120                 125

Phe Val Ala Ala Thr Ala Pro Phe Thr Pro Phe Tyr Arg Ala Leu Asp
130                 135                 140

Trp Ile Val Thr Asp Pro Leu Ala Ala Ile Lys Asp Glu Ile Asn Ala
```

-continued

```
            145                 150                 155                 160
His Gln Gly Glu Tyr Asp Leu Leu Met Val Met Ser His Val Gly Ile
                165                 170                 175

Phe Phe Asp Glu Lys Leu Cys Gln Glu Ile Pro Glu Ile Asp Val Ile
                180                 185                 190

Phe Gly Ser His Thr His His His Phe Glu His Gly Glu Ile Asn Asn
                195                 200                 205

Gly Val Leu Met Ala Ala Ala Gly Lys Tyr Gly Tyr Tyr Leu Gly Glu
                210                 215                 220

Val Asn Ile Thr Ile Glu Asn Gly Lys Ile Val Asp Lys Ile Ala Lys
225                 230                 235                 240

Ile His Pro Ile Glu Thr Leu Pro Leu Val Glu Thr His Phe Glu Glu
                245                 250                 255

Glu Gly Arg Ala Leu Leu Ser Lys Pro Val Val Asn His His Val Asn
                260                 265                 270

Leu Val Lys Arg Thr Asp Val Val Thr Arg Thr Ser Tyr Leu Leu Ala
                275                 280                 285

Glu Ser Val Tyr Glu Phe Ser Arg Ala Asp Cys Ala Ile Val Asn Ala
                290                 295                 300

Gly Leu Ile Val Asn Gly Ile Glu Ala Asp Lys Val Thr Glu Tyr Asp
305                 310                 315                 320

Ile His Arg Met Leu Pro His Pro Ile Asn Ile Val Arg Val Arg Leu
                325                 330                 335

Thr Gly Lys Gln Leu Lys Gln Val Ile Gln Lys Ser Gln Lys Gln Glu
                340                 345                 350

Tyr Met His Glu His Ala Gln Gly Leu Gly Phe Arg Gly Asp Ile Phe
                355                 360                 365

Gly Gly Tyr Ile Leu Tyr Asn Leu Gly Phe Ile Glu Ser Glu Asp Arg
                370                 375                 380

Tyr Phe Ile Gly Asp Glu Glu Ile Gln Asn Asp Lys Gln Tyr Thr Leu
385                 390                 395                 400

Gly Thr Val Asp Met Tyr Thr Phe Gly Arg Tyr Phe Pro Leu Leu Lys
                405                 410                 415

Gly Leu Ser Thr Asp Tyr Ile Met Pro Glu Phe Leu Arg Asp Ile Phe
                420                 425                 430

Lys Glu Lys Leu Leu Lys Leu
                435

<210> SEQ ID NO 46
<211> LENGTH: 203
<212> TYPE: PRT
<213> ORGANISM: Staphylococcus epidermidis

<400> SEQUENCE: 46

Met Glu Lys Val Ile Tyr Leu Ala Gly His Ile Leu Asn Glu Ala Met
1               5                   10                  15

Val Asp Tyr Arg Glu Lys Gln His Asn Gln Val Glu Ala Ile Glu Gly
                20                  25                  30

Val Lys Pro Tyr Ser Pro His Gln Asp Lys Ser Ile Asn Asp Lys Ser
                35                  40                  45

Asn Ala Val Gln Glu Gly Leu Ala Glu Arg Ile Leu Lys Asn Asp Phe
                50                  55                  60

Thr Ala Met Glu Lys Ser Asp Ile Tyr Val Leu Asp Val Leu Asn Glu
65                  70                  75                  80

Gly Leu Gly Thr Ile Ser Glu Leu Gly Ile Ile Ile Gly Met Lys Lys
```

```
                85                  90                  95
Gln Ala Gln Lys Thr Ile Asp Arg Leu Ser Val Leu Ser Glu Glu Ile
            100                 105                 110

Lys His Asp Val Tyr Gly Asp Gln Thr Glu Ala Tyr Asp Leu Ile Gln
            115                 120                 125

Asp Glu Ile Tyr Lys Gln Glu Lys Ile Leu Asn Lys Thr Val Leu Cys
        130                 135                 140

Tyr Cys Ser Asp Ile Arg Gln Gly His Gly Lys Pro Tyr Thr Asp Pro
145                 150                 155                 160

Asp Arg Ala Glu Phe Ser Thr Asn Gln Phe Val Tyr Gly Met Val Leu
                165                 170                 175

Glu Ala Thr Asn Gly Glu Gly Phe Ile Thr Trp Asp Gln Val Leu His
            180                 185                 190

Arg Leu Asp Leu Phe Gly Ser Gly Leu Ile Val
            195                 200

<210> SEQ ID NO 47
<211> LENGTH: 59
<212> TYPE: PRT
<213> ORGANISM: Staphylococcus epidermidis

<400> SEQUENCE: 47

Met Ser Lys Lys Phe Arg Val Glu Asp Lys Glu Thr Ile Ala Asp Cys
1               5                   10                  15

Leu Asp Arg Met Lys Lys Glu Gly Phe Met Pro Ile Arg Arg Ile Glu
            20                  25                  30

Lys Pro Val Tyr Lys Glu Asn Lys Asp Gly Ser Ile Glu Ile Leu Lys
        35                  40                  45

Gln Asp Ile Ile Phe Val Gly Ala Leu Ile Gln
    50                  55

<210> SEQ ID NO 48
<211> LENGTH: 3692
<212> TYPE: PRT
<213> ORGANISM: Staphylococcus epidermidis

<400> SEQUENCE: 48

Met Asn Leu Phe Arg Lys Gln Lys Phe Ser Ile Arg Lys Phe Asn Ile
1               5                   10                  15

Gly Ile Phe Ser Ala Leu Ile Ala Thr Val Ala Phe Leu Ala His Pro
            20                  25                  30

Gly Gln Ala Thr Ala Ser Glu Leu Glu Pro Ser Gln Asn Asn Asp Thr
        35                  40                  45

Thr Ala Gln Ser Asp Gly Gly Leu Glu Asn Thr Ser Gln Ser Asn Pro
    50                  55                  60

Ile Ser Glu Glu Thr Thr Asn Thr Leu Ser Gly Gln Thr Val Pro Ser
65                  70                  75                  80

Ser Thr Glu Asn Lys Gln Thr Gln Asn Val Pro Asn His Asn Ala Gln
                85                  90                  95

Pro Ile Ala Ile Asn Thr Glu Glu Ala Glu Ser Ala Gln Thr Ala Ser
            100                 105                 110

Tyr Thr Asn Ile Asn Glu Asn Asn Asp Thr Ser Asp Asp Gly Leu His
        115                 120                 125

Val Asn Gln Pro Ala Lys His His Ile Glu Ala Gln Ser Glu Asp Val
    130                 135                 140

Thr Asn His Thr Asn Ser Asn His Ser Asn Ser Ser Ile Pro Glu Asn
145                 150                 155                 160
```

```
Lys Ala Thr Thr Glu Ser Ser Lys Pro Lys Lys Arg Gly Lys Arg
            165                 170                 175

Ser Leu Asp Thr Asn Asn Gly Asn Asp Thr Thr Ser Thr Thr Gln Asn
            180                 185                 190

Thr Asp Pro Asn Leu Ser Asn Thr Gly Pro Asn Gly Ile Asn Thr Val
            195                 200                 205

Ile Thr Phe Asp Asp Leu Gly Ile Lys Thr Ser Thr Asn Arg Ser Arg
210                 215                 220

Pro Glu Val Lys Val Val Asp Ser Leu Asn Gly Phe Thr Met Val Asn
225                 230                 235                 240

Gly Gly Lys Val Gly Leu Leu Asn Ser Val Leu Glu Arg Thr Ser Val
            245                 250                 255

Phe Asp Ser Ala Asp Pro Lys Asn Tyr Gln Ala Ile Asp Asn Val Val
            260                 265                 270

Ala Leu Gly Arg Ile Lys Gly Asn Asp Pro Asn Asp His Asp Gly Phe
            275                 280                 285

Asn Gly Ile Glu Lys Glu Phe Ser Val Asn Pro Asn Ser Glu Ile Ile
            290                 295                 300

Phe Ser Phe Asn Thr Met Thr Ala Lys Asn Arg Lys Gly Gly Thr Gln
305                 310                 315                 320

Leu Val Leu Arg Asn Ala Glu Asn Asn Gln Glu Ile Ala Ser Thr Asp
            325                 330                 335

Ile Gln Gly Gly Gly Val Tyr Arg Leu Phe Lys Leu Pro Asp Asn Val
            340                 345                 350

His Arg Leu Lys Val Gln Phe Leu Pro Met Asn Glu Ile His Ser Asp
            355                 360                 365

Phe Lys Arg Ile Gln Gln Leu His Asp Gly Tyr Arg Tyr Tyr Ser Phe
            370                 375                 380

Ile Asp Thr Ile Gly Val Asn Ser Gly Ser His Leu Tyr Val Lys Ser
385                 390                 395                 400

Arg Gln Val Asn Lys Asn Val Lys Asn Gly Lys Glu Phe Glu Val Asn
            405                 410                 415

Thr Arg Ile Glu Asn Asn Gly Asn Phe Ala Ala Ile Gly Gln Asn
            420                 425                 430

Glu Leu Thr Tyr Lys Val Thr Leu Pro Glu Asn Phe Glu Tyr Val Asp
            435                 440                 445

Asn Ser Thr Glu Val Ser Phe Val Asn Gly Asn Val Pro Asn Ser Thr
450                 455                 460

Val Asn Pro Phe Ser Val Asn Phe Asp Arg Gln Asn His Thr Leu Thr
465                 470                 475                 480

Phe Ser Ser Asn Gly Leu Asn Leu Gly Arg Ser Ala Gln Asp Val Ala
            485                 490                 495

Arg Phe Leu Pro Asn Lys Ile Leu Asn Ile Arg Tyr Lys Leu Arg Pro
            500                 505                 510

Val Asn Ile Ser Thr Pro Arg Glu Val Thr Phe Asn Glu Ala Ile Lys
            515                 520                 525

Tyr Lys Thr Phe Ser Glu Tyr Ile Asn Thr Asn Asp Asn Thr Val
            530                 535                 540

Thr Gly Gln Gln Thr Pro Phe Ser Ile Asn Val Ile Met Asn Lys Asp
545                 550                 555                 560

Asp Leu Ser Glu Gln Val Asn Lys Asp Ile Ile Pro Ser Asn Tyr Thr
            565                 570                 575

Leu Ala Ser Tyr Asn Lys Tyr Asn Lys Leu Lys Glu Arg Ala Gln Thr
```

```
                580                 585                 590
Val Leu Asp Glu Glu Thr Asn Asn Thr Pro Phe Asn Gln Arg Tyr Ser
            595                 600                 605

Gln Thr Gln Ile Asp Asp Leu Leu His Glu Leu Gln Thr Thr Leu Ile
        610                 615                 620

Asn Arg Val Ser Ala Ser Arg Glu Ile Asn Asp Lys Ala Gln Glu Met
625                 630                 635                 640

Thr Asp Ala Val Tyr Asp Ser Thr Glu Leu Thr Glu Glu Lys Asp
                    645                 650                 655

Thr Leu Val Asp Gln Ile Glu Asn His Lys Asn Glu Ile Ser Asn Asn
            660                 665                 670

Ile Asp Asp Glu Leu Thr Asp Asp Gly Val Glu Arg Val Lys Glu Ala
        675                 680                 685

Gly Leu His Thr Leu Glu Ser Asp Thr Pro His Pro Val Thr Lys Pro
        690                 695                 700

Asn Ala Arg Gln Val Val Asn Asn Arg Ala Asp Gln Gln Lys Thr Leu
705                 710                 715                 720

Ile Arg Asn Asn His Glu Ala Thr Thr Glu Glu Gln Asn Glu Ala Ile
                    725                 730                 735

Arg Gln Val Glu Ala His Ser Ser Asp Ala Ile Ala Lys Ile Gly Glu
            740                 745                 750

Ala Glu Thr Asp Thr Thr Val Asn Glu Ala Arg Asp Asn Gly Thr Lys
        755                 760                 765

Leu Ile Ala Thr Asp Val Pro Asn Pro Thr Lys Lys Ala Glu Ala Arg
770                 775                 780

Ala Ala Val Thr Asn Ser Ala Asn Ser Lys Ile Lys Asp Ile Asn Asn
785                 790                 795                 800

Asn Thr Gln Ala Thr Leu Asp Glu Arg Asn Asp Ala Ile Ala Leu Val
                    805                 810                 815

Asn Arg Ser Lys Asp Glu Ala Ile Gln Asn Ile Asn Thr Ala Gln Gly
            820                 825                 830

Asn Asp Asp Val Thr Glu Ala Gln Asn Asn Gly Thr Asn Thr Ile Gln
        835                 840                 845

Gln Val Pro Leu Thr Pro Val Lys Arg Gln Asn Ala Ile Ala Thr Ile
        850                 855                 860

Asn Ala Lys Ala Asp Glu Gln Lys Arg Leu Ile Gln Ala Asn Asn Asn
865                 870                 875                 880

Ala Thr Thr Glu Glu Lys Ala Asp Ala Glu Arg Lys Val Asn Glu Ala
                    885                 890                 895

Val Ile Thr Ala Asn Gln Asn Ile Thr Asn Ala Thr Asn Arg Asp
            900                 905                 910

Val Asp Gln Ala Gln Thr Thr Gly Ser Gly Ile Ile Ser Ala Ile Ser
        915                 920                 925

Pro Ala Thr Lys Ile Lys Glu Asp Ala Arg Ala Ala Val Glu Ala Lys
        930                 935                 940

Ala Ile Ala Gln Asn Gln Gln Ile Asn Ser Asn Asn Met Ala Thr Thr
945                 950                 955                 960

Glu Glu Lys Glu Asp Ala Leu Asn Gln Val Glu Ala His Lys Gln Ala
                    965                 970                 975

Ala Ile Ala Thr Ile Asn Gln Ala Gln Ser Thr Gln Val Ser Glu
            980                 985                 990

Ala Lys Asn Asn Gly Ile Asn Thr  Ile Asn Gln Asp Gln Pro Asn Ala
        995                 1000                1005
```

-continued

```
Val Lys Lys Asn Asn Thr Lys Ile Ile Leu Glu Gln Lys Gly Asn
1010                1015                1020

Glu Lys Lys Ser Ala Ile Ala Gln Thr Pro Asp Ala Thr Thr Glu
1025                1030                1035

Glu Lys Gln Glu Ala Val Ser Ala Val Ser Gln Ala Val Thr Asn
1040                1045                1050

Gly Ile Thr His Ile Asn Gln Ala Asn Ser Asn Asp Val Asp
1055                1060                1065

Gln Glu Leu Ser Asn Ala Glu Gln Ile Ile Thr Gln Thr Asn Val
1070                1075                1080

Asn Val Gln Lys Lys Pro Gln Ala Arg Gln Ala Leu Ile Ala Lys
1085                1090                1095

Thr Asn Glu Arg Gln Ser Thr Ile Asn Thr Asp Asn Glu Gly Thr
1100                1105                1110

Ile Glu Glu Lys Gln Lys Ala Ile Gln Ser Leu Asn Asp Ala Lys
1115                1120                1125

Asn Leu Ala Asp Glu Gln Ile Thr Gln Ala Ala Ser Asn Gln Asn
1130                1135                1140

Val Asp Asn Ala Leu Asn Ile Gly Ile Ser Asn Ile Ser Lys Ile
1145                1150                1155

Gln Thr Asn Phe Thr Lys Lys Gln Gln Ala Arg Asp Gln Val Asn
1160                1165                1170

Gln Lys Phe Gln Glu Lys Glu Ala Glu Leu Asn Ser Thr Pro His
1175                1180                1185

Ala Thr Gln Asp Glu Lys Gln Asp Ala Leu Thr Arg Leu Thr Gln
1190                1195                1200

Ala Lys Glu Thr Ala Leu Asn Asp Ile Asn Gln Ala Gln Thr Asn
1205                1210                1215

Gln Asn Val Asp Thr Ala Leu Thr Ser Gly Ile Gln Asn Ile Gln
1220                1225                1230

Asn Thr Gln Val Asn Val Arg Lys Lys Gln Glu Ala Lys Thr Thr
1235                1240                1245

Ile Asn Asp Ile Val Gln Gln His Lys Gln Thr Ile Gln Asn Asn
1250                1255                1260

Asp Asp Ala Thr Thr Glu Lys Glu Val Ala Asn Asn Leu Val
1265                1270                1275

Asn Ala Ser Gln Gln Asn Val Ile Ser Lys Ile Asp Asn Ala Thr
1280                1285                1290

Thr Asn Asn Gln Ile Asp Gly Ile Val Ser Asp Gly Arg Gln Ser
1295                1300                1305

Ile Asn Ala Ile Thr Pro Asp Thr Ser Ile Lys Arg Asn Ala Lys
1310                1315                1320

Asn Asp Ile Asp Ile Lys Ala Ala Asp Lys Lys Ile Lys Ile Gln
1325                1330                1335

Arg Ile Asn Asp Ala Thr Asp Glu Glu Ile Gln Glu Ala Asn Arg
1340                1345                1350

Lys Ile Glu Glu Ala Lys Ile Glu Ala Lys Asp Asn Ile Gln Arg
1355                1360                1365

Asn Ser Thr Arg Asp Gln Val Asn Glu Ala Lys Thr Asn Gly Ile
1370                1375                1380

Asn Lys Ile Glu Asn Ile Thr Pro Ala Thr Thr Val Lys Ser Glu
1385                1390                1395

Ala Arg Gln Ala Val Gln Asn Lys Ala Asn Glu Gln Ile Asn His
1400                1405                1410
```

```
Ile Gln Asn Thr Pro Asp Ala Thr Asn Glu Glu Lys Gln Glu Ala
1415                1420                1425

Ile Asn Arg Val Ser Ala Glu Leu Ala Arg Val Gln Ala Gln Ile
1430                1435                1440

Asn Ala Glu His Thr Thr Gln Gly Val Lys Thr Ile Lys Asp Asp
1445                1450                1455

Ala Ile Thr Ser Leu Ser Arg Ile Asn Ala Gln Val Val Glu Lys
1460                1465                1470

Glu Ser Ala Arg Asn Ala Ile Glu Gln Lys Ala Thr Gln Gln Thr
1475                1480                1485

Gln Phe Ile Asn Asn Asn Asp Asn Ala Thr Asp Glu Glu Lys Glu
1490                1495                1500

Val Ala Asn Asn Leu Val Ile Ala Thr Lys Gln Lys Ser Leu Asp
1505                1510                1515

Asn Ile Asn Ser Leu Ser Ser Asn Asn Asp Val Glu Asn Ala Lys
1520                1525                1530

Val Ala Gly Ile Asn Glu Ile Ala Asn Val Leu Pro Ala Thr Ala
1535                1540                1545

Val Lys Ser Lys Ala Lys Lys Asp Ile Asp Gln Lys Leu Ala Gln
1550                1555                1560

Gln Ile Asn Gln Ile Gln Thr His Gln Thr Ala Thr Thr Glu Glu
1565                1570                1575

Lys Glu Ala Ala Ile Gln Leu Ala Asn Gln Lys Ser Asn Glu Ala
1580                1585                1590

Arg Thr Ala Ile Gln Asn Glu His Ser Asn Asn Gly Val Ala Gln
1595                1600                1605

Ala Lys Ser Asn Gly Ile His Glu Ile Glu Leu Val Met Pro Asp
1610                1615                1620

Ala His Lys Lys Ser Asp Ala Lys Gln Ser Ile Asp Asn Lys Tyr
1625                1630                1635

Asn Glu Gln Ser Asn Thr Ile Asn Thr Thr Pro Asp Ala Thr Asp
1640                1645                1650

Glu Glu Lys Gln Lys Ala Leu Asp Lys Leu Lys Ile Ala Lys Asp
1655                1660                1665

Ala Gly Tyr Asn Lys Val Asp Gln Ala Gln Thr Asn Gln Gln Val
1670                1675                1680

Ser Asp Ala Lys Thr Glu Ala Ile Asp Thr Ile Thr Asn Ile Gln
1685                1690                1695

Ala Asn Val Ala Lys Lys Pro Ser Ala Arg Val Glu Leu Asp Ser
1700                1705                1710

Lys Phe Glu Asp Leu Lys Arg Gln Ile Asn Ala Thr Pro Asn Ala
1715                1720                1725

Thr Glu Glu Lys Gln Asp Ala Ile Gln Arg Leu Asn Gly Lys
1730                1735                1740

Arg Asp Glu Val Lys Asn Leu Ile Asn Gln Asp Arg Arg Asp Asn
1745                1750                1755

Glu Val Glu Gln His Lys Asn Ile Gly Leu Gln Glu Leu Glu Thr
1760                1765                1770

Ile His Ala Asn Pro Thr Arg Lys Ser Asp Ala Leu Gln Glu Leu
1775                1780                1785

Gln Thr Lys Phe Ile Ser Gln Thr Glu Leu Ile Asn Asn Asn Lys
1790                1795                1800

Asp Ala Thr Asn Glu Glu Lys Asp Glu Ala Lys Arg Leu Leu Glu
```

-continued

```
            1805                1810                1815

Ile Ser Lys Asn Lys Thr Ile Thr Asn Ile Asn Gln Ala Gln Thr
    1820                1825                1830

Asn Asn Gln Val Asp Asn Ala Lys Asp Asn Gly Met Asn Glu Ile
    1835                1840                1845

Ala Thr Ile Ile Pro Ala Thr Thr Ile Lys Thr Asp Ala Lys Thr
    1850                1855                1860

Ala Ile Asp Lys Lys Ala Glu Gln Gln Val Thr Ile Ile Asn Gly
    1865                1870                1875

Asn Asn Asp Ala Thr Asp Glu Glu Lys Ala Glu Ala Arg Lys Leu
    1880                1885                1890

Val Glu Lys Ala Lys Ile Glu Ala Lys Ser Asn Ile Thr Asn Ser
    1895                1900                1905

Asp Thr Glu Arg Glu Val Asn Gly Ala Lys Thr Asn Gly Leu Glu
    1910                1915                1920

Lys Ile Asn Asn Ile Gln Pro Ser Thr Gln Thr Lys Thr Asn Ala
    1925                1930                1935

Lys Gln Glu Ile Asn Asp Lys Ala Gln Glu Gln Leu Ile Gln Ile
    1940                1945                1950

Asn Asn Thr Pro Asp Ala Thr Glu Glu Lys Gln Glu Ala Thr
    1955                1960                1965

Asn Arg Val Asn Ala Gly Leu Ala Gln Ala Ile Gln Asn Ile Asn
    1970                1975                1980

Asn Ala His Ser Thr Gln Glu Val Asn Glu Ser Lys Thr Asn Ser
    1985                1990                1995

Ile Ala Thr Ile Lys Ser Val Gln Pro Asn Val Ile Lys Lys Pro
    2000                2005                2010

Thr Ala Ile Asn Ser Leu Thr Gln Glu Ala Asn Asn Gln Lys Thr
    2015                2020                2025

Leu Ile Gly Asn Asp Gly Asn Ala Thr Asp Asp Glu Lys Glu Ala
    2030                2035                2040

Ala Lys Gln Leu Val Thr Gln Lys Leu Asn Glu Gln Ile Gln Lys
    2045                2050                2055

Ile His Glu Ser Thr Gln Asp Asn Gln Val Asp Asn Val Lys Ala
    2060                2065                2070

Gln Ala Ile Thr Ala Ile Lys Leu Ile Asn Ala Asn Ala His Lys
    2075                2080                2085

Arg Gln Asp Ala Ile Asn Ile Leu Thr Asn Leu Ala Glu Ser Lys
    2090                2095                2100

Lys Ser Asp Ile Arg Ala Asn Gln Asp Ala Thr Thr Glu Glu Lys
    2105                2110                2115

Asn Thr Ala Ile Gln Ser Ile Asp Asp Thr Leu Ala Gln Ala Arg
    2120                2125                2130

Asn Asn Ile Asn Gly Ala Asn Thr Asn Ala Leu Val Asp Glu Asn
    2135                2140                2145

Leu Glu Asp Gly Lys Gln Lys Leu Gln Arg Ile Val Leu Ser Thr
    2150                2155                2160

Gln Thr Lys Thr Gln Ala Lys Ala Asp Ile Ala Gln Ala Ile Gly
    2165                2170                2175

Gln Gln Arg Ser Thr Ile Asp Gln Asn Gln Asn Ala Thr Thr Glu
    2180                2185                2190

Glu Lys Gln Glu Ala Leu Glu Arg Leu Asn Gln Glu Thr Asn Gly
    2195                2200                2205
```

-continued

Val Asn Asp Arg Ile Gln Ala Ala Leu Ala Asn Gln Asn Val Thr
2210            2215            2220

Asp Glu Lys Asn Asn Ile Leu Glu Thr Ile Arg Asn Val Glu Pro
2225            2230            2235

Ile Val Ile Val Lys Pro Lys Ala Asn Glu Ile Ile Arg Lys Lys
2240            2245            2250

Ala Ala Glu Gln Thr Thr Leu Ile Asn Gln Asn Gln Asp Ala Thr
2255            2260            2265

Leu Glu Glu Lys Gln Ile Ala Leu Gly Lys Leu Glu Glu Val Lys
2270            2275            2280

Asn Glu Ala Leu Asn Gln Val Ser Gln Ala His Ser Asn Asn Asp
2285            2290            2295

Val Lys Ile Val Glu Asn Asn Gly Ile Ala Lys Ile Ser Glu Val
2300            2305            2310

His Pro Glu Thr Ile Ile Lys Arg Asn Ala Lys Gln Glu Ile Glu
2315            2320            2325

Gln Asp Ala Gln Ser Gln Ile Asp Thr Ile Asn Ala Asn Asn Lys
2330            2335            2340

Ser Thr Asn Glu Glu Lys Ser Ala Ala Ile Asp Arg Val Asn Val
2345            2350            2355

Ala Lys Ile Asp Ala Ile Asn Asn Ile Thr Asn Ala Thr Thr Thr
2360            2365            2370

Gln Leu Val Asn Asp Ala Lys Asn Ser Gly Asn Thr Ser Ile Ser
2375            2380            2385

Gln Ile Leu Pro Ser Thr Ala Val Lys Thr Asn Ala Leu Ala Ala
2390            2395            2400

Leu Ala Ser Glu Ala Lys Asn Lys Asn Ala Ile Ile Asp Gln Thr
2405            2410            2415

Pro Asn Ala Thr Ala Glu Glu Lys Glu Glu Ala Asn Asn Lys Val
2420            2425            2430

Asp Arg Leu Gln Glu Glu Ala Asp Ala Asn Ile Leu Lys Ala His
2435            2440            2445

Thr Thr Asp Glu Val Asn Asn Ile Lys Asn Gln Ala Val Gln Asn
2450            2455            2460

Ile Asn Ala Val Gln Val Glu Val Ile Lys Lys Gln Asn Ala Lys
2465            2470            2475

Asn Gln Leu Asn Gln Phe Ile Asp Asn Gln Lys Lys Ile Ile Glu
2480            2485            2490

Asn Thr Pro Asp Ala Thr Leu Glu Glu Lys Ala Glu Ala Asn Arg
2495            2500            2505

Leu Leu Gln Asn Val Leu Thr Ser Thr Ser Asp Glu Ile Ala Asn
2510            2515            2520

Val Asp His Asn Asn Glu Val Asp Gln Ala Leu Asp Lys Ala Arg
2525            2530            2535

Pro Lys Ile Glu Ala Ile Val Pro Gln Val Ser Lys Lys Arg Asp
2540            2545            2550

Ala Leu Asn Ala Ile Gln Glu Ala Phe Asn Ser Gln Thr Gln Glu
2555            2560            2565

Ile Gln Glu Asn Gln Glu Ala Thr Asn Glu Glu Lys Thr Glu Ala
2570            2575            2580

Leu Asn Lys Ile Asn Gln Leu Leu Asn Gln Ala Lys Val Asn Ile
2585            2590            2595

Asp Gln Ala Gln Ser Asn Lys Asp Val Asp Ser Ala Lys Thr Arg
2600            2605            2610

```
Ser Ile Gln Asp Ile Glu Gln Ile Gln Pro His Pro Gln Thr Lys
2615                2620                2625

Ala Thr Gly Arg His Arg Leu Asn Glu Lys Ala Asn Gln Gln Gln
2630                2635                2640

Ser Thr Ile Ala Thr His Pro Asn Ser Thr Ile Glu Glu Arg Gln
2645                2650                2655

Glu Ala Ser Ala Lys Leu Gln Glu Val Leu Lys Lys Ala Ile Ala
2660                2665                2670

Lys Ile Asp Lys Gly Gln Thr Asn Asp Asp Val Glu Lys Thr Val
2675                2680                2685

Val Asn Gly Ile Ala Glu Ile Glu Asn Ile Leu Pro Ala Thr Thr
2690                2695                2700

Val Lys Asp Lys Ala Lys Ala Asp Val Asn Ala Glu Lys Glu Glu
2705                2710                2715

Lys Asn Leu Gln Ile Asn Ser Asn Asp Glu Ala Thr Thr Glu Glu
2720                2725                2730

Lys Leu Val Ala Ser Asp Asn Leu Asn His Val Val Glu Thr Thr
2735                2740                2745

Asn Gln Ala Ile Glu Asp Ala Pro Asp Thr Asn Gln Val Asn Val
2750                2755                2760

Glu Lys Asn Lys Gly Ile Gly Thr Ile Arg Asp Ile Gln Pro Leu
2765                2770                2775

Val Val Lys Lys Pro Thr Ala Lys Ser Lys Ile Glu Ser Ala Val
2780                2785                2790

Glu Lys Lys Lys Thr Glu Ile Asn Gln Thr Gln Asn Ala Thr His
2795                2800                2805

Asp Glu Val Arg Glu Gly Leu Asn Gln Leu Asn Gln Ile His Glu
2810                2815                2820

Lys Ala Lys Asn Asp Val Asn Gln Ser Gln Thr Asn Gln Gln Val
2825                2830                2835

Glu Asn Ala Glu Gln Asn Ser Leu Asp Gln Ile Asn Asn Phe Arg
2840                2845                2850

Pro Asp Phe Ser Lys Lys Arg Asn Ala Val Ala Glu Ile Val Lys
2855                2860                2865

Ala Gln Gln Asn Lys Ile Asp Glu Ile Glu Gln Glu Phe Ser Ala
2870                2875                2880

Thr Gln Glu Glu Lys Asp Asn Ala Leu Gln His Leu Asp Glu Gln
2885                2890                2895

Val Lys Glu Ile Ile Asn Ser Ile Asn Gln Ala Asn Thr Asp Asn
2900                2905                2910

Glu Val Asp Asn Ala Lys Thr Ser Gly Leu Asn Asn Ile Thr Glu
2915                2920                2925

Tyr Arg Pro Glu Tyr Asn Lys Lys Lys Asn Ala Ile Leu Lys Leu
2930                2935                2940

Tyr Asp Val Ser Asp Thr Gln Glu Ala Ile Ile Asn Gly Tyr Pro
2945                2950                2955

Asp Ala Thr Glu Asp Glu Leu Gln Glu Ala Asn Ser Lys Leu Asn
2960                2965                2970

Lys Ile Leu Leu Asp Ala Lys Lys Gln Ile Gly Leu Ala His Thr
2975                2980                2985

Asn Asn Glu Val Asp Asp Ile Tyr Asn Glu Val Ser Gln Lys Met
2990                2995                3000

Lys Thr Ile Leu Pro Arg Val Asp Thr Lys Ala Val Ala Arg Ser
```

```
                     3005                3010                3015

Val Leu Asn Ala Leu Ala Lys Gln Leu Ile Lys Thr Phe Glu Asn
        3020                3025                3030

Thr Ala Asp Val Thr His Glu Glu Arg Asn Asp Ala Ile Asn His
        3035                3040                3045

Val Lys Glu Gln Leu Ser Leu Val Phe Asn Ala Ile Glu Lys Asp
        3050                3055                3060

Arg Lys Asp Ile Gln Val Ala Gln Asp Glu Leu Phe Gly Leu Asn
        3065                3070                3075

Glu Leu Asn Ser Ile Phe Ile Asn Ile Thr Gln Lys Pro Thr Ala
        3080                3085                3090

Arg Lys Ala Ile Ser Gly Met Ala Ser Gln Leu Asn Asn Ser Ile
        3095                3100                3105

Asn Asn Thr Pro Tyr Ala Thr Glu Glu Arg Gln Ile Ala Leu
        3110                3115                3120

Asn Lys Val Lys Ala Ile Val Asp Asp Ala Asn Glu Lys Ile Arg
        3125                3130                3135

Glu Ala Asn Thr Asp Ser Glu Val Leu Gly Thr Lys Ser Asn Ala
        3140                3145                3150

Ile Thr Leu Leu Gln Ala Ile Ser Ala Asp Val Gln Val Lys Pro
        3155                3160                3165

Gln Ala Phe Glu Glu Ile Asn Ala Gln Ala Glu Ile Gln Arg Glu
        3170                3175                3180

Arg Ile Asn Gly Asn Ser Asp Ala Thr Arg Glu Glu Lys Glu Glu
        3185                3190                3195

Ala Leu Lys Gln Val Asp Thr Leu Val Asn His Ser Phe Ile Thr
        3200                3205                3210

Ile Asn Asn Val Asn Lys Asn Gln Glu Val Tyr Asp Thr Lys Asp
        3215                3220                3225

Lys Thr Ile Glu Ala Ile His Lys Ile Lys Pro Ile Ser Thr Ile
        3230                3235                3240

Lys Pro Gln Ala Leu Asn Glu Ile Thr Ile Gln Leu Asp Thr Gln
        3245                3250                3255

Arg Asp Leu Ile Lys Asn Asn Lys Glu Ser Thr Val Glu Glu Lys
        3260                3265                3270

Ala Ser Ala Ile Asp Lys Leu Ile Lys Thr Ala Ala Arg Ile Ala
        3275                3280                3285

Glu Ser Ile Asp Lys Ala Gln Thr Asn Glu Glu Val Lys Asn Ile
        3290                3295                3300

Lys Lys Gln Ser Ile Asp Glu Ile Ser Lys Ile Leu Pro Val Ile
        3305                3310                3315

Glu Ile Lys Ser Ala Ala Arg Asn Glu Ile His Gln Lys Ala Glu
        3320                3325                3330

Val Ile Arg Gly Leu Ile Asn Asp Asn Glu Glu Ala Thr Lys Glu
        3335                3340                3345

Glu Lys Asp Ile Ala Leu Asn Gln Leu Asp Thr Thr Leu Thr Gln
        3350                3355                3360

Ala Asn Val Ser Ile Asp Gln Ala Leu Thr Asn Glu Ala Val Asn
        3365                3370                3375

Arg Ala Lys Glu Ile Ala Asn Ser Glu Ile Asn Lys Ile Ser Val
        3380                3385                3390

Ile Ala Ile Lys Lys Pro Glu Ala Ile Ala Glu Ile Gln Glu Leu
        3395                3400                3405
```

Ala Asp Lys Lys Leu Asn Lys Phe Lys Gln Ser Gln Glu Ala Thr
3410            3415                3420

Ile Glu Glu Lys Gln Ser Ala Ile Asn Glu Leu Glu Gln Ala Leu
   3425             3430                3435

Lys Ser Ala Ile Asn His Ile His Gln Ser Gln Asn Asn Glu Ser
3440            3445                3450

Val Ser Ala Ala Leu Lys Glu Ser Ile Ser Leu Ile Asp Ser Ile
3455            3460                3465

Glu Ile Gln Ala His Lys Lys Leu Glu Ala Lys Ala Tyr Ile Asp
3470            3475                3480

Gly Tyr Ser Asp Asp Lys Ile Asn Asp Ile Ser Ser Arg Ala Thr
3485            3490                3495

Asn Glu Glu Lys Gln Ile Phe Val Ser Lys Leu Lys Ala Leu Ile
3500            3505                3510

Asn Arg Thr His Lys Gln Ile Asp Glu Ala Glu Thr Phe Val Ser
3515            3520                3525

Val Glu Thr Ile Val Arg Asn Phe Lys Val Glu Ala Asp Lys Leu
3530            3535                3540

Asn Ser Ile Val Arg Lys Lys Ala Lys Ala Ser Lys Glu Ile Glu
3545            3550                3555

Leu Glu Ala Asp His Val Lys Gln Met Ile Asn Ala Asn Leu Ser
3560            3565                3570

Ala Ser Thr Arg Val Lys Gln Asn Ala Arg Thr Leu Ile Asn Glu
3575            3580                3585

Ile Val Ser Asn Ala Leu Ser Gln Leu Asn Lys Val Thr Thr Asn
3590            3595                3600

Lys Glu Val Asp Glu Ile Val Asn Glu Thr Ile Glu Lys Leu Lys
3605            3610                3615

Ser Ile Gln Ile Arg Glu Asp Lys Ile Leu Ser Ser Gln Arg Ser
3620            3625                3630

Ser Thr Ser Met Thr Glu Lys Ser Asn Gln Cys Tyr Ser Ser Glu
3635            3640                3645

Asn Asn Thr Ile Lys Ser Leu Pro Glu Ala Gly Asn Ala Asp Lys
3650            3655                3660

Ser Leu Pro Leu Ala Gly Val Thr Leu Ile Ser Gly Leu Ala Ile
3665            3670                3675

Met Ser Ser Arg Lys Lys Lys Lys Asp Lys Lys Val Asn Asp
3680            3685                3690

<210> SEQ ID NO 49
<211> LENGTH: 439
<212> TYPE: PRT
<213> ORGANISM: Staphylococcus epidermidis

<400> SEQUENCE: 49

Leu Asp Ile Lys Met Pro Lys Leu Gly Glu Ser Val His Glu Gly Thr
1               5                   10                  15

Ile Glu Gln Trp Leu Val Ser Val Gly Asp His Val Asp Glu Tyr Glu
            20                  25                  30

Pro Leu Cys Glu Val Ile Thr Asp Lys Val Thr Ala Glu Val Pro Ser
        35                  40                  45

Thr Ile Ser Gly Thr Ile Thr Glu Leu Val Glu Glu Gly Gln Thr
    50                  55                  60

Val Asn Ile Asn Thr Val Ile Cys Lys Ile Asp Ser Glu Asn Gly Gln
65                  70                  75                  80

```
Asn Gln Thr Glu Ser Ala Asn Glu Phe Lys Glu Gln Asn Gln His
                 85                  90                  95

Ser Gln Ser Asn Ile Asn Val Ser Gln Phe Glu Asn Asn Pro Lys Thr
            100                 105                 110

His Glu Ser Glu Val His Thr Ala Ser Ser Arg Ala Asn Asn Asn Gly
        115                 120                 125

Arg Phe Ser Pro Val Val Phe Lys Leu Ala Ser Glu His Asp Ile Asp
    130                 135                 140

Leu Thr Gln Val Lys Gly Thr Gly Phe Glu Gly Arg Val Thr Lys Lys
145                 150                 155                 160

Asp Ile Gln Asn Ile Ile Asn Asn Pro Asn Asp Gln Glu Lys Glu Lys
                165                 170                 175

Glu Phe Lys Gln Thr Asp Lys Lys Asp His Ser Thr Asn His Cys Asp
            180                 185                 190

Phe Leu His Gln Ser Ser Thr Lys Asn Glu His Ser Pro Leu Ser Asn
        195                 200                 205

Glu Arg Val Val Pro Val Lys Gly Ile Arg Lys Ala Ile Ala Gln Asn
    210                 215                 220

Met Val Thr Ser Val Ser Glu Ile Pro His Gly Trp Met Met Val Glu
225                 230                 235                 240

Ala Asp Ala Thr Asn Leu Val Gln Thr Arg Asn Tyr His Lys Ala Gln
                245                 250                 255

Phe Lys Gln Asn Glu Gly Tyr Asn Leu Thr Phe Phe Ala Phe Phe Val
            260                 265                 270

Lys Ala Val Ala Glu Ala Leu Lys Val Asn Pro Leu Leu Asn Ser Thr
        275                 280                 285

Trp Gln Gly Asp Glu Ile Val Ile His Lys Asp Ile Asn Ile Ser Ile
    290                 295                 300

Ala Val Ala Asp Asp Lys Leu Tyr Val Pro Val Ile Lys Asn Ala
305                 310                 315                 320

Asp Glu Lys Ser Ile Lys Gly Ile Ala Arg Glu Ile Asn Asp Leu Ala
                325                 330                 335

Thr Lys Ala Arg Leu Gly Lys Leu Ala Gln Ser Asp Met Gln Asn Gly
            340                 345                 350

Thr Phe Thr Val Asn Asn Thr Gly Ser Phe Gly Ser Val Ser Ser Met
        355                 360                 365

Gly Ile Ile Asn His Pro Gln Ala Ala Ile Leu Gln Val Glu Ser Val
    370                 375                 380

Val Lys Lys Pro Val Val Ile Asp Asp Met Ala Ile Arg Asn Met
385                 390                 395                 400

Val Asn Leu Cys Ile Ser Ile Asp His Arg Ile Leu Asp Gly Val Gln
                405                 410                 415

Thr Gly Lys Phe Met Asn Leu Val Lys Lys Ile Glu Gln Tyr Ser
            420                 425                 430

Ile Glu Asn Thr Ser Ile Tyr
        435

<210> SEQ ID NO 50
<211> LENGTH: 295
<212> TYPE: PRT
<213> ORGANISM: Staphylococcus epidermidis

<400> SEQUENCE: 50

Met Asn Thr Ile Ile Glu Glu Tyr Leu Asn Phe Ile Gln Ile Glu Lys
1               5                   10                  15
```

```
Gly Leu Ser Asn Asn Thr Ile Gly Ala Tyr Arg Arg Asp Leu Lys Lys
            20                  25                  30

Tyr Lys Asp Tyr Leu Glu Asp Asn Lys Ile Ser His Ile Asp Phe Ile
        35                  40                  45

Asp Arg Gln Ile Ile Gln Glu Cys Leu Gly His Leu Ile Asp Met Gly
    50                  55                  60

Gln Ser Ser Lys Ser Leu Ala Arg Phe Ile Ser Thr Ile Arg Ser Phe
65                  70                  75                  80

His Gln Phe Ala Leu Arg Glu Lys Tyr Ala Ala Lys Asp Pro Thr Val
                85                  90                  95

Leu Ile Glu Thr Pro Lys Tyr Glu Lys Lys Leu Pro Asp Val Leu Glu
            100                 105                 110

Ile Asp Glu Val Ile Ala Leu Leu Glu Thr Pro Asp Leu Thr Lys Asn
        115                 120                 125

Asn Gly Tyr Arg Asp Arg Thr Met Leu Glu Leu Leu Tyr Ala Thr Gly
    130                 135                 140

Met Arg Val Thr Glu Ile Ile Gln Leu Asp Val Glu Asp Val Asn Leu
145                 150                 155                 160

Met Met Gly Phe Val Arg Val Phe Gly Lys Gly Asn Lys Glu Arg Ile
                165                 170                 175

Val Pro Leu Gly Asp Thr Val Ile Glu Tyr Leu Thr Thr Tyr Ile Glu
            180                 185                 190

Thr Val Arg Pro Gln Leu Leu Lys Gln Thr Thr Thr Gln Ala Leu Phe
        195                 200                 205

Leu Asn Met His Gly Lys Ser Leu Ser Arg Gln Gly Ile Trp Lys Ile
    210                 215                 220

Ile Lys Gln Tyr Gly Leu Lys Ala Asn Ile Asn Lys Thr Leu Thr Pro
225                 230                 235                 240

His Thr Leu Arg His Ser Phe Ala Thr His Leu Leu Glu Asn Gly Ala
                245                 250                 255

Asp Leu Arg Ala Val Gln Glu Met Leu Gly His Ser Asp Ile Ser Thr
            260                 265                 270

Thr Gln Leu Tyr Thr His Val Ser Lys Ser Gln Ile Arg Lys Met Tyr
        275                 280                 285

Thr Gln Phe His Pro Arg Ala
    290                 295

<210> SEQ ID NO 51
<211> LENGTH: 800
<212> TYPE: PRT
<213> ORGANISM: Staphylococcus epidermidis

<400> SEQUENCE: 51

Met Ser Leu Val Tyr Leu Met Ala Thr Asn Leu Leu Val Met Leu Ile
1               5                   10                  15

Val Leu Phe Thr Leu Ser His Arg Gln Leu Arg Lys Val Ala Gly Tyr
            20                  25                  30

Val Ala Leu Ile Ala Pro Ile Val Thr Ser Thr Tyr Phe Ile Met Lys
        35                  40                  45

Ile Pro Asp Val Ile Arg Asn Lys Phe Ile Ala Val Arg Leu Pro Trp
    50                  55                  60

Met Pro Ser Ile Asp Ile Asn Leu Asp Leu Arg Leu Asp Gly Leu Ser
65                  70                  75                  80

Leu Met Phe Gly Leu Ile Ile Ser Leu Ile Gly Val Gly Val Phe Phe
                85                  90                  95
```

```
Tyr Ala Thr Gln Tyr Leu Ser His Ser Thr Asp Asn Leu Pro Arg Phe
            100                 105                 110

Phe Ile Tyr Leu Leu Phe Met Phe Ser Met Ile Gly Ile Val Ile
            115                 120                 125

Ala Asn Asn Thr Ile Leu Met Tyr Val Phe Trp Glu Leu Thr Ser Ile
130                 135                 140

Ser Ser Phe Leu Leu Ile Ser Tyr Trp Tyr Asn Asn Gly Glu Ser Gln
145                 150                 155                 160

Leu Gly Ala Ile Gln Ser Phe Met Ile Thr Val Phe Gly Gly Leu Ala
                165                 170                 175

Leu Leu Thr Gly Phe Ile Ile Leu Tyr Ile Ile Thr Gly Thr Asn Thr
            180                 185                 190

Ile Thr Asp Ile Leu Asn Gln Arg Asn Ala Ile Ser Arg His Pro Leu
            195                 200                 205

Phe Ile Pro Met Ile Leu Met Leu Leu Leu Gly Ala Phe Thr Lys Ser
            210                 215                 220

Ala Gln Phe Pro Phe His Ile Trp Leu Pro Lys Ala Met Ala Ala Pro
225                 230                 235                 240

Thr Pro Val Ser Ala Tyr Leu His Ser Ala Thr Met Val Lys Ala Gly
                245                 250                 255

Ile Phe Leu Leu Phe Arg Phe Thr Pro Leu Leu Gly Leu Ser Asn Val
            260                 265                 270

Tyr Ile Tyr Thr Val Thr Phe Val Gly Leu Ile Thr Met Leu Phe Gly
            275                 280                 285

Ser Leu Thr Ala Leu Arg Gln Tyr Asp Leu Lys Gly Ile Leu Ala Tyr
290                 295                 300

Ser Thr Ile Ser Gln Leu Gly Met Ile Met Thr Met Val Gly Leu Gly
305                 310                 315                 320

Gly Gly Tyr Ala Gln His Thr Ser Asp Glu Leu Ser Lys Phe Tyr Ile
                325                 330                 335

Leu Val Leu Phe Ala Gly Leu Phe His Leu Met Asn His Ala Val Phe
            340                 345                 350

Lys Cys Ala Leu Phe Met Gly Val Gly Ile Ile Asp His Glu Ser Gly
            355                 360                 365

Thr Arg Asp Ile Arg Leu Leu Asn Gly Met Arg Lys Val Phe Pro Lys
370                 375                 380

Met His Ile Val Met Leu Leu Ala Ala Leu Ser Met Ala Gly Val Pro
385                 390                 395                 400

Phe Leu Asn Gly Phe Leu Ser Lys Glu Met Phe Leu Asp Ser Leu Thr
                405                 410                 415

Lys Ala Asn Glu Leu Asp Gln Tyr Gly Phe Val Leu Thr Phe Val Ile
            420                 425                 430

Ile Ser Ile Gly Val Ile Ala Ser Ile Leu Thr Phe Thr Tyr Ala Leu
            435                 440                 445

Tyr Met Ile Lys Glu Thr Phe Trp Gly Asn Tyr Asn Ile Glu Lys Phe
            450                 455                 460

Lys Arg Lys Gln Ile His Glu Pro Trp Leu Phe Ser Leu Pro Ala Val
465                 470                 475                 480

Ile Leu Met Leu Leu Ile Pro Val Ile Phe Val Pro Asn Val Phe
                485                 490                 495

Gly Asn Phe Val Ile Leu Pro Ala Thr Arg Ser Val Ser Gly Ile Gly
                500                 505                 510

Ala Glu Val Asp Ala Phe Val Pro His Ile Ser Gln Trp His Gly Val
            515                 520                 525
```

```
Asn Leu Pro Leu Ile Leu Ser Ile Val Val Ile Ile Gly Leu Ile
    530                 535                 540

Leu Ala Leu Val Val Asn Trp Lys Glu Val Thr His Gln Ile Ile Lys
545                 550                 555                 560

Ser Ala Ser Ile Thr Asp Gly Tyr Arg Lys Ile Tyr Arg Glu Phe Glu
                565                 570                 575

Leu Tyr Ser Ala Arg Gly Ile Arg Ala Leu Met Asn Asn Lys Leu Asn
            580                 585                 590

Tyr Tyr Ile Met Ile Thr Leu Phe Ile Phe Val Ala Ile Val Val Tyr
        595                 600                 605

Gly Tyr Leu Thr Val Gly Phe Pro His Val His Gln Leu His Ile Ser
    610                 615                 620

Ser Phe Gly Pro Leu Glu Val Ile Leu Ser Val Val Thr Leu Ile Ile
625                 630                 635                 640

Gly Ile Ser Leu Ile Phe Ile Arg Gln Arg Leu Thr Met Val Val Leu
                645                 650                 655

Asn Gly Met Ile Gly Phe Ala Val Thr Leu Tyr Phe Ile Ala Met Lys
            660                 665                 670

Ala Pro Asp Leu Ala Leu Thr Gln Leu Val Val Glu Thr Ile Thr Thr
        675                 680                 685

Ile Leu Phe Ile Val Ser Phe Ser Arg Leu Pro Asn Ile Pro Arg Val
    690                 695                 700

Lys Ala Asn Leu Lys Lys Glu Thr Phe Lys Ile Ile Val Ser Leu Val
705                 710                 715                 720

Met Ala Leu Thr Val Val Ser Leu Ile Phe Val Ala Gln Gln Ala Asp
                725                 730                 735

Gly Met Pro Ser Ile Ala Lys Phe Tyr Glu Asp Ala Tyr Glu Leu Thr
            740                 745                 750

Gly Gly Lys Asn Ile Val Asn Ala Ile Leu Gly Asp Phe Arg Ala Leu
        755                 760                 765

Asp Thr Met Phe Glu Gly Leu Val Leu Ile Ile Ala Gly Leu Gly Ile
    770                 775                 780

Tyr Thr Leu Leu Asn Tyr Lys Asp Arg Arg Gly Gln Asp Glu Arg Glu
785                 790                 795                 800

<210> SEQ ID NO 52
<211> LENGTH: 892
<212> TYPE: PRT
<213> ORGANISM: Staphylococcus epidermidis

<400> SEQUENCE: 52

Leu Phe Gly Leu Gly His Asn Glu Ala Lys Ala Glu Glu Asn Thr Val
1               5                   10                  15

Gln Asp Val Lys Asp Ser Asn Met Asp Asp Glu Leu Ser Asp Ser Asn
            20                  25                  30

Asp Gln Ser Ser Asn Glu Glu Lys Asn Asp Val Ile Asn Asn Ser Gln
        35                  40                  45

Ser Ile Asn Thr Asp Asp Asn Gln Ile Lys Lys Glu Glu Thr Asn
    50                  55                  60

Ser Asn Asp Ala Ile Glu Asn Arg Ser Lys Asp Ile Thr Gln Ser Thr
65                  70                  75                  80

Thr Asn Val Asp Glu Asn Glu Ala Thr Phe Leu Gln Lys Thr Pro Gln
                85                  90                  95

Asp Asn Thr Gln Leu Lys Glu Glu Val Val Lys Glu Pro Ser Ser Val
            100                 105                 110
```

```
Glu Ser Ser Asn Ser Ser Met Asp Thr Ala Gln Gln Pro Ser His Thr
            115                 120                 125
Thr Ile Asn Ser Glu Ala Ser Ile Gln Thr Ser Asp Asn Glu Glu Asn
        130                 135                 140
Ser Arg Val Ser Asp Phe Ala Asn Ser Lys Ile Ile Glu Ser Asn Thr
145                 150                 155                 160
Glu Ser Asn Lys Glu Asn Thr Ile Glu Gln Pro Asn Lys Val Arg
                165                 170                 175
Glu Asp Ser Ile Thr Ser Gln Pro Ser Ser Tyr Lys Asn Ile Asp Glu
            180                 185                 190
Lys Ile Ser Asn Gln Asp Glu Leu Leu Asn Leu Pro Ile Asn Glu Tyr
        195                 200                 205
Glu Asn Lys Val Arg Pro Leu Ser Thr Thr Ser Ala Gln Pro Ser Ser
        210                 215                 220
Lys Arg Val Thr Val Asn Gln Leu Ala Ala Glu Gln Gly Ser Asn Val
225                 230                 235                 240
Asn His Leu Ile Lys Val Thr Asp Gln Ser Ile Thr Glu Gly Tyr Asp
                245                 250                 255
Asp Ser Asp Gly Ile Ile Lys Ala His Asp Ala Glu Asn Leu Ile Tyr
            260                 265                 270
Asp Val Thr Phe Glu Val Asp Asp Lys Val Lys Ser Gly Asp Thr Met
        275                 280                 285
Thr Val Asn Ile Asp Lys Asn Thr Val Pro Ser Asp Leu Thr Asp Ser
        290                 295                 300
Phe Ala Ile Pro Lys Ile Lys Asp Asn Ser Gly Glu Ile Ile Ala Thr
305                 310                 315                 320
Gly Thr Tyr Asp Asn Thr Asn Lys Gln Ile Thr Tyr Thr Phe Thr Asp
                325                 330                 335
Tyr Val Asp Lys Tyr Glu Asn Ile Lys Ala His Leu Lys Leu Thr Ser
            340                 345                 350
Tyr Ile Asp Lys Ser Lys Val Pro Asn Asn Asn Thr Lys Leu Asp Val
        355                 360                 365
Glu Tyr Lys Thr Ala Leu Ser Ser Val Asn Lys Thr Ile Thr Val Glu
        370                 375                 380
Tyr Gln Lys Pro Asn Glu Asn Arg Thr Ala Asn Leu Gln Ser Met Phe
385                 390                 395                 400
Thr Asn Ile Asp Thr Lys Asn His Thr Val Glu Gln Thr Ile Tyr Ile
                405                 410                 415
Asn Pro Leu Arg Tyr Ser Ala Lys Glu Thr Asn Val Asn Ile Ser Gly
            420                 425                 430
Asn Gly Asp Glu Gly Ser Thr Ile Ile Asp Asp Ser Thr Ile Ile Lys
        435                 440                 445
Val Tyr Lys Val Gly Asp Asn Gln Asn Leu Pro Asp Ser Asn Arg Ile
450                 455                 460
Tyr Asp Tyr Ser Glu Tyr Glu Asp Val Thr Asn Asp Asp Tyr Ala Gln
465                 470                 475                 480
Leu Gly Asn Asn Asn Asp Val Asn Ile Asn Phe Gly Asn Ile Asp Ser
                485                 490                 495
Pro Tyr Ile Ile Lys Val Ile Ser Lys Tyr Asp Pro Asn Lys Asp Asp
            500                 505                 510
Tyr Thr Thr Ile Gln Gln Thr Val Thr Met Gln Thr Thr Ile Asn Glu
        515                 520                 525
Tyr Thr Gly Glu Phe Arg Thr Ala Ser Tyr Asp Asn Thr Ile Ala Phe
```

```
              530                 535                 540
Ser Thr Ser Ser Gly Gln Gly Gln Gly Asp Leu Pro Pro Glu Lys Thr
545                 550                 555                 560

Tyr Lys Ile Gly Asp Tyr Val Trp Glu Asp Val Asp Lys Asp Gly Ile
                565                 570                 575

Gln Asn Thr Asn Asp Asn Glu Lys Pro Leu Ser Asn Val Leu Val Thr
            580                 585                 590

Leu Thr Tyr Pro Asp Gly Thr Ser Lys Ser Val Arg Thr Asp Glu Glu
        595                 600                 605

Gly Lys Tyr Gln Phe Asp Gly Leu Lys Asn Gly Leu Thr Tyr Lys Ile
    610                 615                 620

Thr Phe Glu Thr Pro Glu Gly Tyr Thr Pro Thr Leu Lys His Ser Gly
625                 630                 635                 640

Thr Asn Pro Ala Leu Asp Ser Glu Gly Asn Ser Val Trp Val Thr Ile
                645                 650                 655

Asn Gly Gln Asp Asp Met Thr Ile Asp Ser Gly Phe Tyr Gln Thr Pro
            660                 665                 670

Lys Tyr Ser Leu Gly Asn Tyr Val Trp Tyr Asp Thr Asn Lys Asp Gly
        675                 680                 685

Ile Gln Gly Asp Asp Glu Lys Gly Ile Ser Gly Val Lys Val Thr Leu
    690                 695                 700

Lys Asp Glu Asn Gly Asn Ile Ile Ser Thr Thr Thr Thr Asp Glu Asn
705                 710                 715                 720

Gly Lys Tyr Gln Phe Asp Asn Leu Asn Ser Gly Asn Tyr Ile Val His
                725                 730                 735

Phe Asp Lys Pro Ser Gly Met Thr Gln Thr Thr Thr Asp Ser Gly Asp
            740                 745                 750

Asp Asp Glu Gln Asp Ala Asp Gly Glu Glu Val His Val Thr Ile Thr
        755                 760                 765

Asp His Asp Asp Phe Ser Ile Asp Asn Gly Tyr Tyr Asp Asp Asp Ser
    770                 775                 780

Asp Ser Asp Ser Asp Ser Asp Ser Asp Asp Ser Asp Ser Asp
785                 790                 795                 800

Ser Asp Ser Asp Ser Asp Ser Asp Ser Asp Ser Asp Ser Asp
                805                 810                 815

Ser Asp Ser Asp Ser Asp Ser Asp Ser Asp Ser Asp Ser Asp
            820                 825                 830

Ser Asp Ser Asp Ser Asp Ser Gly Leu Asp Asn Ser Ser Asp Lys Asn
        835                 840                 845

Thr Lys Asp Lys Leu Pro Asp Thr Gly Ala Asn Glu Asp His Asp Ser
850                 855                 860

Lys Gly Thr Leu Leu Gly Ala Leu Phe Ala Gly Leu Gly Ala Leu Leu
                865                 870                 875                 880

Leu Gly Lys Arg Arg Lys Asn Arg Lys Asn Lys Asn
                885                 890

<210> SEQ ID NO 53
<211> LENGTH: 484
<212> TYPE: PRT
<213> ORGANISM: Staphylococcus epidermidis

<400> SEQUENCE: 53

Met Ser Glu Arg Ile Arg Val Arg Tyr Ala Pro Ser Pro Thr Gly Tyr
1               5                   10                  15

Leu His Ile Gly Asn Ala Arg Thr Ala Leu Phe Asn Tyr Leu Phe Ala
```

```
                20                  25                  30
Lys His Tyr Asn Gly Asp Phe Val Arg Ile Glu Asp Thr Asp Ser
        35                  40                  45
Lys Arg Asn Leu Glu Asp Gly Glu Ser Ser Gln Phe Asp Asn Leu Lys
50                  55                  60
Trp Leu Gly Leu Asp Trp Asp Glu Ser Val Asp Lys Asp Lys Gly Phe
65                  70                  75                  80
Gly Pro Tyr Arg Gln Ser Glu Arg Ala Glu Ile Tyr Asn Pro Leu Ile
            85                  90                  95
Gln Gln Leu Leu Glu Glu Asp Lys Ala Tyr Lys Cys Tyr Met Thr Glu
            100                 105                 110
Glu Glu Leu Glu Ala Glu Arg Glu Ala Gln Ile Ala Arg Gly Glu Met
            115                 120                 125
Pro Arg Tyr Gly Gly Gln His Ala His Leu Thr Glu Glu Gln Arg Gln
            130                 135                 140
Gln Tyr Glu Ala Glu Gly Arg Lys Pro Ser Ile Arg Phe Arg Val Pro
145                 150                 155                 160
Lys Asp Gln Thr Tyr Thr Phe Asn Asp Met Val Lys Gly Glu Ile Ser
                165                 170                 175
Phe Glu Ser Asp Asn Ile Gly Asp Trp Val Ile Val Lys Lys Asp Gly
                180                 185                 190
Val Pro Thr Tyr Asn Phe Ala Val Ala Val Asp Asp His Tyr Met Gln
                195                 200                 205
Ile Ser Asp Val Ile Arg Gly Asp Asp His Val Ser Asn Thr Pro Lys
            210                 215                 220
Gln Leu Met Ile Tyr Glu Ala Phe Gly Trp Glu Ala Pro Arg Phe Gly
225                 230                 235                 240
His Met Ser Leu Ile Val Asn Glu Glu Arg Lys Lys Leu Ser Lys Arg
                245                 250                 255
Asp Gly Gln Ile Leu Gln Phe Ile Glu Gln Tyr Arg Asp Leu Gly Tyr
                260                 265                 270
Leu Pro Glu Ala Leu Phe Asn Phe Ile Thr Leu Leu Gly Trp Ser Pro
            275                 280                 285
Glu Gly Glu Glu Glu Ile Phe Ser Lys Glu Glu Phe Ile Lys Ile Phe
290                 295                 300
Asp Glu Lys Arg Leu Ser Lys Ser Pro Ala Met Phe Asp Arg Gln Lys
305                 310                 315                 320
Leu Ala Trp Val Asn Asn Gln Tyr Met Lys Thr Lys Asp Thr Glu Thr
                325                 330                 335
Val Phe Glu Leu Ala Leu Pro His Leu Ile Lys Ala Asn Leu Ile Pro
            340                 345                 350
Glu Asn Pro Ser Glu Lys Asp Arg Glu Trp Gly Arg Lys Leu Ile Ala
            355                 360                 365
Leu Tyr Gln Lys Glu Met Ser Tyr Ala Gly Glu Ile Val Pro Leu Ser
            370                 375                 380
Glu Met Phe Phe His Glu Met Pro Glu Leu Gly Lys Asp Glu Gln Glu
385                 390                 395                 400
Val Leu Gln Gly Glu Gln Val Pro Glu Leu Met Asn His Leu Tyr Gly
                405                 410                 415
Lys Leu Glu Ser Leu Glu Ser Phe Glu Ala Thr Glu Ile Lys Lys Met
            420                 425                 430
Ile Lys Glu Val Gln Lys Glu Thr Gly Ile Lys Gly Lys Gln Leu Phe
            435                 440                 445
```

```
Met Pro Ile Arg Val Ala Val Thr Gly Gln Met His Gly Pro Glu Leu
450                 455                 460

Pro Asn Thr Ile Glu Val Leu Gly Lys Asp Lys Val Leu Ser Arg Leu
465                 470                 475                 480

Lys Asn Leu Val

<210> SEQ ID NO 54
<211> LENGTH: 296
<212> TYPE: PRT
<213> ORGANISM: Staphylococcus epidermidis

<400> SEQUENCE: 54

Met Glu Tyr Lys Asp Ile Ala Thr Pro Ser Arg Thr Arg Ala Leu Leu
1               5                   10                  15

Asp Gln Tyr Gly Phe Asn Phe Lys Lys Ser Leu Gly Gln Asn Phe Leu
            20                  25                  30

Ile Asp Val Asn Ile Ile Asn Lys Ile Glu Ala Ser His Ile Asp
        35                  40                  45

Cys Thr Thr Gly Val Ile Glu Val Gly Pro Gly Met Gly Ser Leu Thr
50                  55                  60

Glu Gln Leu Ala Lys Asn Ala Lys Val Met Ala Phe Glu Ile Asp
65                  70                  75                  80

Gln Arg Leu Ile Pro Val Leu Lys Asp Thr Leu Ser Pro Tyr Asp Asn
                85                  90                  95

Val Thr Ile Ile Asn Glu Asp Ile Leu Lys Ala Asp Ile Ala Lys Ala
            100                 105                 110

Val Asp Thr His Leu Gln Asp Cys Asp Lys Ile Met Val Val Ala Asn
        115                 120                 125

Leu Pro Tyr Tyr Ile Thr Thr Pro Ile Leu Leu Asn Leu Met Gln Gln
    130                 135                 140

Asp Val Pro Ile Asp Gly Phe Val Val Met Met Gln Lys Glu Val Gly
145                 150                 155                 160

Glu Arg Leu Asn Ala Gln Val Gly Thr Lys Ala Tyr Gly Ser Leu Ser
                165                 170                 175

Ile Val Ala Gln Tyr Tyr Thr Glu Thr Ser Lys Val Leu Thr Val Pro
            180                 185                 190

Lys Thr Val Phe Met Pro Pro Asn Val Asp Ser Ile Val Val Lys
        195                 200                 205

Leu Met Gln Arg Gln Glu Pro Leu Val Gln Val Asp Asp Glu Glu Gly
210                 215                 220

Phe Phe Lys Leu Ala Lys Ala Ala Phe Ala Gln Arg Arg Lys Thr Ile
225                 230                 235                 240

Asn Asn Asn Tyr Gln Asn Phe Phe Lys Asp Gly Lys Lys Asn Lys Glu
                245                 250                 255

Thr Ile Arg Gln Trp Leu Glu Ser Ala Gly Ile Asp Pro Lys Arg Arg
            260                 265                 270

Gly Glu Thr Leu Thr Ile Gln Asp Phe Ala Thr Leu Tyr Glu Gln Lys
        275                 280                 285

Lys Lys Phe Ser Glu Leu Thr Asn
    290                 295

<210> SEQ ID NO 55
<211> LENGTH: 106
<212> TYPE: PRT
<213> ORGANISM: Staphylococcus epidermidis

<400> SEQUENCE: 55
```

Met Thr Ser Asn His His Ala Pro Tyr Asp Leu Gly Tyr Thr Arg Ala
1               5                   10                  15

Thr Met Asp Asn Thr Lys Gly Ser Glu Thr Ala Arg Ser Ser Lys Ser
            20                  25                  30

His Lys Val Val Leu Ser Ser Asp Cys Ser Leu Gln Leu Asp Tyr Met
        35                  40                  45

Lys Leu Glu Ser Leu Val Ile Val Asp Gln His Ala Thr Val Asn Thr
    50                  55                  60

Phe Pro Gly Leu Val His Thr Ala Arg His Thr Thr Arg Val Cys Asn
65                  70                  75                  80

Thr Arg Ser Arg Trp Ser Asn His Leu Glu Leu Ala Val Glu Gly Gly
            85                  90                  95

Thr Asn Asp Trp Gly Glu Val Val Thr Arg
            100                 105

<210> SEQ ID NO 56
<211> LENGTH: 442
<212> TYPE: PRT
<213> ORGANISM: Staphylococcus epidermidis

<400> SEQUENCE: 56

Met Phe Phe Lys Gln Phe Tyr Asp Lys His Leu Ser Gln Ala Ser Tyr
1               5                   10                  15

Leu Ile Gly Cys Gln Lys Thr Gly Glu Ala Met Ile Ile Asp Pro Ile
            20                  25                  30

Arg Asp Leu Ser Ser Tyr Ile Arg Val Ala Asp Glu Glu Gly Leu Thr
        35                  40                  45

Ile Thr His Ala Ala Glu Thr His Ile His Ala Asp Phe Ala Ser Gly
    50                  55                  60

Ile Arg Asp Val Ala Ile Lys Leu Asn Ala Ser Ile Tyr Val Ser Gly
65                  70                  75                  80

Glu Ser Asp Asp Thr Leu Gly Tyr Lys Asn Met Pro Asn Gln Thr His
            85                  90                  95

Phe Val Gln His Asn Asp Asp Ile Tyr Val Gly Asn Ile Lys Leu Lys
            100                 105                 110

Val Leu His Thr Pro Gly His Thr Pro Glu Ser Ile Ser Phe Leu Leu
        115                 120                 125

Thr Asp Glu Gly Ala Gly Ala Gln Val Pro Met Gly Leu Phe Ser Gly
    130                 135                 140

Asp Phe Ile Phe Val Gly Asp Ile Gly Arg Pro Asp Leu Leu Glu Lys
145                 150                 155                 160

Ala Val Lys Val Glu Gly Ser Ser Glu Ile Gly Ala Lys Gln Met Phe
            165                 170                 175

Lys Ser Ile Glu Ser Ile Lys Asp Leu Pro Asn Tyr Ile Gln Ile Trp
            180                 185                 190

Pro Gly His Gly Ala Gly Ser Pro Cys Gly Lys Ser Leu Gly Ala Ile
        195                 200                 205

Pro Thr Ser Thr Leu Gly Tyr Glu Lys Gln Thr Asn Trp Ala Phe Ser
    210                 215                 220

Glu Asn Asn Glu Ala Thr Phe Ile Asp Lys Leu Ile Ser Asp Gln Pro
225                 230                 235                 240

Ala Pro Pro His His Phe Ala Gln Met Lys Lys Ile Asn Gln Phe Gly
            245                 250                 255

Met Asn Leu Tyr Gln Pro Tyr Thr Val Tyr Pro Ala Thr Asn Thr Asn
            260                 265                 270

```
Arg Leu Thr Phe Asp Leu Arg Ser Lys Glu Ala Tyr His Gly Gly His
        275                 280                 285

Ile Glu Gly Thr Ile Asn Ile Pro Tyr Asp Lys Asn Phe Ile Asn Gln
        290                 295                 300

Ile Gly Trp Tyr Leu Asn Tyr Asp Gln Glu Ile Asn Leu Ile Gly Glu
305                 310                 315                 320

Tyr His Leu Val Ser Lys Ala Thr His Thr Leu Gln Leu Ile Gly Tyr
                325                 330                 335

Asp Asp Val Ala Gly Tyr Gln Leu Pro Gln Ser Lys Ile Gln Thr Arg
            340                 345                 350

Ser Ile His Ser Glu Asp Ile Thr Gly Asn Glu Ser His Ile Leu Asp
        355                 360                 365

Val Arg Asn Asp Asn Glu Trp Asn Asn Gly His Leu Ser Gln Ala Val
370                 375                 380

His Val Pro His Gly Lys Leu Leu Glu Thr Asp Leu Pro Phe Asn Arg
385                 390                 395                 400

Asn Asp Val Ile Tyr Val His Cys Gln Ser Gly Ile Arg Ser Ser Ile
                405                 410                 415

Ala Ile Gly Ile Leu Glu His Lys Gly Tyr His Asn Ile Ile Asn Val
            420                 425                 430

Asn Glu Gly Tyr Lys Asp Ile His Leu Ser
            435                 440

<210> SEQ ID NO 57
<211> LENGTH: 285
<212> TYPE: PRT
<213> ORGANISM: Staphylococcus epidermidis

<400> SEQUENCE: 57

Leu Lys Lys Ile Leu Val Leu Ser Leu Thr Ala Phe Leu Val Leu Ala
1               5                   10                  15

Gly Cys Asn Ser Gly Asp Lys Thr Asp Thr Lys Asp Lys Lys Glu Glu
            20                  25                  30

Thr Lys Gln Thr Ser Lys Ala Asn Lys Glu Asn Lys Glu Gln His His
        35                  40                  45

Lys Gln Glu Asn Asp Asn Lys Ala Ser Thr Gln Leu Ser Glu Lys Glu
    50                  55                  60

Arg Leu Ala Leu Ala Phe Tyr Ala Asp Gly Val Glu Lys Tyr Met Leu
65                  70                  75                  80

Thr Lys Asn Glu Val Leu Thr Gly Val Tyr Asp Tyr Gln Lys Gly Asn
                85                  90                  95

Glu Thr Glu Lys Lys Gln Met Glu Gln Leu Met Leu Glu Lys Ala Asp
            100                 105                 110

Ser Met Lys Asn Ala Pro Lys Asp Met Lys Phe Tyr Gln Val Tyr Pro
        115                 120                 125

Ser Lys Gly Gln Phe Ala Ser Ile Val Gly Val Asn Lys Asn Lys Ile
    130                 135                 140

Phe Ile Gly Ser Thr Gln Gly Ala Leu Ile Asp Tyr Gln Thr Leu Leu
145                 150                 155                 160

Asn Asn Gly Lys Glu Leu Asp Ile Ser Gln Leu Tyr Glu Asp Asn Lys
                165                 170                 175

Asp Asn Arg Ser Leu Glu Glu Met Lys Asn Lys Ile Glu Ile Val Asp
            180                 185                 190

Ser Gly Ala Ala Gln Lys Ala Asp Asp Pro Asp Lys Asn Ser Ala Asn
        195                 200                 205
```

Thr Met Ala His Met Arg Ser Gln Ile Tyr Glu Lys Ile Ser Asp Phe
    210                 215                 220

Asp Gly Lys Leu Asp Asn Lys Thr Tyr Leu Trp Asp Asn Ile Arg Ile
225                 230                 235                 240

Asn Asp Asp Gly Asn Trp Thr Val His Tyr Arg Asn His Asp Gly Glu
                245                 250                 255

Ile Met Gly Thr Tyr Lys Ser Glu Lys Asn Lys Ile Ile Lys Leu Asp
            260                 265                 270

Gln Asn Gly Asn Lys Ile Lys Glu Gln Gln Met Ser Asn
        275                 280                 285

<210> SEQ ID NO 58
<211> LENGTH: 498
<212> TYPE: PRT
<213> ORGANISM: Staphylococcus epidermidis

<400> SEQUENCE: 58

Met Ala Asn Lys Glu Ser Lys Asn Val Val Ile Ile Gly Ala Gly Val
1               5                   10                  15

Leu Ser Thr Thr Phe Gly Ser Met Ile Lys Glu Leu Glu Pro Asp Trp
            20                  25                  30

Asn Ile Lys Leu Tyr Glu Arg Leu Asp Arg Pro Gly Ile Glu Ser Ser
        35                  40                  45

Asn Glu Arg Asn Asn Ala Gly Thr Gly His Ala Ala Leu Cys Glu Leu
    50                  55                  60

Asn Tyr Thr Val Gln Gln Pro Asp Gly Ser Ile Asp Ile Glu Lys Ala
65                  70                  75                  80

Lys Glu Ile Asn Glu Gln Phe Glu Ile Ser Lys Gln Phe Trp Gly His
                85                  90                  95

Leu Val Lys Ser Gly Asn Ile Ser Asn Pro Arg Asp Phe Ile Asn Pro
            100                 105                 110

Leu Pro His Ile Ser Phe Val Arg Gly Lys Asn Asn Val Lys Phe Leu
        115                 120                 125

Lys Asn Arg Tyr Glu Ala Met Arg Asn Phe Pro Met Phe Asp Asn Ile
    130                 135                 140

Glu Tyr Thr Glu Asp Ile Glu Glu Met Arg Lys Trp Met Pro Leu Met
145                 150                 155                 160

Met Thr Gly Arg Thr Gly Asn Glu Ile Met Ala Ala Ser Lys Ile Asp
                165                 170                 175

Glu Gly Thr Asp Val Asn Tyr Gly Glu Leu Thr Arg Lys Met Ala Lys
            180                 185                 190

Ser Ile Glu Lys His Pro Asn Ala Asp Val Gln Tyr Asn His Glu Val
        195                 200                 205

Ile Asn Phe Asn Arg Arg Lys Asp Gly Ile Trp Glu Val Lys Val Lys
    210                 215                 220

Asn Arg Asn Ser Gly Asp Val Glu Thr Val Leu Ala Asp Tyr Val Phe
225                 230                 235                 240

Ile Gly Ala Gly Gly Ala Ile Pro Leu Leu Gln Lys Thr Gly Ile
                245                 250                 255

Pro Glu Ser Lys His Leu Gly Gly Phe Pro Ile Ser Gly Gln Phe Leu
            260                 265                 270

Ile Cys Thr Asn Pro Asp Val Ile Asn Glu His Asp Val Lys Val Tyr
        275                 280                 285

Gly Lys Glu Pro Pro Gly Thr Pro Pro Met Thr Val Pro His Leu Asp
    290                 295                 300

```
Thr Arg Tyr Ile Asp Gly Glu Arg Thr Leu Leu Phe Gly Pro Phe Ala
305                 310                 315                 320

Asn Ile Gly Pro Lys Phe Leu Arg Asn Gly Ser Asn Leu Asp Leu Phe
            325                 330                 335

Lys Ser Val Lys Pro Tyr Asn Ile Thr Thr Leu Leu Ala Ser Ala Val
        340                 345                 350

Lys Asn Leu Pro Leu Ile Lys Tyr Ser Ile Asp Gln Val Leu Met Thr
            355                 360                 365

Lys Glu Gly Cys Met Asn His Leu Arg Thr Phe Tyr Pro Glu Ala Arg
        370                 375                 380

Asp Glu Asp Trp Gln Leu Tyr Thr Ala Gly Lys Arg Val Gln Val Ile
385                 390                 395                 400

Lys Asp Thr Lys Glu His Gly Lys Gly Phe Ile Gln Phe Gly Thr Glu
            405                 410                 415

Val Val Asn Ser Lys Asp His Ser Val Ile Ala Leu Leu Gly Glu Ser
        420                 425                 430

Pro Gly Ala Ser Thr Ser Val Ser Val Ala Leu Glu Val Leu Glu Lys
            435                 440                 445

Asn Phe Ala Glu Tyr Glu Lys Asp Trp Thr Pro Lys Leu Gln Lys Met
    450                 455                 460

Ile Pro Ser Tyr Gly Lys Ser Leu Ile Asp Asp Val Lys Leu Met Arg
465                 470                 475                 480

Ala Thr Arg Lys Gln Thr Ser Lys Asp Leu Glu Leu Asn Tyr Tyr Glu
            485                 490                 495

Ser Lys

<210> SEQ ID NO 59
<211> LENGTH: 516
<212> TYPE: PRT
<213> ORGANISM: Staphylococcus epidermidis

<400> SEQUENCE: 59

Met Lys Ile Phe Lys Thr Leu Ser Ser Ile Leu Val Thr Ser Val Leu
1               5                   10                  15

Ser Val Thr Val Ile Pro Ser Thr Phe Ala Ser Thr Glu Ser Thr Ala
            20                  25                  30

Thr Asn Gln Thr Gln Thr Val Leu Phe Asp Asn Ser His Ala Gln
        35                  40                  45

Thr Ala Gly Ala Ala Asp Trp Val Ile Asp Gly Ala Phe Ser Asp Tyr
50                  55                  60

Ala Asp Ser Met Arg Lys Gln Gly Tyr Gln Val Lys Glu Leu Glu Gly
65                  70                  75                  80

Glu Ser Asn Ile Ser Asp Gln Ser Leu Gln Gln Ala His Val Leu Val
            85                  90                  95

Ile Pro Glu Ala Asn Asn Pro Phe Lys Glu Asn Glu Gln Lys Ala Ile
            100                 105                 110

Ile Asn Phe Val Lys Asn Gly Gly Ser Val Ile Phe Ile Ser Asp His
        115                 120                 125

Tyr Asn Ala Asp Arg Asn Leu Asn Arg Ile Asp Ser Ser Glu Ser Met
        130                 135                 140

Asn Gly Tyr Arg Arg Gly Ala Tyr Glu Asn Met Thr Lys Asp Met Asn
145                 150                 155                 160

Asn Glu Glu Lys Asn Ser Asn Val Met His Asn Val Lys Ser Ser Asp
            165                 170                 175
```

```
Trp Leu Ser Gln Asn Phe Gly Val Arg Phe Arg Tyr Asn Ala Leu Gly
            180                 185                 190

Asp Ile Asn Thr Gln Asn Ile Val Ser Ser Lys Asp Ser Phe Gly Ile
        195                 200                 205

Thr Lys Gly Val Gln Ser Val Ser Met His Ala Gly Ser Thr Leu Ala
    210                 215                 220

Ile Thr Asp Pro Asn Lys Ala Lys Gly Ile Ile Tyr Met Pro Glu His
225                 230                 235                 240

Leu Thr His Ser Gln Lys Trp Pro His Ala Val Asp Gln Gly Ile Tyr
            245                 250                 255

Asn Gly Gly Gly Ile Asn Glu Gly Pro Tyr Val Ala Ile Ser Lys Ile
            260                 265                 270

Gly Lys Gly Lys Ala Ala Phe Ile Gly Asp Ser Ser Leu Val Glu Asp
        275                 280                 285

Arg Ser Pro Lys Tyr Leu Arg Glu Asp Asn Gly Lys Pro Lys Lys Thr
    290                 295                 300

Tyr Asp Gly Phe Lys Glu Gln Asp Asn Gly Lys Leu Leu Asn Asn Leu
305                 310                 315                 320

Thr Thr Trp Leu Gly Lys Lys Glu Ser Gln Ser Ser Met Lys Asp Met
            325                 330                 335

Gly Ile Lys Leu Asp Asn Lys Thr Pro Leu Leu Asn Phe Glu Gln Pro
            340                 345                 350

Glu Asn Ser Ile Glu Pro Gln Lys Glu Pro Trp Thr Asn Pro Ile Glu
        355                 360                 365

Gly Tyr Lys Trp Tyr Asp Arg Ser Thr Phe Lys Thr Gly Ser Tyr Gly
    370                 375                 380

Ser Asn Gln Arg Gly Ala Asp Asp Gly Val Asp Asp Lys Ser Ser Ser
385                 390                 395                 400

His Gln Asn Gln Asn Ala Lys Val Glu Leu Thr Leu Pro Gln Asn Ile
            405                 410                 415

Gln Pro His His Pro Phe Gln Phe Thr Ile Lys Leu Thr Gly Tyr Glu
            420                 425                 430

Pro Asn Ser Thr Ile Ser Asp Val Arg Val Gly Leu Tyr Lys Asp Gly
        435                 440                 445

Gly Lys Gln Ile Gly Ser Phe Ser Ser Asn Arg Asn Gln Phe Asn Thr
    450                 455                 460

Leu Gly Tyr Ser Pro Gly Gln Ser Ile Lys Ala Asn Gly Ala Gly Glu
465                 470                 475                 480

Ala Ser Phe Thr Leu Thr Ala Lys Val Thr Asp Glu Ile Lys Asp Ala
            485                 490                 495

Asn Ile Arg Val Lys Gln Gly Lys Lys Ile Leu Leu Thr Gln Lys Met
            500                 505                 510

Asn Glu Asn Phe
        515

<210> SEQ ID NO 60
<211> LENGTH: 84
<212> TYPE: PRT
<213> ORGANISM: Staphylococcus epidermidis

<400> SEQUENCE: 60

Gly Thr Pro Leu Glu Leu Val Phe Val Asn Thr Leu Gly Pro Lys Pro
1               5                   10                  15

Cys Phe Ala Lys Pro Asn Lys Ile Leu Leu Glu Tyr Ile Pro Leu
            20                  25                  30
```

```
Phe Val Ala Asp Ala Ala Val Lys Thr Thr Lys Leu Thr Met Pro
        35                  40                  45

Ala Ala Lys Gly Thr Pro Ile Ser Val Asn Asn Leu Thr Asn Gly Leu
 50                  55                  60

Leu Ser Gly Ser Thr Leu Asn His Gly Met Thr Asp Met Ile Thr Ser
 65                  70                  75                  80

Lys Pro Pro Ile

<210> SEQ ID NO 61
<211> LENGTH: 54
<212> TYPE: PRT
<213> ORGANISM: Staphylococcus epidermidis

<400> SEQUENCE: 61

Ser Ser Leu Ser Thr Ile Ile Pro Phe Ser Leu Gly Ala Leu Gly Lys
 1               5                  10                  15

Phe Asn Ser Phe Ile Glu Gln Ile Ile Pro Leu Glu Ser Thr Pro Arg
                20                  25                  30

Asn Trp Ala Ser Leu Ile Thr Ile Pro Leu Gly Ile Thr Ala Pro Thr
         35                  40                  45

Phe Ala Thr Thr Thr Phe
     50

<210> SEQ ID NO 62
<211> LENGTH: 116
<212> TYPE: PRT
<213> ORGANISM: Staphylococcus aureus

<400> SEQUENCE: 62

Met Lys Phe Lys Lys Tyr Ile Leu Thr Gly Thr Leu Ala Leu Leu Leu
 1               5                  10                  15

Ser Ser Thr Gly Ile Ala Thr Ile Glu Gly Asn Lys Ala Asp Ala Ser
                20                  25                  30

Ser Leu Asp Lys Tyr Leu Thr Glu Ser Gln Phe His Asp Lys Arg Ile
         35                  40                  45

Ala Glu Glu Leu Arg Thr Leu Leu Asn Lys Ser Asn Val Tyr Ala Leu
 50                  55                  60

Ala Ala Gly Ser Leu Asn Pro Tyr Tyr Lys Arg Thr Ile Met Met Asn
 65                  70                  75                  80

Glu Tyr Arg Ala Lys Ala Ala Leu Lys Lys Asn Asp Phe Val Ser Met
                85                  90                  95

Ala Asp Ala Lys Val Ala Leu Glu Lys Ile Tyr Lys Glu Ile Asp Glu
                100                 105                 110

Ile Ile Asn Arg
        115

<210> SEQ ID NO 63
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 63

Lys Leu Lys Leu Leu Leu Leu Leu Lys Leu Lys
 1               5                  10

<210> SEQ ID NO 64
<211> LENGTH: 36
<212> TYPE: PRT
```

```
<213> ORGANISM: Artificial Sequence
<220> FEATURE:
<223> OTHER INFORMATION: Synthetic Peptide

<400> SEQUENCE: 64

Arg Leu Ala Gly Leu Leu Arg Lys Gly Gly Glu Lys Ile Gly Glu Lys Leu Lys
1               5                   10                  15

Lys Ile Gly Gln Lys Ile Lys Asn Phe Phe Gln Lys Leu Val Pro Gln Pro Glu
        20                  25                  30                  35
```